United States Patent [19]

Böhringer et al.

[11] Patent Number: 5,494,666
[45] Date of Patent: Feb. 27, 1996

[54] β-LACTAM COMPOUNDS

[75] Inventors: Markus Böhringer, Möhlin, Switzerland; Christian Hubschwerlen, Durmenach, France; Philippe Pflieger, Folgensburg, France; Jean-Luc Specklin, Kembs-Loechle, France

[73] Assignee: Hoffmann-La Roche Inc., Nutley, N.J.

[21] Appl. No.: 489,195

[22] Filed: Jun. 9, 1995

Related U.S. Application Data

[62] Division of Ser. No. 398,411, Mar. 3, 1995, Pat. No. 5,464,617.

[30] Foreign Application Priority Data

Mar. 11, 1994 [CH] Switzerland ................. 751/94
Jan. 31, 1995 [CH] Switzerland ................. 260/95

[51] Int. Cl.⁶ .................. C07D 513/04; A61K 31/54
[52] U.S. Cl. .................. 424/114; 540/205; 540/214; 514/210; 514/224.5
[58] Field of Search .................. 424/114; 514/210, 514/224.5; 540/214, 209, 215, 203

[56] References Cited

U.S. PATENT DOCUMENTS

| | | |
|---|---|---|
| 3,950,352 | 4/1976 | Wolfe . |
| 4,018,782 | 4/1977 | Wolfe ................. 540/205 |
| 4,140,688 | 2/1979 | Perchonck . |
| 4,220,766 | 9/1980 | Tsuji et al. ................. 540/203 |
| 4,525,304 | 6/1985 | Hull et al. ................. 540/203 |
| 4,956,358 | 9/1990 | Morimoto et al. ................. 540/214 |
| 5,055,463 | 10/1991 | Greenlee et al. ................. 540/203 |

FOREIGN PATENT DOCUMENTS

| | | |
|---|---|---|
| 508234 | 10/1992 | European Pat. Off. . |
| 93/15085 | 8/1993 | WIPO . |

OTHER PUBLICATIONS

Derwent Abstract No. AN 92-341562/42. (1992).
Chemical Abstracts, vol. 119:11702s (1993).

*Primary Examiner*—Nicholas Rizzo
*Attorney, Agent, or Firm*—George M. Gould; George W. Johnston; Alan P. Kass

[57] ABSTRACT

Compounds of the formula

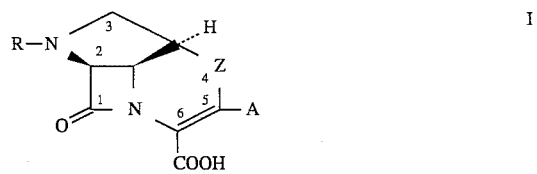

where Z, A, and R are as disclosed herein and pharmaceutically compatible, readily hydrolyzable esters and salts of these compounds are disclosed.

The compounds have β-lactamase inhibiting properties and are useful in the control of β-lactamase-forming pathogens in combination with β-lactam antibiotics. They also exhibit antibacterial activity of their own and can accordingly be used themselves in the control or treatment of infectious diseases.

75 Claims, No Drawings

β-LACTAM COMPOUNDS

This is a divison, of application Ser. No. 08/398,411, filed Mar. 3, 1995, now U.S. Pat. No. 5,464,617.

The present invention is concerned with compounds of the formula

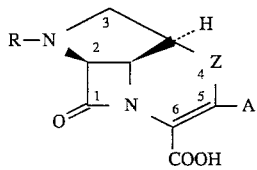

in which Z signifies methylene, oxygen or sulphur and R signifies hydrogen, lower (cyclo)alkyl optionally substituted by carboxy, lower alkoxycoabonyl, carbamoyl, lower alkylcarbamoyl, phenylcarbamoyl or hydroxyphenylcarbamoyl, lower alkenylmethyl, lower alkenylmethoxycoabonyl, formyl, lower (cyclo)alkanoyl or (cyclo)alkylsulphonyl optionally substituted by halogen, cyano, carbamoyl-loweralkoxy, carbamoyl-lower alkylthio or carbamoyl-lower alkylamino, carbamoyl optionally substituted by lower (cyclo)alkyl, lower alkoxycoabonyl-lower alkyl, benzyloxycoabonyl-lower alkyl or coaboxy-lower alkyl or a ring structure of the formulae

wherein Q, represents a 5- or 6-membered ring optionally containing nitrogen, sulphur and/or oxygen and X represents a direct bond or one of the groups —CH₂—, —CH₂CH₂—, —CH=CH—, —NH—, —NHCH₂—, —CH₂NH—, —CH(NH₂)—, —CH₂CH₂NH—, —C(=NOCH₃)—, —OCH₂— and —SCH₂—; and wherein further A signifies lower alkyl, hydroxy-lower alkyl, vinyl, cyanovinyl, lower alkoxy, optionally phenyl-substituted lower (cyclo)alkanoyloxy or (cyclo)alkylsulphonyloxy, optionally lower-(cyclo)alkyl-substituted benzoyloxy or phenylsulphonyloxy, a residue —S-Het or —S—CH₂-Het, wherein Het represents a 5- or 6-membered heterocycle containing nitrogen, sulphur and/or oxygen, or a residue —CH₂—L, wherein L represents optionally phenyl-substituted lower (cyclo)alkanoyloxy or (cyclo)alkylsulphonyloxy, optionally lower (cyclo)alkyl-substituted benzoyloxy or phenylsulphonyloxy, carbamoyloxy, lower (cyclo)alkoxycarbonyl, carboxy, azido, amino, lower (cyclo)alkanoylamino, lower (cyclo)alkylsulphonylamino, lower (cyclo)alkylamino, di-lower (cyclo)alkylamino, a 5- or 6-membered ring bonded to a nitrogen atom or a residue —S-Het or —S—CH₂-Het, wherein Het has the above significance, and pharmaceutically compatible, readily hydrolyzable esters and salts of these compounds.

These compounds are distinguished by therapeutically valuable properties. In particular, they have pronounced β-lactamase inhibiting properties and are accordingly useful in the control of β-lactamase forming pathogens in combination with β-lactam antibiotics such as penicillins, cephalosporins, pomems and carbapenems. They also have an antibacterial activity and can accordingly also be used alone against pathogens.

Objects of the present invention are β-lactams of formula I above and pharmaceutically compatible salts thereof per se and as pharmaceutically active substances, the making of these compounds and intermediates for the manufacture of these compounds, medicaments containing a compound of formula I or pharmaceutically compatible salt thereof and the production of such medicaments, as well as the use of compounds of general formula I and of pharmaceutically compatible salts thereof in the control or prevention of illnesses in mammals, both human and non-human.

The terms in parentheses set forth in the above definition, e.g. "lower (cyclo)alkyl", "lower (cyclo)alkanoyl" and "lower (cyclo)alkylphenylsulphonyloxy" are to be understood as being optional, and accordingly not only "lower alkyl", "lower alkanoyl" and "lower alkylphenylsulphonyloxy" but also "lower cycloalkyl", "lower cycloalka-noyl" and "lower cycloalkyl-phenylsulphonyloxy" are provided for.

The term "lower alkyl", taken alone or in combinations such as "lower alkoxy", "lower alkylamino", "di-lower alkylamino", "lower alkylsulphonyloxy", "lower alkoxycarbonyl", "lower alkanoyl" (="lower alkylcarbonyl"), "lower alkanoyloxy" and the like, signifies straight-chain or branched saturated hydrocarbon residues with a maximum of 7, preferably a maximum of 4, carbon atoms such as methyl, ethyl, n-propyl, isopropyl, n-butyl, isobutyl, sec-butyl, t-butyl and the like.

"Lower cycloalkyl", taken alone or in corresponding combinations, signifies cyclic hydrocarbon residues with 3–6 carbon atoms, i.e. cydopropyl, cyclobutyl, cyclopentyl or cyclohexyl.

"Halogen" signifies fluorine, chlorine, bromine or iodine, especially fluorine. s The "5- or 6-membered, rings optionally containing nitrogen, sulphur and/or oxygen" are e.g. phenyl, saturated heterocyclenes such as pyrrolidinyl, piperidinyl, piperazinyl, morpholinyl, thiomorpholinyl, tetrahydrothienyl and tetrahydrofuryl, and aromatic heterocycles such as 2-furyl, 3-furyl, thiazolyl, thiadiazolyl, oxathiazolyl, 2-thienyl, 3-thienyl, 2-pyrrolyl, 3-pyrrolyl, 1-pyridinio, 2-pyridyl, 3-pyridyl, 4-pyridyl, oxazolyl, isoxazolyl, imidazolyl, pyrazolyl, triazolyl, tetrazolyl, pyrazinyl, pyridazinyl and pyrimidinyl. These groups can also be substituted, e.g. by lower alkyl, lower alkoxy, lower alkylthio, hydroxy, carbamoyl, carbamoylmethyl, carbamoylamino, sulphamoyl, lower alkanoyloxy, sulphonyloxy, halogen, amino, methylamino, dimethylamino, chloroacetylamino and pyridin- 1-ylio-acetylarnino. N-Heterocycles can, in addition, also be substituted by oxo. Examples of such substituted rings are 4-tolyl, 4-sulphamoylphenyl, 4-hydroxyphenyl, 4-carbamoylphenyl, 3,4-dihydroxyphenyl, 3-methyl-(2-furyl), 1-methyl-1H-tetrazol-5-yl, 4-anisyl, 3,4,5-trimethoxyphenyl, 4-chlorophenyl, 4-fluoro-(2-pyridyl), 2-amino-4-thiazolyl, 5-methyl-1,3,4-thiadiazol-2-yl, p-amino-phenyl, p-(chloroacetylamino)-phenyl, 3,4-disulphonyloxy-phenyl, 3,4-diacetoxyphenyl, 2-oxo-pyrrolidinyl-3-yl, 2-oxo-tetrahydrothien-3-yl, 3-methoxy-isoxazol-5-yl, 1,1-dioxo-tetrahydrothien-3-yl, 3-hydroxy-isoxazol-5-yl, 5-amino-1,3,4-thiadiazol-2-yl, 5-(pyridin-1-ylio-acetylamino)- 1,3,4-thiadiazol-2-yl and 1-methyl-pyridin-4-ylio. A further ring can be fused on, especially a phenyl ring, such as e.g. in indolyl, 1H-benzotriazol-2-yl, 2-oxo-2H-1-benzopyran-7-yl or 2-oxo-4-is (trifluoromethyl)-2H-1-benzopyran-7-yl, a saturated 5- or 6-membered carbocyclic ring, such as e.g. in 2,3-cyclopenteno-4-pyridyl (1-pyrindin-4-yl) or 2,3-cyclohexeno-4-pyridyl, or also a 5- to 6-membered heterocycle, such as e.g. in benzimidazol-5-yl, 1H-benzotriazol-4-yl or 2-carbamoyl-5-methyl-[1,2,4]triazolo[1,5-a]pyrimidin-7-yl.

Under "5- or 6-membered rings bonded to a nitrogen atom" there are to be understood N-quaternary rings which can be not only aromatic (such as in the case of 1-pyridinio) but also saturated (such as in the case of 1-methyl-1-pyrrolidinio or 1-methyl-1-piperidinio); or also N-tertiary rings (such as e.g. 5-methylsulphanyl-1H-tetrazol-1-yl).

A preferred subgroup of R has the formula

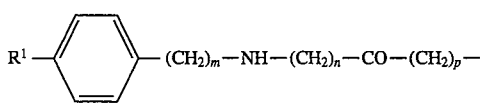

wherein R₁ represents hydrogen, hydroxy, carbamoyl or sulphamoyl and each of m, n and p represent 0 or 1.

Preferred sub-groups of (b) are:

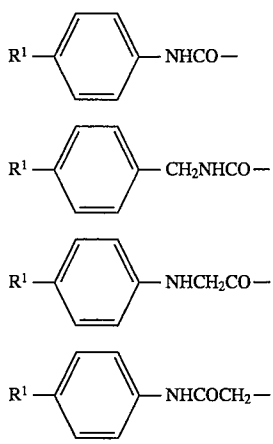

Preferred are:

(b1) with $R^1$=hydroxy or carbamoyl, i.e. 4-hydroxyphenylcarbamoyl and 4-carbamoylphenylcarbamoyl.

Further preferred groups R are the optionally fluoro- or cyano-substituted lower alkanoyl and, lower alkylsulphonyl groups. Formyl, acetyl, trifluoroacetyl, cyanoacetyl and methylsulphonyl are especially preferred.

Further preferred meanings for R include:

Hydrogen,
2-oxo-pyrrolidin-3-ylcarbamoyl,
thien-2-yl-methylcarbamoyl,
3,4-dihydroxy-benzylcarbmoyl,
2-oxo-tetrahydrothien-3-ylcarbamoyl,
4-sulphamoyl-benzylcarbamoyl,
3-methoxy-isoxazol-5-ylmethylcarbamoyl,
3-hydroxy-isoxazol-5-ylmethylcarbamoyl,
1,1-dioxo-tetrahydrothien-3-ylmethylcarbamoyl,
(2-amino-thiazol-4-yl)-methoxyiminoacetyl,
1-methyl-1H-tetrazol-5-ylsulphanylacetyl,
3-carbamoyl-pyridin-1-ylioacetyl,
2-t-butoxycarbonyl-ethylcarbamoyl,
4-hydroxy-benzylcarbamoyl,
trifluoromethylsulphonyl,
benzyloxycarbonylmethylcarbamoyl,
benzylcarbamoyl,
cyclopropylcarbamoyl,
4-sulphamoyl-benzylcarbamoyl,
2-thiophen-2-yl-ethylcarbamoyl,
5-methyl-1,3,4-thiadiazol-2-yl-sulphonylacetyl,
5-amino-1,3,4-thiadiazol-2-yl-sulphonylacetyl,
pyridin-4-ylsulphanylacetyl,
phenylaminoacetyl,
4-hydroxy-phenylcarbamoylmethyl,
methoxycarbonylmethyl,
ethyl,
carbamoylmethyl,
pyridin-4-ylsulphanylacetyl,
3-carbamoyl-pyridin-1-ylioacetyl,
carbamoylmethylsulphanylacetyl,
(R)-(N-benzyloxycarbonyl)-2-phenylglycyl,
(R)-2-phenylglycyl,
carboxymethylcarbamoyl.

The group L present in the residue —CH₂-L set forth under A can, inter alia, also signify "carbamoyloxy". Such carbamoyloxy groups can be characterized by the formula

wherein $R^2$ signifies hydrogen and $R^3$ signifies hydrogen, lower (cyclo)alkyl, halo-lower alkyl, carbamoylmethyl or a residue —(CH₂)$_q$Q, in which q is 0, 1 or 2 and Q, has the above significance, or $R^2$ and $R^3$ together with the nitrogen atom to which they are bound represent a saturated N-heterocycle optionally containing sulphur, oxygen or additional nitrogen.

Examples of substituents $R^3$ include:

Methyl,
cyclopropyl,
2,2,2-trifluoroethyl,
phenyl,
p-hydroxyphenyl,
benzyl,
p-hydroxybenzyl,
4-pyridylmethyl,
carbamoylmethyl,
1H-tetrazol-5-yl.

Examples of saturated heterocycles —NR²R³ include:

Piperazinyl,
4-methyl-piperazinyl,
4-morpholinyl,
4-thiomorpholinyl.

$R^2$ and $R^3$ are both preferably hydrogen and thus (c) represents the carbamoyloxy group, i.e. A is preferably carbamoyloxymethyl.

The definitions —S-Het, —SCH₂-Het, —CH₂S-Het and —CH₂SCH₂-Het falling under A include a sub-group of substituents of the

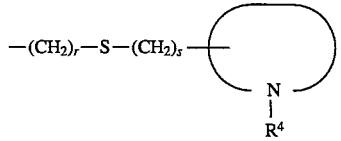

in which each of r and s represent 0 or 1 and

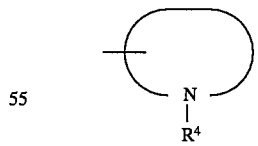

represents a 5- or 6-membered N-heterocycle optionally containing a sulphur or oxygen atom; and in which $R^4$ signifies lower alkyl, sulphonyl methyl or a group of the formula

and $R^5$ signifies hydrogen and $R^6$ signifies hydrogen, lower (cyclo)alkyl, hydroxy, carbamoylmethyl, halo-lower alkyl or a residue —(CH₂)$_q$Q, wherein q is 0, 1 or 2 and Q has the above significance, or $R^5$ and $R^6$ together with the nitrogen atom to which they are bound represent a saturated N-heterocycle optionally containing sulphur, oxygen or additional nitrogen.

The above N-heterocycle

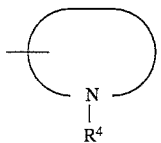

is preferably a 1-$R^4$-substituted 1H-tetrazol-5-yl residue of the formula

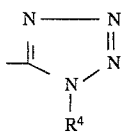

Examples of substituents $R^6$ include:
Methyl,
cyclopropyl,
phenyl,
p-hydroxyphenyl,
benzyl,
phenethyl,
carbamoylmethyl,
hydroxy.

Examples of saturated heterocycles —$NR^5R^6$ include:
Piperazinyl,
4-methyl-piperazinyl,
4-morpholinyl,
4-thiomorpholinyl.

Preferably, $R^4$ is methyl or carbamoylmethyl (i.e. $R^5$ and $R^6$ are both hydrogen); especially preferred groups A are 1-methyl-1H-tetrazol-5-ylsulphanylmethyl and 1-carbamoylmethyl-1H-tetrazol-5-ylsulphanylmethyl.

Further preferred sub-groups of A are of the formula

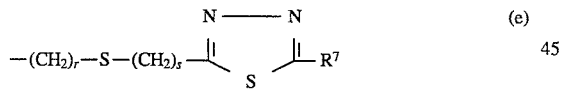 (e)

in which each of r and s represent 0 or 1 and $R^7$ represents methyl, amino, acetylamino or pyridinioacetylamino.

5-Amino-1,3,4-thiadiazol-2-yl-sulphanylmethyl and 5-amino-1,3,4-thiadiazol-2-yl-sulphanyl are especially preferred.

Further preferred sub-groups of A are of the formula

 (f)

in which each of r and s represent 0 or 1 and $R^8$ represents the pyridin-4-yl group or the group

 (g)

and $R^9$ signifies methyl, benzyl, carboxymethyl or carbamoylmethyl.

Pyridin-4-yl-sulphanylmethyl is preferred.
Further preferred meanings for A include:
1-Methyl-1H-tetrazol-5-ylsulphanyl, 5-methyl-1,3,4-thiadiazol-2-ylsulphanyl,
5-(pyridin-1-ylioacetylamino)-1,3,4-thiadiazol-2-yl-sulphanyl,
1-methyl-pyridin-4-yliosulphanylmethyl,
pyridin-1-yliomethyl,
methylsulphonyloxy,
4-methyl-phenylsulphonyloxy,
carboxymethyl,
methoxycarbonylmethyl,
methyl,
vinyl,
acetoxymethyl,
2-carbamoyl-5-methyl[1,2,4]triazolo[1,5-a]pyrimidin-7-ylsulphanylmethyl,
1-(cyclopropyl-carbamoylmethyl)-1H-tetrazol-5-yl-sulphanylmethyl,
1-(phenylethyl-carbamoylmethyl)-1H-tetrazol-5-yl-sulphanylmethyl,
1-(carbamoylmethyl-carbamoylmethyl)-1H-tetrazol-5-yl-sulphanylmethyl,
1-methylcarbamoylmethyl-1H-tetrazol-5-ylsulphanylmethyl,
1-(2-morpholin-4-yl-2-oxo-ethyl)-1H-tetrazol-5-yl-sulphanylmethyl,
1-(4-hydroxyphenyl-carbamoylmethyl)-1H-tetrazol-5-yl-sulphanylmethyl,
1-(hydroxy-carbamoylmethyl)-1H-tetrazol-5-ylsulphanylmethyl,
1-sulphonylmethyl-1H-tetrazol-5-ylsulphanylmethyl,
1-methyl-imidazol-2-ylsulphanylmethyl,
5-hydroxy-4-methyl-4H-[1,2,4]triazol-3-ylsulphanylmethyl,
6,7-dihydro-5H-1-pyrindin-4-ylsulphanylmethyl,
5-methyl-1,3,4-thiadiazol-2-ylsulphanylmethyl,
1-methyl-1H-tetrazol5-yl-methylsulphanylmethyl,
5-methylsulphanyl-1H-tetrazol-1-ylmethyl,
4-methyl-4-pyridiniosulphanyl,
carbamoylmethylsulphanyl,
5-(1,4-dimethyl-1H-1,2,4-triazol-4-ium)-methylsulphanylpyridin-4-ylsulphanyl,
5-acetylamino-1,3,4-thiadiazol-2-ylsulphanylmethyl,
2-cyanovinyl (Z and E isomers),
1-carboxymethyl-pyridin-4-yliosulphanylmethyl,
1-carbamoylmethyl-pyridin-4-yliosulphanylmethyl,
1-benzyl-pyridin-4-yliosulphanylmethyl,
2,5-dihydro-6-hydroxy-2-methyl-5-oxo-1,2,4-triazin-3-ylsulphanylmethyl,
piperidin-1-ylmethyl,
3-benzyloxycarbonylmethyl-pyridin-1-yliomethyl,
3-carboxymethyl-pyridin-1-yliomethyl,
4-pyridin-3-yl-thiazol-2-ylsulphanylmethyl,
pyrimidin-2-ylsulphanyl,
1H-1,2,4-triazol-3-ylsulphanylmethyl,
azidomethyl,
acetylammomethyl,
methylsulphonylaminomethyl,
4-hydroxy-phenylcarbamoyoxymethyl,
2,2,2-trifluoroethylcarbamoyloxymethyl, cyclopropylcarbamoyloxymethyl,
carbamoylmethylcarbamoyloxymethyl,
methylcarbamoyloxymethyl,
pyridinylcarbamoyloxymethyl,
4-hydroxy-benzylcarbamoyloxymethyl,
4-methyl-piperazin-1-ylcarbonyloxymethyl,
1H-tetrazol-5-yl-amino-carbonyloxymethyl,
methoxy.

As mentioned above, particularly preferred meanings for A include:
Carbamoyloxymethyl,
pyridin-4-ylsulphanylmethyl,
1-methyl-1H-tetrazol-5-ylsulphanylmethyl,
1-carbamoylmethyl-1H-tetrazol-5-ylsulphanylmethyl,
5-amino-1,3,4-thiadiazol-2-ylsulphanylmethyl,
5-amino-1,3,4-thiadiazol-2-ylsulphanyl.

Especially preferred compounds of formula I and, respectively, their salts include:

(1aS,3aR,6bR)-5-Carbamoyloxymethyl-2-(4-hydroxyphenylcarbamoyl)-1-oxo-1a,2,3,3a,4,6b-hexahydro-1H-2,6a-diazacyclobut[cd]indene-6-carboxylic acid, (1aS,3aR,6bR)-5-carbamoyloxymethyl-2-(4-carbamoyl-phenylcarbamoyl)-1-oxo-1a,2,3,3a,4,6b-hexahydro-1H-2,6a-diazacyclobut[cd]indene-6-carboxylic acid, (1aS,3aR,6bR)-2-(4-carbamoyl-phenylcarbamoyl)-1-oxo-5-(pyridin-4-ylsulphanylmethyl)-1a,2,3,3a,4,6b-hexahydro-1H-2,6a-diazacyclobut[cd]indene-6-carboxylic acid, (1aS,3aR,6bR)-5-(5-amino-1,3,4-thiadiazol-2-ylsulphanylmethyl)-2-(4-hydroxy-phenylcarbamoyl)-1-oxo-1a,2,3,3a,4,6b-hexahydro-1H-2,6a-diazacyclobut[cd]indene-6-carboxylic acid, (1aS,3aR,6bR)-5-(5-amino-1,3,4-thiadiazol-2-ylsulphanyl)-2-(4-hydroxyphenylcarbamoyl)-1-oxo-1a,2,3,3a,4,6b-hexahydro-1H-2,6a-diazacyclobut[cd]indene-6-carboxylic acid, (1aS,3aR,6bR)-5-carbamoyloxymethyl-1-oxo-2-trifluoroacetyl-1a,2,3,3a,4,6b-hexahydro-1H-2,6a-diazacyclobut[cd]indene-6-carboxylic acid, (1aS,3aR,6bR)-1-oxo-5-(pyridin-4-ylsulphanylmethyl)-2-trifluoroacetyl-1a,2,3,3a,4,6b-hexahydro-1H-2,6a-diazacyclobut[cd]indene-6-carboxylic acid, (1aS,3aR,6bR)-5-(1-carbamoylmethyl-1H-tetrazol-5-ylsulphanylmethyl)-2-formyl-1-oxo-1a,2,3,3a,4,6b-hexahydro-1H-2,6a-diazacyclobut[cd]indene-6-carboxylic acid, (1aS,3aR,6bR)-2-methylsulphonyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid, (1aS,3aR,6bR)-2-acetyl-5-(1-carbamoylmethyl-1H-tetrazol-5-ylsulphanylmethyl)-1-oxo-1a,2,3,3a,4,6b-hexahydro-1H-2,6a-diazacyclobut[cd]indene6-carboxylic acid and (1aS,3aR,6bS)-2-acetyl-5-(1-methyl-1H-tetrazol-5-ylsulphanylmethyl)-1-oxo-1,1a,2,3,3a,6b-hexahydro-4-oxa-2,6a-diazacyclobut[cd]indene6-carboxylic acid as well as corresponding pharmaceutically compatible salts thereof, especially the sodium salts.

Other preferred compounds of formula I and, respectively, their salts include:

(1aS,3aR,6bR)-2-(4-Hydroxy-phenylcarbamoyl)-5-(1-methyl-1H-tetrazol-5-ylsulphanyl)-1-oxo-1a,2,3,3a,4,6b-hexahydro-1H-2,6a-diazacclobut[cd]indene-6-carboxylic acid, (1aS,3aR,6bR)-2-(4-carbamoyl-phenylcarbamoyl)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid, (1aS,3aR,6bR)-2-[(S)-2-oxo-pyrrolidin-3-ylcarbamoyl]-5-(1-methyl-1H-tetrazol-5-ylsulphanyl)-1-oxo-1a,2,3,3a,4,6b-hexahydro-1H-2,6a-diazacyclobut[cd]indene-6-carboxylic acid, (1aS,3aR,6bR)-5-(1-methyl-1H-tetrazol-5-ylsulphanyl)-1-oxo-2-(thien-2-ylmethylcarbamoyl)-1a,2,3,3a,4,6b-hexahydro-1H- 2,6a-diazacyclobut[cd]indene-6-carboxylic acid, (aS,3aR,6bR)-2-(3,4-dihydroxy-benzylcarbamoyl)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid, (1aS,3aR,6bR)-5-(1-methyl-1H-tetrazol-5-ylsulphanyl)-1-oxo-2-[(R)- and [(S)-2-oxo-tetrahyclro-thien-3-ylcarbamoyl]-1a,2,3,3a,4,6b-hexahydro-1H-2,6a-diazacyclobut[cd]indene-6-carboxylic acid, (1aS,3aR,6bR)-5-(1-methyl-1H-tetrazol-5-ylsulphanyl)-1-oxo-2-(4-sulphamoyl-benzylcarbamoyl)-1a,2,3,3a,4,6b-hexahydro-1H- 2,6a-diazacyclobut[cd]indene-6-carboxylic acid, (1aS,3aR,6bR)-2-(3-methoxy-isoxazol-5-ylmethylcarbamoyl)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid, (1aS,3aR,6bR)-2-[(R)- and [(S)-1,1-dioxo-tetrahydrothien-3-ylcarbamoyl]-5-(1-methyl-1H-tetrazol-5-ylsulphanyl)-1-oxo-1a,2,3,3a,4,6b-hexahydro-1H-2, 6a-diazacyclobut[cd]indene-6-carboxylic acid, (1aS,3aR,6bR)-2-(4-hydroxyphenylcarbamoyl)-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid, (1aS,3aR,6bR)-2-(4-carbamoyl-phenylcarbamoyl)-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid, (1aS,3aR,6bR)-5-(5-amino-1,3,4-thiadiazol-2-ylsulphanyl)-2-(4-carbamoyl-amino-phenylcarbamoyl)-1-oxo-1a,2,3,3a,4,6b-hexahydro-1H-2,6a-diazacyclobut[cd]indene-6-carboxylic acid, (1aS,3aR,6bR)-2-(4-hydroxy-phenylcarbamoyl)-1-oxo-5-(5-pyridin-1-ylacetylamino-1,3,4-thiadiazol-2-ylsulphanyl)-1a,2,3,3a,4,6b-hexahydro-1H-2,6a-diazacyclobut[cd]indene-6-carboxylic acid, (Z)-(1aS,3aR,6bR)-2-[(2-amino-thiazol-4-yl)-methoxyimino-acetyl]-1-oxo-5-(1-methyl-1H-tetrazol-5-ylsulphanyl)-1a,2,3,3a,4,6b-hexahydro-1H-2,6a-diazacyclobut[cd]indene-6-carboxylic acid, (1aS,3aR,6bR)-2-(4-hydroxy-phenylcarbamoyl)-5-methyl-sulphonyloxy-1-oxo-1a,2,3,3a,4,6b-hexahydro-1H-2,6a-diazacyclobut[cd]indene-6-carboxylic acid, (1aS,3aR,6bR)-2-(4-carbamoyl-phenylcarbamoyl)-5-methylsulphonyloxy-1-oxo-1a,2,3,3a,4,6b-hexahydro-1H-2,6a-diazacyclobut[cd]indene-6-carboxylic acid, (1aS,3aR,6bR)-5-methylsulphonyloxy-2-(thien-2-ylmethylcarbamoyl)-1-oxo-1a,2,3,3a,4,6b-hexahydro-1H-2,6a-diazacyclobut[cd]indene-6-carboxylic acid, (1aS,3aR,6bR)-2-(3,4-dihydroxy-benzylcarbamoyl)-5-methylsulphonyloxy-1-oxo-1a,2,3,3a,4,6b-hexahydro-1H-2,6a-diazacyclobut[cd]indene-6-carboxylic acid, (1aS,3aR,6bR)-5-methylsulphonyloxy-1-oxo-2-[(S)-2-oxo-pyrrolidin-3-ylcarbamoyl]-1a,2,3,3a,4,6b-hexahydro-1H-2,6a-diazacyclobut[cd]indene-6-carboxylic acid, (1aS,3aR,6bR)-5-methylsulphonyloxy-1-oxo-2-[(R) and -[(S)-2-oxo-tetrahydro-thien-3-ylcarbamoyl]-1a,2,3,3a,4,6b-hexahydro-1H- 2,6a-diazacyclobut[cd]indene-6-carboxylic acid, (1aS,3aR,6bR)-2-[(R)- and [(S)-1,1-dioxo-tetrahydrothien-3-ylcarbamoyl]-5-methylsulphonyloxy-1-oxo-1a,2,3,3a,4,6b-hexahydro-1H-2,6a-diazacyclobut[cd]indene-6-carboxylic acid, (1aS,3aR,6bR)-5-methylsulphonyloxy-1-oxo-2-(4-sulphamoylbenzylcarbamoyl)-1a,2,3,3a,4,6b-hexahydro-1H-2,6a-diaza-cyclobut[cd]indene-6-carboxylate, (1aS,3aR,6bR)-2-(4-hydroxy-phenylcarbamoyl)-5-(4-methyl-phenylsulphonyloxy)-1-oxo-1a,2,3,3a,4,6b-hexahydro-1H-2,6a-diazacyclobut[cd]indene-6-carboxylic acid, (1aS,3aR,6bR)-2-(3-carbamoyl-pyridin-1-ylioacetyl)-5-methylsulphonyloxy-1-oxo-1a,2,3,3a,4,6b-hexahydro-1H-2,6a-diazacyclobut[cd]indene-6-carboxylate, (1aS,3aR,6bR)-5-methylsulphonyloxy-2-(1-methyl-1H-tetrazol-5-ylsulphanylacetyl)-1-oxo-1a,2,3,3a,4,6b-hexahydro-1H-2,6a-diazacyclobut[cd]indene-6-carboxylic acid, (1aS,3aR,6bR)-5-carboxymethyl-2-(4-hydroxy-phenylcarbamoyl)-1-oxo-1a,2,3,3a,4,6b-hexahydro-1H-2,6a-diaza-cyclobut[cd]indene-6-carboxylic acid, (1aS,3aR,6bR)-2-(4-hydroxy-phenylcarbamoyl)-5-methoxy-carbonylmethyl-1-oxo-1a,2,3,3a,4,6b-hexahydro-1H-2,6a-diazacyclobut[cd]indene-6-carboxylic acid, (1aS,3aR,6bR)-2-(4-hydroxy-phenylcarbamoyl)-5-(1-methyl-1H-tetrazol-5-ylsulphanylmethyl)-1-oxo-1a,2,3a,4,6b-hexahydro-1H-2,6a-diazacyclobut[cd]indene-6-carboxylic acid, (1aS,3aR,6bR)-2-(4-carbamoyl-phenylcarbamoyl)-5-(1-methyl-1H-tetrazol-5-ylsulphanylmethyl)-1-oxo-1a,2, 3,3a,4,6b-hexahydro-1H-2,6a-diazacyclobut[cd]indene-6-carboxylic acid, (1aS,3aR,6bR)-2-[(S)-2-oxo-pyrrolidin-3-ylcarbamoyl]-5-(1-methyl-1H-tetrazol-5-ylsulphanylmethyl]-1-oxo-1a,2,3,3a, 4,6b-hexahydro-1H-2,6a-diazacyclobut[cd] indene-6-carboxylic acid, (1aS,3aR,6bR)-2-acetyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid, (1aS,3aR,6bR)-2-acetyl-1-oxo-5-(pyridin-4-ylsulphanylmethyl)-1a,2,3,3a,4,6b-hexahydro-1H-2,6a-diazacyclobut[cd]indene-6carboxylic acid, (1aS,3aR,6bR)-2-(4-carbamoyl-phenylcarbamoyl)-5-(1-methyl-pyridin-1-yliosulphanylmethyl)-1-oxo-1a,2,3, 3a,4,6b-hexahydro-1H-2,6a-diazacyclobut[cd]indene-6-carboxylate, (1aS,3aR,6bR)-2-(4-hydroxy-phenylcarbamoyl)-1-oxo-5-(pyridin-1-yliomethyl)-1a,2,3,3a,4,6b-hexahydro-1H-2,6a-diazacyclobut[cd]indene-6-carboxylate, (1aS,3aR,6bR)-2-(3-hydroxy-isoxazol-5-ylmethylcarbamoyl)-1-oxo-5-(pyridin-1-yliomethyl)-1a,2,3,3a,4, 6b-hexahydro-1H-2,6a-diazacyclobut[cd]indene-6-carboxylate, (1aS,3aR,6bR)-2-(4-carbamoyl-phenylcarbamoyl)-1-oxo-5-(pyridin-1-yliomethyl)-1a,2,3,3a,4,6b-hexahydro-1H-2,6a-diazacyclobut[cd]indene-6-carboxylate, (1aS,3aR,6bR)-2-acetyl-1-oxo-5-(pyridin-1-yliomethyl)-1a,2,3,3a,4,6b-hexahydro-1H-2,6a-diazacyclobut[cd] indene-6-carboxylate, (1aS,3aR,6bR)-1-oxo-5-(pyridin-1-yliomethyl)-2-trifluoroacetyl-1a,2,3,3a,4,6b-hexahydro-1H-2,6a-diazacyciobut[cd]indene-6-carboxylate and (1aS,3aR,6bR)-5-acetoxymethyl-2-(4-hydroxy-phenylcarbamoyl)-1-oxo-1a,2,3,3a,4,6b-hexahydro-1H-2,6a-diazacyclobut[cd]indene-6-carboxylic acid, as well as corresponding pharmaceutically compatible salts thereof, especially the sodium salts.

The term "amino protecting groups" refers to protecting groups conventionally used to replace an acidic proton of an amino group. Examples of such groups are described in Green, T., Protective Groups in Organic Synthesis, Chapter 7, John Wiley and Sons, Inc. (1981), pp. 218–287, herein incorporated by reference. These examples include the carbamates of methyl, cyclopropylmethyl, 1-methyl-1-cyclopropylmethyl, diisopropylmethyl, 9-fluorenylmethyl, 9-(2-sulfo)fluorenylmethyl, 2-furanylmethyl, 2,2,2-trichloroethyl, 2-haloethyl, 2-iodoethyl, 2-trimethylsilylethyl, 2-methylthioethyl, 2-methylsulfonylethyl, 2-(p-toluenesulfonyl)ethyl, 2-phosphonioethyl, 1,1-dimethyl-3-(N,N-dimethylcarboxamido)-propyl, 1,1-diphenyl-3-(N,N-diethylamino)propyl, 1-methyl-1-(1-adamantyl)ethyl, 1-methyl-1-phenylethyl, 1-methyl-1-(3,5-dimethoxyphenyl)ethyl, 1-methyl-1-(4-biphenylyl)ethyl, 1-methyl-1-(p-phenylazophenyl)ethyl, 1,1-dimethyl-2-haloethyl, 1,1-dimethyl-2,2,2-trichloroethyl, 1,1-diemthyl-2-cyanoethyl, isobutyl, t-butyl, t-amyl, cyclobutyl, 1-methylcyclobutyl, cyclopentyl, cyclohexyl, 1-methylcyclohexyl, 1-adamantyl, isobornyl, vinyl, allyl, cinnamyl, phenyl, 2,4, 6-tri-t-butylphenyl, m-nitrophenyl, S-phenyl, 8-quinolyl, N-hydroxypiperidinyl, 4-(1,4-dimethylpiperdinyl), 4,5-diphenyl-3-oxazolin-2-one, benzyl, 2,4,6-trimethylbenzyl, p-methoxybenzyl, 3,5-dimethoxybenzyl, p-decyloxybenzyl, p-nitrobenzyl, o-nitrobenzyl, 3,4-dimethoxy-6-nitrobenzyl, p-bromobenzyl, chlorobenzyl, 2,4-dichlorobenzyl, p-cyanobenzyl, o-(N,N-dimethylcarboxamide)benzyl, m-chloro-p-acyloxybenzyl, p-(dihydroxyboryl)benzyl, p-(phenylazo)benzyl, p-(p'-methoxyphenylazo)benzyl, 5-benzisoxazolylmethyl, 9-anthrylmethyl, diphenylmethyl, phenyl(o-nitrophenyl)methyl, di(2-pyridyl)methyl, 1-methyl-1-(4-pyridyl)ethyl, isonicotinyl, S-benzyl, N'-piperidinylcarbonyl, N'-p-touluenesulfonyl-aminocarbonyl, N'-phenylaminothiocarbonyl; the amides of N-formyl, N-acetyl, N-chloroacetyl, N-dichloroacetyl, N-trichloroacetyl, N-trifluoroacetyl, N-o-nitrophenylacetyl, N-o-nitrophenoxyacetyl, N-acetoacetyl, N-acetylpyridinium, N-(N'-dithiobenzyloxycarbonylamino)acetyl, N-3-phenylpropionyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)-propionyl, N-4-chlorobutyryl, N-isobutyryl, N-o-nitrocinnamoyl, N-picolinoyl, N-(N'acetylmethionyl), N-(N'benzoylphenylalkanyl), N-benzoyl, N-p-phenylbenzoyl, N-p-methoxybenzoyl, N-o-nitrobenzoyl, N-o-(benzoyloxymethyl)benzoyl, N-p-P-benzoyl; the cyclic imides of N-phthaloyl, N-2,3-diphenylmaleoyl, N-dithiasuccinoyl; N-allyl, N-phenacyl, N-3-acetoxypropyl, N-(4-nitro-1-cyclohexyl-2-oxo-3-pyrrolin-3-yl), quaternary ammonium salts, N-methoxymethyl, N-2-chloroethoxymethyl, N-benzyloxymethyl, N-pivaloyloxymethyl, N-[1-(alkoxycarbonylamino)-2,2,2-trifluoro]ethyl, N-[1-trifluoromethyl-1-(p-chlorophenoxymethoxy)-2,2,2-trifluoro]ethyl, N-2-tetrahydro-pyranyl, N-2,4-dinitrophenyl, N-benzyl, N-3,4-dimethoxybenzyl, N-o-nitrobenzyl, N-di(p- methoxyphenyl)methyl, N-triphenylmethyl, N-(p-methoxyphenyl)diphenylmethyl, N-diphenyl-4-pyridylmethyl, M-2-picolyl N'-oxide, N-5-dibenzosuberyl, N-(N',N'-dimethylaminomethylene), N,N'-isopropylidene, N-benzylidene, N-p-methoxybenzyidene, N-p-nitrobenzylidene, N-salicylidene, N-5-chlorosalicylidene, N-diphenylmethylene, N-(5-chloro-2-hydroxyphenyl)phenyl-methylene, N-(acylvinyl), N-(5,5-dimethyl-3-oxo-1-cyclohexenyl), N-borane, N-[phenyl(penmcarbonylchromium or -tungsten)]carbonyl, N-copper or N-zinc chelate, N-nitro, N-nitroso, N-oxide, N-diphenyl-phosphinyl, N-dimethylthiophosphinyl, N-diphenylthiophosphinyl, N-diethyl phosphoryl, N-dibenzyl phosphoryl, N-diphenyl phosphoryl, N-trtmethylsilyl, N-benzenesulfenyl, N-o-nitrobenzenesulfenyl, N-2,4-dinitrobenzenesulfenyl, N-2-nitro-4-methoxybenzenesulfenyl, N-triphenylmethylsulfenyl, N-benzenesulfonyl, N-p-methoxybenzenesulfonyl, N-2,4,6-trimethylbenzensulfonyl, N-toluenesulfonyl, N-benzylsulfonyl, N-p-methylbenzylsulfonyl, N-trifluoromethylsulfonyl, N-phenacylsulfonyl.

The term "carboxylic acid protecting group" refers to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981), incorporated herein by reference. These examples include methoxymethyl, methylthiomethyl, tetrahydropyranyl, tetrahydrofuranyl, methoxyethoxymethyl, benzyloxymethyl, phenacyl, p-bromophenacyl, a-methylphenacyl, p-methoxyphenacyl, diacylmethyl, N-phthalimidomethyl, ethyl, 2,2,2-trichloroethyl, 2-haloethyl, w-chloroalkyl, 2-(trimethylsilyl)ethyl, 2-methylthioethyl, 2-(p-nitrophenylsulfenyl)ethyl, 2-(p-toluenesulfonyl)ethyl, 1-methyl-1-phenylethyl, t-butyl, cyclopentyl, cyclohexyl, allyl, cinnamyl, phenyl, p-methylthiophenyl, benzyl, triphenylmethyl, diphenylmethyl, bis(o-nitrophenyl)methyl, 9-anthrylmethyl, 2-(9,10-dioxo)anthrylmethyl, 5-dibenzosuberyl, 2,4,6-trimethylbenzyl, p-bromobenzyl, o-nitrobenzyl, p-nitrobenzyl, p-methoxybenzyl, piperonyl, 4-picolyl, trimethylsilyl, triethylsilyl, t-butyldimethylsilyl, i-propyl-dimethylsilyl, phenyldimethylsilyl, S-t-butyl, S-phenyl, S-2-pyridyl, N-hydroxypiperidinyl, N-hydroxysuccinimidoyl, N-hydroxyphthalimidoyl, N-hydroxybenzotriazolyl, O-acyl oximes, 2,4-dinitrophenylsulfenyl, 2-alkyl-1,3-oxazolines, 4-alkyl-5-oxo-1,3-oxazolidines, 5-alkyl-4-oxo-1,3-dioxolanes, triethylstannyl, tri-n-butylstannyl; the amides or hydrazides of N,N-dimethylamino, pyrrolidinyl, piperidinyl, o-nitrophenyl, 7-nitroindolyl, 8-nitrotetra-hydroquinolyl, p-benzenesulfonamide, hydrazides, N-phenylhyctrazide, N,N'-diisopropylhydrazide.

As readily hydrolyzable esters of the compound of formula I there are to be understood compounds of formula I in which the carboxy group or carboxy groups (e.g. the 6-carboxy group) is/are present in the form of a readily hydrolyzable ester group. Examples of such esters, which can be of the conventional type, are the lower alkanoyloxyalkyl esters, e.g. the acetoxymethyl, pivaloyloxymethyl, 1-acetoxyethyl and 1-pivaloyloxyethyl ester; the lower alkoxycarbonyloxyalkyl esters, e.g. the methoxy-carbonyloxymethyl, 1-ethoxycarbonyloxyethyl and 1-isopropoxycarbonyloxyethyl ester; the 1-cyclohexyloxycarbonyloxyethyl ester; the (5-methyl-2-oxo-1,3-dioxol-4-yl)-methyl ester; the lactonyl esters, e.g. the phthalidyl and thiophthalidyl esters; the lower alkoxymethyl esters, e.g. the methoxymethyl ester, and the lower alkanoylaminomethyl esters, e.g. the acetamidomethyl ester. Other esters, e.g. the benzyl and cyanomethyl esters, can also be used. Further readily hydrolyzable esters are the (2,2-dimethyl-1-oxopropoxy)methyl ester, the 2-[(2-methylpropoxy)carbonyl]-2-pentenyl ester, the 1-[(1- methylethoxy)carbonyl]oxy]-ethyl ester and the 3,3dimethyl-2-oxobutyl ester.

Examples of salts of the compounds of formula I are alkali metal salts such as the sodium salt and the potassium salt, ammonium salts; alkaline earth metal salts such as the calcium salt; salts with organic bases such as salts with amines, e.g. salts with N-ethylpiperidine, procaine, dibenzylamine, N,N'-dibenzylethylenediamine, alkylamines or dialkylamines, as well as salts with amino acids such as e.g. salts with arginine or lysine.

Compounds of formula I, insofar as they have a basic functional group such as e.g. an amino group, also form addition salts with organic or inorganic acids. Examples of such salts are hydrohalides, for example hydrochlorides, hydrobromides and hydroiodides, as well as other mineral acid salts such as sulphates, nitrates, phosphates and the like, alkylsulphonates and monoarylsulphonates such as ethanesulphonates, toluene-sulphonates, benzenesulphonates and the like and other organic acid salts such as acetates, triflouroacetates, tartrates, maleares, citrates, benzoates, salicylates, ascorbates and the like.

The β-lactams of formula I in accordance with the invention as well as their pharmaceutically compatible salts can be made in accordance with the invention by a) cleaving off the carboxy protecting group and an amino protecting group which may be present in a compound of the formula

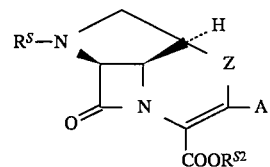

in which A and Z have the significance given above, $R^S$ has the significance given for R or signifies an amino protecting group and $R^{S2}$ represents a carboxy protecting group, and, if desired, treating an acid addition salt of a compound of the formula

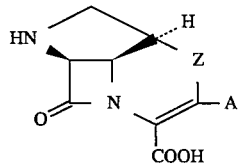

in which A and Z have the above significance, which may be obtained with agents yielding the residue R and, where required, cleaving off any protecting groups still present, or b) for the making of a readily hydrolyzable ester of a compound of formula I, subjecting a carboxylic acid of formula I to a corresponding esterification, or c) for the making of pharmaceutically compatible salts of a compound of formula I, converting a compound of formula I into such a salt.

When Z=methylene, the preferred cleavage of protecting groups in compounds of formula II is effected with $R^{S2}$=t-butyl and, $R^S$=t-butoxycarbonyl and by treatment with an acidic agent, preferably with trifluoroacetic acid, in an organic solvent such as methylene chloride, optionally in the presence of anisole, phenol, cresol or triethylsilane, or also with hydrogen chloride in an organic solvent such as dioxan, tetrahydrofuran or methylene chloride. The temperature preferably lies between −20° C. and room temperature; at lower temperatures, about −20° to −10° C. only the t-butoxycarbonyl group in the 2-position is preferentially cleaved off, so that in the reaction product after the introduction of a residue R the t-butyl protecting group in position 6 must be cleaved off in the above manner. The residue R thereby remains intact.

When Z=oxygen or sulphur, the preferred cleavage of protecting groups in compounds of formula II is effected with $R^{S2}$=allyl and, $R^S$=allyloxycarbonyl and by treatment with a palladium catalyst, such as e.g. bis-(triphenylphosphine)-palladium(II) dichloride or tetrakis-palladiumtriphenylphosphine and a p-allyl complex scavenger such as tributyltin hydride. The reaction is effected in an aprotic organic solvent such as ethyl acetate, tetrahydrofuran or methylene chloride and preferably at room temperature.

For the cleavage of allyloxycarbonyl and, allyl groups see also J. Org. Chem. 1982, 47, 587.

Analogous intermediates with other protecting groups (e.g. benzyloxycarbonyl or chloroacetyl in position 2; p-nitrobenzyl, benzyl or benzhydryl in position 6) are also suitable for the above protecting group cleavage. The starting materials are prepared analogously, and the protecting group cleavage is carried out in a manner known per se, e.g.:

Position 2

Benzyloxycarbonyl: hydrogenation with palladium/carbon or treatment with palladium/carbon and 1,4-cyclohexadiene in an organic solvent such as ethanol, tetrahydrofuran, dioxan, ethyl acetate or dimethylformamide (optionally aqueous) at about 0°–80° C.;

Chloroacetyl: with thiourea in a polar solvent, preferably in water at neutral pH, and about 0°–30° C.; or also with an alkali metal bicarbonate, e.g. sodium bicarbonate, in methanol and/or tetrahydrofuran (optionally aqueous) at about 0°–30° C.;

Position 6

Benzyl and p-nitrobenzyl: hydrogenation with palladium-carbon or palladium oxide at about 0° C. to 80° C. in an organic solvent such as ethyl acetate, methanol or tetrahydrofuran or in water, optionally in the presence of an acid such as acetic acid or hydrochloric acid; or hydrolysis in the presence of sodium sulphide at (or below) 0° C. to room temperature in a solvent such as e.g. dimethylformamide (preferably aqueous);

Benzhydryl: with m-cresol at about 50° C.

It will be appredated that the choice of protecting groups in positions 2 and 6, respectively, 6 depends on the reactivity of other groups in the molecule. For example, in the case of a double bond in the end product (e.g. when A=lower alkenyl) no hydrogenolytically cleavable protecting groups must be chosen for positions 2 (benzyloxycarbonyl) and 6 (benzyl or p-nitrobenzyl), because the lower alkenyl group A would be saturated. It must also be noted that the olefinic protecting groups (allyloxy-carbonyl and, allyl) cannot be subjected to a hydrogenation, because they then become saturated and subsequently cannot be cleaved off using conventional methods.

For the introduction of a residue R in position 2, the compound of formula III is e.g. acylated with an acid of the formula ROH or with one of its reactive derivatives. Acylating agents which come into consideration are: corresponding acids of the formula ROH in the presence of 2-halopyridinium salts, e.g. of 2-chloro- or 2-fluoro-1-methylpyridinium chloride or tosylate, or also in the presence of carbonyldiimidazole or N,N'-dicyclo-hexylcarbodiimide, the latter preferably together with N-hydroxybenztriazole, N-hydroxysuccinimide or N-hydroxyphthalimide. Corresponding reactive derivatives of carboxylic acids can also be used, such as e.g. the acid halide (preferably the chloride), acid anhydride or acid azide. Also usable are the corresponding thiol esters such as e.g. 2-benzthiazolyl thioesters as well as hydroxybenztriazole esters, N-hydroxysuccinimide esters or N-hydroxyphthalimide esters. The reaction is preferably carried out in an organic solvent or solvent mixture, e.g. acetone, methylene chloride, tetrahydrofuran, dioxan, dimethylacetamide, dimethyl-formamide, dimethyl sulphoxide or acetonitrile. The temperature generally lies between −30° C. and room temperature.

For the making of the readily hydrolyzable esters of the carboxylic acids of formula I in accordance with variant b) of the process in accordance with the invention, the carboxylic acid is preferably reacted with the corresponding halide, preferably with the iodide, which contains the ester group. The reaction can be accelerated with the aid of a base, e.g. an alkali metal hydroxide or carbonate or an organic amine such as triethylamine. The esterification reaction is preferably carried out in an inert organic solvent such as dimethylacetamide, hexamethylphosphoric acid triamide, dimethyl sulphoxide or, preferably, dimethylformamide. The temperature preferably lies in the range of about 0°–40° C.

The making of the salts of the compounds of formula I in accordance with variant c) of the process in accordance with the invention can be effected in a manner known per se, e.g. by reacting the carboxylic acid of formula I with an equimolar amount of the desired base, conveniently in a solvent such as water or in an organic solvent such as ethanol, methanol, acetone and the like. Salt formation is also brought about by addition of an organic or inorganic acid. The temperature of the salt formation is not critical, it generally lies at room temperature, but can also lie thereover or thereunder, for instance in the range of 0° C. to +50° C.

The following Reaction Schemes I and II illustrate the process for the making of the products in accordance with the invention and, the intermediates which occur in the synthesis.

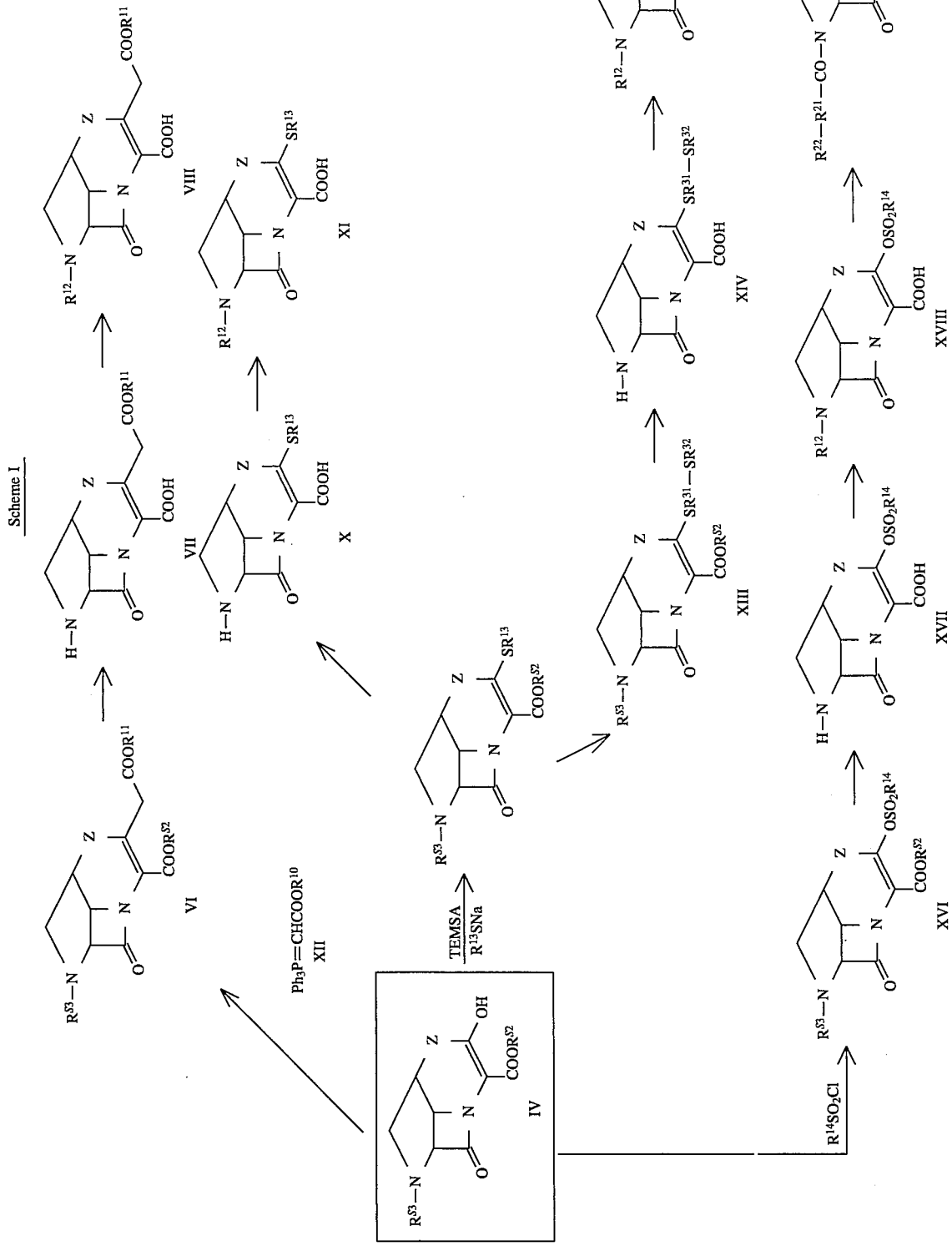

-continued
Scheme I
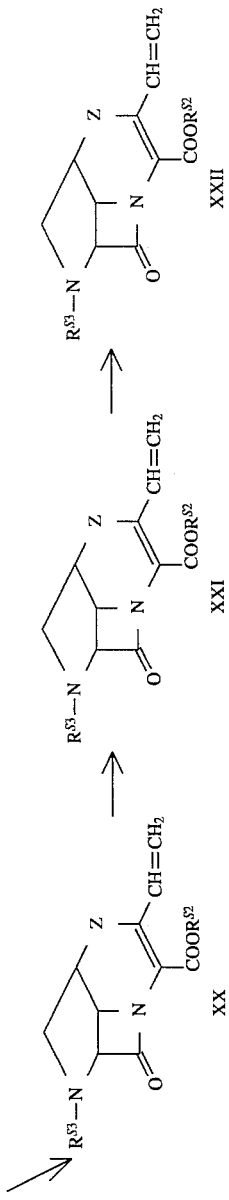

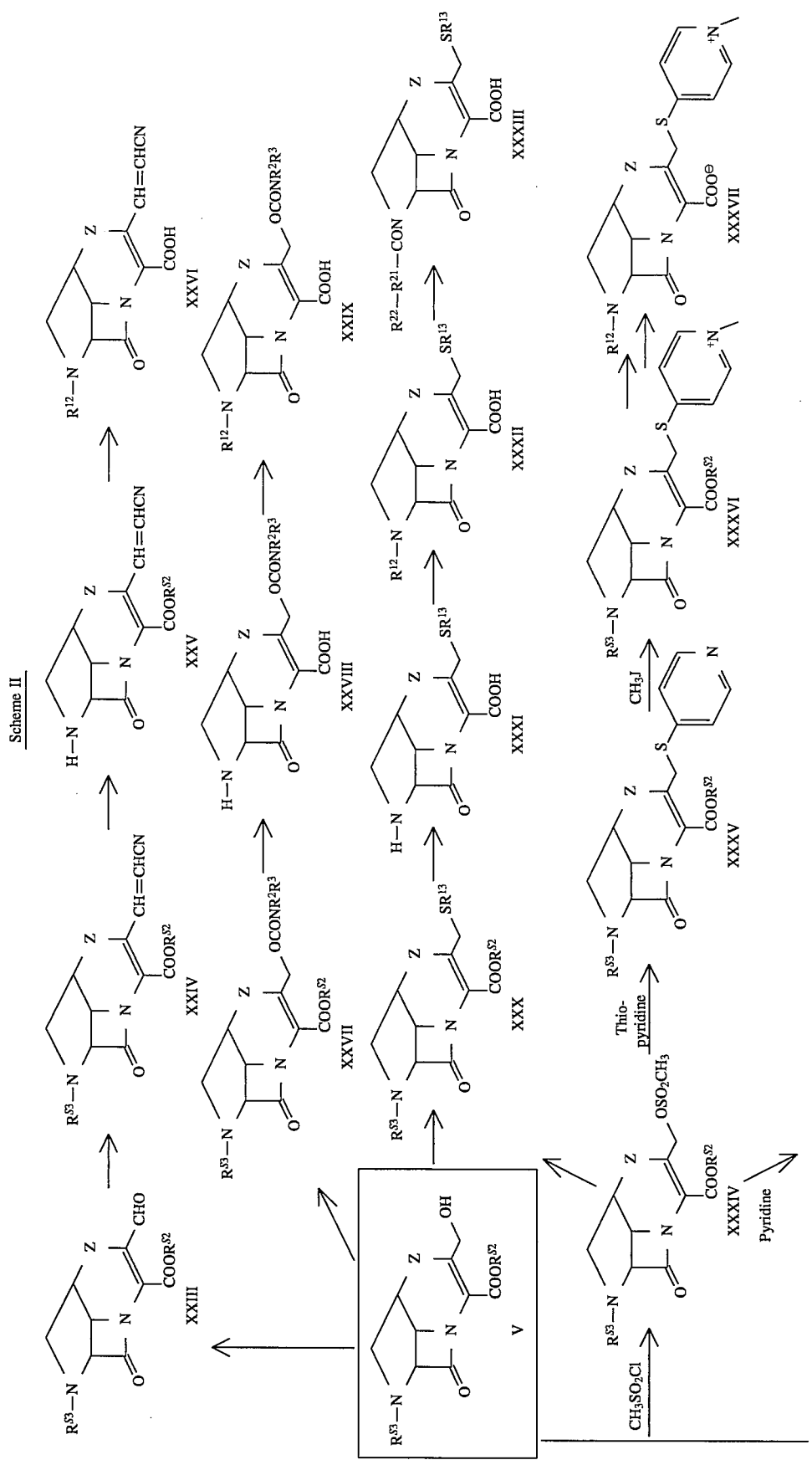

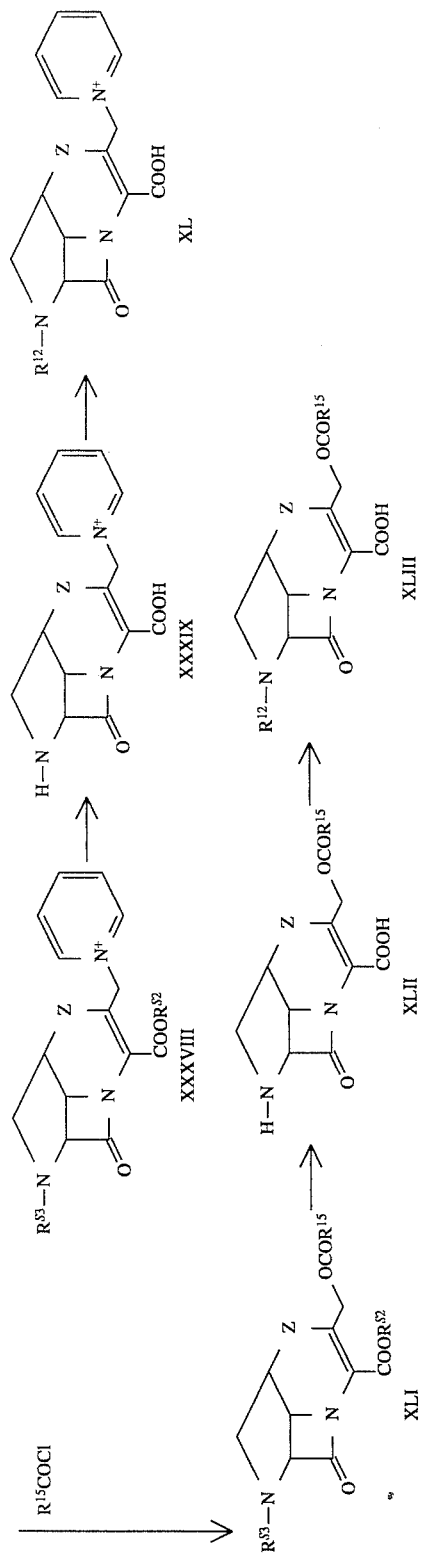

The symbols have the following meanings in Schemes I and II:

Z=methylene, oxygen or sulphur
$R^{S2}$=a carboxy protecting group, preferably t-butyl (when Z=methylene) or allyl (when Z =oxygen or sulphur)
$R^{S3}$=an amino protecting group, preferably t-butoxycarbonyl (when Z=methylene) or allyloxycarbonyl (when Z=oxygen or sulphur)
TFMSA=trifluoromethanesulphonic anhydride
$R^{10}$=benzyl or lower alkyl
$R^{11}$=hydrogen or lower alkyl
$R^{12}$=the same significance as R, excluding hydrogen
$R^{22}$—$R^{21}$—CO=a group (a) provided with a subsequently introduced ring
$R^{13}$="Het" with the above significance
$R^{31}$—$R^{32}$=a group "Het" provided with a subsequently introduced substituent
$R^{14}$=lower (cyclo)alkyl, phenyl or lower (cyclo)alkylphenyl
$R^{15}$=lower alkyl When in Reaction Scheme II in the case of the reactions XXXIV→XL another N-tertiary, N-heterocyclic compound (e.g. 1-methyl-1-pyrrolidine) is used in place of pyridine, there are obtained correspondingly substituted reaction products having the corresponding quaternary nitrogen ring. If an N-saturated ring compound (e.g. 1H-tetrazole or 5-methylsulphanyl-1H-tetrazole) is used in place of pyridine, there are obtained corresponding compounds having a tertiary nitrogen ring. If ammonia or a lower alkylamine or di-lower alkyl-amine is used in place of pyridine, there are obtained corresponding compounds of formula I in which A represents aminomethyl, lower alkylaminomethyl or di-lower alkylaminomethyl. Azidomethyl or aminomethyl groups A can be introduced by reacting the compound XXXIV with sodium azide and, if desired, hydrogenating the azidomethyl compound obtained, e.g. with palladium-carbon.

As mentioned, the synthesis can also be carried out via intermediates which are substituted in the 2- and 6-position by protecting groups other than t-butoxycarbonyl and, t-butyl (e.g. benzyloxycarbonyl or chloroacetyl in position 2; p-nitrobenzyl, benzyl or benzhydryl in position 6). These intermediates are obtainable in analogy to the described process.

The "building blocks" of formulae IV and V referred to in Reaction Schemes I and II can be prepared in the manner described in Examples 1, 14, 28 and 40 or in an analogous manner. It will be appreciated that groups falling under the definition of R, which are inert in the synthesis, can also be chosen as amino protecting groups $R^{S3}$ in compounds IV and V. Such groups are e.g. lower alkanoyl groups, e.g. acetyl, which are intended to appear in the end product and accordingly do not have to be cleaved off. The preparation of such a "building block" of formula V (with $R^{S3}$=acetyl) has been described in Example 35.

As mentioned earlier, the compounds of formula I and pharmaceutically compatible salts thereof with bases exhibit pronounced β-lactamase inhibiting activities against β-lactamases from various bacterial strains. As illustrated hereinafter, these therapeutically valuable properties can be determined in vitro on isolated β-lactamases:

A. Isolation of the β-lactamases

Various β-lactamases can be isolated from penicillin- or cephalosporin-resistant bacterial strains such as Klebsiella pneumoniae NCTC 418, Promus vulgaris 1028, *Bacillus licheniformis* 749/C, Escherichia coli SN01, *Pseudomonas aeruginosa* 18SH and *Citrobacter freundii* 1203. For this purpose, the corresponding strains are cultivated in Tryptic Soy Broth (Difco) and harvested by centrifugation in the last logarithmic growth phase (when necessary 50–100 mg/l of ampicillin are added to the medium towards the end of the log-phase in order to induce the β-lactamase). The thus-obtained bacterial mass is treated with 20 mM Tris-HCl buffer (pH 7.0); the cells are broken open with a French press while cooling. The mixture is centrifuged (20,000 r/min.) for 20–30 minutes and a clear crude extract is obtained. The purification of the proteins is effected according to the method of Cartwright, S. J. & Waley, S. G. [Biochem. J. 221, 505–512 (1980)] and, for B. licheniformis, Ellerby, L. M. et al. [Biochemistry 29, 5797–5806 (1990)].

B. Determination of the β-lactamase activity

The determination of the activity of the isolated β-lactamases can be carried out according to the method of O'Callaghan, C. H. et al. [Antimicr. Ag. Chemother. 1, 283–288 (1972)] using the chromogenic cephalosporin nitrocefin (87/312 from Glaxo). The requisite test batch contains per ml of water: 50 mM phosphate buffer (pH 7.0), 0.1 mM nitrocefin and sufficient enzyme (β-lactamase) to achieve a DA/min. of about 0.1. The cleavage of the substrate, which is accompanied by a change in colour, is effected at 37° C. and is followed quantitatively at 482 nm using a spectral photometer.

C. Determination of the β-lactamase inhibiting activity of the compounds of formula I The above-described cleavage of the chromogenic substrate by β-lactamases (Test B.) can be inhibited by the addition of compounds of formula I (inhibitors). Since it has been found that the inhibitors irreversibly inactivate the β-lactamase in a time-dependent reaction, the reaction (cleaveage of the substrate) is in each case started by addition of the substrate after a pre-incubation period of β-lactamase with inhibitor of 15 minutes. As a measurement for the affinity of the particular tested inhibitor to the β-lactamase, which is a measurement of the strength of the inhibitor, there serves that concentration which inhibits by 50% (IC 50 in mM) the cleavage of the substrate (nitrocefin) effected under the above test conditions (Test B.) in the absence of an inhibitor. 4 to 6 tests with different concentrations of inhibitor were carried out in order to determine the IC 50. The determination of the IC 50 was effected by means of a graph.

The results obtained in the above test (Test C) are presented in Table 1 hereinafter.

TABLE 1

(Test organism: *Citrobacter freundii* 1982)
The IC 50 value in mM is given for the end products of the following working Examples. This is a measurement of the β-lactamase inhibition. An IC 50 value of 1 mM (micromolar) or less is considered to be significant.

| Example No. | IC 50 μM |
| --- | --- |
| 2(b) | 0.074 |
| 3(a) | 0.010 |
| 3(b) | 0.004 |
| 3(c) | 0.012 |
| 3(d) | 0.022 |
| 3(e) | 0.010 |
| 3(f) | 0.006 |
| 3(g) | 0.009 |
| 3(h) | 0.010 |
| 3(i) | 0.009 |
| 3(j) | 0.007 |
| 3(k) | 0.013 |
| 3(l) | 0.010 |

TABLE 1-continued (Test organism: *Citrobacter freundii* 1982)
The IC 50 value in mM is given for the end products of the following working Examples. This is a measurement of the β-lactamase inhibition. An IC 50 value of 1 mM (micromolar) or less is considered to be significant.

| Example No. | IC 50 μM |
|---|---|
| 3(m) | 0.007 |
| 4 | 2.7 |
| 5 | 0.011 |
| 7 | 4.16 |
| 8 | 29.3 |
| 9(a) | 0.012 |
| 9(b) | 0.010 |
| 9(c) | 0.026 |
| 9(d) | 0.017 |
| 9(e) | 0.012 |
| 9(f) | 0.041 |
| 9(g) | 0.027 |
| 9(h) | 0.018 |
| 9(i) | 0.013 |
| 10(a) | 0.010 |
| 10(d) | 0.015 |
| 11(a) | 0.060 |
| 11(b) | 0.009 |
| 12(b) | 35 |
| 13(a) | 0.038 |
| 13(b) | 0.014 |
| 18(a) | 0.011 |
| 18(b) | 0.012 |
| 18(c) | 0.010 |
| 19(a) | 0.021 |
| 20 | 58 |
| 21 | 0.043 |
| 22 | 2.7 |
| 23(a) | 0.082 |
| 23(b) | 0.15 |
| 23(c) | 0.023 |
| 25 | 0.004 |

D. Determination of the β-lactamase inhibiting activity by combination of a compound of formula I with ceftriaxone The minimum inhibitory concentration in vitro (MIC in mg/ml) of a 1:4 combination of ceftriaxone with a compound of formula I against Citrobacter freundii 1982 was measured and compiled in Table 2 hereinafter.

TABLE 2

| Example No. | MIC C. freundii 1982 μg/ml |
|---|---|
| 2(b) | 1 |
| 3(a) | 0.25 |
| 3(b) | 0.25 |
| 3(c) | 0.25 |
| 3(d) | 1 |
| 3(e) | 2 |
| 3(f) | 0.06 |
| 3(g) | 0.5 |
| 3(h) | 2 |
| 3(i) | 0.06 |
| 3(k) | 0.5 |
| 3(l) | 0.5 |
| 3(m) | 0.25 |
| 5 | 2 |
| 7 | 16 |
| 8 | 1 |
| 9(a) | 0.12 |
| 9(b) | 0.25 |
| 9(c) | 1 |
| 9(d) | 2 |
| 9(e) | 0.25 |
| 9(f) | 0.12 |
| 9(g) | 0.25 |
| 9(h) | 0.5 |
| 9(i) | 2 |
| 10(a) | 1 |
| 10(d) | 8 |
| 11(b) | 0.5 |
| 12(b) | 4 |
| 13(a) | 1 |
| 13(b) | 0.25 |
| 18(a) | 0.25 |
| 18(b) | 0.25 |
| 18(c) | 0.25 |
| 20 | 1 |
| 21 | 0.5 |
| 22 | 4 |
| 23(a) | 1 |
| 23(b) | 1 |
| 23(c) | 0.25 |
| 25 | 0.25 |
| Ceftriaxone alone (control) | 128 |

The compounds in accordance with the invention also exhibit some antibacterial activity which is illustrated on the basis of the following test results:

E. Antibacterial activity

The antibacterial activity of the products per se is illustrated on the basis of Table 3 hereinafter, the minimum inhibitory concentration (mg/ml) in vitro against *E. coil* 1346 being determined using the serial dilution method in liquid medium:

TABLE 3

| Example No. | MIC E. coli 1346 μg/ml |
|---|---|
| 2(a) | 4 |
| 2(b) | 4 |
| 3(a) | 128 |
| 3(d) | 32 |
| 3(e) | 32 |
| 3(g) | 16 |
| 3(h) | 16 |
| 3(j) | 32 |
| 3(l) | 8 |
| 7 | 64 |
| 8 | 2 |
| 9(a) | 32 |
| 9(b) | 0.5 |
| 9(c) | 8 |
| 9(d) | 32 |
| 9(f) | 32 |
| 9(h) | 32 |
| 9(i) | 16 |
| 11(a) | 32 |
| 11(b) | 16 |
| 12(b) | 8 |
| 13(a) | 4 |
| 15 | 2 |
| 18(a) | 32 |
| 18(b) | 32 |
| 18(c) | 32 |
| 19(a) | 0.5 |
| 20 | ≦0.5 |
| 22 | 4 |

Corresponding test data for additional products from the working Examples given hereinafter are compiled in Table 4 hereinafter with reference to the above tests C, D and E (see Tables 1, 2 and 3):

TABLE 4

| Example No. | IC 50 μM (C) | MIC C. freundii 1982 μg/ml (D) | MIC E. coli 1346 μg/ml (E) |
| --- | --- | --- | --- |
| 2(d) | 0.34 | 64 | >32 |
| 2(f) | 13.2 | 2 | 8 |
| 3(n) | 0.008 | 1 | >32 |
| 3(o) | 0.016 | 1 | >32 |
| 3(p) | 0.014 | 1 | 32 |
| 3(q) | 0.242 | 2 | >32 |
| 3(aa) | 0.033 | 2 | 8 |
| 3(ab) | 0.027 | 16 | 32 |
| 3(ac) | 0.012 | 4 | 8 |
| 3(ad) | 0.039 | 8 | 16 |
| 3(ae) | 0.030 | 4 | 4 |
| 3(ag) | 0.028 | 2 | 8 |
| 3(ah) | 0.012 | 2 | 8 |
| 3(ai) | 0.026 | 32 | >32 |
| 3(ak) | 0.461 | 4 | 16 |
| 3(al) | — | 2 | 8 |
| 3(an) | 0.071 | 32 | 32 |
| 3(ao) | 1.020 | 8 | >32 |
| 18(f) | 0.013 | 1 | 4 |
| 18(g) | 0.011 | 0.5 | — |
| 18(h) | 0.004 | 0.5 | 16 |
| 18(i) | 0.002 | 4 | 32 |
| 18(j) | 0.006 | 0.5 | >32 |
| 19(c) | 0.005 | 0.5 | 2 |
| 19(d) | 0.009 | 0.25 | 2 |
| 19(f) | 0.034 | 4 | — |
| 19(h) | 0.018 | 0.5 | 2 |
| 19(i) | 0.031 | 1 | 0.5 |
| 19(j) | 0.034 | 2 | 0.5 |
| 19(k) | 0.038 | 0.25 | 0.5 |
| 23(f) | 0.320 | 4 | >32 |
| 25(b) | 0.018 | 0.25 | 4 |
| 25(c) | 0.033 | 1 | 4 |
| 25(d) | 0.019 | 0.5 | 4 |
| 27(c) | 0.008 | 0.25 | >32 |
| 27(d) | 0.011 | 0.25 | 32 |
| 27(e) | 0.006 | 0.5 | 32 |
| 27(f) | 0.008 | 0.25 | ≦0,25 |
| 27(g) | 0.005 | 0.5 | >32 |
| 27(h) | 0.003 | 0.25 | >32 |
| 29(a) | 0.790 | 1 | 1 |
| 29(b) | 0.275 | 2 | >16 |
| 29(c) | 0.380 | 0.5 | 2 |
| 29(d) | 0.430 | 8 | 4 |
| 29(e) | 0.036 | 0.5 | 1 |
| 29(e) Byproduct | 0.003 | 1 | 4 |
| 29(g) | 0.056 | 8 | 8 |
| 29(h) | 0.218 | 32 | >32 |
| 29(i) | 0.823 | 8 | 8 |
| 29(j) | 0.045 | 4 | 8 |
| 29(k) | 0.034 | 8 | 32 |
| 29(l) | 0.056 | 32 | >32 |
| 30 | 0.019 | 1 | 8 |
| 31(a) | 0.010 | 0.5 | 8 |
| 31(b) | 0.011 | 0.2 | 8 |
| 31(c) | 0.016 | — | — |
| 31(d) | 0.005 | 1 | >32 |
| 31(e) | 0.011 | 0.5 | >32 |
| 31(g) | 51 | 16 | 0,5 |
| 31(h) | 0.006 | 0.5 | 8 |
| 31(i) | 0.011 | 0.5 | 8 |
| 32(a) | 0.516 | 16 | >32 |
| 32(c) | 0.030 | 32 | 4 |
| 32(d) | 0.017 | 16 | 16 |
| 32(e) | 0.019 | 2 | 4 |
| 32(f) | — | 8 | 4 |
| 32(h) | 0.022 | 64 | >32 |
| 33 | 0.037 | 2 | 2 |
| 34 | 0.025 | 1 | 8 |
| 37 | 0.171 | 32 | 32 |
| 38(b) | 0.222 | 4 | 8 |
| 38(d) | 0.326 | 128 | >32 |
| 39 | 0.010 | 2 | 8 |
| 40(a) | 0.011 | 0.5 | 16 |
| 40(c) | 0.053 | 0.5 | >32 |
| 40(d) | 0.218 | 2 | 8 |
| 40(e) | 0.078 | 1 | 32 |
| 40(f) | 0.029 | 2 | 32 |
| 40(g) | 0.317 | 4 | >32 |
| 40(h) | 0.069 | 0.5 | 8 |
| 41(a) | 0.001 | 2 | >32 |
| 41(b) | 0.019 | 4 | >32 |
| 41(c) | 0.010 | 1 | >32 |
| 41(d) | 0.010 | 0.5 | >32 |
| 41(d) Byproduct | 0.090 | 1 | >32 |
| 42(a) | 0.020 | 1 | 2 |
| 42(b) | 0.050 | 2 | 0.5 |
| 42(c) | 0.011 | 0.2 | 16 |
| 43 | 12.6 | 4 | >32 |
| 44 | 13.1 | 4 | 32 |
| 46(a) | 0.004 | 1 | 64 |
| 46(b) | 0.004 | 0.5 | >32 |
| 47 | 0.025 | 4 | 8 |
| 48(a) | 3.48 | 4 | 16 |
| 48(b) | 0.53 | 2 | 4 |
| 49(a) | 0.010 | 2 | >32 |
| 49(b) | 0.010 | 1 | 4 |
| 50 | 3 | 2 | 4 |
| 51 | 0.198 | 1 | >32 |
| 52(a) | 0.298 | 4 | 8 |
| 52(b) | 0.024 | 1 | 2 |
| 52(c) | 0.033 | — | — |
| 52(d) | 0.022 | 1 | 2 |
| 53 | 0.338 | 4 | 2 |
| 54 | 0.007 | 0.25 | 32 |
| 57(a) | 0.007 | — | — |
| 57(b) | 0.041 | 0.25 | >32 |
| 58(a) | 0.011 | 2 | >32 |
| 58(b) | 0.011 | 0.5 | 16 |
| 58(c) | 0.020 | 0.5 | 0.5 |
| 58(e) | 0.009 | 0.25 | 8 |
| 58(f) | 0.013 | 0.12 | 8 |
| 58(g) | 0.013 | 0.25 | 8 |
| 58(h) | 0.009 | 1 | 32 |
| 59(a) | 0.019 | 1 | 2 |
| 59(b) | 0.006 | 0.5 | 2 |
| 59(c) | 0.163 | 2 | 8 |
| 59(d) | 0.030 | 1 | 8 |
| 60 | 0.149 | 2 | >32 |
| 61(a) | 0.004 | 0.25 | — |
| 61(b) | 0.004 | 2 | 16 |
| 62 | 0.008 | 0.5 | 16 |
| 63 | 0.032 | 2 | 8 |
| 64 | 0.010 | 0.5 | >32 |
| 65(a) | 0.032 | 1 | 0.5 |
| 65(b) | 0.010 | 1 | 2 |
| 65(c) | 0.003 | 1 | 2 |
| 65(d) | 0.124 | 2 | 16 |
| 65(e) | 0.045 | 0.5 | 1 |
| 65(f) | 0.008 | 0.5 | 2 |
| 65(g) | ≦0.001 | 0.5 | 8 |
| 66 | 0.053 | 8 | 4 |
| 67(a) | 0.013 | 8 | 0.5 |
| 67(b) | 0.030 | 8 | 4 |
| 69 | 0.209 | 0.5 | 2 |
| 70(b) | 0.012 | 0.5 | 1 |
| 71 | 0.119 | 2 | 8 |
| 72(a) | 0.041 | 4 | 2 |
| 72(b) | 0.011 | 2 | 4 |
| 73 | 0.159 | 1 | 1 |
| 74(a) | 0.006 | 1 | 2 |
| 74(b) | 0.005 | 1 | 1 |
| 75 | 0.127 | 1 | 4 |
| 76(a) | 0.037 | 1 | 2 |
| 76(b) | 0.072 | 0.5 | ≦0.25 |
| 77 | 0.322 | 2 | 2 |

TABLE 4-continued

| Example No. | IC 50 µM (C) | MIC C. freundii 1982 µg/ml (D) | MIC E. coli 1346 µg/ml (E) |
|---|---|---|---|
| 78(a) | 0.014 | 0.5 | 1 |
| 78(b) | 0.01.3 | 1 | 1 |
| 79 | 0.134 | 4 | 2 |
| 80(a) | 0.008 | 4 | 0.5 |
| 80(b) | 0.004 | — | — |
| 81 | 0.127 | 1 | 1 |
| 82 | 0.013 | 0.25 | 16 |
| 83(a) | 0.016 | 0.5 | 2 |
| 83(b) | 0.010 | 0.5 | 0.5 |
| 84 | 50 | 4 | 2 |
| 85 | 0.019 | 0.5 | >32 |
| 86 | 0.060 | 2 | 16 |
| 87 | 8.7 | 4 | 16 |
| 88(a) | 0.436 | 4 | 16 |
| 88(b) | 0.092 | 2 | 4 |
| 89 | 0.040 | 2 | 4 |
| 90(a) | 0.015 | 1 | 0.5 |
| 90(b) | 0.015 | 1 | 0.5 |
| 91 | 0.080 | 2 | 4 |
| 92(a) | 0.020 | 2 | 4 |
| 92(b) | 0.014 | 2 | 4 |
| 93 | 0.068 | 2 | 8 |
| 94(a) | 0.021 | 2 | 2 |
| 94(b) | 0.012 | 1 | 2 |
| 95 | 0.150 | 0.5 | 4 |
| 96(a) | 0.042 | 2 | 8 |
| 96(b) | 0.005 | 0.5 | 2 |
| 97 | 0.124 | 1 | 4 |
| 98(a) | 0.033 | 1 | 2 |
| 98(b) | 0.010 | 1 | 2 |
| 99 | 0.059 | 2 | 4 |
| 100(a) | 0.018 | 1 | 1 |
| 100(b) | 0.004 | 1 | 2 |
| 100(d) | 0.019 | 2 | 0.5 |
| 101 | 0.038 | 1 | 2 |
| 102(a) | 0.016 | 2 | 0.5 |
| 102(b) | 0.013 | 2 | 1 |
| 103 | 0.047 | 2 | 1 |
| 108 | 0.107 | 1 | 32 |

Test data for particularly preferred products are compiled in Table 5 hereinafter:

TABLE 5

| Example No. | IC 50 µM (C) | MIC C. freundii 1982 µg/ml (D) | MIC E. coli 1346 µg/ml (E) |
|---|---|---|---|
| 3(l) | 0.010 | 0.5 | 8 |
| 18(d) | 0.009 | ≦0.06 | 32 |
| 18(e) | 0.007 | 0.12 | >32 |
| 19(e) | 0.015 | 0.25 | 1 |
| 19(g) | 0.010 | 1 | 1 |
| 27(a) | 0.031 | ≦0.06 | >32 |
| 27(b) | 0.006 | ≦0.06 | >32 |
| 35 | 0.015 | 1 | 0.5 |
| 58(d) | 0.005 | 0.5 | 1 |
| 70(a) | 0.024 | 0.5 | 1 |
| 70(c) | 0.018 | 0.25 | 1 |

The products in accordance with the invention can be used as medicaments, e.g. in the form of pharmaceutical preparations or compositions which contain them or their salts in admixture with a pharmaceutical, organic or inorganic inert carrier material which is suitable for parenteral or enteral administration, such as e.g. water, gelatine, gum arabic, lactose, starch, magnesium stearate, talc, vegetable oils, polyalkylene glycols, Vaseline, etc. The pharmaceutical preparations or compositions can be present in unit dosage forms as in solid form, e.g. as tablets, dragées, suppositories, capsules (hard or soft gelatin); or in liquid form, e.g. as solutions, suspensions or emulsions. They may be sterilized and/or may contain adjuvants such as preservatives, stabilizers, wetting agents or emulsifiers, salts for varying the osmotic pressure, anaesthetics or buffers. They come into consideration for parenteral administration and also for enteral administration.

As mentioned earlier, the compounds in accordance with the invention can be used in the control or prevention of illnesses, especially in the control of β-lactamase-forming pathogens, alone or, especially, in combination with β-lactam antibiotics, i.e. antibiotics which contain a β-lactam ring, for example penicillins such as benzylpenicillin, piperacillin, phenoxymethylpenicillin, carbenicillin, apalcillin, methicillin, propicillin, tricarcillin, ampicillin, amoxicillin or mecillinam or cephalosporins such as ceftriaxone, ceftazidime, cefetamet, cefetamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R, 7R)-7-[(Z)-2-(2-amino-4-thiazolyl)-2-(methoxyimino)acetamido]-3-(azidomethyl)-8-oxo-5-thia-1-azabicyclo[4.2.01]oct-2-ene-2-carboxylic acid or (E)-2-(isobutoxycarbonyl)-2-pentenyl (6R,7R)-7-[(Z)-2-(2-amino-4-thiazolyl)-2-(methoxyimino)acetamido]-3-(azidomethyl)-8-oxo-5-thia-1-azabicyclo[4.2.0]oct-2-en-2-carboxylate or also penems or carbapenems, such as imipenem and meropenem. Thereby, the compounds of formula I or pharmaceutically compatible salts thereof with bases can be administered before, simultaneously with or after the administration or intake of β-lactam antibiotics. When the products in accordance with the invention are administered simultaneously with a β-lactam antibiotic, then this can be effected by administration as an ad-hoc combination or in the form of a pharmaceutical combination which contains a compound of formula I or a pharmaceutically compatible salt thereof with a base and a β-lactam antibiotic; such pharmaceutical combinations are also an object of the present invention.

The dosage of the compounds of formula I and of the pharmaceutically compatible salts thereof with bases can vary within wide limits and will, of course, in each particular case be fitted to the individual requirements and to the β-lactamase producing pathogen to be controlled. In general, a daily dosage of about 0.1 to about 2.0 g should be appropriate. The ratio of β-lactamase inhibitor (compound of formula I or pharmaceutically compatible salt thereof with a base) to β-lactam antibiotic can also vary within wide limits and will be fitted to the individual requirements in each particular case. In general, a ratio of about 1:20 to about 1:1 should be appropriate.

As mentioned earlier, medicaments containing a compound of formula I or a pharmaceutically compatible, readily hydrolyzable ester or corresponding salt thereof are also an object of the present invention, furthermore also a process for the production of such medicaments which comprises bringing one or more compounds of formula I or pharmaceutically compatible esters or salts thereof and, if desired, one or more therapeutically valuable substances into a galenical administration form; in this connection, reference is again made to the pharmaceutical compositions mentioned above which are likewise an object of the present invention. In particular, pharmaceutical combinations containing a compound of formula I or a pharmaceutically compatible, readily hydrolyzable ester or corresponding salt thereof and a β-lactam antibiotic, e.g. a penicillin such as benzylpenicillin, piperacillin, phenoxymethylpenicillin, carbenicillin, apalcillin, methicillin, propicillin, tricarcillin, ampicillin, amoxicillin or mecillinam or a cephalosporin such as ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R,7R)-7-[(Z)-2-(2-amino-4-thiazolyl)-2-(methoxyimino)acetamidol -3-(azidomethyl)-8-oxo-5-thia-1-azabicyclo[4.2.0]oct-2-ene-2-carboxylic acid or (E)-2-(isobutoxycarbonyl)-2-pentenyl (6R,7R)-7-[(Z)-2-(2-amino-4-thiazolyl)-2-(methoxyimino)acetamido]-3-(azidomethyl)-8-oxo-5-thia-1-azabicyclo[4.2.0]oct-2-en-2-carboxylate or also a penem or carbapenem, such as imipenem and meropenem, are objects of the present invention. Such combinations are suitable for the control of pathogens which produce β-lactamase.

In the following Examples DMF signifies dimethylformamide and THF signifies tetrahydrofuran.

EXAMPLE 1 di-t-Butyl (1a S,3aR,6R)-5-hydroxy-1-oxo-1a,2,3,3a,4,6b-hexahydro-2,6a-diazacyclobut[cd]indene-2,6-dicarboxylate (5-hydroxy "building block")

This compound was obtained by the following reaction sequence a)–j):

a) Benzyl (2S,3S)-1-(3,4-dimethoxybenzyl)-2-[(R)-2-oxo-1,3-dioxolan-4-yl]-4-oxo-3-azetidine carbamate 215.23 g (0.5 mol) of benzyl (2S,3S)-1-(3,4-dimethoxybenzyl)-2-[1(R),2-dihydroxyethyl]-4-oxo-3-azetidinecarbamate were dissolved In 3 l of THF at the boiling temperature. 12.61 g (0.75 mol) of 1,1'-carbonyldiimidazole were added. The mixture was boiled under reflux for 4 hours. The THF was subsequently removed by concentration, the oily residue was taken up in 1.5 l of dichloromethane, washed once with 500 ml of 1N aqueous hydrochloric acid, twice with 1 l of water each time and once with 500 ml of saturated, aqueous sodium chloride solution and dried over magnesium sulphate with the addition of about 7 g of fuller's earth. The solvent was removed by concentration. After drying there were obtained without further purification 220.3 g (yield: 96%) of pure product. M.p.: 135°–136° C.

MS (EI): 456 (M$^+$) Microanalysis: $C_{23}H_{24}N_2O_8$ Calc. C 60.52 H 5.30 N 6.14 Found C 60.48 H 5.39 N 6.28 b) Benzyl (1S,4S,5S)-6-(3,4-dimethoxybenzyl)-4-hydroxy-7-oxo-2,6-diazabicyclo[3.2.0]heptane-2-carboxylate Benzyl (2S,3S)-1-(3,4-dimethoxybenzyl)-2-[(R)-2-oxo-1,3-dioxolan-4-yl]-4-oxo-3-azetidinecarbamate (220.3 g, 0.483 mol) was dissolved in 3 l of DMF, treated with 25.4 g (0.121 mol) of tetraethylammonium bromide and stirred vigorously at 140° C. internal temperature under argon for 5 hours. The DMF was removed at 60° C. by concentration under severely reduced pressure. The yellow oily residue was taken up in 1 l of ethyl acetate and extracted twice with 1 l of water and once with 500 ml of saturated aqueous sodium chloride solution. Drying was carried out over magnesium sulphate with the addition of 7 g of fuller's earth. After concentration there was obtained a yellow oil which was purified by chromatography over 2 kg of silica gel with 1) ethyl acetate/n-hexane (3:1) and 2) ethyl acetate. Yield: 172 g (86%) as a light yellow oil which crystallizes from ethyl acetate or isopropanol. M.p.: 100°–102° C. (ethyl acetate).

IR (KBr): 1731, 1707 cm$^{-1}$ Microanalysis: $C_{22}H_{24}N_2O_6$ Calc. C 64.07 H 5.87 N 6.79 Found C 64.00 H 5.80 N 6.80 c) Benzyl (1S,5S)-6-(3,4-dimethoxybenzyl)-4,7-dioxo-2,6-diazabicyclo[3.2.0]heptane-2-carboxylate Oxalyl chloride (25.0 ml, 290.7 mmol) was dissolved in abs. methylene chloride and cooled to −78° C. Abs. dimethyl sulphoxide (40.8 ml, 572 mmol) was added dropwise within one hour at between −70° and −76° C. After 30 minutes at this temperature benzyl (1S,4S,5S)-6-(3,4-dimethoxybenzyl)-4-hydroxy-7-oxo-2,6-diazabicyclo[3.2.0]heptane-2-carboxylate (100 g, 242.4 mmol) in methylene chloride (300 ml) was added dropwise during 2 hours at between −74° and −76° C. After 1 hour at this temperature the mixture was diluted with methylene chloride (640 ml) at below −70° C. and treated with ethyldiisopropylamine (120 ml, 701 mmol) at between −74° C. and −78° C. within 1 hour. After 30 minutes at this temperature the mixture was left to rise to −40° C. The reaction mixture was subsequently poured into 1N aqueous hydrochloric acid while stirring. The organic phase was separated and washed in succession with 1N aqueous hydrochloric add (600 ml), a saturated aqueous sodium chloride solution (600 ml), a saturated aqueous sodium bicarbonate solution (1200 ml) and again with a saturated aqueous sodium chloride solution (1200 ml), dried with magnesium sulphate and concentrated. Yield: 98.4 g (99%) as a colourless solid foam.

IR (KBr): 1760, 1709 cm$^{-1}$ MS (EI): (M$^+$) 410 d) Benzyl (Z)- and (E)-(1S,5R)-4-benzyloxycarbonylmethylene-6-(3,4-dimethoxybenzyl)-7-oxo-2,6-diazabicyclo[3.2.0]-heptane-2-carboxylate Benzyl (1S,5S)-6-(3,4-dimethoxybenzyl)-4,7-dioxo-2,6-diazabicyclo[3.2.0]heptane-2-carboxylate (70.1 g; 170.8 mmol) was dissolved in abs. THF (570 ml) and cooled to −10° C. Benzyloxycarbonylmethylenetriphenylphosphorane (70.1 g; 170.8 mmol) was added portionwise within 15 minutes without the temperature rising above 0° C. After 3 hours at −10° C. the suspension was suction filtered and the mother liquor was concentrated. The oil obtained was dissolved in methylene chloride (20 ml) and chromatographed over silica gel (600 g; 0.040–0.063 mm particle size) with ethyl acetate/n-hexane 2:8 to 1:1. The combined pure fractions were then concentrated to about 200 ml, the separated triphenylphosphine oxide was filtered off under suction and the mother liquor was concentrated. Yield: 78 g (84%) as a colourless foam.

IR (film): 2835, 1762, 1710, 1590, 1516, 1237, 1132 cm$^{-1}$ Microanalysis: $C_{30}H_{28}N_2O_7$ Calc. C 68.17 H 5.34 N 5.30 Found C 68.11 H 5.54 N 4.99 e) (1S,4R,5R)-2-t-Butoxycarbonyl-6-(3,4-dimethoxybenzyl)-7-oxo-2,6-diazabicyclo[3.2.0]hept-4-yl-acetic acid Benzyl (Z)- and (E)-(1S,5R)-4-benzyloxycarbonylmethylene-6-(3,4-dimethoxybenzyl)-7-oxo-2,6-diazabicyclo [3.2.0]heptane-2-carboxylate (78 g; 143.8 mmol) was dissolved in DMF (400 ml) and methanol (1400 ml). After the addition of di-t-butyl dicarbonate (50 ml; 215.6 mmol) the reaction mixture was hydrogenated over 10% Pd/C (26 g) overnight. The dark suspension obtained was filtered and concentrated. The viscous oil obtained was treated with water (850 ml), triturated with saturated aqueous sodium bicarbonate solution (150 ml) and washed with ether (4×1000 ml). After the addition of 1N aqueous hydrochloric acid (100 ml; pH=5) the milky emulsion was extracted with ethyl acetate (1000 ml). The same procedure was repeated and the combined organic phases were dried over magnesium sulphate and concentrated. Yield: 42.2 g (71%) as a yellowish foam.

IR (film): 2600, 1757, 1699, 1675, 1594, 1571 cm$^{-1}$ MS (EI): (M−tBuO) 347 f) t-Butyl (1S,4R,5R)-4-benzyloxycarbonylmethyl-6-(3,4-dimethoxybenzyl)-7-oxo-2,6-diazabicyclo[3.2.0]heptane-2-carboxylate (1S,4R,S R)-2-t-Butoxycarbonyl-6-(3,4-dimethoxybenzyl)-7-oxo-2,6-diazabicyclo[3.2.0]hept-4-yl-acetic acid (41.2 g; 98.9 mmol) was dissolved in methylene chloride (70 ml). Benzyl alcohol (12 ml; 118.7 mmol) and 4-dimethylaminopyridine (1.3 g; 9.89 mmol) were added. Subsequently, the solution was cooled to −10° C. and dicyclohexylcarbodiimide (24.7 g; 118.7 mmol) was added portionwise such that the temperature did not rise above +10° C. The suspension obtained was stirred at room temperature for 20 hours and subsequently suction filtered and concentrated. The oil obtained was chromatographed over silica gel (800 g; 0.040–0.063 mm particle size) with ethyl acetate/n-hexane 1:1. Yield: 37.8 g (75.5%) as a colourless foam.

IR (KBr): 1758, 1697, 1517, 1261, 1160, 1027 cm$^{-1}$ MS (ISP): (M+H$^+$) 511.6 g) t-Butyl (1S,4R,5R)-4-benzyloxycarbonylmethyl-7-oxo-2,6-diazabicyclo[3.2.0]heptane-2-carboxylate t-Butyl (1S,4R,5R)-4-benzyloxycarbonylmethyl-6-(3,4-dimethoxybenzyl)-7-oxo-2,6-diazabicyclo[3.2.0]heptane-2-carboxylate (37.8 g; 74.18 mmol) was placed in acetonitrile (500 ml) and water (240 ml). The solution was heated to 60° C. and treated with potassium persulphate (84 g; 310 mmol) in 4 portions in each case 1 hour apart. Simultaneously, the pH value was held at 5 with a 15% aqueous sodium carbonate solution. After 3 hours at 60° C. the suspension obtained was cooled, the pH was adjusted to 7, the mixture was then diluted with water (200 ml) and extracted with ethyl acetate (2×1000 ml). The combined organic phases were washed with saturated aqueous sodium chloride solution (500 ml), dried over magnesium sulphate and concentrated. The residue was chromatographed over silica gel (1000 g; 0.040–0.063 mm particle size) with ethyl acetate/n-hexane 1:1. Yield: 18.5 g (69.1%) as a colourless solid. M.p.: 135° C.

IR (KBr): 3196, 1750, 1733, 1705, 1160 cm$^{-1}$
Microanalysis: $C_{19}H_{24}N_2O_5$ Calc. C 63.32 H 6.71 N 7.77 Found C 63.22 H 6.88 N 7.58 h) t-Butyl (1S,4R,5R)-4-benzyloxycarbonylmethyl-6-t-butoxycarbonylmethyl-7-oxo-2,6-diazabicyclo[3.2.0]heptane-2-carboxylate t-Butyl (1S,4R,5R)-4-benzyloxycarbonylmethyl-7-oxo-2,6-diazabicyclo[3.2.0]heptane-2-carboxylate (18.0 g; 49.94 mmol) was placed in abs. THF (200 ml) at −78° C. A 1M bistrimethylsilyllithium amide solution in THF (55.1 ml; 55.1 mmol) was added in such a manner that the temperature did not rise above −70° C. (20 minutes). After 10 minutes at this temperature t-butyl bromoacetate (8.8 ml; 60.1 mmol) was added and the reaction mixture was stirred at 0° C. for 1 hour. The orange solution obtained was poured into 1N aqueous hydrochloric acid (250 ml) and ice (150 g) and subsequently extracted with ethyl acetate (2×450 ml). The combined organic phases were washed with saturated aqueous sodium chloride solution (3×300 ml), dried over magnesium sulphate and concentrated. The viscous oil was subsequently triturated with n-hexane (250 ml) and the crystals obtained were filtered off under suction. Yield: 19.2 g (81.1%) as colourless crystals.

IR (KBr): 1771, 1737, 1700, 1157 cm$^{-1}$ MS (FAB): (M+H$^+$) 475.4 i) (1S,4R,5R)-2-t-Butoxycarbonyl-6-t-butoxycarbonylmethyl-7-oxo-2,6-diazabicyclo[3.2.0]hept-4-yl-acetic acid t-Butyl (1S,4R,5R)-4-benzyloxycarbonylmethyl-6-t-butoxycarbonylmethyl-7-oxo-2,6-diazabicyclo[3.2.0]heptane-2-carboxylate (19.0 g; 40.0 mmol) in ethyl acetate (500 ml) was hydrogenated over 10% Pd/C (2 g). The suspension obtained was suction filtered, concentrated, then triturated with water (220 ml), saturated aqueous sodium bicarbonate solution (110 ml) and ether (220 ml). The aqueous phase was treated with 1N aqueous hydrochloric acid (about 110 ml) until a permanent, strong turbidity resulted (pH=5). After extraction with ethyl acetate (300 ml) 1N aqueous hydrochloric acid (about 22 ml; pH=1) was again added and the mixture was extracted with ethyl acetate (300 ml). The combined organic phases were washed with saturated aqueous sodium chloride solution (270 ml) and subsequently dried over magnesium sulphate and concentrated. Yield: 14.5 g (94.3%) as a colourless solid. M.p.: 46°–48° C.

IR (KBr): 3247, 2626, 1772, 1738, 1704, 1158 cm$^{-1}$ MS (ISP): (M+H$^+$) 385.3 j) Di-t-butyl (1aS,3aR,6R)-5-hydroxy-1-oxo-1a,2,3,3a,4,6b-hexahydro-2,6a-diazacyclobut[cd]indene-2,6-dicarboxylate (1S,4R,S R)-2-t-Butoxycarbonyl-6-t-butoxycarbonylmethyl-7-oxo-2,6-diazabicyclo[3.2.0]hept-4-yl-acetic acid (13.13 g; 34.2 mmol) was dissolved in abs. THF (200 ml) and treated with 1,1-carbonyldiimidazole (8.33 g; 51.33 mmol). The suspension obtained was stirred at room temperature for 5 hours, Subsequently, the reaction mixture was cooled to −78° C. and a 1M bistrimethylsilyllithium amide solution in THF (75.3 ml; 75.33 mmol) was added dropwise during 2 hours without the temperature rising above −74° C. After 7 hours the reaction mixture was poured into 1N aqueous hydrochloric acid (150 ml) and ice (50 g) and extracted with ethyl acetate. The combined organic phases were washed in succession with saturated aqueous sodium bicarbonate solution (150 ml) and saturated aqueous sodium chloride solution (2×150 ml) and subsequently dried over magnesium sulphate and concentrated. The residue was suspended in ether (175 ml) and washed thoroughly in succession with 1N aqueous hydrochloric acid (3×175 ml), saturated aqueous sodium bicarbonate solution (2×50 ml) and saturated aqueous sodium chloride solution (2×100 ml). The organic phase was dried over magnesium sulphate and concentrated. Subsequently, the beige solid obtained was triturated with n-hexane (50 ml) for 2 hours and filtered off under suction. Yield: 6.2 g (49%) as colourless crystals. M.p.: 127°–129° C.

IR: 3440, 2979, 1772, 1703, 1657, 1619 cm$^{-1}$
Microanalysis: $C_{18}H_{26}N_2O_6$ Calc. C 59.00 H 7.15 N 7.65 Found C 59.18 H 7.30 N 7.35

EXAMPLE 2

(a) (1aS,3aR,6bR)-5-(1-Methyl-1H-tetrazol-5-ylsulphanyl)-1-oxo-1a,2,3,3a,4,6b-hexahydro-1H-2,6a-diazacyclobut[cd]indene-6-carboxylic acid trifluoroacetate A solution of di-t-butyl (1as,3aR,6bR)-5-(1-methyl-1H-tetrazol-5-ylsulphanyl)-1-oxo-1a,2,3,3a,4,6b-hexahydro-1H-2,6a-diazacyclobut[cd]indene-2,6-dicarboxylate (3.0 g; 6.46 mmol) in abs. methylene chloride (8 ml) was added dropwise to abs. trifluoroacetic acid (32 ml) at between −20° C. and −18° C. After 2 hours at this temperature the solution was diluted with abs. methylene chloride (64 ml) and stirred at room temperature for a further 2 hours. The reaction mixture was concentrated. The residue was triturated with abs. ether (300 ml) and washed with ether (2×50 ml). The crystals were dried in a high vacuum for 10 hours. Yield: 2.9 g (98%) as a beige solid.

IR (KBr): 2683, 1788, 1675 cm$^{-1}$ MS (ISN): (M−H)− 307.0

The di-t-butyl (1aS,3aR,6bR)-5-(1-methyl-1H-tetrazol-5-ylsulphanyl)-1-oxo-1a,2,3,3a,4,6b-hexahydro-1H-2,6a-diazacyclobut[cd]indene-2,6-dicarboxylate used as the starting material can be prepared as follows:

Di-t-butyl (1aS,3aR,6bR)-5-hydroxy-1-oxo-1a,2,3,3a,4,6b-hexahydro-2,6a-diazacyclobut[cd]indene-2,6-dicarboxylate (4.0 g; 10.92 mmol; from Example 1) was dissolved in abs. methylene chloride (110 ml) at room temperature and cooled to −78° C. N-Ethyldiisopropylamine (2.1 ml; 12 mmol) was carefully added dropwise without the temperature rising above −76° C. (about 10 minutes). After 10 minutes trifluoromethanesulphonic anhydride (2.0 ml; 12 mmol) was added dropwise at between −78° C. and −76° C. and the mixture was subsequently stirred at −78° C. for a further 20 minutes. The reaction mixture was diluted with methylene chloride (300 ml) and washed in succession with water (3×160 ml) and saturated aqueous sodium chloride solution (80 ml). The organic phase was dried over magnesium sulphate and concentrated. The residue was dissolved in abs. THF (110 ml) and treated at room temperature with 5-mercapto-1-methyl-1H-tetrazole sodium salt (1.51 g; 10.92 mmol). After 6 days 5-mercapto-1-methyltetrazole sodium salt (0.75 g; 5.46 mmol) was again added. Subsequently, the mixture was stirred for a further 9 days. The suspension was suction filtered and the solid obtained was washed with a small amount of ethyl acetate. Yield: 3.0 g (60%) as a colourless solid. M.p. 222° C.

IR (KBr): 1784, 1692, 1248, 1163 cm$^{-1}$ Microanalysis: $C_{20}H_{28}N_6O_5S$ Calc. C 51.71 H 6.08 N 18.09 Found C 51.61 H 6.09 N 18.08

In analogy to this there were prepared:

(b) (1aS,3aR,6bR)-5-(5-Methyl-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate Starting from di-t-butyl (1aS,3aR,6bR)-5-(5-methyl-1,3,4-thiadiazol-2-ylsulphanyl)-1-oxo-1a,2,3,3a,4,6b-hexahydro-1H-2,6a-diazacyclo[cd]indene-2,6-dicarboxylate (660 mg; 0.37 mmol) there were obtained 360 mg (62%) as a colourless solid.

IR (KBr): 1785, 1674 cm$^{-1}$ MS (ISN): (M−H)$^−$+ NH$_3$:340.0 (MS artefact)

The di-t-butyl (1aS,3aR,6bR)-5-(5-methyl-1,3,4-thiadiazol-2-ylsulphanyl)-1-oxo-1a,2,3,3a,4,6b-hexahydro-1H-2,6a-diazacyclobut[cd]indene-2,6-dicarboxylate used as the starting material was obtained starting from di-t-butyl (1aS,3aR,6bR)-5-hydroxy-1-oxo-1a,2,3,3a,4,6b-hexahydro-2,6a-diazacyclobut[cd]indene-2,6-dicarboxylate (2.15 g; 5.87 mmol; from Example 1): 960 mg (40%) of product as a colourless solid. M.p.: 175° C.

IR (KBr): 1779, 1701, 1243, 1161 cm$^{-1}$ Microanalysis: $C_{21}H_{28}N_4O_5S_2$ Calc. C 52.48 H 5.87 N 11.66 Found C 52.34 H 5.91 N 11.62

(c) (1aS,3aR,6bR)-5-(5-Amino-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate Starting from di-t-butyl (1aS,3aR,6bR)-5-(5-amino-1,3,4-thiadiazol-2-ylsulphanyl)-1-oxo-1a,2,3,3a,4,6b-hexahydro-1H-2,6a-diazacyclobut[cd]indene-2,6-dicarboxylate (510 mg; 1.03 mmol) there were obtained 400 mg (89%) as a beige solid.

IR (KBr): 1776, 1678, 1619, 1390, 1204 cm$^{-1}$ MS (ISN): (M−H)$^−$324.2

The di-t-butyl (1aS,3aR,6bR)-5-(5-amino-1,3,4-thiadiazol-2-ylsulphanyl)-1-oxo-1a,2,3,3a,4,6b-hexahydro-1H-2,6a-diazacyclobut[cd]indene-2,6-dicarboxylate used as the starting material was obtained starting from di-t-butyl (1aS,3aR,6bR)-5-hydroxy-1-oxo-1a,2,3,3a,4,6b-hexahydro-2,6a-diazacyclobut[cd]indene-2,6-dicarboxylate (500 mg; 1.36 mmol; from Example 1): 280 mg (41%) of product as a yellow solid. M.p. 204° C. (dec.).

IR (KBr): 3317, 1777, 1700, 1616, 1244, 1161 cm$^{-1}$ Microanalysis: $C_{20}H_{27}N_5O_5S_2$ Calc. C 48.28 H 5.47 N 14.07 Found C 48.58 H 5.60 N 14.21

(d) (1aS,3aR,6bR)-1-Oxo-5-(pyridin-4-ylsulphanyl)-1a,2,3,3a,4,6b-hexahydro-1H-2,6a-diazacyclobut[cd]indene-6-carboxylic acid trifluoroacetate Starting from di-t-butyl (1aS,3aR,6bR)-1-oxo-5-(pyridin-4-ylsulphanyl)-1a,2,3,3a,4,6b-hexahydro-1H-2,6a-diazacyclobut[cd]indene-2,6-dicarboxylate (177 mg; 0.38 mmol) there were obtained 119 mg (58%) as a yellowish solid.

IR (KBr): 1786, 1678, 1624, 1479, 1199, 1135 cm$^{-1}$ MS (ISP): (M+H)$^+$ 304.3

The di-t-butyl (1aS,3aR,6bR)-1-oxo-5-(pyridin-4-ylsulphanyl)-1a,2,3,3a,4,6b-hexahydro-1H-2,6a-diazacyclobut[cd]indene-2,6-dicarboxylate used as the starting material was prepared as follows:

Di-t-butyl (1aS,3aR,6bR)-1-oxo-5-trifluoromethylsulphonyloxy-1a,2,3,3a,4,6b-hexahydro-1H-2,6a-diazacyclobut[cd]indene-2,6-dicarboxylate.

Di-t-butyl (1aS,3aR,6bR)-5-hydroxy-1-oxo-1a,2,3,3a,4,6b-hexahydro-2,6a-diazacyclobut[cd]indene-2,6-dicarboxylate (1.8 g; 4.91 mmol; from Example 1) was dissolved in absolute methylene chloride (50 ml) and cooled to −78° C. At a temperature of <−70° C. there was added dropwise firstly N-ethyldiisopropylamine (0.99 ml; 5.78 mmol), then trifluoromethanesulphonic anhydride (0.90 ml; 5.49 mmol) and finally the mixture was stirred for a further 1.5 hours. The reaction mixture was washed with water (1×100 ml, 2×50 ml). The organic phase was dried over magnesium sulphate and concentrated. The residue was dissolved in diethyl ether. Addition of n-hexane yielded 2.25 g (90%) of a beige precipitate.

MS (EI): 425 (M−OC$_4$H$_9$)$^+$

Di-t-butyl (1aS,3aR,6bR)-1-oxo-5-(pyridin-4-ylsulphanyl)-1a,2,3,3a,4,6b-hexahydro-1H-2,6a-diazacyclobut[cd]indene-2,6-dicarboxylate A mixture of 4-mercaptopyridine (118 mg; 1.06 mmol) and sodium hydride (51 mg; about 1.16 mmol) was suspended in THF (10 ml). At −45° C. to −40° C. there was added dropwise a solution of di-t-butyl (1aS,3aR,6bR)-1-oxo-5-trifluoromethylsulphonyloxy-1a,2,3,3a,4,6b-hexahydro-1H-2,6a-diazacyclobut[cd]indene-2,6-dicarboxylate (499 mg; 1.00 mmol) in THF (5 ml) and the mixture was subsequently stirred for 7.5 hours. The reaction mixture was diluted with 40 ml of a mixture consisting of 20 ml of saturated, aqueous sodium chloride solution, 10 ml of water and 10 ml of an aqueous 2M dipotassitun hydrogen phosphate/potassium dihydrogen phosphate buffer, pH 6. The reaction mixture was extracted with ethyl acetate (2×60 ml). The organic phases were washed with saturated, aqueous sodium chloride solution (40 ml), combined, dried over magnesium sulphate and concentrated. The residue was chromatographed twice on silica gel, with the eluent being methylene chloride/acetone 9:1 and, respectively, 4:1 in the first chromatography and ethyl acetate/n-hexane 4:1 in the second chromatography. 407 mg (88%) were obtained as a white foam.

IR (KBr): 1779, 1703, 1572, 1406, 1368, 1162 cm$^{-1}$ MS (MALDI): (M+H)$^+$ 460.8

(e) (1aS,3aR,6bR)-4-(6-Carboxy-1-oxo-1a,2,3,3a,4,6b-hexahydro-1H-2,6a-diazacyclobut[cd]indene-5-ylsulphanyl)-1-methyl-pyridinium trifluoromethanesulphonate-trifluoroacetate (1:1)

Starting from (1aS,3aR,6bR)-4-(2,6-bis-t-butoxycarbonyl-1-oxo-1a,2,3,3a,4,6b-hexahydro-1H-2,6a-diazacyclobut[cd]inden-5-ylsulphanyl)-1-methyl-pyridinium trifluoromethanesulphonate (840 mg; 1.35 mmol) there were obtained 640 mg (78%) as a yellowish solid.

IR (KBr): 1782, 1731, 1225, 1175, 827 cm$^{-1}$ MS (ISP): M$^+$ 318.3 Microanalysis: $C_{16}H_{16}N_3O_6S_2F_3 \cdot 0.95CF_3COOH$.

0.11CH$_3$OSO$_2$CF$_3$. 0.07 (C$_2$H$_5$)$_2$O.0.66 H$_2$O Calc. C 36.18 H 3.18 N 6.88 S 11.07 F 19.22 Found C 36.19 H 3.35 N 6.80 S 11.17 F 19.23

The (1aS,3aR,6bR)-4-(2,6-bis-t-butoxycarbonyl-1-oxo-1a,2,3,3a,4,6b-hexahydro-1H-2,6a-diazacyclobut[cd]inden-5-ylsulphanyl)-1-methyl-pyridinium trifluoromethanesulphate used as the starting material was prepared as follows:

Methyl trifluoromethanesulphonate (0.21 ml; 1.91 mmol) was added dropwise at 0° C. to a solution of di-t-butyl (1aS,3aR,6bR)-1-oxo-5-(pyridin-4-ylsulphanyl)-1a,2,3,3a,4,6b-hexahydro-1H-2,6a-diazacyclobut[cd]indene-2,6-dicarboxylate (730 mg; 1.6 mmol; from Example 2(d)) in methylene chloride (10 ml). The mixture was stirred at 0° C. for a further 2 hours, then the solvent was removed. The residue was treated with n-hexane and stirred. The precipitate which thereby forms was filtered off under suction and dried. 870 mg (82%) were obtained as a yellowish solid.

IR(KBr): 1783, 1722, 1699, 1369, 1263, 1160 cm$^{-1}$ MS (ISP): M$^+$474.5 Microanalysis: C$_{25}$H$_{32}$N$_3$O$_8$S$_2$F$_3$.0.1CH$_3$OSO$_2$CF$_3$.0.25C$_6$H$_{14}$.0.5 H$_2$O Calc. C 47.82 H 5.53 N 6.27 S 10.04 F 9.35 Found C 47.60 H 5.69 N 6.21 S 10.32 F 9.69

(f) (1aS,3aR,6bR)-5-Carbamoylmethylsulphanyl-1-oxo-1a,2,3,3a,4,6b-hexahydro-1H-2,6a-diazacyclobut[cd]indene-6-carboxylic acid trifluoroacetate Starting from di-t-butyl (1aS,3aR,6bR)-5-carbamoylmethylsulphanyl-1-oxo-1a,2,3,3a,4,6b-hexahydro-1H-2,6a-diazacyclobut[cd]indene-2,6-dicarboxylate (140 mg; 0.32 mmol) there were obtained 88 mg (70%) as a brownish solid.

IR (KBr): 3429, 1776, 1677, 1378, 1202 cm$^{-1}$ MS (ISN): (M−H)$^-$ 396.3

The di-t-butyl (1aS,3aR,6bR)-5-carbamoylmethylsulphanyl-1-oxo-1a,2,3,3a,4,6b-hexahydro-1H-2,6a-diazacyclobut[cd]indene-2,6-dicarboxylate used as the starting material was prepared in analogy to Example 2(d) from di-t-butyl (1aS,3aR,6bR)-1-oxo-5-trifluoromethylsulphonyloxy-1a,2,3,3a,4,6b-hexahydro-1H-2,6a-diazacyclobut[cd]indene-2,6-dicarboxylate (600 mg; 1.2 mmol; from Example 2(d)) and mercaptoacetamide (120 mg; 1.3 mmol). 120 mg (23%) of a yellowish solid were obtained.

IR (KBr): 1773, 1691, 1618, 1252 cm$^{-1}$ MS (ISP): 457.4 (M+NH$_4$)$^+$; 440.4 (M+H)$^+$ (g) (1aS,3aR,6bR)-5-(6-Carboxy-1-oxo-1a,2,3,3a,4,6b-hexahydro-1H-2,6a-diazacyclobut[cd]inden-5-ylsulphanylmethyl)-1,4-dimethyl-1H-1,2,4-triazol-4-ium trifluoromethanesulphonate trifluoroacetate Starting from (1aS,3aR,6bR)-5-(2,6-bis-t-butoxycarbonyl-1-oxo-1a,2,3,3a,4,6b-hexahydro-1H-2,6a-diazacyclobut[cd]inden-5-ylsulphanylmethyl)-1,4-dimethyl-1H-1,2,4-triazol-4-ium trifluoromethanesulphonate (980 mg; 1.5mmol) there were obtained 865 mg (94%) as a yellow solid.

IR (KBr): 1781, 1682, 1629, 1264 cm$^{-1}$ MS (ISP): (M)$^+$336.2

The (1aS,3aR,6bR)-5-(2,6-bis-t-butoxycarbonyl-1-oxo-1a,2,3,3a,4,6b-hexahydro-1H-2,6a-diazacyclobut[cd]inden-5-ylsulphanylmethyl)-1,4-dimethyl-1H-1,2,4-triazol-4-ium trifluoromethanesulphonate used as the starting material was prepared as follows:

A solution of di-t-butyl (1aS,3aR,6bR)-1-oxo-5-trifluoromethylsulphonyloxy-1a,2,3,3a,4,6b-hexahydro-1H-2,6a-diazacyclobut[cd]indene-2,6-dicarboxylate (205 mg; 0.41 mmol; from Example 2(d)) in THF (4 ml) was treated at −76° C. with a solution of 1,4-dimethyl-5-mercaptomethyl-1H-1,2,4-triazol-4-ium trifluoromethanesulphonate (137 mg; 0.47 mmol) in THF (3 ml) and a solution of diisopropylethylamine in THF (2 ml), The mixture was warmed to room temperature within 3 hours and then stirred for a further 3 hours, The reaction mixture was diluted with ethyl acetate (100 ml) and extracted with 50 ml of a mixture consisting of 25 ml of saturated, aqueous sodium chloride solution, 12.5 ml of water and 12.5 ml of an aqueous 2M dipotassium hydrogen phosphate/potassium dihydrogen phosphate buffer of pH 6, The aqueous phase was re-extracted with ethyl acetate (100 ml) the organic phases are washed with saturated, aqueous sodium chloride solution (50 ml), combined, dried over magnesium sulphate and concentrated, Chromatography of the residue on silica gel (eluent methylene chloride/methanol 9:1, then 6:1) gave 111 mg (42%) as a white solid.

IR (KBr): 1773, 1694, 1566, 1260, 1160 cm$^{-1}$ MS (ISP): 492,4 (M-trifluoromethanesulphonate)$^+$

EXAMPLE 3

(a) (1aS,3aR,6bR)-2-(4-Hydroxy-phenylcarbamoyl)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid sodium salt (1aS,3aR,6bR)-5-(1-Methyl-1H-tetrazol-5-ylsulphanyl)-1-oxo-1a,2,3,3a,4,6b-hexahydro-1H-2,6a-diazacyclo[cd]indene-6-carboxylic acid trifluoroacetate (200 mg; 0.474 mmol; from Example 2(a)) was placed in acetonitrile/water 1:1 (6 ml) and cooled to 0° C. The solution was treated with sodium bicarbonate (80 mg; 0,948 mmol) and 4-hydroxyphenylcarbamic acid 2,5-dioxo-pyrrolidin-1-yl ester (118 mg; 0.474 mmol). After 10 minutes at 0° C. the mixture was stirred at room temperature for 1 to 2 hours (followed by thin-layer chromatography). Subsequently, the reaction mixture was diluted s with water (5 ml), washed with methylene chloride (3×10 ml) and lyophilized. The residue was dissolved in a small amount of water and chromatographed over a polymeric hydrophobic gel with water and lyophilized. Yield: 78 mg (35%) as a colourless powder.

IR (KBr): 3416, 1756, 1615, 1513, 1389, 1240 cm$^{-1}$ MS (ISN): (M−Na$^+$) 442.4

In analogy thereto, starting from (1aS,3aR,6bR)-5-(1-methyl-1H-tetrazol-5-ylsulphanyl)-1-oxo-1a,2,3,3a,4,6b-hexahydro-1H-2,6a-diazacyclo[cd]indene-6-carboxylic acid there were prepared:

(b) (1aS,3aR,6bR)-2-(4-Carbamoyl-phenylcarbamoyl)-5-(1-methyl-1H-tetrazol-5-ylsulphanyl)-1-oxo-1a,2,3,3a,4,5b-hexahydro-1H-2,6a-diazacyclobut[cd]indene-6-carboxylic acid sodium salt. Yield: 21% as a colourless powder.

IR (KBr): 3424, 1756, 1658, 1608, 1526, 1390 cm$^{-1}$ Microanalysis: C$_{19}$H$_{17}$N$_8$O$_5$SNa Calc. C 42.41 H 4.13 N 20.82 Found C 42.59 H 4.01 N 20.61

(c) (1aS,3aR,6bR)-2-[(S)-2-Oxo-pyrrolidin-3-ylcarbamoyl]-5-(1-methyl-1H-tetrazol-5-ylsulphanyl)-1-oxo-1a,2,3,3a,4,6b-hexahydro-1H-2,6a-diazacyclobut[cd]indene-6-carboxylic acid sodium salt. Yield: 17% as a colourless powder.

IR (KBr): 1758, 1702 cm$^{-1}$ MS (ISN): (M−Na)$^-$433.2

(d) (1aS,3aR,6bR)-5-(1-Methyl-1H-tetrazol-5-ylsulphanyl)-1-oxo-2-(thien-2-ylmethylcarbamoyl)-1a,2,3,3a,4,6b-hexahydro-1H-2,6a-diazacyclobut[cd]indene-6-carboxylic acid sodium salt. Yield: 19% as a colourless powder.

IR (KBr): 3410, 1756, 1619, 1525, 1394 cm$^{-1}$ MS (ISN): (M−Na)$^-$446.2

(e) (1aS,3aR,6bR)-2-(3,4-Dihydroxy-benzylcarbamoyl)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid salt. Yield: 16% as a colourless powder.

IR (KBr): 3411, 1756, 1618, 1529, 1392 cm$^{-1}$ MS (ISN): (M–Na)$^-$472.3
(f) (1aS,3aR,6bR)-5-(1-Methyl-1H-tetrazol-5-ylsulphanyl)-1-oxo-2-[(R)- and [(S)-2-oxo-tetrahydro-thien-3-ylcarbamoyl]-1a,2,3,3a,4,6b-hexahydro-1H-2,6a-diazacyclobut[cd]indene-6-carboxylic add sodium salt. Yield: 40% as a colourless powder.
IR (KBr): 3426, 1758, 1699, 1620, 1534, 1393 cm$^{-1}$ is MS (ISN): (M–Na)$^-$450.3
(g) (1aS,3aR,6bR)-5-(1-Methyl-1H-tetrazol-5-ylsulphanyl)-1-oxo-2-(4-sulphamoyl-benzylcarbamoyl)-1a,2,3,3a,4,6b-hexahydro-1H-2,6a-diazacyclobut[cd]indene-6-carboxylic acid sodium salt. Yield: 36% as a colourless powder.
IR (KBr): 3371, 1756, 1615, 1539, 1377, 1323, 1160 cm$^{-1}$ Microanalysis: $C_{19}H_{19}N_8O_6S_2Na$ Calc. C 42.06 H 3.53 N 20.65 Found C 41.81 H 3.71 N 20.32
(h) (1aS,3aR,6bR)-2-(3-Methoxy-isoxazol-5-ylmethylcarbamoyl)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid sodium salt. Yield: 28% as a colourless powder.
IR (KBr): 3280, 1751, 1620, 1518, 1409 cm$^{-1}$ MS (ISN): [(M–Na)$^-$+ NH$_3$] 478.3 (MS artefact), (M+Na)$^-$461.5
(i) (1aS,3aR,6bR)-2-[(R)- and [(S)-1,1-dioxo-tetrahydrothien-3-ylcarbamoyl)-5-(1-methyl-1H-tetrazol-5-ylsulphanyl)-1-oxo- 1a,2,3,3a,4,6b-hexahydro-1H-2,6a-diazacyclobut[cd]indene-6-carboxylic acid sodium salt. Yield: 30% as a colourless powder.
IR (KBr): 3300, 1764, 1633, 1534, 1394, 1305, 1118 cm$^{-1}$ MS (ISN): (M+Na)$^-$468.6
In analogy to Example 3(a), starting from (1aS,3aR,6bR)-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate (from Example 2b) there were prepared:
(j) (1aS,3aR,6bR)-2-(4-Hydroxyphenylcarbamoyl)-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid sodium salt. Yield: 35% as a colourless powder.
IR (KBr): 3280, 1756, 1612, 1539, 1387 cm$^{-1}$ Microanalysis: $C_{19}H_{16}N_5O_5S_2Na$ Calc. C 47.40 H 3.35 N 14.55 Found C 47.44 H 3.22 N 14.45
(k) (1aS,3aR,6bR)-2-(4-Carbamoyl-phenylcarbamoyl)-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid sodium salt. Yield: 19% as a colourless powder.
IR (KBr): 3416, 3240, 1756, 1660, 1607, 1525, 1385 cm$^{-1}$ Microanalysis: $C_{20}H_{17}N_6O_5S_2Na$ Calc. C 47.24 H 3.37 N 16.53 Found C 47.16 H 3.74 N 16.35
In analogy to Example 3(a), starting from (1aS,3aR,6bR)-5-(5-amino-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate (from Example 2c) they were prepared:
(1) (1aS,3aR,6bR)-5-(5-Amino-1,3,4-thiadiazol-2-ylsulphanyl)-2-(4-hydroxyphenylcarbamoyl)-1-oxo-1a,2,3,3a,4,6b-hexahydro-1H-2,6a-diazacyclobut[cd]indene-6-carboxylic acid sodium salt. Yield: 32% as a colourless powder.
IR (KBr): 3411, 3300, 3180, 1751, 1611, 1513, 1389, 1238 cm$^{-1}$ MS (ISN): (M+Na)$^-$458.9
(m) (1aS,3aR,6bR)-5-(5-Amino-1,3,4-thiadiazol-2-ylsulphanyl)-2-(4-carbamoyl-amino-phenylcarbamoyl)-1-oxo-1a,2,3,3a,4,6b-hexahydro-1H-2,6a-diazacyclobut[cd]indene-6-carboxylic acid sodium salt. Yield: 26% as a colourless powder.
IR (KBr): 3394, 1751, 1657, 1606, 1523, 1389 cm$^{-1}$ MS (ISN): (M+Na)$^-$486.2 Microanalysis: $C_{19}H_{16}N_7O_5S_2Na$ Calc. C 44.79 H 3.17 N 19.24 Found C 44.82 H 3.29 N 19.60

In analogy to Example 3(a) there were prepared:
(n) (1aS,3aR,6bR)-2-(4-Carbamoyl-phenylcarbamoyl)-1-oxo-5-(pyridin-4-ylsulphanyl)-1a,2,3,3a,4,6b- hexahydro-1H-2,6a-diazacyclobut[cd]indene-6-carboxylic acid sodium salt
Starting from (1aS,3a-R,6bR)-1-oxo-(5-pyridin-4-ylsulphanyl)-1a,2,3,3a,4,6b-hexahydro-1H-2,6a-diazacyclobut[cd]indene-6-carboxylic acid trifluoroacetate (105 mg; 0.20 mmol; from Example 2(d)) there were isolated 31 mg (32%) as a white powder.
IR (KBr): 3422, 1759, 1662, 1611, 1383 cm$^{-1}$ MS (ISN): (M–H+NH$_3$)$^-$481.4; (M–Na)$^-$464
(o) ((1aS,3aR,6bR)-2-(4-Hydroxy-phenylcarbamoyl)-1-oxo-5-(pyridin-4-ylsulphanyl)-1a,2,3,3a,4,6b-hexahydro-1H-2,6a-diazacyclobut[cd]indene-6-carboxylic acid sodium salt.
Starting from (1aS,3aR,6bR)-1-oxo-5-(pyridin-4-ylsulphanyl)-1a,2,3,3a,4,6b-hexahydro-1H-2,6a-diazacyclobut[cd]indene-6-carboxylic acid trifluoroacetate (100 mg; 0.19 mmol; from Example 2(d)) there were isolated 51 mg (54%) as a white powder.
IR (KBr): 3406, 1756, 1613, 1438, 1237, 832 cm$^{-1}$ MS (ISP): (M+H+Na)$^+$ 461.5; (M+H)$^+$ 439.5 Microanalysis: $C_{21}H_{17}N_4O_5SNa.1.99 H_2O$ Calc. C 50.83 H 4.26 N 11.26 S 6.46 Found C 49.78 H 4.18 N 11.09 S 6.68
(p) (1aS,3aR,6bR)-5-Carbamoylmethylsulphanyl-2-(4-hydroxyphenylcarbamoyl)-1-oxo-5-(pyridin-4-ylsulphanyl)-1a,2,3,3a,4,6b-hexahydro-1H-2,6a-diazacyclobut[cd]indene-6-carboxylic acid sodium salt
Starting from (1aS,3aR,6bR)-5-carbamoylmethylsulphanyl-1-oxo-1a,2,3,3a,4,6b-hexahydro-1H-2,6a-diazacyclobut[cd]indene-6-carboxylic acid trifluoroacetate (120 mg; 0.30 mmol; from Example 2(f)) there were isolated 25 mg(19%) as a white powder.
IR (KBr): 3410, 1748, 1670, 1605, 1512, 1384, 1238, 838 cm$^{-1}$ MS (ISN): (M+NH$_3$–Na)$^-$434.3; (M–Na)$^-$417.3
(q) (1aS,3aR,6bR)-5-[(1,4-Dimethyl-1H-1,2,4-triazol-5-ylio)methylsulphanyl]-2-(4-hydroxy-phenylcarbamoyl)-1-oxo-1a,2,3,3a,4,6b-hexahydro-1H-2,6a-diazacyclobut[cd]indene-6-carboxylate
Starting from (1aS,3aR,6bR)-5-(6-carboxy-1-oxo-1a,2,3,3a,4,6b-hexahydro-1H-2,6a-diazacyclobut[cd]inden-5-ylsulphanylmethyl)-1,4-dimethyl-1H-1,2,4-triazol-4-ium trifluoromethanesulphonate trifluoroacetate(150 mg; 0.25 mmol; from Example 2(g)) there were isolated 22 mg (14%) as a white powder.
IR (KBr): 3411, 1761, 1711, 1607, 1370, 1240, 1195 cm$^{-1}$ MS (ISN): (M–H)$^-$469.3
(aa) (1aS,3aR,6bR)-2-Acetyl-5-(1-methyl -1H-tetrazol-5-ylsulphanyl)-1-oxo-1a,2,3,3a,4,6b-hexahydro-1H-2,6a-diazacyclobut[cd]indene-6-carboxylic acid sodium salt
Acetyl chloride (26 ml; 0.36 mmol) was added at 0° C. to a solution of (1aS,3aR,6bR)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid trifluoroacetate (200 mg; 0.36 mmol; from Example 2(a)) and sodium hydrogen carbonate (121 mg; 1.44 mmol) in DMF (2 ml). The mixture was stirred at 0° C. for 0.5 hour and then concentrated. The residue was dissolved in a small mount of water and chromatographed over a hydrophobic polymer (eluent: water/acetonitrile). 24 mg (185) of a yellowish powder were obtained.
IR (KBr): 1760, 1618, 1395 cm$^{-1}$ MS (ISN): (M–Na+NH$_3$)$^-$366.3 (MS artefact); (M–Na)$^-$ 349,3
(ab) (1aS,3aR,6bR)-5-(1-Methyl-1H-tetrazol-5-ylsulphanyl)-1-oxo-2-trifluoroacetyl-1a,2,3,3a,4,6b-hexahydro-1H-2,6a-diazacyclobut[cd]indene-6-carboxylic acid sodium salt To a solution of (1aS,3aR,6bR)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid trifluoroacetate (200 mg; 0.36 mmol; from Example 2(a)) in DMF (4 ml) was added N-methyl-N-trimethylsilyltrifluoroacemmide (80 ml; 0.27 mmol), then dicyclohexylcarbodiimide (89 mg; 0.43 mmol) and trifluoroacetic acid. The mixture was stirred at room temperature for 1 hour. The resulting precipitate was filtered off and rinsed with a small amount of DMF. The filtrate was concentrated. The residue was dissolved in s a small amount of water. The solution was adjusted to pH$_7$ with sodium hydrogen carbonate and chromatographed over a hydrophobic polymer (eluent: water/acetonitrile). 12 mg (9%) of a white powder were obtained.

IR (KBr): 1768, 1696, 1621, 1394, 1172 cm$^{-1}$ MS (ISP): (M+H)$^+$427.3; (M–Na+H+NH$_4$)$^+$422.4; (M–Na+2H)$^+$ 405.3

(ac) (1aS,3aR,6bR)-2-Acetyl-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid sodium salt Starting from (1aS,3aR,6bR)-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate (100 mg; 0.23 mmol; from Example 2(b)) there were obtained in analogy to Example 3(aa) 30 mg (34%) of a yellowish powder.

IR (KBr): 1759, 1620, 1397 cm$^{-1}$ MS (ISN): (M–Na)$^-$ 365.3

(ad) (1aS,3aR,6bR)-5-(5-Methyl-1,3,4-thiadiazol-2-yl sulphanyl)-1-oxo-2-trifluoracetyl-1a,2,3,3a,4,6b-hexahydro-1H-2,6a-diazacyclobut[cd]indene-6-carboxylic acid sodium salt A solution of (1aS,3aR,6bR)-5-(5-methyl-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate (90 mg; 0.21 mmol; from Example 2(b)) and sodium hydrogen carbonate (53 mg; 0.63 mmol) in DMF (1 ml) was treated with 2-(trifluoroacetoxy)pyridine (29 ml; 0.21 mmol) at 0° C. The mixture was stirred at room temperature for 1.5 hours and then concentrated. The residue was dissolved in a small amount of water and chromatographed over a hydrophobic polymer (eluent: water/acetonitrile). 23 mg (24%) of a white powder were obtained.

IR (KBr): 1766, 1697, 1618, 1343, 1180 cm$^{-1}$ MS (ISP): (M+H)$^+$443.4; (M–Na+H+NH$_4$)$^+$438.4; (M–Na+2H)$^+$ 421.4

(ae) (1aS,3aR,6bR)-2-Acetyl-5-(5-amino-1,3,4-thiadiazol-2-ylsulphanyl)-1-oxo-1a,2,3,3a,4,6b-hexahydro-1H-2,6a-diazacyclobut[cd]indene-6-carboxylic acid sodium salt Starting from (1aS,3aR,6bR)-5-(5-amino-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate (100 mg; 0.23 mmol; from Example 2(c)) there were obtained in analogy to Example 3(aa) 61 mg (49%) of a yellowish powder.

IR (KBr): 1756, 1617, 1400, 1405, 807 cm$^{-1}$ MS (ISN): (M–Na)$^-$ 366.3 Microanalysis: C$_{13}$H$_{12}$N$_5$O$_4$S$_2$Na.2.37 H$_2$O.0.3NaHCO$_3$ Calc. C 34.93 H 3.76 N 15.32 S 14.02 Na 6.54 Found C 34.90 H 3.45 N 15.41 S 13.43 Na 6.49

(af) (1aS,3aR,6bR)-5-(5-Amino-1,3,4-thiadiazol-2-ylsulphanyl)-2-methylsulphonyl-1-oxo-1a,2,3,3a,4,6b-hexahydro-1H-2,6a-diazacyclobut[cd]indene-6-carboxylic acid 20 sodium salt Starting from (1aS,3aR,6bR)-5-(5-amino-1,3,4-thiadiazol-2-ylsulphanyl)-1-oxo-1a,2,3,3a,4,6b-hexahydro-1H-2,6a-diazacyclobut[cd]indene-6-carboxylic acid trifluoroacetate (120 mg; 0.27 mmol; from Example 2(c)) there were obtained in analogy to Example 3(aj) 23 mg (20%) of a yellowish powder.

IR (KBr): 3400, 3286, 1754, 1613, 1397, 1333, 1154 cm$^{-1}$ MS (ISP): (M+Na)$^+$448.3; (M+H)$^+$426.4; (M–Na+H+NH$_4$)$^+$ 421.4; (M–Na+2H)$^+$404.4

(ag) (1aS,3aR,6bR)-5-(5-Amino-1,3,4-thiadiazol-2-ylsulphanyl)-2-cyanoacetyl-1-oxo-1a,2,3,3a,4,6b-hexahydro-1H-2,6a-diazacyclobut[cd]indene-6-carboxylic acid sodium salt Starting from (1aS,3aR,6bR)-5-(5-amino-1,3,4-thiadiazol-2-ylsulphanyl)-1-oxo-1a,2,3,3a,4,6b-hexahycdro-1H-2,6a-diazacyclobut[cd]indene-6-carboxylic acid trifluoroacetate (300 mg; 0.68 mmol; from Example 2(c)) there were obtained in analogy to Example 3(ah) 26 mg (9%) of a white powder.

IR (KBr): 2408, 2236, 1755, 1613, 1395 cm$^{-1}$ MS (ISP): (M+Na)$^+$437; (M+H)$^+$ 414

(ah) (1aS,3aR,6bR)-2-Acetyl-1-oxo-5-(pyridin-4-ylsulphanyl)-1a,2,3,3a,4,6b-hexahydro-1H-2,6a-diazacyclobut[cd]indene-6-carboxylic acid sodium salt Sodium hydrogen carbonate (67 mg; 0.80 mmol) and 2,5-dioxo-pyrrolidin-1-yl acetate (43 mg; 0.28 mmol) were added at 0° C. to a solution of (1aS,3aR,6bR)-1-oxo-5-(pyridin-4-ylsulphanyl)-1a,2,3,3a,4,6b-hexahydro-1H-2,6a-diazacyclobut[cd]indene-6-carboxylic acid trifluoroacetate (105 mg; 0.20 mmol; from Example 2(d)) in acetonitrile/water 1:1 (5 ml). The mixture was stirred at room temperature for 3 hours and then concentrated. The residue was taken up in water (20 ml) and extracted with methylene chloride (4×10 ml). The aqueous phase was concentrated. The residue was dissolved in a small amount of water and chromatographed over a hydrophobic polymer (eluent: as water/acetonitrile). 35 mg (45%) of a yellowish powder were obtained.

IR (KBr): 1760, 1620, 1573, 1405, 807 cm$^{-1}$ MS (ISN): (M–Na+NH$_3$)$^-$361.4 (MS artefact)

(ai) (1aS,3aR,6bR)-1-Oxo-5-(pyridin-4-ylsulphanyl)-2-trifluoracetyl-1a,2,3,3a,4,6b-hexahydro-1H-2,6a-diazacyclobut[cd]indene-6-carboxylic acid sodium salt Starting from (1aS,3aR,6bR)-1-oxo-5-(pyridin-4-ylsulphanyl)-1a,2,3,3a,4,6b-hexahydro-1H-2,6a-diazacyclobut[cd]indene-6-carboxylic acid trifluoroacetate (87 mg; 0.18 mmol; from Example 2(d)) there were isolated in analogy to Example 3(ad) 35 mg (47%) as a yellowish powder.

IR (KBr): 1766, 1692, 1618, 1399, 1208, 1179 cm$^{-1}$ MS (ISP): (M–Na+2H)$^+$400.4

(aj) (1aS,3aR,6bR)-2-Methylsulphonyl-1-oxo-5-(pyridin-4-ylsulphanyl)-1a,2,3,3a,4,6b-hexahydro-1H-2,6a-diazacyclobut[cd]indene-6-carboxylic acid sodium salt N-methyl-N-trimethylsilyltrifluoroacetamide (300 ml; 1.6 mmol) was added to a suspension of (1aS,3aR,6bR)-1-oxo-5-(pyridin-4-ylsulphanyl)-1a,2,3,3a,4,6b-hexahydro-1H-2,6a-diazacyclobut[cd]indene-6-carboxylic acid trifluoroacetate (120 mg; 0.24 mmol; from Example 2(d)) in methylene chloride (5 ml). The suspension was stirred at room temperature for 0.5 hour, with all solid material passing into solution. This solution was treated with sodium hydrogen carbonate (28 mg; 0.33 mmol) and mesyl chloride (21 ml; 0.27 mmol), stirred for 23 hours and then poured into water (5 ml). The pH of the aqueous phase was adjusted to 7 by the addition of sodium hydrogen carbonate. The solvent was removed. The residue was dissolved in a small amount of water and chromatographed over a hydrophobic polymer (eluent: water/acetonitrile). 17 mg (17%) of a yellowish-powder were obtained.

IR (KBr): 1756, 1616, 1577, 1398, 1333, 1153 cm$^{-1}$ MS (ISN): (M–Na)$^-$380.2

(ak) (1aS,3aR,6bR)-2-Acetyl-5-carbamoylmethylsulphanyl-1-oxo-1a,2,3,3a,4,6b-hexahydro-1H-2,6a-diazacyclobut[cd]

indene-6-carboxylic acid sodium salt

Starting from (1aS,3aR,6bR)-5-carbamoylmethylsulphanyl-1-oxo-1a,2,3,3a,4,6b-hexahydro-1H-2,6a-diazacyclobut[cd]indene-6-carboxylic acid trifluoroacetate (200 mg; 0.50 mmol; from Example 2(f)) there were obtained in analogy to Example 3(aa) 22 mg (13%) of a yellowish powder.

IR (KBr): 1752, 1673, 1614, 1394 cm$^{-1}$ MS (ISP): (M−Na+2H)$^+$326.2; (M+H)$^+$348.2

(al) (1aS,3aR,6bR)-5-Carbamoylmethylsulphanyl-1-oxo-2-trifluoroacetyl-1a,2,3,3a,4,6b-hexahydro-1H-2,6a-diazacyclobut[cd]indene6-carboxylic acid sodium salt Starting from (1aS,3aR,6bR)-5-carbamoylmethylsulphanyl-1-oxo-1a,2,3,3a,4,6b-hexahydro-1H-2,6a-diazacyclobut[cd]indene-6-carboxylic acid trifluoroacetate (120 mg; 0.30 mmol; from Example 2(f)) there were isolated in analogy to Example 3(ab) 12 mg (10%) as a yellowish powder.

IR (KBr): 3425, 1759, 1688, 1605, 1396, 1178 cm$^{-1}$ MS (ISP): (M+H)$^+$402.2; (M−Na+H+NH$_4$)$^+$397.2; (M−Na+2H)$^+$380.2

(am) (1aS,3aR,6bR)-5-Carbamoylmethylsulphanyl-2-methyl-sulphonyl-1-oxo-1a,2,3,3a,4,6b-hexahydro-1H-2,6a-diazacyclobut[cd]indene-6-carboxylic-acid sodium salt Starting from (1aS,3aR,6bR)-5-carbamoylmethylsulphanyl-1-oxo-1a,2 ,3 ,3 a,4,6b-hexahydro-1H-2,6a-diazacyclobut[cd]indene-6-carboxylic acid trifluoroacetate (112 mg; 0.28 mmol; from Example 2(f)) there were obtained in analogy to Example 3(aj) 17 mg (16%) of a white powder.

IR (KBr): 3421, 1752, 1675, 1603, 1396, 1329, 1152 cm$^{-1}$ MS (ISN): (M−Na+NH$_3$)$^-$377.3 (MS artefact)

(an) (1aS,3aR,6bR)-5-[(1,4-Dimethyl-1H-1,2,4-triazol-5-ylio)methylsulphanyl]-1-oxo-2-trifluoroacetyl-1a,2,3,3a,4,6b-hexahydro-1H-2,6a-diazacyclobut[cd]indene-6-carboxylate Starting from (1aS,3aR,6bR)-5-(6-carboxy-1-oxo-1a,2,3,3a,4,6b-hexahydro-1H-2,6a-diazacyclobut[cd]indene-5-ylsulphanylmethyl)-1,4-dimethyl-1H-1,2,4-triazol-4-ium trifluoromethanesulphonate trifluoroacetate (150 mg; 0.25 mmol; from Example 2(g)) there were isolated in analogy to Example 3(ab) 48 mg (40%) as a yellowish powder.

IR (KBr): 1766, 1693, 1613, 1386, 1180 cm$^{-1}$ MS (ISP): (M+H)$^+$432.3 Microanalysis: C$_{16}$H$_{16}$N$_5$O$_4$F$_3$S.2.5 H$_2$O Calc. C 40.34 H 4.44 N 14.70 F 11.96 S 6.73 Na 0.00 Found C 40.94 H 4.53 N 14.56 F 10.60 S 6.47 Na 0.12

(ao) (1aS,3aR,6bR)-2-Acetyl-5-[(1,4-dimethyl-1H-1,2,4-triazol-5-ylio)-methylsulphanyl]-1-oxo-1a,2,3,3a,4,6b-hexahydro-1H-2,6a-diazacyclobut[cd]indene-6-carboxylate Starting from (1aS,3aR,6bR)-5-(6-carboxy-1-oxo-1a,2,3,3a,4,6b-hexahydro-1H-2,6a-diazacyclobut[cd]inden-5-ylsulphanylmethyl)-1,4-dimethyl-1H-1,2,4-triazol-4-ium trifluoromethanesulphonate trifluoroacetate (150 mg; 0.25 mmol; from Example 2(g)) there were obtained in analogy to Example 3(aa) 23 mg (24%) of a yellowish powder.

IR (KBr): 1757, 1614, 1386 cm$^{-1}$ MS (ISP): (M+H)$^+$378.3

EXAMPLE 4

(1aS,3aR,6bR)-1-Oxo-5-[5-(pyridin-1-ylioacetylamino)-1,3,4-thiadiazol-2-ylsulphanyl]-1a,2,3,3a,4,6b-hexahydro-1H-2,6a-diazacyclobut[cd]indene-6-carboxylate trifluoroacetate hydrobromide This compound was prepared in the same manner as given in Example 2(a) starting from (1aS,3aR,6bR)-1-[5-( 2,6,-bis-t-butoxycarbonyl-1-oxo-1a,2,3,3a,4,6b-hexahydro-1H-2,6a-diazacyclobut[cd]inden-5-ylsulphanyl)-1,3,4-thiadiazol-2-ylcarbamoyhnethyl]-pyridinium bromide (340 mg; 0.49 mmol). Yield: 280 mg (81%) as a beige solid.

IR (KBr): 2744, 1780, 1679, 1551, 1490, 1425, 1203 cm$^{-1}$ MS (ISP): M$^+$445.2

The above starting material was prepared as follows:
Di-t-butyl (1aS,3aR,6bR)-5-[5-(2-bromo-acetylamino)-1,3,4-thiadiazol-2-ylsulphanyl]-1-oxo-1a,2,3,3a,4,6b-hexahydro-1H-2,6-a-diazacyclobut[cd]indene-2,6-dicarboxylate Di-t-butyl (1aS,3aR,6bR)-5-(5-amino-1,3,4-thiadiazol-2-ylsulphanyl)-1-oxo-1a,2,3,3a,4,6b-hexahydro-1H-2,6a-diazacyclobut[cd]indene-2,6-dicarboxylate (400 mg; 0.804 mmol; Example 2c)) was placed in abs. methylene chloride at −20° C. and treated with pyridine (0.078 ml; 0.965 mmol) and bromoacetyl bromide (0.084 ml; 0.965 mmol). After 30 minutes at −20° C. the reaction mixture was poured into 1N aqueous hydrochloric acid (50 ml) and ice (20 g) while stirring vigorously. Subsequently, the mixture was extracted with ethyl acetate (2×100 ml). The combined organic phases were washed with saturated sodium chloride solution, dried over magnesium sulphate and concentrated. Yield: 470 mg (95%) as a yellow solid.

IR (KBr): 1771, 1700, 1660, 1544, 1246 cm$^{-1}$ MS (FAB): (M+H)$^+$604.1

(1aS,3aR,6bR)-1-[(5-(2,6-bis-t-Butoxycarbonyl-1-oxo-1a,2,3,3a,4,6b-hexahydro-1H-2,6a-diazacyclobut[cd]indene-5-ylsulphanyl)-1,3,4-thiadiazol-2-ylcarbamoylmethyl]-pyridinium bromide Di-t-butyl (1aS,3aR,6bR)-5-[5-(2-bromo-acetylamino)-1,3,4-thiadiazol-2-ylsulphanyl]-1-oxo-1a,2,3,3a,4,6b-hexahydro-1H-2,6a-diazacyclobut[cd]indene-2,6-dicarboxylate (470 mg; 0.78 mmol) was dissolved in abs. methylene chloride (5 ml) and treated with pyridine (0.14 ml; 1.74 mmol); After 5 hours at room temperature the solution was concentrated, titurated with ether and the resulting crystals were filtered off under suction. Yield: 460 mg (86%) as a beige solid. M.p.: >180° C.

IR (KBr): 1777, 1700, 1635, 1543 cm$^{-1}$ Microanalysis: C$_{27}$H$_{33}$N$_6$O$_7$S$_2$Br Calc. C 46.69 H 4.77 N 12.05 Found C 46.64 H 5.06 N 11.96

EXAMPLE 5

(1aS,3aR,6bR)-2-(4-Hydroxy-phenylcarbamoyl)-1-oxo-5-[5-(pyridin-1-ylioacetylamino)-1,3,4-thiadiazol-2-ylsulphanyl]-1a,2,3,3a,4,6b-hexahydro-1H-2,6a-diazacyclobut[cd]indene-6-carboxylic acid This compound was prepared in the same manner as given in Example 2(a) from (1aS,3aR,6bR)-1-oxo-5-[5-(pyridin-1-ylioacetylamino)-1,3,4-thiadiazol-2-ylsulphanyl]-1a,2,3,3a,4,6b-hexahydro-1H-2,6a-diazacyclobut[cd]indene-6-carboxylate trifluoroacetate hydrobromide (240 mg; 0.34 mmol; from Example 4). Yield: 74 mg (37%) as a beige solid.

IR (KBr): 3399, 1761, 1700, 1634, 1610, 1513, 1434, 1234 cm$^{-1}$ MS (EI): (M+H)$^+$580.0

EXAMPLE 6

(1aS,3aR,6bR)-2-t-Butoxycarbonyl-5-(1-methyl-1H-tetrazol-5-ylsulphanyl)-1-oxo-1a,2,3,3a,4,6b-hexahydro-1H-2,6a-diazacyclobut[cd]indene-6-carboxylic acid (1aS,3aR,6bR)-5-(1-Methyl-1H-tetrazol-5-ylsulphanyl)-1-oxo-1a,2,3,3a,4,6b-hexahydro-1H-2,6a-diazacyclobut[cd]indene-6-carboxylic acid trifluoroacetate (100 mg; 0.22 mmol; from Example 2 (a)) was dissolved in dioxan/water (2 ml) and treated with sodium bicarbonate (41 mg, 0.49 mmol) and di-t-butyl dicarbonate (0.078 ml, 0.34 mmol). After 2 hours water (2 ml) was added and the mixture was washed with methylene chloride (3×5 ml). The aqueous phase was subsequently chromatographed over a polymeric hydrophobic gel with water and lyophilized. Yield: 53 mg (56%) as a colourless powder.

IR (KBr): 1758, 1695, 1615, 1579, 1409, 1163 cm$^{-1}$ MS (ISN): [(M–Na)$^-$+NH$_3$]: 424.5 (MS artefact)

The product can be converted with trifluoroacetic acid according to Example 2(a) into (1aS,3aR,6bR)-5-(1-methyl-1H-tetrazol-5-ylsulphanyl)-1-oxo-1a,2,3,3a,4,6b-hexahydro-1H-2,6a-diazacyclobut[cd]indene-6-carboxylic acid trifluoroacetate.

EXAMPLE 7

(Z)-(1aS,3aR,6bR)-2-[(2-Amino-thiazol-4-yl)-methoxyiminoacetyl]-1-oxo-5-(1-methyl-1H-tetrazol-5-ylsulphanyl)-1a,2,3,3a,4,6b-hexahydro-1H-2,6a-diazacyclobut[cd]indene-6-carboxylic acid sodium salt t-Butyl (Z)-(1aS,3aR,6bR)-2-[(2-amino-thiazol-4-yl)metlaoxyiminoacetyl]-1-oxo-5-(1-methyl-1H-tetrazol-5-ylsulphanyl)- 1a,2,3,3a,4,6b-hexahydro-1H-2,6a-diazacyclobut[cd]indene-6-carboxylate (180 mg; 0.32 mmol) was dissolved in phenol/p-cresol 1:1 (0.7 ml) and treated with trifluoroacetic acid (0.5 ml). After 3 hours at room temperature the trifluoroacetic acid was removed under a vacuum, and abs. ether (10 ml) was added. The suspension was suction filtered, the solid was washed with ether (2×10 ml), taken up in water (2 ml) and the pH was adjusted to 6 with saturated aqueous sodium bicarbonate solution. The turbid solution obtained was chromatographed over a poylmeric hydrophobic gel with water; the pure fractions were lyophilized. Yield: 40 mg (25%) as a colourless lyophilizate.

IR (KBr): 3426, 3197, 1764, 1622, 1534, 1392, 1048 cm$^{-1}$ MS (ISN): [(M–Na)$^-$+NH$_3$]507.2 (MS artefact)

The t-butyl (Z)-(1aS,3aR,6bR)-2-[(2-amino-thiazol-4-yl)methoxyiminoacetyl]-1-oxo-5-(1-methyl-1H-tetrazol-5-ylsulphanyl)-1a,2,3,3a,4,6b-hexahydro-1H-2,6a-diazacyclobutcd]indene-6-carboxylate used as the starting material was prepared as follows:

t-Butyl (1aS,3aR,6bR)-5-(1-methyl-1H-tetrazol-5-ylsulphanyl)-1-oxo-1a,2,3,3a,4,6b-hexahydro-1H-2,6a-diazacyclobut[cd]indene-6-carboxylate trifluoroacetate Di-t-butyl (1aS,3aR,6bR)-5-(1-methyl-1H-tetrazol-5-ylsulphanyl)-1-oxo-1a,2,3,3a,4,6b-hexahydro-1H-2,6a-diazacyclobut[cd]indene-2,6-dicarboxylate (580 mg; 1.24 mmol; from Example 2(a)) was added in several portions (15 minutes) to trifluoroacetic acid (2 ml) pre-cooled at –15° C. Thereafter, the mixture was stirred at –15° C. for 2 hours and subsequently diluted with abs. ether (20 ml) and suction filtered. Yield: 510 mg (86%) as a colourless solid. M.p. 157°–159° C. (ether).

IR (KBr): 1783, 1694, 1673, 1620, 1164 cm$^-$ Microanalysis: C$_{17}$H$_{21}$N$_6$O$_5$F$_3$S Calc. C 42.68 H 4.42 N 17.57 Found C 42.61 H 4.38 N 17.54 t-Butyl (Z)-(1aS,3aR,6bR)-2-[(2-amino-thiazol-4-yl)-methoxyiminoacetyl]-1-oxo-5-(1-methyl-1H-tetrazol-5-ylsulphanyl)-1a,2,3,3a,4,6b-hexahydro-1H-2,6a-diazacyclobut[cd]indene-6-carboxylate t-Butyl (1aS,3aR,6bR)-5-(1-methyl-1H-tetrazol-5-ylsulphanyl)-1-oxo-1a,2,3,3a,4,6b-hexahydro-1H-2,6a-diazacyclobut[cd]indene-6-carboxylate trifluoroacetate (190 mg; 0.397 mmol) was dissolved in acetonitrile/water 1:1 (8 ml) and treated with S-(2-benzotriazol)-2-amino-4-thiazolethioglyoxylate (Z)-O-methyl oxime (140 mg; 0.397 mmol) in DMF (2 ml) and sodium bicarbonate (67 mg; 0.794 mmol), After 3 hours at room temperature the acetonitrile was removed under a vacuum and the suspension obtained was suction filtered, Yield: 180 mg (83%) as a Colourless solid. M.P. >200° C.

IR (KBr): 3359, 1784, 1721, 1655, 1615, 1533, 1260, 1044 cm$^{-1}$ MS (ISP): (M+H$^+$) 548.3.

EXAMPLE 8

(a) (1aS,3aR,6bR)-5-Methylsulphonyloxy-1-oxo-1a,2,3,3a,4,6b-hexahydro-1H-2,6a-diazacyclobut[cd]indene-6-carboxylic acid trifluoroacetate In analogy to Example 2(a), starting from di-t-butyl (1aS,3aR,6bR)-5-methylsulphonyloxy-1-oxo-1a,2,3,3a,4,6b-hexahydro-1H-2,6a-diazacyclobut[cd]indene-2,6-dicarboxylate (780 mg; 1.98 mmol) there were isolated 880 mg (98%) as a colourless solid.

IR (KBr): 2662, 1783, 1720, 1680, 1610, 1357 cm$^{-1}$ MS (ISN): (M–H)$^-$287.0

The di-t-butyl (1aS,3aR,6bR)-5-methylsulphonyloxy-1-oxo-1a,2,3,3a,4,6b-hexahydro-1H-2,6a-diazacyclobut[cd]indene-2,6-dicarboxylate used as the starting material is prepared as follows:

Di-t-butyl (1aS,3aR,6bR)-5-hydroxy-1-oxo-1a,2,3,3a,4,6b-hexahydro-2,6a-diazacyclobut[cd]indene-2,6-dicarboxylate (360 mg; 1 mmol; from Example 1) was placed in abs. methylene chloride (10 ml), cooled to –78° C. and treated with methanesulphochloride (0.19 ml; 1.1 mmol). After 1 hour at this temperature the reaction mixture was poured into 1N aqueous hydrochloric acid (10 ml) and extracted with ethyl acetate (3×10 ml). The combined organic phases were washed in succession with saturated aqueous sodium bicarbonate solution (10 ml) and saturated aqueous sodium chloride solution, then dried over magnesium sulphate and concentrated. The residue was triturated with n-hexane (10 ml) and filtered off under suction. Yield 340 mg (77%) as a colourless solid. M.p. 130°–133° C.

Microanalysis: C$_{19}$H$_{28}$N$_2$O$_8$S 1:0.1 C$_6$H$_{14}$ Calc. C51.97 H 6.54 N 6.18 Found C52.03 H 6.41 N 6.14

In an analogous manner there was prepared: (b) (1aS,3aR,6bR)-5-(4-Methyl-phenylsulphonyloxy)-1-oxo-1a,2,3,3a,4,6b-hexahydro-1H-2,6a-diazacyclobut[cd]indene-6-carboxylic acid trifluoroacetate Starting from di-t-butyl (1aS,3aR,6bR)-5-(4-methylphenylsulphonyloxy)-1-oxo-1a,2,3,3a,4,6b-hexahydro-1H-2,6a-diazacyclobut[cd]indene-2,6-dicarboxylate (230 mg; 0.44 mmol) there were obtained 150 mg (86%) as a beige solid.

IR (KBr): 1789, 1622, 1596, 1364, 1195 cm$^{-1}$ MS (ISP): (M+H)$^+$365.0

The di-t-butyl (1aS,3aR,6bR)-5-(4-methyl-phenylsulphonyloxy)-1-oxo-1a,2,3,3a,4,6b-hexahydro-1H-2,6a-diazacyclobut[cd]indene-2,6-dicarboxylate used as the starting material was prepared starting from di-t-butyl (1aS,3aR,6bR)-5-hydroxy-1-oxo-1a,2,3,3a,4,6b-hexahydro-2,6a-diazacyclobut[cd]indene-2,6-dicarboxylate (750 mg; 2.04 mmol; from Example 1). There were obtained 270 mg (25%) as a light yellow solid. M.p. 137°–140° C. (ether).

Microanalysis: C$_{25}$H$_{32}$N$_2$O$_8$S Calc. C 57.68 H 6.20 N 5.38 Found C 57.86 H 6.34 N 5.22

EXAMPLE 9

The following compounds were prepared in analogy to Example 3(a) starting from (1aS,3aR,6bR)-5-methylsulphonyloxy-1-oxo-1a,2,3,3a,4,6b-hexahydro-1H-2,6a-diazacyclobut[cd]indene-6-carboxylic acid trifluoroacetate (100 mg; 0.25 mmol):

(a) (1aS,3aR,6bR)-2-(4-Hydroxy-phenylcarbamoyl)-5-methylsulphonyloxy-1-oxo-1a,2,3,3a,4,6b-hexahydro-1H-2,6a-diazacyclobut[cd]indene-6-carboxylic acid sodium salt. Yield: 40 mg (36%) as a colourless powder.

IR (KBr): 3408, 3260, 1751, 1650, 1615, 1513, 1357, 1235, 1154, 833, 809 cm$^{-1}$ Microanalysis: $C_{17}H_{16}N_3O_8SNa$ Calc. C 45.85 H 3.62 N 9.43 Found C 45.62 H 3.50 N 9.50

(b) (1aS,3aR,6bR)-2-(4-Carbamoyl-phenylcarbamoyl)-5-methylsulphonyloxy-1-oxo-1a,2,3,3a,4,6b-hexahydro-1H-2,6a-diazacyclobut[cd]indene-6-carboxylic acid sodium salt. Yield: 44% as a colourless solid.

IR (KBr): 3434, 3240, 1757, 1657, 1615, 1525, 1412, 1325, 1185 cm$^{-1}$ Microanalysis: $C_{18}H_{17}N_4O_8SNa$ Calc. C 45.77 H 3.63 N 11.86 Found C 45.65 H 3.41 N 11.96

(c) (1aS,3aR,6bR)-5-Methylsulphonyloxy-2-(thien-2-ylmethylcarbamoyl)-1-oxo-1a,2,3,3a,4,6b-hexahydro-1H-2,6a-diazacyclobut[cd]indene-6-carboxylic acid sodium salt. Yield: 20% as a brown solid.

IR (KBr): 3431, 3280, 1764, 1705, 1629, 1530 cm$^{-1}$ MS (ISN): (M–Na)$^-$ 426.3

(d) (1aS,3aR,6bR)-2-(3,4-Dihydroxy-benzylcarbamoyl)-5-methylsulphonyloxy-1-oxo-1a,2,3,3a,4,6b-hexahydro-1H-2,6a-diazacyclobut[cd]indene-6-carboxylic acid sodium salt. Yield: 23% as a colourless solid.

IR (KBr): 3425, 1758, 1620, 1530, 1396, 1330, 1154 cm$^{-1}$ MS (ISN): (M–Na)$^-$ 452.2

(e) (1aS,3aR,6bR)-5-Methylsulphonyloxy-1-oxo-2-[(S)-2-oxo-pyrrolidin-3-ylcarbamoyl]-1a,2,3,3a,4,6b-hexahydro-1H-2,6a-diazacyclobut[cd]indene-6-carboxylic acid sodium salt. Yield: 12% as a colourless solid.

IR (KBr): 3412, 1762, 1702, 1622, 1538, 1395, 1352, 1153 cm$^{-1}$ MS (M–Na)$^-$ 413.1

(f) (1aS,3aR,6bR)-5-Methylsulphonyloxy-1-oxo-2-[(R) and [(S)-2-oxo-tetrahydro-thien-3-ylcarbamoyl]-1a,2,3,3a,4,6b-hexahydro-1H-2,6a-diazacyclobut[cd]indene-6-carboxylic acid sodium salt. Yield: 18% as a colourless solid.

IR (KBr): 3412, 3300, 1765, 1699, 1644, 1534, 1154 cm$^{-1}$ MS (ISN): [(M–Na)$^-$+NH$_3$] 447.3 (MS artefact)

(g) (1aS,3aR,6bR)-2-[(R)- and [(S)-1,1-Dioxo-tetrahydrothien-3-ylcarbamoyl]-5-methylsulphonyloxy-1-oxo-1a,2,3,3a,4,6b-hexahydro-1H-2,6a-diazacyclobut[cd]indene-6-carboxylic acid sodium salt. Yield: 15% as a colourless solid.

IR (KBr): 3280, 1768, 1716, 1644, 1536, 1303, 1119 cm$^{-1}$ MS (ISN): [(M–H)$^-$+NH$_3$] 465.1 (MS artefact)

(h) (1aS,3aR,6bR)-5-Methylsulphonyloxy-1-oxo-2-(4-sulphamoylbenzylcarbamoyl)-1a,2,3,3a,4,6b-hexahydro-1H-2,6a-diazacyclobut[cd]indene-6-carboxylic acid sodium salt. Yield: 13% as a colourless solid.

IR (KBr): 3350, 1762, 1644, 1323, 1300, 1160 cm$^{-1}$ MS (ISN): (M–Na)$^-$ 499.3

In analogy to Example 3(a), likewise starting from (1aS,3aR, 6bR)-5-(4-methyl-phenylsulphonyloxy)-1-oxo-1a,2,3,3a,4,6b-hexahydro-1H-2,6a-diazacyclobut[cd]indene-6-carboxylic acid trifluoroacetate, there was prepared:

(i) (1aS,3aR,6bR)-2-(4-Hydroxy-phenylcarbamoyl)-5-(4-methylphenylsulphonyloxy)-1-oxo-1a,2,3,3a,4,6b-hexahydro-1H-2,6a-diazacyclobut[cd]indene-6-carboxylic acid sodium salt. Yield: 56% as a colourless solid.

IR (KBr): 3421, 1760, 1619, 1400, 1235 cm$^{-1}$ MS (ISN): (M–Na)$^-$ 498.4

EXAMPLE 10

(a) (1aS,3aR,6bR)-2-t-Butoxycarbonyl-5-methylsulphonyloxy-1-oxo-1a,2,3,3a,4,6b-hexahydro-1H-2,6a-diazacyclobut[cd]indene6-carboxylic acid sodium salt.

(1aS,3aR,6bR)-5-Methylsulphonyloxy-1-oxo-1a,2,3,3a,4,6b-hexahydro-1H-2,6a-diazacyclobut[cd]indene-6-carboxylic acid trifluoroacetate (62 mg; 0.15 mmol); from Example 8(a)) was dissolved in dioxan/water 1:1 (2 ml) and treated with sodium bicarbonate (26 mg; 0.31 mmol) and di-t-butyl dicarbonate (0.053 ml; 0.23 mmol). After 2 hours water (2 ml) was added and the mixture was washed with methylene chloride (3×5 ml). The pH value of the aqueous phase was adjusted to 2 with 1N aqueous hydrochloric acid; subsequently the mixture was extracted with ethyl acetate (2×10 ml). The ethyl acetate phases were dried over magnesium sulphate and concentrated. The residue was dissolved in ethyl acetate (0.2 ml), treated with a 2N sodium ethylcaproate solution in ethyl acetate (0.07 ml; 0.14 mmol), diluted with ether (5 ml) and suction filtered. Yield: 43 mg (68%) as a colourless solid. M.p. 164°–172° C.

IR (KBr): 1765, 1699, 1618, 1406, 1364, 1156 cm$^{-1}$ Microanalysis: $C_{15}H_{19}N_2O_8SNa$ Calc. C 43.90 H 4.67 N 6.83 Found C 43.56 H 4.95 N 6.53

The product can be converted with trifluoroacetic acid according to Example 2(a) into (1a,3aR,6bR)-5-methylsulphonyloxy-1-oxo-1a,2,3,3a,4,6b-hexahydro-1H-2,6a-diazacyclobut[cd]indene-6-carboxylic acid trifluoroacetate.

In an analogous manner there were prepared:

(b) (1a,3aR,6bR)-2-Acetyl-5-methylsulphonyloxy-1-oxo-1a,2,3,3a,4,6b-hexahydro-1H-2,6a-diazacyclobut[cd]indene-6-carboxylic acid (1aS,3a-R,6bR)-5-Methylsulphonyloxy-1-oxo-1a,2,3,3a,4,6b-hexahydro-1H-2,6a-diazacyclobut[cd]indene-6-carboxylic acid trifluoroacetate (100 mg; 0.25 mmol; from Example 8(a)) was dissolved in ethyl acetate (1 ml) and treated at room temperature with acetic anhydride (0.12 ml). After 30 minutes the solution was concentrated and chromatographed over a polymeric hydrophobic gel with water/acetonitrile. Yield: 35 mg (43%) as a colourless powder.

IR (KBr): 2550, 1772, 1727, 1646, 1360 cm$^{-1}$ MS (ISN): (M–H+NH$_3$)$^-$ 346.2 (MS artefact)

(c) (1aS,3 aR,6bR)-2-Formyl-5-methylsulphonyloxy-1-oxo-1a,2,3,3a,4,6b-hexahydro-1H-2,6a-diazacyclobut[cd]indene-6-carboxylic acid (1aS,3aR,6bR)-5-Methylsulphonyloxy-1-oxo-1a,2,3,3a,4,6b-hexahydro-1H-2,6a-diazacyclobut[cd]indene-6-carboxylic acid trifluoroacetate (250 mg; 0.62 mmol; from Example 8(a)) was suspended in chloroform (12 ml) and acetonitrile (2 ml) and treated with pentafluorophenyl formate (395 mg; 1.86 mmol) and sodium bicarbonate (104 mg; 1.24 mmol). After 2 hours at room temperature the suspension was concentrated, triturated with ether (12 ml) and suction filtered. The beige solid obtained was dissolved in water (2 ml) and chromatographed over a polymeric hydrophobic gel with water/acetonitrile. Yield: 67 mg (32%) as a beige powder.

IR (KBr): 1761, 1658, 1618, 1395, 1354, 1153 cm$^{-1}$ MS (ISN): [(M–Na$^+$+NH$_3$] 332.2

In analogy to this, starting from (1aS,3aR,6bR)-5-(4-methylsulphonyloxy)-1-oxo-1a,2,3,3a,4,6b-hexahydro-1H-2,6a-diazacyclobut[cd]indene-6-carboxylic acid trifluoroacetate (from Example 8(b)) there was prepared:

(d) (1aS,3aR,6bR)-2-t-Butoxycarbonyl-5-(4-methyl-phenylsulphonyloxy)-1-oxo-1a,2,3,3a,4,6b-hexahydro-1H-2,6a-diazacyclobut[cd]indene-6-carboxylic acid sodium salt. Yield: 57% as a colourless solid. M.p. 153°–166° C. (dec.).

IR (KBr): 1766, 1700, 1621, 1403, 1366, 1160 cm$^{-1}$ Microanalysis: $C_{21}H_{23}N_2O_8SNa$ Calc. C 51.85 H 4.77 N 5.76 Found C 51.83 H 5.05 N 6.01

The product can be converted with trifluoroacetic acid according to Example 2(a) into (1aS,3aR,6bR)-5-(4-methylphenylsulphonyloxy)-1-oxo-1a,2,3,3a,4,6b-hexahydro-1H-2,6a-diazacyclobut[cd]indene-6-carboxylic acid trifluoroacetate.

EXAMPLE 11

(a) (1aS,3aR,6bR)-2-(3-Carbamoyl-pyridin-1-ylioacetyl)-5-methylsulphonyloxy-1a,2,3,3a,4,6b-hexahydro-1H-2,6a-diazacyclobut[cd]indene-6-carboxylate (1aS,3aR,6bR)-5-Methylsulphonyloxy-1-oxo-1a,2,3,3a,4,6b-hexahydro-1H-2,6a-diazacyclobut[cd]indene-6-carboxylic acid trifluoroacetate (500 mg; 1.24 mmol; from Example 8(a)) was suspended in abs. methylene chloride (10 ml) and treated with N-methyl-N-trimethylsilyltrifluoroacetamide (0.53 ml). After 10 minutes at room temperature the solution obtained was cooled to −20° C., treated with pyridine (0.18 ml; 2.2 mmol) and subsequently with bromoacetyl bromide (0.14 ml; 1.6 mmol). The reaction mixture was stirred at 0° C. for an additional 1 hour, diluted with water (25 ml) and extracted with ethyl acetate (3×100 ml). The combined organic phases were washed with saturated aqueous sodium chloride solution (25 ml), dried over magnesium sulphate and concentrated. The residue was triturated with n-hexane (20 ml) and filtered off under suction. There were obtained 390 mg (66%) of (1aS,3a-R,6bR)-2-bromoacetyl-5-methylsulphonyloxy-1-oxo-1a,2,3,3a,4,6a-hexahydro-1H-2,6a-diazacyclobut[cd]indene-6-carboxylic acid as a colourless solid.

IR (KBr): 2800, 1778, 1727, 1657, 1350, 1230, 1156 cm$^{-1}$ MS (ISN): M−H$^-$ 407

(1aS,3aR,6bR)-2-Bromoacetyl-5-methylsulphonyloxy-1-oxo-1a,2,3,3a,4,6a-hexahydro-1H-2,6a-diazacyclobut[cd]indene-6-carboxylic acid (300 mg; 0.73 mmol) was dissolved in DMF (12 ml) and treated with nicotinamide (180 mg; 1.47 mmol). After 20 hours at room temperature the solution was concentrated. The residue was dissolved in water (2 ml) and chromatographed over a polymeric hydrophobic gel with water. Yield: 40 mg (12%) as a colourless powder.

IR (KBr): 1764, 1669, 1616, 1506, 1394, 1347, 1153 cm$^{-1}$ MS (ISP): (M+H$^+$) 451.4

In analogy to this there was prepared:
(1aS,3aR,6bR)-5-Methylsulphonyloxy-2-(1-methyl-1H-tetrazol-5-ylsulphanylacetyl)-1-oxo-1a,2,3,3a,4,6b-hexahydro-1H-2,6a-diazacyclobut[cd]indene-6-carboxylic acid sodium salt.

Starting from (1aS,3aR,6bR)-2-bromoacetyl-5-methylsulphanyloxy-1-oxo-1a,2,3,3a,4,6b-hexahydro-1H-2,6a-diazacyclobut[cd]indene-6-carboxylic acid (200 mg; 0.49 mmol) there were obtained 42 mg (18%) as a colourless lyophilizate.

IR (KBr): 1761, 1649, 1619, 1398, 1352, 1154 cm$^{-1}$ MS (ISN): [(M−H)$^-$+NH$_3$]: 460.4 (MS artefact)

EXAMPLE 12

(a) (1aS,3aR,6bR)-5-Carboxymethyl-1-oxo-1a,2,3,3a,4,6b-hexahydro-1H-2,6a-diazacyclobut[cd]indene-6-carboxylic acid trifluoroacetate In the same manner as given in Example 2(a) there were obtained starting from (1aS,3aR,6bR)-(2,6-bis-t-butoxycarbonyl-1-oxo-1a,2,3,3a,4,6,b-hexahydro-1H-2,6a-diazacyclobut[cd]inden-5-yl)acetic acid (250 mg; 0.6 mmol) 180 mg (81%) as a colourless solid.

IR (KBr): 2700, 1778, 1711, 1197 cm$^{-1}$ MS (ISN): (M−H)$^-$ 251.2

The starting material used was prepared as follows:
Di-t-butyl (1aS,3aR,6bR)-5-benzyloxycarbonylmethyl-1-oxo-1a,2,3,3a,4,6b-hexahydro-1H-2,6a-diazacyclobut[cd]indene-2,6-dicarboxylate Di-t-butyl (1aS,3aR,6bR)-5-hydroxy-1-oxo-1a,2,3,3a,4,6b-hexahydro-2,6a-diazacyclobut[cd]indene-2,6-dicarboxylate (500 mg; 1.36 mmol; from Example 1) was placed in 1,2-dichloroethane (50 ml) and heated under reflux conditions for 48 hours with benzyloxycarboxymethylenetriphenylphosphorane (840 mg; 2.05 mmol). The reaction mixture was subsequently poured into 1N aqueous hydrochloric acid (50 ml) and ice (50 g) while stirring vigorously and extracted with ethyl acetate. The combined organic phases were washed with saturated aqueous sodium chloride solution (100 ml), dried over magnesium sulphate and concentrated. The residue was chromatographed over silica gel (50 g, 0.040–0.063 mm particle size) with ethyl acetate/n-hexane 3:7. Yield: 480 mg (71%) as a colourless solid.

IR (KBr): 1763, 1725, 1710, 1695 cm$^{-1}$ MS (ISP): (M+H)$^+$ 499.2

(1aS,3aR,6bR)-(2,6-bis-t-Butoxycarbonyl-1-oxo-1a,2,3,3a,4,6b-hexahydro-1H-2,6a-diazacyclobut[cd]inden-5-yl)-acetic acid Di-t-butyl (1aS,3aR,6bR)-5-benzyloxycarbonylmethyl-1-oxo-1a,2,3,3a,4,6b-hexahydro-1H-2,6a-diazacyclobut[cd]indene-2,6-dicarboxylate (300 mg; 0.60 mmol) was hydrogenated over 10% Pd/C (50 mg) in methanol. The suspension was subsequently filtered under suction and concentrated. Yield: 220 mg (90%) as a colourless solid.

IR (KBr): 2700, 1770, 1731, 1703 cm$^{-1}$ MS (ISN): (M−H)$^-$ 407.3

In an analogous manner there was prepared:
(b) (1aS,3aR,6bR)-5-Methoxycarbonylmethyl-1-oxo-1a,2,3,3a,4,6b-hexahydro-1H-2,6a-diazacyclobut[cd]indene-6-carboxylic acid trifluoroacetate Starting from di-t-butyl (1aS,3aR,6bR)-5-methoxycarbonylmethyl-1-oxo-1a,2,3,3a,4,6b-hexahydro-1H-2,6a-diazacyclobut[cd]indene-2,6-dicarboxylate (300 mg; 0.70 mmol) there were obtained 240 mg (91%) as a beige solid.

IR (KBr): 1779, 1732, 1678, 1640, 1202 cm$^{-1}$ MS (ISN): (M+H)$^+$ 267.3

The starting material was obtained starting from di-t-butyl (1aS,3aR,6bR)-5-hyclroxy-1-oxo-1a,2,3,3a,4,6b-hexahydro-2,6a-diazacyclobut[cd]indene-2,6-dicarboxylate (500 mg; 1.36 mmol; from Example 1). 260 mg (45%) as a colourless solid.

IR (KBr): 1765, 1735, 1704, 1638, 1252, 1164 cm$^{-1}$ MS (ISP): (M+H)$^+$ 423.4

EXAMPLE 13

(a) (1aS,3aR,6bR)-5-Carboxymethyl-2-(4-hydroxy-phenylcarbamoyl)-1-oxo-1a,2,3,3a,4,6b-hexahydro-1H-2,6a-diazacyclobut[cd]indene-6-carboxylic acid sodium salt This compound was prepared as given in Example 3(a) starting from (1aS,3aR,6bR)-5-carboxymethyl-1-oxo-1a,2,3,3a,4,6b-hexahydro-1H-2,6a-diazacyclobut[cd]indene-6-carboxylic acid trifluoroacetate (120 mg; 0.36 mmol; from Example 12(a). Yield: 45 mg (31%) as a colourless powder.

IR (KBr): 1735, 1635, 1589, 1378 cm$^{-1}$ Microanalysis: $C_{18}H_{15}N_3O_7Na$ Cal. C 52.95 H 3.70 N 10.29 Found C 53.33 H 3.73 N 10.19

In analogy to this there was prepared:
(b) (1aS,3aR,6bR)-2-(4-Hydroxy-phenylcarbamoyl)-5-methoxycarbonylmethyl-1-oxo-1a,2,3,3a,4,6b-hexahydro-1H-2,6a-diazacyclobut[cd]indene-6-carboxylic acid sodium salt In analogy to Example 3(a), starting from (1aS,3aR6bR)-5-methoxycarbonylmethyl-1-oxo-1a,2,3,3a,4,6b-hexahydro-1H-2,6a-diazacyclobut[cd]indene-6-carboxylic acid trifluoroacetate (200 mg; 0.55 mmol; from Example 12(b)) there were obtained 82 mg (35%) as a colourless powder.

IR (KBr): 1736, 1638, 1610, 1540, 1513 cm$^{-1}$ MS (ISN): (M−H)$^-$ 400.3

EXAMPLE 14

Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (5-hydroxymethyl "building block")

This compound was obtained by the following reaction sequence a)–f):

a) Mixture of benzyl (E)- and (Z)-(1S,5R)-6-(3,4-dimethoxy benzyl)-7-oxo-4-[2-oxo-3-(2-trimethylsilanyl-ethoxy)propylidene]-2,6-diazabicyclo[3.2.0]heptane-2-carboxylate Benzyl (1S,5S)-6-(3,4-dimethoxybenzyl)-4,7-dioxo-2,6-diazabicyclo[3.2.0]heptane-2-carboxylate (49 g; 119.4 mmol; from Example 1) was placed in abs. methylene chloride (250 ml) and treated dropwise (40 minutes) with 1-[2-(trimethyl-silanyl)-ethoxy]-3-triphenylphosphoranylidene-propan-2-one (51.9 g; 119.4 mmol) in abs. methylene chloride (125 ml). After 2.5 hours at room temperature the reaction mixture was poured into 1N aqueous hydrochloric acid (650 ml) and extracted with methylene chloride (2×300 ml). The combined organic phases were washed with water (3×500 ml) and saturated aqueous sodium chloride solution (500 ml), dried over magnesium sulphate and concentrated. The residue was chromatographed over silica gel (1.7 kg, 0.040–0.063 mm particle size) with ethyl acetate/n-hexane 7.3. Yield: 51.4 g (76%) as a colourless oil.

IR (film): 2840, 1763, 1711 cm$^{-1}$ MS (ISP): (M+H)$^+$ 567.5 b) t-Butyl (1S,4R,5R)-6-(3,4-dimethoxybenzyl)-7-oxo-4-[2-oxo-3-(2-trimethylsilanyl-ethoxy)-propyl]-2,6-diazabicyclo[3.2.0]heptane-2-carboxylate The above-prepared mixture of (E)- and (Z)-(1S,5R)-6-(3,4-dimethoxybenzyl)-7-oxo-4-[2-oxo-3-(2-trimethylsilanyl-ethoxy)propylidene]-2,6-diazabicyclo[3.2.0]heptane-2-carboxylate (51.4 g; 90.7 mmol) was placed in methanol (2 l), treated with di-t-butyl dicarbonate (29.7 ml; 136 mmol) and hydrogenated over Pd/C (15 g.). After 15 hours the reaction mixture was suction filtered, concentrated and chromatographed over silica gel (1 kg, 0.040–0.063 mm particle size) with ethyl acetate/n-hexane 1:1. Yield: 25.7 g (53%) as a colourless foam.

IR (film): 1760, 1699, 1591, 1517, 1160, 887, 765 cm$^{-1}$ MS (ISP): (M+H)$^+$ 535.4 Microanalysis: $C_{27}H_{42}N_2O_7Si$ Calc. C 60.65 H 7.92 N 5.24 Found C 60.48 H 8.27 N 4.91 c) t-Butyl (1S,4R,5R)-7-oxo-4-[2-oxo-3-(2-trimethylsilanylethoxy)-propyl]-2,6-diazabicyclo[3.2.0]heptane-2-carboxylate This compound was prepared in analogy to Example 1g) starting from t-butyl (1S,4R, 5R)-6-(3,4-dimethoxybenzyl)-7-oxo-4-[2-oxo-3-(2-trimethylsilanyl-ethoxy)-propyl]-2,6-diazabicyclo[3.2.0]heptane-2-carboxylate (25.7 g; 48 mmol). Yield: 12.7 g (69%) as a colourless solid. M.p. 89°–91° C. (ethyl acetate).

IR (KBr). 3294, 1784, 1729, 1696, 1514, 1250 cm$^{-1}$ Microanalysis: $C_{18}H_{32}N_2O_5Si$ Calc. C 56.22 H 8.39 N 7.28 Found C 55.93 H 8.22 N 7.00

Di-t-butyl (1aS,3aR,6bR)-5-(2-trimethylsilanl-ethoxymethyl)-1-oxo-1a,2,3,3a,4,6b-hexahydro-1H-2,6a-diazacyclobut[cd]indene-2,6-dicarboxylate t-Butyl (1S,4R,5R)-7-oxo-4-[2-oxo-3-(2-trimethylsilanylethoxy)-propyl]-2,6-diazabicyclo[3.2.0]heptane-2-carboxylate (12.7 g; 33 mmol) and methyl-diisopropylamine (7.0 ml; 39.6 mmol) were pre-cooled to −5° C. and added to a suspension of calcium carbonate (13.1 g; 131 mmol) and t-butyl-oxalyl chloride (6 ml; 39.6 mmol) in abs. methylene chloride (30 ml) while cooling with an ice bath. After 2 hours at 0° C. the suspension was diluted with ethanol-free chloroform (120 ml) and filtered over silica gel (70 g; 0.040–0.063 mm particle size). Subsequently, the column was rinsed with chloroform (120 ml). The combined organic phases were diluted with abs. toluene (900 ml), treated with triethyl phosphite (11.5 ml; 66 mmol) at room temperature and heated under reflux conditions for 15 hours. The solution obtained was concentrated. The residue was dissolved in ethyl acetate (1200 ml), washed in succession with water (600 ml) and saturated aqueous sodium chloride solution (600 ml) and dried over magnesium sulphate. After concentration the residue was chromatographed over silica gel (600 g; 0.040–0.063 mm particle size) with n-hexane/acetone 9:1. Yield: 8.7 g (55%) as a colourless solid.

IR (KBr): 1764, 1706, 1248, 836, 776 cm$^{-1}$ MS (ISP): (M+H)$^+$481.6 e) t-Butyl (1aS,3aR,6bR)-5-hydromethyl-1-oxo-1a,2,3,3a,4,6b-hexahydro-1H-2,6a-diazacyclobut[cd]indene-6-carboxylate.

Di-t-butyl (1aS,3aR,6bR)-5-(2-trimethylsilanyl-ethoxymethyl)-1-oxo-1a,2,3,3a,4,6b-hexahydro-1H-2,6-a-diazacyclobut[cd]indend-2,6-dicarboxylate (8.7 g; 18.1 mmol) was dissolved in methylene chloride (30 ml) and added dropwise while stirring vigorously to trifluoroacetic acid (80 ml) pre-cooled to −20° C. (the temperature was held at between −18° and −20° C.). After 3 hours at −20° C. the reaction mixture was concentrated at the same temperature, treated with abs. ether (670 ml) and suction filtered. Yield: 5.3 g (74%) as a beige solid.

IR (I<Br). 3426, 1773, 1710, 1670, 1180, 1077 cm$^{-1}$ MS (ISP): (M+H)$^+$ 281.2 f) Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate t-Butyl (1aS,3aR,6bR)-5-hydroxymethyl-1-oxo-1a,2,3,3a,4,6b-hexahydro-1H-2,6a-diazacyclobut[cd]indene-6-carboxylate (5.3 g; 3.4 mmol) was placed in dioxan/water 1:1 (150 ml) and treated with sodium bicarbonate (2.2 g; 26.7 mmol) and di-t-butyl dicarbonate (3.7 ml; 16 mmol) at room temperature. After 1 hour the reaction mixture was poured into saturated aqueous sodium chloride solution (150 ml), extracted with ethyl acetate (3×150 ml), dried over magnesium sulphate and concentrated. The residue was chromatographed over silica gel (150 g, 0.040–0.063 mm particle size) with ethyl acetate. Yield: 3.2 g (63%) as a colourless solid. M.p. 175° C.

IR (KBr). 1761, 1705, 1631, 1253, 1161, 1117, 1087 cm$^{-1}$ MS (ISP): (M+H)$^+$ 381.4

The 5-hydroxymethyl "building block" can also be obtained according to the following improved method (reaction sequence a1)–g1))

a1) n-Butyl (t-butyl-dimethyl-silanyloxy)-acetate n-Butyl glycolate (231 g; 1.75 mol) and imidazole (345.1 g; 5.07 mol) are placed together at 0° C. The suspension obtained was treated portionwise with t-butyldimethylchlorosilane (303 g; 2.01 mol) during 1.5 hours. After 20 hours at room temperature the reaction mixture was diluted with ether/n-hexane 1:1 (1 l) and suction filtered. The crystals were rinsed thoroughly with ether/n-hexane hexane 1:1 (200 ml). The filtrate was washed in succession with water (2×700 ml) and saturated aqueous sodium chloride solution (500 ml), dried over magnesium sulphate and concentrated. The oil obtained was distilled over a Vigreux column (7.5 cm). Yield: 405 g (94%) as a colourless oil (b.p. 78° C./0.98 mmHg).

IR (film): 1760, 1225, 1206, 1148, 838, 780 cm$^{-1}$ MS (EI): (M+H)$^+$ 247 b1) [3-(t-Butyl-dimethyl-silanyloxy)-propyl]-phosporic acid dimethyl ester

Methanephosphoric acid dimethyl ester (70 ml; 634.8 mmol) was placed in tetrahydrofuran (1.6 l) at −75° C. and treated at this temperature with 1.6M n-butyllithium in tetrahydrofuran (437 ml; 700 mmol). After 1.5 hours at −75° C. n-butyl (t-butyl-dimethylsilanyloxy)-acetate (52.1 g; 211.6 mmol) in tetrahydrofuran (110 ml) was added and the mixture was stirred at −30° C. for 2 hours. The reaction mixture was subsequently poured into ice-cold aqueous 1N hydrochloric acid (800 ml) and extracted rapidly with ethyl acetate (2×1 l). The combined organic phases were washed in succession with water (2×1 l) and saturated aqueous sodium chloride solution (500 ml), dried over magnesium sulphate and concentrated. The residue was azeotroped with toluene (2×300 ml) and distilled (b.p.: 89°–95° C.; 0.42 mmHg). Yield: 57.2 g (92%) as a colourless oil.

IR (film): 1734, 1257, 1033, 840, 780 cm$^{-1}$ MS (EI): (M+H)$^+$ 297 c1) Benzyl (Z) and (E)-(1S,5R)-4-[3-(t-butyl-dimethylsilanyloxy)-2-oxo-propylidene]-6-(2,4-dimethoxy-benzyl)-7-oxo-2,6-diazabicyclo[3.2.0]heptane-2-carboxylate

[3-(t-Butyl-dimethyl-silanyloxy)-propyl]-phosphonic acid dimethyl ester (39.4 g; 133.2 mmol) was dissolved in THF (177 ml) and cooled to 0° C. Sodium hydride (4.25 g of a 55 to 60% suspension in oil) was added portionwise such that the temperature does not rise above +5° C. After 40 minutes at 0° C. a solution, pre-cooled to −20° C., of benzyl (1S,5S)-6-(2,4-dimethoxybenzyl)-4,7-dioxo-2,6-diazabicyclo[3.2.0]heptane-2-carboxylate (European Patent Publication No. 508 234 discloses the corresponding 3,4-dimethoxybenzyl compound) in ethylene chloride (750 ml) was added in one portion. The reaction mixture was stirred at between −6° and −7° C. for 1 hour, poured into ice-cold aqueous 1N hydrochloric acid (140 ml) and extracted with ethyl acetate (2×1 l). The combined organic phases were washed with saturated aqueous sodium chloride solution (1 l), dried over magnesium sulphate and concentrated. Yield: 76 g as a yellow oil which was used in the next step without further purification.

IR (KBr): 1763, 1711, 1293, 1133, 1034, 838, 781 cm$^{-1}$ MS (ISP): (M+H)$^+$ 581.4 d1) t-Butyl (1S,4R,5R)-4-[3-(t-butyl-dimethyl-silanyloxy)-2-oxo-propyl]-6-(2,4-dimethoxy-benzyl)-7-oxo-2,6-diazabicyclo[3.2.0]heptane-2-carboxylate The above-prepared mixture of benzyl (Z) and (E)-(1S,5R)-4-[3-(t-butyl-dimethyl-silanyloxy)-2-oxo-propylidene]-6-(2,4-dimethoxybenzyl)-7-oxo-2,6-diazabicyclo[3.2.0]heptane-2-carboxylate (76 g; maximum 73.8 mmol) was dissolved in methanol (900 ml), treated with di-t-butyl dicarbonate (24.4 ml; 112 mmol) and hydrogenated over 10% Pd/C (9 g). After 1.5 hours the reaction mixture was suction filtered, concentrated and chromatographed over silica gel (400 g; 0.063–0.2 mm particle size) with ethyl acetate/n-hexane 1:4. The solid residue obtained was triturated with n-hexane (200 ml) and filtered off under suction. Yield: 17 g (42%) as a colourless powder.

IR (KBr): 1760, 1740, 1688, 1613, 1365, 1261, 1161, 1035, 840, 780 cm$^{-1}$ MS (ISP): (M+H)$^+$ 549.5 e1) t-Butyl (1S,4R,5R)-4-[3-(t-butyl-dimethyl-silanyloxy)-2-oxo-propyl]-7-oxo-2,6-diazabicyclo[3.2.0]heptane-2-carboxylate This compound was prepared in analogy to Example 1g) starting from t-butyl (1S,4R,5R)-4-[3-(t-butyl-dimethyl-silanyloxy)-2-oxo-propyl]-6-(2,4-dimethoxy-benzyl)-7-oxo-2,6-diazabicyclo[3.2.0]heptane-2-carboxylate (17 g; 31.0 mmol). The residue obtained was chromatographed over silica gel (400 g; 0.063–0.2 mm particle size) with ethyl acetate/n-hexane 7:3 and subsequently crystallized from n-hexane. Yield: 7.17 g (58%) as a colourless powder.

IR (KBr): 1772, 1740, 1700, 1257, 1164, 1107, 839, 780 cm$^{-1}$ MS (ISP): (M+H)$^+$ 399.5; (M+NH$_4$)$^+$ 416.5 f1) Di-t-Butyl (1aS,3aR,6bR)-5-(t-butyl-dimethylsilanyloxymethyl)-1-oxo-1a,2,3,3a,4,6b-hexahydro-1H-2,6a-diazacyclobut[cd]indene-2,6-dicarboxylate t-Butyl (1S,4R,5R)-4-[3-(t-butyl-dimethyl-silanyloxy)-2-oxo-propyl]-7-oxo-2,6-diazabicyclo[3.2.0]heptane-2-carboxylate (7.17 g; 18.0 mmol) and ethyldiisopropylamine (3.7 ml; 21.6 mmol) were pre-cooled to 0° C. in abs. methylene chloride (70 ml) and added to a suspension of calcium carbonate (7.1 g; 71 mmol) and t-butyl-oxalyl chloride (3.55 g; 21.6 mmol) in abs. methylene chloride (50 ml) while cooling with an ice bath. After 1.5 hours at 0° C. the reaction mixture was diluted with methylene chloride (200 ml) and washed in succession with ice-cold aqueous 1N hydrochloric acid (100 ml), ice-cold water (2×100 ml) and ice-cold saturated aqueous sodium chloride solution (100 ml), dried over magnesium sulphate and concentrated. The residue was dissolved in abs. toluene (250 ml), treated at room temperature with triethyl phosphite (6.26 ml; 36 mmol) in abs. toluene (50 ml) and heated under reflux conditions for 15 hours. The reaction mixture was taken up in ethyl acetate (100 ml) and washed in succession with water (20 ml) and saturated aqueous sodium chloride solution (2×20 ml), dried over magnesium sulphate and concentrated. The solid residue was triturated with n-hexane (200 ml) and filtered off under suction. Yield: 5.61 g (63%) as a colourless powder.

IR (KBr): 1783, 1703, 1695, 1624, 1258, 1163, 1098, 838, 778 cm$^{-1}$ MS (EI): (M-$^t$BuO.) 421 Microanalysis: C$_{25}$H$_{42}$N$_2$O$_6$Si Calc. C 60.70 H 8.56 N 5.66 Found C 60.59 H 8.76 N 5.49 g1) Di-t-butyl (1aS,3a-R,6bR)-5-hydroxymethyl-1-oxo-1a,2,3,3a,4,6b-hexahydro-1H-2,6a-diazacyclobut[cd]indene-2,6-dicarboxylate Di-t-butyl (1aS,3aR,6bR)-5-(t-butyl-dimethyl-silanyloxymethyl)-1-oxo-1a,2,3,3a,4,6b-hexahydro-1H-2,6a-diazacyclobut[cd]indene-2,6-dicarboxylate (5.61 g; 11.34 mmol) was dissolved in tetrahydrofuran (80 ml) and treated at room temperature with 1N aqueous hydrochloric acid (23 ml). After 1 hour the reaction mixture was diluted with ethyl acetate (200 ml) and washed in succession with aqueous sodium bicarbonate solution (50 ml) and saturated aqueous sodium chloride solution (50 ml), dried over magnesium sulphate and concentrated. The residue was crystallized from n-hexane. Yield: 3.93 g (91%) as a colourless powder. M.p. 184° C.

IR (KBr). 1761, 1705, 1631, 1253, 1161, 1117, 1087 cm$^{-1}$ MS (ISP): (M+H)$^+$ 381.4

EXAMPLE 15

(1aS,3aR,6bR)-5-(1-Methyl-1H-tetrazol-5-ylsulphanylmethyl)-1-oxo-1a,2,3,3a,4,6b-hexahydro-1H-2,6a-diazacyclobut[cd]indene-6-carboxylic acid trifluoroacetate This material was prepared in the same manner as given in Example 2(a) starting from di-t-butyl (1aS,3aR,6bR)-5-(1-methyl-1H-tetrazol-5-ylsulphanylmethyl)-1-oxo-1a,1,2,3,3a,4,6b-hexahydro-1H-2,6a-diazacyclobut[cd]indene-2,6-dicarboxylate (190 mg; 0.039 mmol). Yield: 150 mg (87%) as a beige solid.

IR (KBr): 1780, 1677, 1198, 1140 cm$^{-1}$ MS (ISP): (M+H)$^+$ 32.3

The starting material used was prepared as follows:

Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (260 mg; 0.67 mmol; from Example 14) was placed in abs. acetonitrile (5 ml) and treated with bis-(5-mercapto-1-methyl-1H-tetrazolyl)-dithiocarbonate (260 mg;

1 mmol) and triethylamine (0.09 ml; 0.67 mmol). After 10 minutes the reaction mixture was diluted with ethyl acetate (30 ml) and washed in succession with 1N aqueous hydrochloric acid (15 ml), saturated aqueous sodium bicarbonate solution (2×10 ml) and saturated aqueous sodium chloride solution (15 ml). The organic phase was dried over magnesium sulphate and concentrated. Yield: 300 mg (93%) as a colourless solid.

IR (KBr): 1776, 1703, 1629, 1251, 1165 cm$^{-1}$ MS (ISP): (M+H)$^+$ 479.5

EXAMPLE 16

(1aS,3aR,6bR)-5-(5-Amino-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacetate This material was prepared in the same manner as given in Example 2(a) starting from di-t-butyl (1aS,3aR,6bR)-5-(5-amino-1,3,4-thiadiazol-2-ylsulphanylmethyl)-1-oxo-1a,2,3,3a,4,6-hexahydro-1H-2,6a-diazacyclobut[cd]indene-2,6-dicarboxylate (229 mg; 0.462 mmol). Yield: 175 mg (74%) as a beige solid.

IR (KBr): 1777, 1677, 1629, 1416 cm$^{-1}$ MS (ISP): (M+H)$^+$ 340.2

The starting material used was prepared as follows:

Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (200 mg; 0.53 mmol; from Example 14) was placed in abs. methylene chloride (2 ml) at −40° C. and treated with triethylamine (0.11 ml; 0.789 mmol) and mesyl chloride (0.061 ml; 0.789 mmol). After 20 minutes the reaction mixture was added to a suspension of 2-amino-5-mercapto-1,3,4-thiadiazole (105 mg; 0.788 mmol) and sodium hydride (32 mg; 0.789 mmol) in THF (3 ml) at 0° C. After 30 minutes at this temperature the reaction mixture was diluted with ethyl acetate (20 ml) and washed with saturated aqueous sodium chloride solution. Subsequently, the organic phase was dried over magnesium sulphate, concentrated and treated with abs. ether (20 ml). The crystals obtained were filtered off under suction and the mother liquor was concentrated. Yield: 229 mg (88%) as a light yellow solid.

IR (KBr): 1776, 1705, 1620, 1250, 1164 cm$^{-1}$ MS (ISP): (M+H)$^+$ 496.4

EXAMPLE 17

(1aS,3aR,6bR)-1-Oxo-5-(pyridin-4-ylsulphanylmethyl)-1a,2,3,3a,4,6b-hexahydro-1H-2,6-a-diazacyclobut[cd]indene-6-carboxylic acid trifluoroacetate This compound was prepared in the same manner as given in Example 2(a) starting from di-t-butyl (1aS,3aR,6bR)-1-oxo-5-(pyridin-4-ylsulphanylmethyl)-1a,2,3,3a,4,6b-hexahydro-1H-2,6a-diazacyclobut[cd]indene-2,6-dicarboxylate (448 mg; 0.946 mmol). Yield: 400 mg (98%) as a beige solid.

IR (KBr): 1781, 1710, 1674, 1196 cm$^{-1}$ MS (ISN): (M−H)$^-$316.2

The starting material used was prepared as follows:

Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (360 mg; 0.95 mmol; from Example 14) was placed in abs. methylene chloride (5 ml) at −40° C. and treated with triethylamine (0.19 ml; 1.3 mmol) and mesyl chloride (0.10 ml; 1.3 mmol). After 30 minutes at this temperature the reaction mixture was diluted with abs. THF (25 ml) and treated with triethylamine (0.15 ml; 1.04 mmol) and 4-thiopyridine (160 mg; 1.4 mmol). Subsequently, the suspension was stirred at 0° C. for 2 hours and suction filtered. The mother liquor was diluted with ethyl acetate (200 ml), washed in succession with water (50 ml) and saturated aqueous sodium chloride solution (50 ml), dried over magnesium sulphate and concentrated. Yield: 440 mg (98%) as a yellow solid.

IR (KBr): 1774, 1704, 1625, 1480, 1250, 1165 cm$^{-1}$ MS (ISP): (M+H)$^+$474.4

EXAMPLE 18

(1aS,3aR,6bR)-2-(4-Hydroxy-phenylcarbamoyl)-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt This compound was prepared in the same manner as given in Example 3(a) starting from (1aS,3aR,6bR)-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid trifluoroacetate (130 mg; 0.30 mmol; from Example 15). Yield: 38 mg (28%) as a colourless solid.

IR (KBr): 1747, 1603, 1512 cm$^{-1}$ MS (ISN): (M−Na)$^-$ 456.2

In analogy to this, starting from the same starting material there were prepared:

(b) (1aS,3aR,6bR)-2-(4-Carbamoyl-phenylcarbamoyl)-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt. Yield: 17% as a colourless powder.

IR (KBr): 1747, 1661, 1603, 1524, 1411 cm$^{-1}$ MS (ISN): (M−Na)$^-$483.2

(c) (1aS,3aR,6bR)-2-[(S)-2-Oxo-pyrrolidin-3-ylcarbamoyl)-5-(1-methyl-1H-tetrazol-5-ylsulphanylmethyl)-1-oxo-1a,2,3,3a, 4,6b-hexahydro-1H-2,6a-diazacyclobut[cd]indene-6-carboxylic acid sodium salt. Yield: 26% as a colourless powder.

IR (KBr): 1746, 1696, 1631, 1602, 1536, 1391 cm$^{-1}$ MS (ISN): (M−Na)$^-$447.3

In analogy to this, starting from (1aS,3aR,6bR)-5-(5-amino-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacetate (from Example 16) there was prepared:

(d) (1aS,3aR,6bR)-5-(5-Amino-1,3,4-thiadiazol-2-ylsulphanylmethyl)-2-(4-hydroxy-phenylcarbamoyl)-1-oxo-1a,2,3,3a,4,6b-hexahydro-1H-2,6a-diazacyclobut[cd]indene-6-carboxylic acid sodium salt. Yield: 45% as a colourless powder.

IR (KBr): 1743, 1640, 1602, 1513, 1391 cm$^{-1}$ MS (ISN): (M−Na)$^-$473.2

In analogy to this, starting from (1aS,3aR,6bR)-1-oxo-5-(pyridin-4-ylsulphanylmethyl)-1a,2,3,3a,4,6b-hexahydro-1H-2,6a-diazacyclobut[cd]indene-6-carboxylic acid trifluoroacetate (from Example 17) there was prepared:

(e) (1aS,3aR,6bR)-2-(4-Carbamoyl-phenylcarbamoyl)-1-oxo-5-(pyridin-4-ylsulphanylmethyl)-1a,2,3,3a,4,6b-hexahydro-1H-2,6a-diazacyclobut[cd]indene-6-carboxylic acid. Yield: 41% as a colourless powder.

IR (KBr): 1748, 1661, 1585, 1525, 1412 cm$^{-1}$ MS (ISN): (M−H)$^-$478.2

(f) (1aS,3aR,6bR)-2-(2-t-Butoxycarbonyl-ethylcarbamoyl)-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt This compound was prepared in analogy to Example 3(a) starting from (1aS,3aR,6bR)-5-(1-methyl-tetrazol-5-yl-sulphanyl-1-oxo-1a,2,3,3a,4,6b-hexahydro-1H-2,6a-diazacyclobut[cd]indene-6-carboxylic acid trfiuoroacetate (400 mg; 0.838 mmol). Yield: 210 mg (49%) as a colourless solid.

IR (KBr): 1738, 1605, 1531, 1392 cm$^{-1}$ MS (ISN): (M–Na)$^-$492.5

By treatment with trifluoroacetic acid as in Example 2(a) there was obtained the corresponding 2-(2-carboxyethylcarbamoyl) compound.

in analogy thereto starting from the same starting material there were prepared:

(g) (1aS,3aR,6bR)-1-Oxo-5-(1-methyl-1H-tetrazol-5-ylsulphanylmethyl)-2-thiophen-2-ylmethylcarbamoyl-1a,2,3,3a,4,6b-hexahydro-1H-2,6a-diazacyclobut[cd]indene-6-carboxylic acid sodium salt Yield: 14% as a colourless solid.

IR (KBr): 1749, 1634, 1603, 1526, 1393 cm$^{-1}$ MS (ISN): (M–Na)$^-$460.4

(h) (1aS,3aR,6bR)-2-(4-Hydroxy-benzylcarbamoyl)-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt Yield: 64% as a light yellow solid.

IR (KBr): 1747, 1609, 1515, 1392 cm$^{-1}$ MS (ISN): (M–Na)$^-$470.5

In analogy thereto, starting from (1aS,3aR,6bR)-1-oxo-5-pyridin-4-ylsulphanylmethyl-1a,2,3,3a,4,6b-hexahydro-1H-2,6a-diazacyclobut[cd]indene-6-carboxylic acid trifluoroacetate there were prepared:

(i) (1aS,3aR,6bR)-2-(4-Hydroxy-benzylcarbamoyl)-1-oxo-5-(pyridin-4-ylsulphanylmethyl)-1a,2,3,3a,4,6b-hexahydro-1H-2,6a-diazacyclobut[cd]indene-6-carboxylic acid sodium salt Yield: 82% as a light yellow solid.

IR (KBr): 1746, 1609, 1582, 1538, 1482, 1392 cm$^{-1}$ MS (ISN): (M–Na)$^-$465.4

(1aS,3aR,6bR)-2-(4-Hydroxy-phenylcarbamoyl)-1-oxo-5-(pyridin-4-ylsulphanylmethyl)-1a,2,3,3a,4,6b-hexahydro-1H-2,6a-diazacyclobut[cd]indene-6-carboxylic acid sodium salt Yield: 83% as a colourless powder.

IR (KBr): 1749, 1604, 1481, 1241 cm$^{-1}$ MS (ISN): (M–Na)$^-$451.4

EXAMPLE 19

(a) (1aS,3aR,6bR)-2-Acetyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt.

(1aS,3aR,6bR)-5-(1-Methyl-1H-tetrazol-5-ylsulphanylmethyl)-1-oxo-1a,2,3,3a,4,6b-hexahydro-1H-2,6a-diazacyclobut[cd]indene-6-carboxylic acid trifluoroacetate (150 mg; 0.3 1 mmol; from Example 15) was placed in methylene chloride (5 ml) and acetonitrile (2 ml) at 0° C. and treated with acetyl chloride (0.025 ml; 0.35 mmol) and sodium bicarbonate (62 mg; 0.74 mmol). After 1 hour at 0° C. the reaction mixture was diluted with water (4 ml) and the pH value was adjusted to 7 by means of saturated aqueous sodium bicarbonate solution. The solution obtained was chromatographed over a polymeric hydrophobic gel with water and the pure fractions are lyophilized. Yield: 43 mg (38%) as a colourless lyophilizate.

IR (KBr): 1749, 1602, 1407 cm$^{-1}$ MS (ISN): (M–Na)$^-$ 363.3

In analogy to this there was prepared:

(b) (1aS,3aR,6bR)-2-Acetyl-1-oxo-5-(pyridin-4-ylsulphanylmethyl)-1a,2,3,3a,4,6b-hexahydro-1H-2,6a-diazacyclobut[cd]indene-6-carboxylic acid Starting from (1aS,3aR,6aR)-1-oxo-5-(pyridin-4-ylsulphanylmethyl)-1a,2,3,3a,4,6b-hexahydro-1H-2,6a-diazacyclobut[cd]indene-6-carboxylic acid trifluoroacetate (200 mg; 0.46 mmol; from Example 17) there was obtained 40 mg (24%) of a colourless powder.

IR (KBr): 1764, 1623, 1417 cm$^{-1}$ MS (ISN): (M–H)$^-$ 358.1

(c) (1aS,3aR,6bR)-5-(1-Methyl-1H-tetrazol-5-ylsulphanylmethyl)-1-oxo-2-trifluoracetyl-1a,2,3,3a,4,6b-hexahydro-1H-2,6a-diazacyclobut[cd]indene-6-carboxylic acid sodium salt (1aS,3aR,6bR)-5-(1-Methyl-tetrazol-5-yl-sulphanylmethyl)-1-oxo-1a,2,3,3a,4,6b-hexahydro-1H-2,6a-diazacyclobut[cd]indene-6-carboxylic acid trifluoroacetate (200 mg; 0.415 mmol) was dissolved in dimethylformamide (4 ml) and treated with trifluoroacetic acid (0.033 ml; 0.41 mmol) and dicyclohexylcarbodiimide (100 mg; 0.48 mmol). After 30 minutes the suspension obtained was suction filtered, concentrated and taken up in a small amount of water. The pH value was adjusted to 7 with saturated aqueous sodium bicarbonate solution. The solution was chromatographed over a polymeric hydrophobic gel with water/acetonitrile and lyophilized. Yield: 75 mg (44%) as a colourless powder.

IR (KBr): 1765, 1697, 1607, 1397 cm$^{-1}$ MS (ISN): (M–Na)$^-$4 17.3

(d) (1aS,3aR,6bR)-2-Cyanoacetyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt (1aS,3aR,6bR)-5-(1-Methyl-tetrazol-5-yl-sulphanylmethyl)-1-oxo-1a,2,3,3a,4,6b-hexahydro-1H-2,6a-diazacyclobut[cd]indene-6-carboxylic acid trifluoroacetate (200 mg; 0.4 15 mmol) was dissolved in dimethylformamide (2 ml) and treated with sodium bicarbonate (91 mg; 1.08 mmol) and 2,5-dioxo-pyrrolidin-1-yl 2-cyanoacetate (91 mg; 0.498 mmol). After 3 hours at room temperature the reaction mixture was concentrated. The residue obtained was taken up in a small amount of water (1 ml) and the pH value was adjusted to 7 with saturated aqueous sodium bicarbonate solution. The solution was chromatographed over a polymeric hydrophobic gel with water/acetonitrile and lyophilized. Yield: 24 mg (16%) as a colourless powder.

IR (KBr): 2260, 1753, 1665, 1605, 1395 cm$^{-1}$ MS (ISN): (M–Na)$^-$388.3

(e) (1aS,3aR,6bR)-2-Methylsulphonyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt (1aS,3aR,6bR)-5-(1-Methyl-tetrazol-5-yl-sulphanyl-1-oxo-1a,2,3,3a,4,6b-hexahydro-1H-2,6a-diazacyclobut[cd]indene-6-carboxylic acid trifluoroacetate (200 mg; 0.4 15 mmol) was suspended in methylene chloride (5 ml) and treated with N-methyl-N-trimethylsilyltrifluoroacetamide (0.2 ml; 1.08 mmol). After 5 minutes methanesulphonyl chloride (0.039 ml; 0.498 mmol) and N-ethyldiisopropylamine (0.085 ml; 0.498 mmol) were added. After 2 hours at room temperature the reaction mixture was concentrated and the residue obtained was taken up in water (1 ml). The pH value was adjusted to 7 with saturated aqueous sodium bicarbonate solution. The solution was chromatographed over a polymeric hydrophobic gel with water/acetonitrile and lyophilized. Yield: 29 mg (17%) as a colourless powder.

IR (KBr): 1763, 1607, 1388, 1337, 1154 cm$^{-1}$ MS (ISN): (M–Na)$^-$399.4

(f) (1aS,3aR,6bR)-5-(1-Methyl-1H-tetrazol-5-ylsulphanylmethyl)-1-oxo-2-trifluormethylsulphonyl-1a,2,3,3a,4,6b-hexahydro-1H-2,6a-diazacyclobut[cd]indene-6-carboxylic acid sodium salt (1aS,3aR,6bR)-5-(1-Methyl-tetrazol-5-yl-sulphanylmethyl)-1-oxo-1a,2,3,3a,4,6b-hexahydro-1H-2,6a-diazacyclobut[cd]indene-6-carbonxylic acid trifluoroacetate (200 mg; 0.415 mmol) was suspended in methylene chloride (5 ml) and treated with N-methyl-N-trimethylsilyluifluoroacetamide (0.2 ml; 1.08 mmol). After 5 minutes the reaction mixture was cooled to 0° C. and trifluoromethanesulphonic anhydride (0.102 ml; 0.6238 mmol) and N-ethyldiisopropylamine (0.107 ml; 0.623 mmol) were added. After 1 hour at this temperature the reaction mixture was concentrated and the residue obtained was taken up in water (1 ml). The pH value was adjusted to 7 with saturated aqueous sodium bicarbonate solution. The solution was chromatographed over a polymeric hydrophobic gel with water/acetonitrile and lyophilized. Yield: 17 mg (9%) as a colourless powder.

IR (KBr): 1777, 1698, 1610, 1393, 1360, 1190, 1144 cm$^{-1}$ MS (ISN): (M+H)$^+$455.4

(g) (1aS,3aR,6bR)-1-Oxo-5-(pyridin-4-ylsulphanylmethyl)-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-1-oxo-5-(pyridin-4-ylsulphanylmethyl)-1a,2,3,3a,4,6b-hexahydro-1H-2,6a-diazacyclobut[cd]indene-6-carboxylic acid trifluoroacetate (165 mg; 0.3 mmol). Yield: 54 mg (52%) as a colourless powder.

IR (KBr): 1764, 1696, 1609, 1403, 1180 cm$^{-1}$ MS (ISN): (M–Na)–412.4

(h) (1aS,3aR,6bR)-5-(5-Amino-1,3,4-thiadiazol-2-ylsulphanylmethyl)-1-oxo-2-trifluoroacetyl-1a,2,3,3a,4,6b-hexahydro-1H-2,6a-diaza-cyclobut[cd]indene-6-carboxylic acid sodium salt This compound was prepared in the same manner as given in Example 19(c) starting from (1aS,3aR,6bR)-5-(5-amino-1,3,4-thiadiazol-2-ylsulphahylmethyl)-1-oxo-1a,2,3,3a,4,6b-hexahydro-1H-2,6a-diazacyclobut[cd]indene-6-carboxylic acid trifluoroacetate (204 mg; 0.4 mmol). Yield: 21 mg (12%) as a colourless powder.

IR (KBr): 1760, 1694, 1606, 1399, 1180 cm$^{-1}$ MS (ISP): (M+H)$^+$436.3

(i) (1aS,3aR,6bR)-2-Acetyl-5-(5-amino-1,3,4-thiadiazol-2-ylsulphanylmethyl)-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-(5-amino-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacetate (180 mg; 0.35 mmol) in DMF (5 ml) at –20° C. Yield: 26 mg (19%) as a brown powder.

IR (KBr): 1750, 1605, 1404 cm$^{-1}$ MS (ISN): (M–Na)$^-$ 380.2

(j) (1aS,3aR,6bR)-2-Acetyl-5-(5-acetylamino-1,3,4-thiadiazol-2-ylsulphanylmethyl)-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-(5-amino-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacetate (204 mg; 0.4 mmol) in DMF (5 ml) at 0° C. Yield: 55 mg (31%) as a yellowish powder.

IR (KBr): 1753, 1690, 1606, 1397 cm$^{-1}$ MS (ISP): (M+H)$^+$ 424.2 (without Na); (M+H)$^+$446.2 (with Na)

(k) (1aS,3aR,6bR)-2-Formyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt (1aS,3aR,6bR)-5-(1-Methyl-1H-tetrazol-5-ylsulphanylmethyl)-1-oxo-1a,2,3,3a,4,6b-hexahydro-1H-2,6a-diazacyclobut[cd]indene-6-carboxylic acid trifluoroacetate (241 mg; 0.5 mmol) was placed in dimethylformamide (4 ml) at 0° C. and treated with concentrated formic acid (0.38 ml; 10 mmol) and dicyclohexylcarbodiimide (226 mg; 1.1 mmol). After 3 hours at 0° C. the suspension obtained was suction filtered and concentrated. The residue was taken up in water (2 ml) and the pH value was adjusted to 7 with saturated aqueous sodium bicarbonate solution. The solution was chromatographed over a polymeric hydrophobic gel with water/acetonitrile and lyophilized. Yield: 61 mg (33%) as an orange powder.

IR (KBr): 1753, 1660, 1597, 1393 cm$^{-1}$ MS (ISP): (M+H)$^+$373.3

EXAMPLE 20

(1aS,3aR,6bR)-5-(1-Methhyl-pyridin-4-yliosulphanylmethyl)-1-oxo-1a,2,3,3a,4,6b-hexahydro-1H-2,6a-diazacyclobut[cd]indene-6-carboxylate trifluoroacetate This compound was prepared in the same manner as in Example 2(a) starting from (1aS,3aR,6bR)-4-(2,6-bis-t-butoxycarbonyl-1-oxo-1a,2,3,3a,4,6b-hexahydro-1H-2,6a-diazacyclobut[cd]inden-5-ylmethylsulphanyl)-1-methyl-pyridinium iodide (355 mg; 0.59 mmol). Yield: 287 mg (100%) as a beige solid.

IR (KBr): 1779, 1681, 1633 cm$^{-1}$ MS (ISP): M$^+$332.3

The starting material was prepared as follows:

Di-t-butyl (1aS,3aR,6bR)-1-oxo-5-(pyridin-4-ylsulphanylmethyl)-1a,2,3,3a,4,6b-hexahydro-1H-2,6a-diazacyclobut[cd]indene2,6-dicarboxylate (440 mg; 0.93 mmol; from Example 17) was placed in dimethylformamide (3 ml) and treated at room temperature with methyl iodide (0.17 ml; 2.8 mmol). After 3 hours the solution was concentrated, treated with saturated, aqueous sodium chloride solution (20 ml) and extracted with methylene chloride (60 ml). Subsequently, the organic phase was dried over magnesium sulphate, concentrated, triturated with absolute ether (20 ml) and suction filtered. Yield: 355 mg (63%) as a beige-brown solid.

IR (KBr): 1775, 1702, 1633, 1163 cm$^{-1}$ MS (ISP): M$^+$488.5

EXAMPLE 21

(1aS,3aR,6bR)-2-(4-Carbamoyl-phenylcarbamoyl)-5-(1-methylpyridin-1-yliosulphanylmethyl)-1-oxo-1a,2,3,3a,4,6b-hexahydro-1H-2,6a-diazacyclobut[cd]Lndene-6-carboxylate This compound was prepared in the same manner as given in Example 3(a) from (1aS,3aR,6bR)-5-(1-methyl-pyridin-4-yliosulphanylmethyl)-1-oxo-1a,2,3,3a,4,6b-hexahydro-1H-2,6a-diazacyclobut[cd]indene-6-carboxylate trifluoroacetate (190 mg, 0.32 mmol; from Example 20). Yield: 50 mg (32%) as a light pink powder.

IR (KBr): 1752, 1661, 1633. 1600, 1524 cm$^{-1}$ Microanalysis: $C_{24}H_{23}N_5O_5S$ Calc. C 58.41 H 4.70 N 14.19 Found C 58.31 H 4.68 N 14.10

EXAMPLE 22

(1aS,3alL6bR)-1-Oxo-5-(pyridin-1-yliomethyl)-1a,2,3,3a,4,6b-hexahydro-1H-2,6a-diazacyclobut[cd]indene-6-carboxylate trifluoroacetate In analogy to Example 2(a), starting from (1aS,3aR,6bR)-1-(2,6-bis-t-butoxycarbonyl-1-oxo-1a,2,3,3a,4,6b-hexahydro-1H-2,6a-diazacyclobut[cd]indene-5-ylmethyl)pyridinium chloride (680 mg; 1.42 mmol) thee were obtained 640 mg (98%) as a colourless solid.

IR (KBr): 2700, 1783, 1719, 1681, 1487 cm$^{-1}$ MS (ISP): M$^+$286.3

The starting material was prepared as follows:

Di-t-butyl (1aS,3aR,6bR)-5-hydroxymethyl-1-oxo-1a,2, 3,3a,4,6b-hexahydro-1H-2,6a-diazacyclobut[cd]indene-2,6-dicarboxylate (900 mg; 2.73 mmol; from Example 14) was dissolved in pyridine (5 ml) at 0° C. and treated with mesyl chloride (0.25 ml; 3.15 mmol). After 16 hours at room temperature the reaction mixture was concentrated. The residue was dissolved in methylene chloride (50 ml) and washed with saturated aqueous sodium chloride solution (3×25 ml). Subsequently, the organic phase was dried over magnesium sulphate and concentrated. The residue was triturated With ether (2×50 ml) and filtered off under suction. Yield: 950 mg (84%) as a colourless solid. M.p. 124° C. (dec.).

IR (KBr): 1780, 1703, 1630, 1250, 1161 cm$^{-1}$ MS (ISP): M$^+$442.5

EXAMPLE 23

(a) (1aS,3aR,6bR)-2-(4-Hydroxy-phenylcarbamoyl)-1-oxo-5-(pyridin-1-yliomethyl)-1a,2,3,3a,4,6b-hexahydro-1H-2, 6a-diazacyclobut[cd]indene-6-carboxylate This compound was prepared in the same manner as given in Example 3(a) starting from (1aS,3aR,6bR)-1-oxo-5-(pyridin-1-yliomethyl)-1a,2,3,3a,4,6b-hexahydro-1H-2,6a-diazacyclobut[cd]indene-6-carboxylate trifluoroacetate (200 mg; 0.44 mmol; from Example 22). Yield: 79 mg (41%) as a colourless powder.

IR (KBr): 3415, 3259, 1758, 1650, 1611, 1530, 1513, 1385 cm$^{-1}$ Microanalysis: $C_{22}H_{20}N_4O_5$ Calc. C 62.85 H 4.80 N 13.33 Found C 62.79 H 4.68 N 13.08

In analogy to this, starting from (1aS,3aR,6bR)-1-oxo-5-(pyridin-1-yliomethyl)-1a,2,3,3a,4,6b-hexahydro-1H-2,6a-diazacyclobut[cd]indene-6-carboxylate trifluoroacetate there were prepared:

(b) (1aS,3aR,6bR)-2-(3-Hydroxy-isoxazol-5-ylmethylcarbamoyl)-1-oxo-5-(pyridin-1-yliomethyl)-1a,2,3,3a,4,6b-hexahydro-1H-2,6a-diazacyclobut[cd]indene-6-carboxylate. Yield: 29% as a colourless powder.

IR (KBr): 1762, 1705, 1629, 1531, 1391 cm$^{-1}$ Microanalysis: $C_{20}H_{19}N_5O_6$ Calc. C 56.47 H 4.50 N 16.46 Found C 56.51 H 4.30 N 16.35

(c) (1aS,3aR,6bR)-2-(4-Carbamoyl-phenylcarbamoyl)-1-oxo-5-(pyridin-1-yliomethyl)-1a,2,3,3a,4,6b-hexahydro-1H-2,6a-diazacyclobut[cd]indene-6-carboxylate. Yield: 43% as a colourless powder.

IR (KBr): 3420, 1758, 1662, 1524, 1384 cm$^{-1}$ Microanalysis: $C_{23}H_{21}N_5O_5$ Calc. C 61.74 H 4.73 N 15.65 Found C 61.67 H 4.53 N 15.39

(d) (1a,3aR,6bR)-2-Acetyl-1-oxo-5-(pyridin-1-yliomethyl)-1a,2,3,3a,4,6b-hexahydro-1H-2,6a-diazacyclobut[cd]indene-6-carboxylate This compound was prepared in the same manner as given in Example 19 starting from (1aS,3aR,6bR)-1-oxo-5-(pyridin-1-yliomethyl)-1a,2,3,3a,4,6b-hexahydro-1H-2,6a-diazacyclobut[cd]indene-6-carboxylate trifluoroacetate (200 mg; 0.43 mmol; from Example 22) Yield: 80 mg (57%) as a yellow powder.

IR (KBr): 1770, 1680, 1424 cm$^{-1}$ MS (ISP): (M+H)$^+$ 328.2

(e) (1aS,3aR,6bR)-1-Oxo-5-(pyridin-1-yliomethyl)-2-trifluoroacetyl-1a,2,3,3a,4,6b-hexahydro-1H-2,6a-diazacyclobut[cd]indene-6-carboxylate (1aS,3aR,6bR)-1-Oxo-5-(pyridin-1-yliomethyl)-1a,2,3, 3a,4,6b-hexahydro-1H-2,6a-diazacyclobut[cd]indene-6-carboxylate trifluoroacetate (188 mg; 0.41 mmol) was placed in methylene chloride (8 ml) at 0° C. and treated with N-methyl-N-trimethylsilyltrifluoroacetamide (91 ml; 0.49 mmol) and dicyclohexylcarbodiimide (103 mg; 0.49 mmol). After 2 hours at room temperature the reaction mixture was concentrated, dissolved in water (1 ml), the pH value was adjusted to 7 with saturated aqueous sodium bicarbonate solution and the mixture was chromatographed over a polymeric hydrophobic gel with water/acetonitrile and lyophilized. Yield: 52 mg (34%) as a yellow powder.

IR (KBr): 1770, 1615, 1390, 1336, 1155 cm$^{-1}$ MS (ISP): [M+H$^+$+H$_2$O]$^+$382.3 (MS artefact)

(1aS,3aR,6bR)-2-(2-t-Butoxycarbonyl-ethylcarbamoyl)-1-oxo-5-(pyridin-1-yliomethyl)-1a,2,3,3a,4,6b-hexahydro-1H-2,6a-diazacyclobut[cd]indene-6-carboxylate This compound was prepared in analogy to Example 3(a) starting from (1aS,3aR,6bR)-1-oxo-5-(pyridin-1-yliomethyl)-1a,2,3,3a,4,6b-hexahydro-1H-2,6a-diazacyclobut[cd] indene-6-carboxylate trifluoroacetate (350 mg; 0.702 mmol; from Example 22). Yield: 154 mg (48%) as an orange powder.

IR (KBr): 1762, 1722, 1632, 1536, 1392, 1216 cm$^{-1}$ MS (ISP): (M+H)$^+$457.4

(g) (1aS,3aR,6bR)-2-Benzyloxycarbonylmethylcarbamoyl-1-oxo-5-(pyridin-1-yliomethyl)-1a,2,3,3a,4,6b-hexahydro-1H-2,6a-diazacyclobut[cd]indene-6-carboxylate.

This compound was prepared in analogy to Example 3(a) starting from (1aS,3aR,6bR)-1-oxo-5-(pyridin-1-yliomethyl)-1a,2,3,3a,4,6b-hexahydro-1H-2,6a-diazacyclobut[cd] indene-6-carboxylate trifluoroacetate (300 mg; 0.602 mmol; from Example 22). Yield: 54 mg (19%) as a brown powder.

IR (KBr): 1758, 1614, 1536, 1390 cm$^{-1}$ MS (ISP): (M+H)$^+$477.4

EXAMPLE 24

(1aS,3aR,6bR)-5-Acetoxymethyl-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-acetoxymethyl-1-oxo-1a,2,3,3a,4,6b-hexahydro-1H-2,6a-diazacyclobut[cd]indene-6-carboxylate (570 mg; 1.35 mmol). Yield: 400 mg (83%) as a beige solid.

IR (KBr): 1784, 1739, 1674, 1234, 1198 cm$^{-1}$ MS (ISN): (M–H)$^-$ 265.2

The starting material was prepared as follows:

Di-t-butyl (1aS,3aR,6bR)-5-hydroxymethyl-1-oxo-1a,2, 3,3a,4,6b-hexahydro-1H-2,6a-diazacyclobut[cd]indene-2,6-dicarboxylate (440 mg; 1.08 mmol; from Example 14) was placed in abs. methylene chloride (8 ml) at 0° C. and treated with pyridine (0.12 ml; 1.4 mmol) and acetyl chloride (0.09 ml; 1.3 mmol). After 2 hours at 0° C. the reaction mixture was diluted with ethyl acetate (40 ml), washed in succession with water (40 ml) and saturated aqueous sodium chloride solution (40 ml), dried over magnesium sulphate and concentrated. Yield: 450 mg (99%) as a colourless powder.

IR (KBr): 1775, 1742, 1705, 1636, 1239, 1162 cm$^{-1}$ MS (ISP): (M+H)$^+$423.6

EXAMPLE 25 a) ((1aS,3aR,6bR)-5-Acetoxymethyl-2-(4-hydroxy-phenylcarbamoyl)-1-oxo-1a,2,3,3a,4,6b-hexahydro-1H-2,6a-diazacyclobut[cd]indene-6-carboxylic acid sodium salt.

This compound was prepared in the same manner as given in Example 3(a) starting from (1aS,3aR,6bR)-5-acetoxymethyl-1-oxo-1a,2,3,3a,4,6b-hexahydro-1H-2,6a-diazacyclobut[cd]indene-6-carboxylic acid trifluoroacetate (390 mg; 1.09 mmol; from Example 24). Yield: 160 mg (35%) as a colourless powder.

IR (KBr): 1750, 1739, 1638, 1610, 1513, 1382, 1238 cm$^{-1}$ MS (ISN): M$^-$400.2

(b) (1aS,3aR,6bR)-5-Acetoxymethyl-2-benzyloxycarbonyl-methylcarbamoyl-1-oxo-1a,2,3,3a,4,6b-hexahydxo-1H-2,6a-diazacyclobut[cd]indene-6-carboxylic acid sodium salt This compound was prepared in analogy to Example 3(a) starting from (1aS,3aR,6bR)-5-acetoxymethyl-1-oxo-1a,2,3,3a,4,6b-hexahydro-1H-2,6a-diazacyclobut[cd]indene-6-carboxylic acid trifluoroacetate (317 mg; 0.86 mmol). Yield: 167 mg (41%) as a colourless powder.

IR (KBr): 1742, 1609, 1532, 1398, 1243 cm$^{-1}$ MS (ISN): (M–Na)$^-$456.4

(c) (1aS,3aR,6bR)-5-Acetoxymethyl-2-acetyl-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-acetoxymethyl-1-oxo-1a,2,3,3a,4,6b-hexahydro-1H-2,6a-diazacyclobut[cd]indene-6-carboxylic acid trifluoroacetate (148 mg; 0.4 mmol) in dimethylformamide (5 ml). Yield: 106 mg (80%) as a yellow powder.

IR (KBr): 1747, 1610, 1411, 1241 cm$^{-1}$ MS (ISN): (M+H)$^+$331.3

(d) (1aS,3aR,6bR)-5-Acetoxymethyl-2-trifluoroacetyl-1-oxo-1a,2,3,3a,4,6b-hexahydro-1H-2,6a-diazacyclobut[cd]indene-6-carboxylic acid sodium salt This compound was prepared in analogy to Example 19(c) starting from 1aS,3aR,6bR)-5-acetoxymethyl-1-oxo-1a,2,3,3a,4,6b-hexahydro-1H-2,6a-diazacyclobut[cd]indene-6-carboxylic acid trifluoroacetate (148 mg; 0.4 mmol). Yield: 44 mg (29%) as a colourless powder.

IR (KBr): 1756, 1699, 1611, 1409, 1168 cm$^{-1}$ MS (ISN): (M–Na)$^-$361.3

EXAMPLE 26

(1aS,3aR,6bR)-5-Carbamoyloxymethyl-1-oxo-1a,2,3,3a,4,6b-hexahydro-1H-2,6a-diazacyclobut[cd]indene-6-carboxylic acid trifluoroacetate This compound was prepared in the same manner as in Example 2(a) starting from (1aS,3aR,6bR)-5-carbamoyloxymethyl-1-oxo-1a,2,3,3a,4,6b-hexahydro-1H-2,6a-diazacyclobut[cd]indene-2.6-dicarboxylate (1,42 mg; 3.36 mmol). Yield: 1.25 g (98%) as a colourless powder.

IR (KBr): 1775, 1678, 1620, 1200 cm$^{-1}$ MS (ISN): (M–H)$^-$266.2

The starting material was prepared as follows:
Di-t-butyl (1aS,3aR,6bR)-5-(2-chloroacetylaminocarbonyloxymethyl)-1-oxo-1a,2,3,3a,4,6b-hexahydro-1H-2,6a-diazacyclobutcd]indene-2,6-dicarboxylate Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (1.9 g; 5.0 mmol; from Example 14) was placed in abs. methylene chloride (25 ml) at 0° C. and treated with chloroacetyl isocyanate (900 mg; 7.5 mmol) abs. methylene chloride (7 ml). After 1 hour the reaction mixture was concentrated, triturated with n-hexane (25 ml) and filtered off under suction. Yield: 2.5 g (100%) as a yellow powder. M.p. 124°–126° C.

IR (KBr): 1776, 1707 cm$^{-1}$ MS (ISP): (M+H)$^+$500.4

Di-t-butyl (1aS,3aR, 6bR)-5-carbamoyloxymethyl-1-oxo1a,2,3,3a,4,6b-hexahydro-1H-2,6a-diazacyclobut[cd]indene-2,6-dicarboxylate Di-t-butyl (1aS,3aR,6bR)-5-(2-chloroacetylaminocarbonyloxymethyl)-1-oxo-1a,2,3,3a,4,6b-hexahydro-1H-2,6a-diazacyclobut[cd]indene-2,6-dicarboxylate (2.0 g; 4 mmol) was dissolved in THF (20 ml) and methanol (8.5 ml) and treated with sodium bicarbonate (670 mg; 8 mmol) in water (8.5 ml). After 18 hours at room temperature the organic solvents were evaporated, the residue was treated with saturated aqueous sodium chloride solution (25 ml) and extracted with ethyl acetate (2×100 ml). The combined organic phases were washed with saturated aqueous sodium chloride solution (2×25 ml), dried over magnesium sulphate and concentrated. The resinous residue obtained was triturated with n-hexane (20 ml) for 2 hours and filtered off under suction. Yield: 1.47 g (87%) as a colourless powder. M.p. 128°–133° C.

Microanalysis: $C_{20}H_{29}N_{23}O_7$ Calc. C 56.73 H 6.90 N 9.92 Found C 56.67 H 6.92 N 9.63

The di-t-butyl (1aS,3aR,6bR)-5-carbamoyloxymethyl-1-oxo-1a,2,3,3a,4,6b-hexahydro-1H-2,6a-diazacyclobut[cd]indene-2,6-dicarboxylate was also prepared in analogy to Example 89 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (3.93 g; 10.33 mmol) and ammonium chloride (1.1 g; 20.6 mmol). Yield 3.84 g (90%) as a colourless powder.

EXAMPLE 27

(a) (1aS,3aR,6bR)-5-Carbamoyloxymerhyl-2-(4-hydroxyphenylcarbamoyl)-1-oxo-1a,2,3,3a,4,6b-hexahydro-1H-2,6a-diazacyclobut[cd]indene-6-carboxylic acid sodium salt This compound was prepared in the same manner as given in Example 3(a) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trffluoroacetate (310 mg; 0.83 mmol; from Example 26). Yield: 215 mg (61%) as a colourless powder.

IR (KBr): 3407, 1758, 1718, 1643, 1610 cm$^{-1}$ MS (ISN): (M–Na)$^-$401.4

In an analogous manner there was prepared:
(b) (1aS,3aR,6bR)-5-Carbamoyloxymethyl-2-(4-carbamoylphenylcarbamoyl)-1-oxo-1a,2,3,3a,4,6b-hexahydro-1H-2,6a-diazacyclobut[cd]indene-6-carboxylic acid sodium salt. Yield: 46% as a colourless powder.

IR (KBr): 3371, 1751, 1713, 1658, 1607, 1525 cm$^{-1}$ MS (ISN): (M–Na)$^-$428.3

(c) (1aS,3aR,6bR)-2-Benzylcarbamoyl-5-carbamoyloxymethyl-1-oxo-1a,2,3,3a,4,6b-hexahydro-1H-2,6a-diazacyclobut[cd]indene-6-carboxylic acid sodium salt This compound was prepared in analogy to Example 3(a) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trifluoroacetate (372 mg; 1.00 mmol). Yield: 83 mg (20%) as a yellow solid.

IR (KBr): 1741, 1608, 1399 cm$^{-1}$ MS (ISN): (M–Na)$^-$ 399.3

In an analogous manner there were prepared:
(d) (1aS,3aR,6bR)-5-Carbamoyloxymethyl-2-cyclopropylcarbamoyl-1-oxo-1a,2,3,3a,4,6b-hexahydro-1H-2,6a-diazacyclobut[cd]indene-6-carboxylic acid sodium salt Yield: 65% as a colourless powder.

IR (KBr): 1747, 1609, 1529, 1400, 1249 cm$^{-1}$ MS (ISN): (M–Na)$^-$ 349.3

(e) (1aS,3aR,6bR)-5-Carbamoyloxymethyl-2-(4-sulphamoylbenzylcarbamoyl)-1-oxo-1a,2,3,3a,4,6b-hexahydro-1H-2,6a-diazacyclobut[cd]indene-6-carboxylic acid sodium salt Yield: 57% as a colourless powder.

IR (KBr): 1746, 1607, 1534, 1398, 1318, 1160 cm$^{-1}$ MS (ISN): (M–Na)$^-$ 478.4.

(f) (1aS,3aR,6bR)-5-Carbamoyloxymethyl-2-(thiophen-2-ylmethylcarbamoyl)-1-oxo-1a,2,3,3a,4,6b-hexahydro-1H-2, 6a-diaza-cyclobut[cd]indene-6-carboxylic acid sodium salt Yield: 53% as a colourless powder.

IR (KBr): 1741, 1609, 1526, 1400, 1246 cm$^{-1}$ MS (ISN): (M–Na)$^-$ 405.4

(g) (1aS,3aR,6bR)-5-Carbamoyloxymethyl-1-oxo-2-(2-thiophen-2-yl-ethylcarbamoyl)-1a,2,3,3a,4,6b-hexahydzo-1H-2,6a-diazacybut[cd]indene-6-carboxylic acid sodium salt Yield: 64% as a colourless powder.

IR (KBr): 1744, 1710, 1608, 1533, 1400 cm$^{-1}$ MS (ISN): (M–Na)$^-$ 419.2

(h) (1aS,3aR,6bR)-5-Carbamoyloxymethyl-2-(4-hydroxybenzylcarbamoyl)-1-oxo-1a,2,3,3a,4,6b-hexahydro-1H-2,6a-diaza-cyclobut[cd]indene-6-carboxylic acid sodium salt Yield: 57% as a colourless powder.

IR (KBr): 1745, 1612, 1514, 1398 cm$^{-1}$ MS (ISN): (M–Na)$^-$ 415.4

EXAMPLE 28

Diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (5-hydroxymethyl "building block")

This compound was obtained by the following reaction sequence a)–h):

a) 1:1 Mixture of (1S,4S,5S)-[2-benzyloxycarbonyl-7-oxo-4-[(R)- and (S)-tetrahydropyran-2-yloxy]-2,6-diazabicyclo[3.2.0]heptan-6-yl]-acetic acid sodium salt (1:1)

(1S,4S,5S)-2-Benzyloxycarbonyl-4-[(R)- and (S)-tetrahydropyran-2-yloxy]-2,6-diazabicyclo[3.2.0]heptane-7-one (1:1 mixture; 62.46 g; 0.18 mol; European Patent Publication 508 234, Example 14) in THF (tetrahydrofuran; 1l) was treated at –78° C. while stirring with a bistrimethylsilyllithium amide solution (396 ml, 1M in THF). Bromoacetic acid (27.56 g, 0.198 mol) in THF (100 ml) was added dropwise and the reaction mixture was stirred at 0° C. for a further two days. The reaction mixture was diluted at –10° C. with ethyl acetate and water. The organic phase was washed with water and the combined aqueous phases were treated with charcoal and filtered. The pH of the solution was adjusted to 3.5° at 0° C. and the solution was extracted with ethyl acetate. The organic solution was washed with a saturated aqueous sodium chloride solution, dried over magnesium sulphate, filtered and concentrated. 65.12 g (89%) of a colourless oil are obtained. A portion of this (0.5 g) was treated with sodium bicarbonate (105 mg) and chromatographed over a hydrophobic polymer (eluent: water). 160 mg of a white powder were obtained.

MS (ISN): 403.5 (M–Na) Microanalysis: $C_{20}H_{23}N_2O_7Na$ Calc. C 56.34 H 5.44 N 6.57 Found C 55.89 H 5.35 N 6.43 b) 1:1 Mixture of (1S,4S,5S)-[7-oxo-4-[(R)- and (S)-tetrahydropyran-2-yloxy]-2,6-diazabicyclo[3.2.0]heptan-6-yl]-acetic acid A solution of (1S,4S,5S)-[2-benzyloxycarbonyl-7-oxo-4-[(R)- and (S)-tetrahydropyran-2-yloxy]-2,6-diazabicyclo[3.2.0]heptan-6-yl]-acetic acid (61.9 g, 0.153 mol) in ethanol (1l) was hydrogenated over palladium-charcoal. The catalyst was filtered off under suction and the solution was concentrated. 43 g of a colourless oil were obtained. A portion of this (0.5 g) was chromatographed over a hydrophobic polymer (eluent: water). 131 mg of a white powder were obtained.

MS (ISN): 269.3 (M–H) Microanalysis: $C_{12}H_{18}N_2O_5$ Calc. C 53.33 H 6.71 N 10.36 Found C 53.39 H 6.53 N 10.45 c) 1:1 Mixture of (1S,4S,5S)-[2-allyloxycarbonyl-7-oxo-4-[(R)- and (S)-tetrahyclropyran-2-yloxy]-2,6-diazabicyclo[3.2.0]heptan-6-yl]-acetic acid sodium salt A solution of (1S,4S,5S)-[7-Oxo-4-[(R)- and (S)-tetrahydropyran-2-yloxy]-2,6-diazabicyclo[3.2.0]heptan-6-yl]-acetic acid (43 g; 0.153 mol) in water (400 ml) is adjusted to pH7.5 with 2N NaOH at 0° C. The solution was treated with allyl chloroformate (22.13 g, 0.183 mol) and stirred at 0° C. for two hours. The solution was treated with charcoal and filtered. The filtrate was adjusted to pH3. The solution was extracted with ethyl acetate, dried and concentrated. 54 g (100%) of a colourless oil were obtained. A portion of this (400 mg) was treated with sodium bicarbonate (126 mg) and chromatographed over a hydrophobic polymer (eluent: water). 264 mg of a white powder were obtained.

MS (ISN): 353.4 (M–Na) Microanalysis: $C_{12}H_{18}N_2O_5$ Calc. C 51.06 H 5.62 N 7.44 Found C 50.73 H 5.90 N 7.42 d) 1:1 Mixture of allyl (1S,4S,5S)-6-allyloxycarbonylmethyl-7-oxo-4-[(R)- and (S)-tetrahydropyran-2-yloxy]-2,6-diazabicyclo[3.2.0]heptan-2-carboxylate A solution of (1S,4S,5S)-[2-allyloxycarbonyl-7-oxo-4-[(R)- and (S)-tetrahydropyran-2-yloxy]-2,6a-diazabicyclo[3.2.0]heptan-6-yl]-acetic acid (54 g; 0.153 mol) in acetone (1 l) was treated with triethylamine (23.4 ml; 0.168 mol) and allyl bromide (28.47 ml; 0.336 mol). The solution was stirred for 24 hours and subsequently concentrated. The residue was dissolved in ethyl acetate, washed with water and saturated sodium chloride solution, dried over magnesium sulphate and concentrated. The residue was chromatographed over silica gel (eluent ethyl acetate/n-hexane 1:1). 43.4 g (72%) of a colourless oil were obtained.

IR (film) 1773, 1740, 1707 cm$^{-1}$ Microanalysis: $C_{19}H_{26}N_2O_7$ Calc. C 57.86 H 6.64 N 7.10 Found C 57.91 H 6.64 N 6.93 e) 1:1:1:1 Mixture of allyl (1S,4S,5S)-6-[(R)- and (S)-1-allyloxycarbonyl-3-(t-butyl-dimethyl-silanyloxy)-2-oxo-propyl]-7-oxo-4-[(R)- and (S)-tetrahydropyran-2-yloxy]-2,6-diazabicyclo[3.2.0]heptane-2-carboxylate A solution of allyl (1S,4S,5S)-6-allyloxycarbonylmethyl-7-oxo-4-[(R)- and (S)-tetrahydropyran-2-yloxy]-2,6-diazabicyclo[3.2.0]heptane-2-carboxylate (49.6 g, 0.125 mol) in THF (500 ml) was placed at –78° C. and treated in succession with bis-trimethylsilyllithium amide (1M in THF, 0.257 mol) and t-butyl-dimethylsilyloxyacetyl chloride (28.7 g, 0.137 mol). After 30 minutes aqueous 1N hydrochloric acid (130 ml) and a saturated sodium chloride solution (130 ml) were added dropwise. The reaction mixture was diluted with ethyl acetate, dried, concentrated and chromatographed over silica gel (eluent ethyl acetate/n-hexane 3.5/6.5). 64 g (90%) of a yellowish oil were obtained.

IR (film) 1779, 1743, 1712 cm$^{-1}$ Microanalysis: $C_{27}H_{42}N_2O_9$ Calc. C 57.22 H 7.47 N 4.94 Found C 57.49 H 7.67 N 4.94 f) 1:1 Mixture of allyl (1S,4S,5S)-6-[(R)- and (S)-1-allyloxycarbonyl-3-(t-butyl-dimethyl-silanyloxy)-2-oxo-propyl]-4-hydroxy-7-oxo-2,6-diazabicyclo [3.2.0]heptane-2-carboxylate A solution of (1S,4S,5S)-6-[(R)- and (S)-1-allyloxycarbonyl-3-(t-butyl-dimethyl-silanyloxy)-2-oxo-propyl]-7-oxo-4-[(R)- and (S)-tetrahydropyran-2-yloxy]-2,6-diazabicyclo[3.2.0]heptane-2-carboxylate (62.12 g; 109 mmol) in ether (1 l) was treated with finely ground magnesium bromide etherate (83 g; 328 mmol). After 45 minutes the suspension was treated dropwise with water (1l). The organic phase was washed with water and saturated aqueous sodium chloride solution, dried and concentrated. The residue was chromatographed over silica gel (eluent ethyl acetate/n-hexane 1:1). 38.8 g (73%) of a yellowish oil were obtained.

IR (film): 3434, 1776, 1746, 1709 cm$^{-1}$ Microanalysis: $C_{22}H_{34}N_2O_8Si$ Calc. C 54.75 H 7.10 N 5.80 Found C 54.95 H 7.22 N 5.49 g) Diallyl (1aS,3aR,6bS)-5-(t-butyl-dimethyl-silanyloxymethyl)-1-oxo-1,1a,2,3,3a,6b-hexahydro-4-oxa-2,6a-diazacyclobut[cd]indene-2,6-dicarboxylate A solution of allyl (1S,4S,5S)-6-[(R)- and (S)-1-allyloxycarbonyl-3-(t-butyl-dimethyl-silanyloxy)-2-oxo-propyl]-4-hydroxy-7-oxo-2,6-diazabicyclo[3.2.0]heptane-2-carboxylate (38.7 g; 80 mmol) in THF (500 ml) was treated in succession while stirring at −25° C. with triphenylphospine (31.47 g, 0.12 mol) and a solution of diethyl azodicarboxylate(19.5 g, 0.112 mol) in THF (20 ml). The reaction mixture was stirred at room temperature for 5 hours. The solvent was evaporated and the residue was dissolved in ethyl acetate and treated with saturated aqueous ammonium chloride solution. The organic phase was washed with water and dried over magnesium sulphate and concentrated. The residue was taken up in ether/n-hexane (1:1; 500 ml) and the crystals obtained were filtered off under suction. The mother liquor was concentrated and chromatographed over silica gel (eluent ethyl acetate/n-hexane 3:7). 24.4 g (65.5%) of a yellowish oil were obtained.

IR (film): 1788, 1716, 1619 cm$^{-1}$ Microanalysis: $C_{22}H_{32}N_2O_7Si$ Calc. C 56.88 H 6.94 N 6.03 Found C 56.92 H 7.11 N 6.05 h) Diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate A solution of diallyl (1aS,3aR,6bS)-5-(t-butyl-dimethylsilanyloxymethyl)-1-oxo-1,1a,2,3,3a,6b-hexahydro-4-oxa-2,6a-diazacyclobut[cd]indene- 2,6-dicarboxylate (24.3 g; 52.3 mmol) in ethanol (200 ml) and water (1 ml) was treated with pyridinium (toluene-4-sulphonate) (6.6 g; 26 mmol) and heated to 50° C. for 4 hours. The solvent was evaporated, the residue was taken up in ethyl acetate and washed with water and saturated aqueous sodium chloride solution, dried and concentrated. The residue was chromatographed on silica gel (eluent ethyl acetate/n-hexane 7:3). 13.43 g (73.3%) of a yellowish oil were obtained.

IR (film): 1783, 1710, 1614, 1413 cm$^{-1}$ Microanalysis: $C_{16}H_{18}N_2O_7$ Calc. C 54.86 H 5.18 N 8.00 Found C 54.32 H 5.35 N 7.77

EXAMPLE 29

(a) (1aS,3aR,6bS)-5-(5-Methyl-1,3,4-thiadiazol-2-yl sulphanylmethyl)-1-oxo-1,1a,2,3,3a,6b-hexahydro-4-oxa-2,6a-diazacyclobut[cd]indene-6-carboxylic acid sodium salt A solution of diallyl (1aS,3aR,6bS)-5-(5-methyl-1,3,4-thiadiazol-2-ylsulphanylmethyl)-1-oxo-1,1a,2,3,3a,6b-hexahydro-4-oxa-2,6a-diazacyclobut[cd]indene-2,6-dicarboxylate (1.25 g; 2.69 mmol) in ethyl acetate (25 ml) was treated with bis(triphenylphosphine)-palladium(II) dichloride (37 mg; 0.054 mmol) and acetic acid (1.23 ml; 21 mmol). The solution obtained was treated dropwise with tributyltin hydride (3.91 g; 13.45 mmol). After stirring for 5 hours the solution was diluted with n-hexane; the crystals obtained were filtered off under suction and dried (740 mg; 81%). These crystals were dissolved in a small amount of water, treated with sodium bicarbonate (180 mg) and chromatographed over a hydrophobic polymer (eluent: water). 158 mg were obtained as a colourless powder.

IR (KBr): 1750, 1626, 1591 cm$^{-1}$ MS(ISP): 341.2 (M+H)$^+$

The starting material used was prepared as follows:

A solution of diallyl (1aS,3aR,6bS)-5-hydroxymethyl-1-oxo-1,1a,2,3,3a,6b- hexahydro-4-oxa-2,6a-diazacycl o but[cd]indene-2,6-dicarboxylate (350 mg; 1 mmol) in THF (10 ml) was treated with 2-mercapto-5-methyl-1,3,4-thiadiazole (158 mg; 1.2 mmol) and triphenylphosphine. The solution obtained was treated dropwise at −20° C. while stirring with a solution of diethyl azodicarboxylate (226 mg; 1.3 mmol) in THF (5 ml). The solution was stirred at 0° C. for 3 hours. The solvent was evaporated and the residue was chromatographed on silica gel with methylene chloride:ether (7:3). A yellowish oil (266 mg; 57%) was obtained.

IR (KBr): 1784, 1712, 1613 cm$^{-1}$ MS(ISP): 465.4 (M+H)$^+$

In analogy thereto there were prepared:

(b) (1aS,3aR,6bS)-1-Oxo-5-(pyridin-4-ylsulphanylmethyl)-1,1a,2,3,3a,6b-hexahydro-4-oxa-2,6a-diazacyclobut[cd]indene-6-carboxylic acid Starting from diallyl (1aS,3aR,6bS)-1-oxo-5-pyridin-4-ylsulphanylmethyl-1,1a,2,3,3a,6b-hexahydro-4-oxa-2,6a-diazacyclobut[cd]indene-2,6-dicarboxylate (1.14 g; 2.57 mmol) there were obtained 40 mg (5%) as a colourless solid.

IR (KBr): 1750, 1623, 1578 cm$^{-1}$ MS(ISP): 320.3 (M−Na+2H)$^+$

The diallyl (1aS,3aR,6bS)-1-oxo-5-(pyridin-4-ylsulphanylmethyl)-1,1a,2,3,3a,6b-hexahydro-4-oxa-2,6a-diazacyclobut[cd]indene-2,6-dicarboxylate used as the starting material was obtained starting from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (1.98 g; 5.66 mmol) and 4-mercaptopyridine (0.756 g; 6.8 mmol) as in Example 29(a): 1.47 g (58%).

IR (KBr): 1784, 1709, 1612, 1573 cm$^{-1}$ MS (EI): 444 (M+H)$^+$, 333 (M−SPh)

(c) (1aS,3aR,6bS)-5-(5-Amino-1,3,4-thiadiazol-2-ylsulphanylmethyl)-1-oxo-4-oxa-1,1a,2,3,3a,6b-hexahydro-2,6a-diazacyclobut[cd]indene-6-carboxylic acid sodium salt Starting from diallyl (1aS,3aR,6bS)-5-(5-amino-1,3,4-thiadiazol-2-ylsulphanylmethyl)-1-oxo-4-oxa-1,1a,2,3,3a,6b-hexahydro-2,6a-diazacyclobut[cd]indene-2,6-dicarboxylate (1.4 g; 3 mmol) there were obtained 320 mg (29%) as a colourless solid.

IR (KBr): 1748, 1622, 1583, 1496 cm$^{-1}$ MS (ISN): 340.2 (M−Na)$^-$ (1aS,3aR,6bS)-2-Allyloxycarbonyl-5-(5-amino-1,3,4-thiadiazol-2-ylsulphanylmethyl)-1-oxo-4-oxa-1,1a,2,3,3a,6b-hexahydro-2,6a-diazacyclobut[cd]indene-6-carboxylic acid sodium salt was isolated as a byproduct: 49 mg (4%).

IR (KBr): 1761, 1704, 1630, 1596, 1494 cm$^{-1}$ MS (ISP): 448 (M+H)$^+$, 426.3 (M−Na+H)

The diallyl (1aS,3aR,6bS)-5-(5-amino-1,3,4-thiadiazol-2-ylsulphanylmethyl)-1-oxo-4-oxa-1,1a,2,3,3a,6b-hexahydro-2,6a-diazacyclobut[cd]indene-2,6-dicarboxylate used as the starting material was prepared in analogy to Example 16 starting from diallyl (1aS,3aL,6bS)-5-hydroxymethyl-1-oxo-1,1a,2,3,3a,6b-hexahydro-4-oxa-2,6a-diazacyclobut[cd]indene-2,6-dicarboxylate (100 mg; 0.28 mmol), 2-amino-5-mercapto-1,3,4-thiadiazole (41 mg; 0.31 mmol) and mesyl chloride (36 mg; 0.31 mmol): 117 mg (90%).

IR (KBr): 1782, 1709, 1611, 1493 cm$^{-1}$ MS (ISP): 488.3 (M +Na)$^+$; 466.3 (M+H)$^+$ (d) (1aS,3aR,6bS)-5-(2-Carbamoyl-5-methyl[1,2,4]triazolo[1,5-a]pyrimidin-7-ylsulphanylmethyl)-1-oxo-1,1a,2,3,3a,6b-hexahydro-4-oxa-2,6a-diazacyclobut[cd]indene-6-carboxylic acid Starting from diallyl (1aS,3aR,6bS)-5-(2-carbamoyl-5-methyl[1,2,4]triazolo[1,5-a]pyrimidin-7-ylsulphanylmethyl)-1-oxo-1,1a,2,3,3a,6b-hexahydro-4-oxa-2,6a-diazacyclobut[cd]indene-2,6-dicarboxylate (190 mg; 3 mmol) there were obtained 62 mg (42%) as a colourless solid.

IR (KBr): 1753, 1691, 1525, 1594, 1512 cm$^{-1}$ MS (ISP): 440.3 (M+Na)$^+$; 418.4 (M+H)$^+$; 390.3 (M−CO)

The diallyl (1aS,3aR,6bS)-5-(2-carbamoyl-5-methyl-[1,2,4]triazolo[1,5-a]pyrimidin-7-ylsulphanylmethyl)-1-oxo-1, 1a,2,3,3a,6b-hexahydro-4-oxa-2,6a-diazacyclobut[cd]indene-2,6-dicarboxylate used as the starting material was prepared starting from (1aS,3aR,6bS)-5-hydroxymethyl-1-oxo-1,1a,2,3,3a,6b-hexahydro-4-oxa-2,6a-diazacyclobut[cd]indene-2,6-dicarboxylate (1.05 g; 3 mmol) and 7-mercapto-5-methyl[1,2,4]triazolo[1,5-a]pyrimidine-2-carboxamide (648 mg; 3 mmol) as in Example 29(c): 1.15 g (70%).

IR (KBr):1785, 1707, 1596, 1511 cm$^{-1}$ Microanalysis: $C_{23}H_{23}N_7O_7S$ Calc. C 51.01 H 4.28 N 18.11 S 5.92 Found C 50.76 H 4.36 N 18.12 S 5.95

(e) (1aS,3aR,6bS)-5-(1-Methyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Starting from diallyl (1aS,3aR,6bS)-5-(1-methyl-1H-tetrazol-5-ylsulphanylmethyl)-1-oxo-1,1a,2,3,3a,6b-hexahydro-4-oxa-2,6a-diazacyclobut[cd]indene-2,6-dicarboxylate (122 mg; 0.25 mmol) there were obtained 31 mg (36%) as a colourless solid.

IR (KBr): 1752, 1626, 1588, 1387 cm$^{-1}$ MS (ISP): 347.3 (M+Na)$^+$; 342.4 (M+NH$_4$)$^+$; 325.3 (M+H)$^+$ (1aS,3aR,6bS)-5-(1-Methyl-1H-tetrazol-5-ylsulphanylmethyl)-1-oxo-1,1a,2,3,3a,6b-hexahydro-4-oxa-2,6a-diazacyclobut[cd]indene-2,6-dicarboxylic acid 2-allyl ester sodium salt was isolated as a byproduct in the form of a colourless solid (34 mg; 32%).

IR (KBr): 1763, 1710, 1631, 1597 cm$^{-1}$ MS (ISP): 431.4 (M+Na)$^+$; 426.4 (M+NH$_4$)$^+$; 409.4 (M+H)$^+$

The diallyl (1aS,3aR,6bS)-5-(1-methyl-1H-tetrazol-5-ylsulphanylmethyl)-1-oxo-1,1a,2,3,3a,6b-hexahydro-4-oxa-2,6a-diazacyclobut[cd]indene-2,6-dicarboxylate used as the starting material was prepared starting from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (3 g; 8, 6 mmol) and bis-(5-mercapto-1-methyltetrazolyl)-dithiocarbonate (2.54 g; 9.84 mmol) in analogy to Example 15: 2.47 g; 64%.

IR (KBr): 1784, 1710, 1615, 1412 cm$^{-1}$ MS (ISP): 471.4 (M+Na)$^+$; 466.4 (M+NH$_4$)$^+$; 449.4 (M+H)$^+$ (f) (1aS,3aR,6bS)-5-(Carbamoyloxymethyl)-1-oxo-1,1a,2,3,3a,6b-hexahydro-4-oxa-2,6a-diazacyclobut[cd]indene-6-carboxylic acid This compound was obtained starting from diallyl (1aS,3aR,6bS)-5-(carbamoyloxymethyl)-1-oxo-1,1a,2,3,3a,6b-hexahydro-4-oxa-2,6a-diazacyclobut[cd]indene-2,6-dicarboxylate.

IR (KBr): 1770, 1692, 1645, 1414 cm$^{-1}$

The diallyl (1aS,3aR,6bS)-5-(carbamoyloxymethyl)-1-oxo-1,1a,2,3,3a,6b-hexahydro-4-oxa-2,6a-diazacyclobut[cd]indene-2,6-dicarboxylate used as the starting material was prepared as follows:

Diallyl (1aS,3aR,6bS)-5-(2-chloracetylaminocarbamoyloxymethyl)-1-oxo-1,1a,2,3,3a,6b-hexahydro-4-oxa-2,6a-diazacyclobut[cd]indene-2,6-dicarboxylate.

Starting from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (2 g; 5.7 mmol) and chloracetyl isocyanate (1.0 g; 8.56 mmol) there were obtained in analogy to Example 26 2.56 g (95%) as a colourless powder.

IR (film): 1787, 1713, 1625, 1497 cm$^{-1}$ Microanalysis: $C_{19}H_{20}N_3O_9Cl$ Calc. C 48.57H 4.29N 8.94 Found C 48.73H 4.51N 8.76

Diallyl (1aS,3aR,6bS)-5-(carbamoyloxymethyl)-1-oxo-1,1a,2,3,3a,6b-hexahydro-4-oxa-2,6a-diazacyclobut[cd]indene-2,6-dicarboxylate Starting from diallyl (1aS,3aR,6bS)-5-(2-chloracetylaminocarbamoyloxymethyl)-1-oxo-1,1a,2,3,3a,6b-hexahydro-4-oxa-2,6a-diazacyclobut[cd]indene-2,6-dicarboxylate (2.56 g; 5.45 mmol) and NaHCO$_3$ (0.915 g; 10.9 mmol) there were obtained in analogy to Example 26 1.33 g (62%) as a colourless powder.

IR (film): 1798, 1708, 1646, 1414 cm$^{-1}$ Microanalysis: C 17H$_{19}$N$_3$O$_8$ Calc. C 51.91H 4.87N 10.68 Found C 51.67H 4.88N 10.52

(g) (1aS,3aR,6bS)-5-(1-(cyclopropyl-carbonylmethyl)-1H-tetrazol-5-ylsulphanylmethyl-1-oxo-1,1a,2,3,3a,6b-hexahydro-4-oxa-2,6a-diazacyclobut[cd]indene-6-carboxylic acid Starting from diallyl (1aS,3aR,6bS)-5-(1-(cyclopropyl-carbamoyl-methyl)-1H-tetrazol-5-ylsulphanylmethyl)-1-oxo-1,1a,2,3,3a,6b-hexahydro-4-oxa-2,6a-diazacyclobut[cd]indene-2,6-dicarboxylate (722 mg; 1.36 mmol) there were obtained 526 mg (95%) as a yellowish solid.

IR (KBr): 3317, 1778, 1694, 1546, 1213 cm$^{-1}$ MS (ISP): 430.3 (M+Na)$^+$; 425 (M+NH$_4$)$^+$; 408.3 (M+H)$^+$

The diallyl (1aS,3aR,6bS)-5-(1-(cyclopropylcarbamoyl-methyl)-1H-tetrazol-5-ylsulphanylmethyl)-1-oxo-1,1a,2,3,3a,6b-hexahydro-4-oxa-2,6a-diazacyclobut[cd]indene-2,6-dicarboxylate used as the starting material was prepared as follows:

A solution of diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (500 mg; 1.4 mmol; from Example 28) in abs. THF was treated at 0° C. with triethylamine (500 ml; 3.6 mmol) and mesyl chloride (127 ml; 1.6 mmol). The mixture was stirred at 0° C. for 0.5 hour and subsequently treated with a solution of N-cyclopropyl-2-(5-mercapto-tetrazol-1-yl)-acetamide (326 mg; 1.6 mmol) in abs. THF (7 ml). The mixture was stirred at room temperature for 3.5 hours. The resulting white suspension was treated with 50 ml of a mixture consisting of 25 ml of saturated, aqueous sodium chloride solution, 12.5 ml of water and 12.5 ml of an aqueous 2M dipotassium hydrogen phosphate/potassium dihydrogen phosphate buffer, pH6. The mixture was extracted with ethyl acetate (2×100 ml). The organic phases were washed with saturated, aqueous sodium chloride solution (50 ml), combined, dried over magnesium sulphate and concentrated. The residue was chromatographed on silica gel with ethyl acetate/n-hexane 4:1. 734 mg (97%) of a white foam were obtained.

IR (KBr): 1782, 1707, 1613, 1546, 1097 cm$^{-1}$ MS (ISP): 532.4 (M+H)$^+$ (h) (1aS,3aR,6bS)-1-Oxo-5-(1-(phenylethyl-carbamoylmethyl)-1H-tetrazol-5-ylsulphanylmethyl)-1,1a,2,3,3a,6b-hexahydro-4-oxa-2,6a-diazacyclobut[cd]indene-6-carboxylic acid Starting from diallyl (1aS,3aR,6bS)-1-oxo-5-(1-(phenylethylcarbamoylmethyl)-1H-tetrazol-5-ylsulphanylmethyl)-1,1a,2,3,3a,6b-hexahydro-4-oxa-2,6a-diazacyclobut[cd]indene-2,6-dicarboxylate (297 mg; 0.50 mmol) there were obtained 218 mg (93%) as a yellow solid.

IR (KBr): 1774, 1680, 1554, 1214, 750, 702 cm$^{-1}$ MS (ISP): 494 (M+Na)$^+$; 489.4 (M+NH$_4$)$^+$; 472.3 (M+H)$^+$

The diallyl (1aS,3aR,6bS)-1-oxo-5-(1-(phenylethylcarbamoylmethyl)-1H-tetrazol-5-ylsulphanylmethyl)-1,1a,2,3,3a,6b-hexahydro-4-oxa-2,6a-diazacyclobut[cd]indene-2,6-dicarboxylate used as the starting material was obtained in analogy to Example 29(g) from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (194 mg; 0.55 mmol; from Example 28) and 2-(5-mercapto-tetrazol-1-yl)-N-phenylethyl-acetamide (167 mg; 0.64 mmol). 303 mg (92%) of a white foam were obtained.

IR (KBr): 3340, 1785, 1708, 1614, 1549, 1214, 759, 701 cm$^{-1}$ MS (ISP): 618 (M+Na)$^+$; 613.3 (M+NH$_4$)$^+$; 596.3 (M+H)$^+$ (i) (1aS,3aR,6bS)-5-(1-(Carbamoylmethyl-carbamoylmethyl)-1H-tetrazol-5-ylsulphanylmethyl)-1-oxo-1,1a,2,3,3a,6b-hexahydro-4-oxa-2,6a-diazacyclobut[cd]indene-6-carboxylic acid Starting from diallyl (1aS,3aR,6bS)-5-(1-(carbamoylmethylcarbamoylmethyl)-1H-tetrazol-5-ylsulphanylmethyl)-1-oxo-1,1a,2,3,3a,6b- hexahydro-4-oxa-2,6a-diazacyclobut[cd]indene-2,6-dicarboxylate (424 mg; 0.77 mmol) there were obtained 119 mg (36%) as a white solid.

IR (KBr): 3407, 1757, 1671, 1630, 1398, 1218 cm$^{-1}$ MS (ISP): 447.2 (M+Na)$^+$; 442.3 (M+NH$_4$)$^+$; 425.3 (M+H)$^+$

The (1aS,3aR,6bS)-5-(1-(carbamoylmethyl-carbamoylmethyl)-1H-tetrazol-5-ylsulphanylmethyl)-1-oxo-1,1a,2,3,3a,6b-hexahydro-4-oxa-2,6a-diazacyclobut[cd]indene-2,6-dicarboxylate used as the starting material was prepared in analogy to Example 29(g) from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (245 mg; 0.70 mmol) and N-carbamoylmethyl-2-(5-mercapto-tetrazol-1-yl)-acemmide (175 mg; 0.81 mmol). 365 mg (95%) of a white foam were obtained.

IR (KBr): 3432, 1784, 1706, 1613 cm$^{-1}$ MS (ISP): 571 (M+Na)$^+$; 566.3(M+NH$_4$)$^+$; 549.3 (M+H)$^+$ (j) (1aS,3aR,6bS)-5-(1-Carbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid Starting from diallyl (1aS,3aR,6bS)-5-(1-carbamoylmethyl-1H-tetrazol-5-ylsulphanylmethyl)-1-oxo-1,1a,2,3,3a,6b-hexahydro-4-oxa-2,6a-diazacyclobut[cd]indene-2,6-dicarboxylate (460 mg; 0.96 mmol) there were obtained 336 mg (95%) as a white solid.

IR (KBr): 3410, 1775, 1695, 1612, 1214 cm$^{-1}$ MS (ISP): 390.2 (M+Na)$^+$; 385.2 (M+NH$_4$)$^+$; 368.2 (M+H)$^+$

The diallyl (1aS,3aR,6bS)-5-(1-carbamoylmethyl-1H-tetrazol-5-ylsulphanylmethyl)-1-oxo-1,1a,2,3,3a,6b-hexahydro-4-oxa- 2,6a-diazacyclobut[cd]indene-2,6-dicarboxylate used as the starting material was prepared in analogy to Example 29(g) from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (400 mg; 1.1 mmol; from Example 28) and 2-(5-mercapto-tetrazol-1-yl)acetamide (210 mg; 1.3 mmol). 445 mg (82%) of a yellowish foam were obtained.

IR (KBr): 3430, 1783, 1707, 1613, 1214 cm$^{-1}$ MS (ISP): 514,2 (M+Na)$^+$; 509.2 (M+NH$_4$)$^+$; 492.2 (M+H)$^+$ (k) (1aS,3aR,6bS)-5-(1-Methylcarbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid Starting from diallyl (1aS,3aR,6bS)-5-(1-methylcarbamoylmethyl-1H-tetrazol-5-ylsulphanylmethyl)-1-oxo-1,1a,2,3,3a,6b-hexahydro-4-oxa-2,6a-diazacyclobut[cd]indene-2,6-dicarboxylate (536 mg; 1.1 mmol) there were obtained 420 mg (100%) as a yellowish solid.

IR (KBr): 3407, 1781, 1693, 1616, 1558, 1411 cm$^{-1}$ MS (ISN): 380.2 (M–H)$^-$

The diallyl (1aS,3aR,6bS)-5-(1-methylcarbamoylmethyl-1H-tetrazol-5-ylsulphanylmethyl)-1-oxo-1,1a,2,3,3a,6b-hexahydro-4-oxa-2,6a-diazacyclobut[cd]indene-2,6-dicarboxylate used as the starting material was prepared in analogy to Example 29(g) from diallyl (1aS,3aR,6bS)-5-hyclroxymethyl-1-oxo-1,1a,2,3,3a,6b-hexahydro-4-oxa-2,6a-diazacyclobut[cd]indene-2,6-dicarboxylate (400 mg; 1.1 mmol; from Example 28) and 2-(5-mercapto-tetrazol-1-yl)-N-methyl-acetamide (240 mg; 1.4 mmol). 511 mg (89%) of a white foam were obtained.

IR (KBr): 3374, 1707, 1614, 1553 cm$^{-1}$ MS (ISP): 528.3 (M+Na)$^+$; 523.3 (M+NH$_4$)$^+$; 506.4 (M+H)$^+$ (1) (1aS,3aR,6bS)-5-(1-(2-Morpholin-4yl-2-oxo-ethyl)-1H-tetrazol-5-ylsulphanylmethyl)-1-oxo-1,1a,2,3,3a,6b-hexahydro-4-oxa-2,6a-diazacyclobut[cd]indene-6-carboxylic acid Starting from diallyl (1aS,3aR,6bS)-5-(1-(2-morpholin-4-yl-2-oxo-ethyl)-1H-tetrazol-5-ylsulphanylmethyl)-1-oxo-1,1a,2,3,3a,6b-hexahydro-4-oxa-2,6a-diazacyclobut[cd]indene-2,6-dicarboxylate (589 mg; 1.1 mmol) there were obtained 395 mg (86%) as a yellowish solid.

IR (KBr): 3432, 1777, 1706, 1663, 1614 cm$^{-1}$ MS (ISN): 436.2 (M–H)$^-$

The diallyl (1aS,3aR,6bS)-5-(1-(2-morpholin-4-yl-2-oxo-ethyl)-1H-tetrazol-5-ylsulphanylmethyl)-1-oxo-1,1a,2,3,3a,6b-hexahydro-4-oxa-2,6a-diazacyclobut[cd]indene-2,6-dicarboxylate used as the starting material was prepared in analogy to Example 29(g) from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (407 mg; 1.2 mmol; from Example 28) and 2-(5-mercapto-tetrazol-1-yl)-1-(morpholino-4-yl)-ethanone (306 mg; 1.3 mmol). 595 mg (91%) of a white foam were obtained.

IR (KBr): 1783, 1710, 1666, 1614, 1241, 975 cm$^{-1}$ MS (ISP): 584.2 (M+Na)$^+$; 579.3, (M+NH$_4$)$^+$; 562.3 (M+H)$^+$ Microanalysis: C$_{23}$H$_{27}$N$_7$O$_8$S.0.236 AcOEt.0.200 H$_2$O Calc. C 49.13 H 5.03 N 16.72 S 5.47 Found C 49.35 H 5.04 N 16.73 S 5.72

(m) (1aS,3aR,6bS)-5-(1-(4-Hydroxyphenyl-carbamoylmethyl)-1H-tetrazol-5-ylsulphanylmethyl)-1-oxo-1,1a,2,3,3a,6b-hexahydro-4-oxa-2,6a-diazacyclobut[cd]indene-6-carboxylic acid Starting from diallyl (1aS,3aR,6bS)-5-(1-(4-hydroxyphenylcarbamoylmethyl)-1H-tetrazol-5-ylsulphanylmethyl)-1-oxo-1,1a,2,3,3a,6b-hexahydro-4-oxa-2,6a-diazacyclobut[cd]indene-2,6-dicarboxylate (390 mg; 0.67 mmol) there were obtained 293 mg (95%) as a yellowish solid.

IR (KBr): 3422, 1775, 1691, 1613, 1513, 836 cm$^{-1}$ MS (EI): 208 (M − [N-(4-hydroxy-phenyl)-2-(5-mercapto-tetrazol-1-yl)-acemmide])$^+$ The diallyl (1aS,3aR,6bS)-5-(1-(4-hydroxyphenylcarbamoylmethyl)-1H-tetrazol-5-ylsulphanylmethyl)-1-oxo-1,1a,2,3,3a,6b-hexahydro-4-oxa-2,6a-diazacyclobut[cd]indene-2,6-dicarboxylate used as the starting material was prepared in analogy to Example 29(g) from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (500 mg; 1.4 mmol; from Example 28) and N-(4-hydroxyphenyl)-2-(5-mercapto-tetrazol-1-yl)-acetamide (431 mg; 1.7 mmol). 636 mg (76%) of a white foam were obtained.

IR (KBr): 3401, 1784, 1707, 1613, 1555, 1513, 836 cm$^{-1}$ MS (ISP): 606.3 (M+Na)$^+$; 601.3, (M+NH$_4$)$^+$; 584.3 (M+H)$^+$ (n) (1aS,3aR,6bS)-1-Oxo-5-(1-(trityloxy-carbamoylmethyl)-1H-tetrazol-5-ylsulphanylmethyl)-1,1a,2,3,3a,6b-hexahydro-4-oxa-2,6a-diazacyclobut[cd]indene-6-carboxylic acid Starting from diallyl (1aS,3aR,6bS)-1-oxo-5-(1-(trityloxycarbamoylmethyl)-1H-tetrazol-5-ylsulphanylmethyl)-1,1a,2,3,3a,6b-hexahydro-4-oxa-2,6a-diazacyclobut[cd]indene-2,6-dicarboxylate (523 mg; 0.68 mmol) there were obtained 381 mg (89%) as a yellowish solid.

IR (KBr): 3426, 1779, 1708, 1613, 1400, 761,704 cm$^{-1}$ MS (ISP): 648.4 (M+Na)$^+$; 643 (M+NH$_4$)$^+$; 626.4 (M+H)$^+$

The compound was converted in the usual manner by acidic hydrolysis (e.g. aqueous hydrochloric acid) or hydrogenolysis with Pd/C into the 1-(hydroxycarbamoylmethyl) compound (with respect to the tetrazolyl group).

The diallyl (1aS,3aR,6bS)-1-oxo-5-(1-(trityloxycarbamoylmethyl)-1H-tetrazol-5-ylsulphanylmethyl)-1,1a,2,3,3a, 6b-hexahydro-4-oxa-2,6a-diazacyclobut[cd]indene-2,6-dicarboxylate used as the starting material was prepared in analogy to Example 29(g) from diallyl (1aS,3aR,6bS)-5-hydroxymethyl-1-oxo-1,1a,2,3,3a,6b-hexahydro-4-oxa-2,6a-diazacyclobut[cd]indene-2,6-dicarboxylate (460 mg; 1.3 mmol; from Example 28) and 2-(5-mercapto-tetrazol-1-yl)-N-trityloxy-acetamide (660 mg; 1.6 mmol). 953 mg. (97%) of a yellow foam were obtained.

IR (KBr): 1786, 1711, 1615, 1448, 763,704 cm$^{-1}$ MS (ISP): 772.2 (M+Na)$^+$; 767.3 (M+NH$_4$)$^+$; 750.3 (M+H)$^+$

EXAMPLE 30

(1aS,3aR,6bS)-2-Ally-5-(1-methyl-1H-tetrazol-5-ylsulphanylmethyl)-1-oxo-4-oxa-1,1a,2,3,3a,6b-hexahydro-2,6a-diazacyclobut[cd]indene-6-carboxylic acid sodium salt A solution of diallyl (1aS,3aR,6bS)-5-(1-methyl-1H-tetrazol-5-ylsulphanylmethyl)-1-oxo-1,1a,2,3,3a,6b-hexahydro-4-oxa-2,6a-diazacyclobut[cd]indene-2,6-dicarboxylate (257 mg; 0.57 mmol; from Example 29(e)) in THF (1 ml) was treated with tetrakis(triphenylphosphine)-palladium (37 mg; 0.027 mmol) and dimedone (240 mg; 1.71 mmol) and stirred at room temperature overnight. The solvent was evaporated. The residue was diluted in ethyl acetate and washed with saturated, aqueous sodium bicarbonate solution (5 ml). The organic phase was washed with water (5 ml). The aqueous phase was lyophilized and chromatographed over a hydrophobic polymer (eluent: water). 41 mg (18%) of a white powder were obtained.

IR (KBr): 1745, 1631, 1595, 1391 cm$^{-1}$ MS (ISP): 365.2 (M+H)$^+$

EXAMPLE 31

(a) (1aS,3aR,6bS)-2-(4-Hydroxy-phenylcarbamoyl)-5-(5-methyl-1,3,4-thiadiazol-2-ylsulphanylmethyl)-1-oxo-1,1a,2,3,3a,6b-hexahydro-4-oxa-2,6a-diazacyclobut[cd]indene-6-carboxylic acid sodium salt This compound was obtained in analogy to Example 3(a) starting from (1aS,3aR,6bS)-5-(5-methyl-1,3,4-thiadiazol-2-ylsulphanylmethyl)-1-oxo-1,1a,2,3,3a,6b-hexahydro-4-oxa-2,6a-diazacyclobut[cd]indene-6-carboxylic acid (from Example 29(a)) and 4-hydroxy-phenylcarbamic acid 2,5-dioxopyrrolidin-1-yl ester in 39% yield as a colourless powder.

IR (KBr): 1759, 1630, 1599, 1513 cm$^{-1}$ MS (ISP): 498.2 (M+Na)$^+$; 493.2 (M+NH$_4$)$^+$; 476.2 (M+H)$^+$

In analogy to this there were prepared:

(b) (1aS,3aR,6bS)-2-(4-Carbamoyl-phenylcarbamoyl)-5-(5-methyl-1,3,4-thiadiazol-2-ylsulphanylmethyl)-1-oxo-1,1a,2,3,3a,6b-hexahyctro-4-oxa-2,6a-diazacyclobut[cd]indene-6-carboxylic acid sodium salt Obtained starting from (1aS,3aR,6bS)-5-(5-methyl-1,3,4-thiadiazol-2-ylsulphanylmethyl)-1-oxo-1,1a,2,3,3a,6b-hexahydro-4-oxa-2,6a-diazacyclobut[cd]indene-6-carboxylic acid and 4-carbamoyl-phenylcarbamic acid 2,5-dioxopyrrolidin-1-yl ester in 50% yield as a colourless powder.

IR (KBr): 1761, 1663, 1596, 1526 cm$^{-1}$ MS (ISN): 501.3 (M−Na)$^-$; 369.3 (M−C$_3$H$_4$N$_2$S$_2$)

(c) (1aS,3aR,6bS)-5-(5-Amino-1,3,4-thiadiazol-2-ylsulphanylmethyl)-2-(4-hydroxy-phenylcarbamoyl)-1-oxo-1,1a,2,3,3a,6b-hexahydro-4-oxa-2,6a-diazacyclobut[cd]indene-6-carboxylic acid sodium salt Obtained starting from (1aS,3aR,6bS)-5-(5-amino-1,3,4-thiadiazol-2-ylsulphanylmethyl)-1-oxo-1,1a,2,3,3a,6b-hexahydro-4-oxa-2,6a-diazacyclobut[cd]indene-6-carboxylic acid and 4-hydroxyphenylcarbamic acid 2,5-dioxopyrrolidin-1-yl ester in 38% yield as a colourless powder.

IR (KBr): 1755, 1629, 1600, 1513 cm$^{-1}$ MS (ISP): 499.3 (M+H)$^+$; 477.3 (M−Na+2H)$^+$ (d) (1aS,3aR,6bS)-2-(4-Hydroxy-phenylcarbamoyl)-1-oxo-5-(pyridin-4-ylsulphanylmethyl)-1,1a,2,3,3a,6b-hexahydro-4-oxa-2,6a-diazacyclobut[cd]indene-6-carboxylic acid sodium salt Obtained starting from (1aS,3aR,6bS)-1-oxo-5-(pyridin-4-ylsulphanylmethyl)-1,1a,2,3,3a,6b-hexahydro-4-oxa-2,6a-diazacyclobut[cd]indene-6-carboxylic acid and 4-hydroxy-phenylcarbamic acid 2,5-dioxopyrrolidin-1-yl ester in 33% yield as a colourless powder.

IR (KBr): 1759, 1626, 1581, 1513 cm$^{-1}$ MS (ISP): 477.4 (M+H)$^+$; 455.4 (M−Na+2H)$^+$ (e) (1aS,3aR,6bS)-2-(4-Carbamoyl-phenylcarbamoyl)-1-oxo-5-(pyridin-4-ylsulphanylmethyl)-1,1a,2,3,3a,6b-hexahydro-4-oxa-2,6a-diazacyclobut[cd]indene-6-carboxylic acid sodium salt Obtained starting from (1aS,3aR,6bS)-1-oxo-5-(pyridin-4-ylsulphanylmethyl)-1,1a,2,3,3a,6b-hexahydro-4-oxa-2,6a-diazacyclobut[cd]indene-6-carboxylic acid and 4-carbamoyl-phenylcarbamic acid 2,5-dioxopyrrolidin-1-yl-ester in 40% yield as a colourless powder.

IR (KBr): 1761, 1664, 1583, 1526 cm$^{-1}$ MS (ISP): 504.4 (M+H)$^+$; 482.4 (M−Na+2H)$^+$ (f) (1aS,3aR,6bS)-2-(4-Carbamoyl-phenylcarbamoyl)-5-(carbamoyloxymethyl)-1-oxo-1,1a,2,3,3a,6b-hexahydro-4-oxa-2,6a-diazacyclobut[cd]indene-6-carboxylic acid sodium salt Obtained starting from (1aS,3aR,6bS)-5-(carbamoyloxymethyl)-1-oxo-1,1a,2,3,3a,6b-hexahydro-4-oxa-2,6a-diazacyclobut[cd]indene-6-carboxylic acid and 4-carbamoyl-phenylcarbamic acid 2,5-dioxopyrrolidin-1-yl ester in 61% yield as a colourless powder.

IR (KBr): 1759, 1718, 1657, 1609, 1524 cm$^{-1}$ MS (ISP): 410.4 (M+Na)$^+$; 405.5 (M+NH$_4$)$^+$; 388.4 (M+H)$^+$ (g) (1aS,3aR,6bS)-5-(Carbamoyloxymethyl)-2-(4-hydroxyphenylcarbamoyl)-1-oxo-1,1a,2,3,3a,6b-hexahydro-4-oxa-2,6a-diazacyclobut[cd]indene-6-carboxylic acid sodium salt Obtained starting from (1aS,3aR,6bS)-5-(carbamoyloxymethyl)-1-oxo-1,1a,2,3,3a,6b-hexahydro-4-oxa-2,6a-diazacyclobut[cd]indene-6-carboxylic acid and 4-hydroxy-phenylcarbamic acid 2,5-dioxopyrrolidin-1-yl ester in 50% yield as a colourless powder.

IR (KBr): 1757, 1716, 1655, 1513 cm$^{-1}$ MS (ISP): 383.4 (M+Na)$^+$; 378.4 (M+NH$_4$)$^+$; 361.4 (M+H)$^+$ (h) (1aS,3aR,6bS)-2-(4-hydroxy-phenylcarbamoyl)-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Obtained starting from (1aS,3aR,6bS)-5-(1-Methyl-1H-tetrazol-5-ylsulphanylmethyl)-1-oxo-1,1a,2,3,3a,6b-hexahydro-4-oxa-2,6a-diazacyclobut[cd]indene-6-carboxylic acid and 4-hydroxyphenylcarbamic acid 2,5-dioxopyrrolidin-1-yl ester in 12% yield as a colourless powder.

IR (KBr): 1758, 1631, 1602, 1513 cm$^{-1}$ MS (ISN): 458.4 (M−Na)$^-$; 414.4 (M−Na−CO$_2$)$^-$ (i) (1aS,3aR,6bS)-2-(4-Carbamoyl-phenylcarbamoyl)-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Obtained starting from (1aS,3aR,6bS)-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylic acid and 4-carbamoylphenylcarbamic acid 2,5- dioxopyrrolidin-1-yl ester in 12% yield as a colourless powder.

IR (KBr): 1761, 1662, 1599, 1526 cm$^{-1}$ MS (ISP): 509.4 (M+H)$^+$; 487.5 (M–Na+2H)$^+$

EXAMPLE 32

(a) (1aS,3aR,6bS)-2-Acetyl-5-(pyridin-4-ylsulphanylmethyl)-1-oxo-1,1a,2,3,3a,6b-hexahydro-4-oxa-2,6a-diazacyclobut[cd]indene-6-carboxylic acid sodium salt Was obtained in analogy to Example 10(b) starting from (1aS,3aR,6bS)-1-oxo-(5-pyridin-4-ylsulphanylmethyl)-1,1a,2,3,3a,6b-hexahydro-4-oxa-2,6a-diazacyclobut[cd]indene-6-carboxylic acid (from Example 29(b)) and acetic anhydride in acetic acid in 48% yield as a colourless powder.

IR (KBr): 1764, 1627, 1580, 1410 cm$^{-1}$ in analogy to this there were prepared:

(b) (1aS,3aR,6bS)-2-Acetyl-5-(carbamoyloxymethyl)-1-oxo-1,1a,2,3,3a,6b-hexahydro-4-oxa-2,6a-diazacyclobut[cd]indene-6-carboxylic acid sodium salt Starting from (1aS,3aR,6bS)-5-(Carbamoyloxymethyl)-1-oxo-1,1a,2,3,3a,6b-hexahydro-4-oxa-2,6a-diazacyclobut[cd]indene-6-carboxylic acid (from Example 29(f)) in 41% yield as a colourless powder.

IR (KBr): 1765, 1723, 1659, 1455, 1348 cm$^{-1}$ (c) (1aS,3aR,6bS)-2-Acetyl-5-(2-carbamoyl-5-methyl[1,2,4]triazolo[1,5-a]pyrimidin-7-ylsulphanylmethyl)-1-oxo-1,1a,2,3,3a,6b-hexahydro-4-oxa-2,6a-diazacyclobut[cd]indene-6-carboxylic acid sodium salt Starting from (1aS,3aR,6bS)-5-(2-carbamoyl-5-methyl[1,2,4]triazolo[1,5-a]pyrimidin-7-ylsulphanylmethyl)-1-oxo-1,1a,2,3,3a,6b-hexahydro-4-oxa-2,6a-diazacyclobut[cd]indene-6-carboxylic acid (from Example 29(d)) in 30% yield as a colourless powder.

IR (KBr): 1762, 1690, 1628, 1595, 1512 cm$^{-1}$ MS (ISP): 504.3 (M+Na)$^+$; 482.2 (M+H)$^+$; 460.5 (M–Na+2H)$^+$ (d) (1aS,3aR,6bS)-2-Acetyl-5-(1-cyclopropylcarbamoylmethyl-1H-tetrazol-5-ylsulphanylmethyl)-1-oxo-1,1a,2,3,3a,6b-hexahydro4-oxa-2,6a-diazacyclobut[cd]indene-6-carboxylic acid sodium salt Starting from (1aS,3aR,6bS)-5-(1-cyclopropylcarbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid (150 mg; 0.37 mmol; Example 29(g)) there were isolated 10 mg (6%) as a white powder.

IR (KBr): 1762, 1630, 1395 cm$^{-1}$ MS (ISP): 472.3 (M+H)$^+$; 450.3 (M–Na+2H)$^+$ (e) (1aS,3aR,6bS)-2-Acetyl-5-(1-carbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Starting from (1aS,3aR,6bS)-5-(1-carbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid (100 mg; 0.27 mmol; Example 29(j)) there were isolated 23 mg (20%) as a white powder.

IR (KBr): 1761, 1694, 1630, 1394, 1084 cm$^{-1}$ MS (ISP): 454.2 (M+Na)$^+$; 432.2 (M+H)$^+$; 410.2 (M–Na+2H)$^+$ (f) (1aS,3aR,6bS)-2-Acetyl-5-(1-methyl-carbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Starting from (1aS,3aR,6bS)-5-(1-methylcarbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid (125 mg; 0.33 mmol; Example 29(k)) there were isolated 7 mg (5%) as a white powder.

IR (KBr): 1763, 1630, 1600, 1408 cm$^{-1}$ MS (ISP): 446.3 (M+H)$^+$; 441.4 (M–Na+H+NH$_4$)$^+$; 424.3 (M–Na+2H)$^+$ (g) (1aS,3aR,6bS)-2-Acetyl-5-(1-(2-morpholin-4-yl-2-oxoethyl)-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Starting from (1aS,3aL,6bS)-5-(1-(2-morpholin-4-yl-2-oxo-ethyl)-1H-tetrazol-5-ylsulphanylmethyl)-1-oxo-1,1a,2,3,3a,6b-hexahydro-4-oxa-2,6a-diazacyclobut[cd]indene-6-carboxylic acid (114 mg; 0.26 mmol; Example 29(1)) there were isolated 26 mg (20%) as a white powder.

IR (KBr): 1764, 1659, 1598, 1395 cm$^{-1}$ MS (ISP): 502.2 (M+H)$^+$; 497.2 (M–Na+H+NH$_4$)$^+$; 480.2 (M–Na+2H)$^+$ (h) (1aS,3aR,6bS)-2-Acetyl-1-oxo-5-(1-(trityloxycarbamoylmethyl)-1H-tetrazol-5-ylsulphanylmethyl)-1,1a,2,3,3a,6b-hexahydro4-oxa-2,6a-diazacyclobut[cd]indene-6-carboxylic acid sodium salt Starting from (1aS,3aR,6bS)-1-oxo-5-(1-(trityloxycarbamoylmethyl)-1H-tetrazol-5-ylsulphanylmethyl)-1,1a,2,3,3a,6b-hexahydro-4-oxa-2,6a-diazacyclobut[cd]indene-6-carboxylic acid (120 mg; 0.19 mmol; Example 29(n)) there were isolated 40 mg (31%) as a white powder.

IR (KBr): 1757, 1690, 1628, 1386, 763, 703 cm$^{-1}$ MS (ISP): 690 (M+H)$^+$; 685.4 (M–Na+H+NH$_4$)$^+$; 668.3 (M–Na+2H)$^+$

EXAMPLE 33

(1aS,3aR,6bS)-2-Acetyl-5-(5-amino-1,3,4-thiadiazol-2-ylsulphanylmethyl)-1-oxo-1,1a,2,3,3a,6b-hexahydro-4-oxa-2,6a-diazacyclobut[cd]indene-6-carboxylic acid sodium salt Was obtained in analogy to Example 19(a) starting from (1aS,3aR,6bS)-5-(5-amino-1,3,4-thiadiazol-2-ylsulphanylmethyl)-1-oxo-1,1a,2,3,3a,6b-hexahydro-4-oxa-2,6a-diazacyclobut[cd]indene-6-carboxylic acid (from Example 29(c)) and acetyl chloride in 39% yield as a pink powder.

IR (KBr): 1758, 1626, 1595, 1495 cm$^{-1}$ MS (ISP): 428.2 (M+Na)$^+$; 406.2 (M+H)$^+$; 384.2 (M–Na+2H)$^+$

EXAMPLE 34

(1aS,3aR,6bS)-2-(1-Methyl-1H-tetrazol-5-ylsulphanylacetyl)-5-(5-methyl-1,3,4-thiadiazol-2-ylsulphanylmethyl)-1-oxo-1,1a,2, 3,3a,6b-hexahydro-4-oxa-2,6a-diazacyclobut[cd]indene-6-carboxylic acid A solution of (1aS,3aR,6bS)-5-(5-methyl-1,3,4-thiadiazol-2-ylsulphanylmethyl)-1-oxo-1,1a,2,3,3a,6b-hexahydro-4-oxa-2,6a-diazacyclobut[cd]indene-6-carboxylic acid (120 mg; 0.246 mmol) in DMF (1 ml) was treated with 2,5-dioxopyrrolidin-1-yl (1-methyl-1H-tetrazol-5-ylsulphanyl)-acetate (80 mg; 0.296 mmol) The solution was stirred for 2 hours, treated with charcoal and filtered. The Filtrate was diluted with ethyl acetate. The crystals were filtered off under suction, dissolved in dimethylformamide (DMF) and treated with 2N sodium 2-ethyl-capronate in ethyl acetate (1 ml). The crystals obtained were filtered off under suction, dissolved in a small mount of water and chromatographed over a hydrophobic polymer (eluent: water). 23 mg (18%) of a white powder were obtained.

IR (KBr): 1760, 1631, 1599, 1388 cm$^{-1}$ MS (ISP): 541.3 (M+Na)$^+$; 519.3 (M+H)$^+$; 497.4 (M–Na+2H)$^+$

EXAMPLE 35

(1aS,3aR,6bS)-2-Acetyl-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Was prepared in analogy to Example 29(a) starting from allyl (1aS,3aR,6bS)-2-acetyl-5-(1-methyl-1H-tetrazol-5-yl-sulphanylmethyl)-1-oxo-1,1a,2,3,3a,6b-hexahydro-4-oxa-2, 6a-diazacyclobut[cd]indene-6-carboxylate in 26% yield as a white powder.

IR(KBr): 1762, 1650, 1631, 1600, 1390 cm$^{-1}$ MS(ISP): 389.3 (M+H); 384.3 (M+NH$_4$+H–Na)$^+$; 367.4 (M–Na+2H)$^+$

The allyl (1aS,3aR,6bS)-2-acetyl-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylate used as the starting material was prepared as follows:

a) 1:1 Mixture of (1S,4S,5S)-4-[(R)- and (S)-tetrahydro pyran-2-yloxy]-2,6-diazabicyclo [3.2.0]heptane-7-one (1S,4S,5S)-2-Benzyloxycarbonyl-4-[(R)-and (S)-tetrahyclropyran-2-yloxy]-2,6-diaza-bicyclo[3.2.0]heptane-7-one (1:1 mixture; 11 g; 0.32 mol; European Patent Publication 508 234, Example 14) in ethanol (250 ml) was hydrogenated over Pd/C (10%; 100 mg). The catalyst was filtered off under suction, the filtrate was concentrated and chromatographed over silica gel with ethyl acetate/methanol 9:1. 3.30 g (49%) of colourless material were obtained.

M.p 153°–54° C. (Ether) Microanalysis: C$_{10}$H$_{16}$N$_2$O$_3$ Calc. C 56.59 H 7.60 N 13.20 Found C 56.55 H 7.64 N 12.96 b) 1:1 Mixture of (1S,4S,5S)-2-acetyl-4-[(R)- und (S)-tetrahydropyran-2-yloxy]-2,6 -diazabicyclo[3.2.0]heptane-7-one A solution of (1S,4S,5S)-4-[(R)- and (S)-tetrahydropyran-2-yloxy]-2,6-diazabicyclo[3.2.0]heptan-7-one (4.84 g, 22.8 mmol) in methylene chloride (100 ml) was placed at 0° C. and treated in succession with pyridine (2 ml; 25 mmol) and a solution of acetic anhydride(2.26 ml; 24 mmol) in methylene chloride(10 ml). After 10 minutes the reaction mixture was diluted with methylene chloride and washed in succession with saturated sodium bicarbonate and sodium chloride solutions. The organic solution was dried and concentrated and the residue was crystallized from ether/n-hexane. 5.44 g (93.6%) of colourless material were obtained.

M.p. 132°–34° C. (ether) Microanalysis: C$_{12}$H$_{18}$N$_2$O$_4$ Calc. C 56.68 H 7.14 N 11.02 Found C 56.58 H 7.22 N 10.88 c) 1:1 Mixture of allyl (1S,4S,5S)-[2-acetyl-7-oxo-4-[(R)- and (S)-tetrahydropyran-$_2$-yloxy]-2,6-diazabicyclo[3.2.0] heptan-6-yl]-acetate A solution of (1S,4S,5S)-2-acetyl-4-[(R)- and (S)-tetrahydropyran-2-yloxy]-2,6-diazabicyclo[3.2.0]heptan-7-one (5.76 g, 22.7 mmol) in THF (100 ml) was placed at –78° C. and treated in succession with bistrimethylsilyllithium amide (1M in THF, 0.27 mol) and allyl bromoacetate (3 ml; 25 mmol). The reaction mixture was stirred at 0° C. for 30 minutes, treated with a saturated aqueous ammonium chloride solution and diluted with ethyl acetate and water. The organic phase was washed with saturated aqueous sodium chloride solution, dried and concentrated. The residue was chromatographed over silica gel with ethyl acetate. 5.0 g (62%) of a yellowish oil were obtained.

IR (film): 1770, 1740, 1655, 1417 cm$^{-1}$ MS (ISP): 370.5 (M+NH$_4$)$^+$; 353.4 (M+H)$^+$; 269.4 (M-dihydropyran)

d) 1:1:1:1 Mixture of allyl [(R)- and (S)-2-(1S,4S,5S)-2-acetyl-7-oxo-4-[(R)- and (S)-(tetrahydropyran-2-yloxy]-2,6-diazabicyclo[3.2.0]heptan-6-yl]-4-(t-butyl-dimethylsilanyl-oxy)-3-oxo-butyrate Was obtained in analogy to Example 28e) starting from a 1:1 mixture of allyl (1S,4S,5S)-[2-acetyl-7-oxo-4-[(R)- and (S)-tetrahydropyran-2-yloxy]-2,6-diazabicyclo[3.2.0]heptan-6-yl]-acetate and (t-butyldimethylsilyl)oxyacetyl chloride in 32% yield as a yellowish oil.

IR (film): 1776, 1740, 1660, 1418 cm$^{-1}$ MS (ISP): 542.5 (M+NH$_4$)$^+$; 525.5 (M+H)$^+$ e) 1:1 Mixture of allyl (R)- and (S)-2-(1S,4S,5S)-(2-acetyl-7-oxo-4-hydroxy-2,6-diazabicyclo[3.2.0]heptan-6-yl)-4-(t-butyldimethylsilanyloxy)-3-oxo-butyrate Was obtained in analogy to Example 28 f) starting from allyl [(R)- and (S)-2-(1S,4S,5S)-2-acetyl-7-oxo-4-[(R) and (S)-tetrahydropyran-2-yloxy]-2,6-diazabicyclo[3.2.0]heptan-6-yl]-4-(t-butyl-dimethylsilanyloxy)-3-oxo-butyrate in 44% yield as colourless crystals (ether).

IR (KBr): 1747, 1640, 1513, 1420 cm$^{-1}$ MS (ISP): 458.5 (M+NH$_4$)$^+$; 441.5 (M+H)$^+$ f) Allyl (1aS,3aR,6bS)-2-acetyl-5-(t-butyl-dimethyl-silanyloxymethyl)-1-oxo-1,1a,2,3,3a,6b-hexahydro-4-oxa-2,6a-diazacyclobut[cd]indene-6-carboxylate Was obtained in analogy to Example 28(g) starting from a 1:1 mixture of allyl (R)- and (S)-2-(1S,4S,5S)-[2-acetyl-7-oxo-4-hydroxy-2,6-diazabicyclo[3.2.0]heptan-6-yl]-4-(t-butyl-dimethylsilanyloxy)-3-oxo-butyrate in 52% yield as a yellowish oil.

IR (film): 1783, 1716, 1666, 1618, 1415 cm$^{-1}$ Microanalysis: C$_{20}$H$_{30}$N$_2$O$_6$Si Calc. C 56.85 H 7.16 N 6.63 Found C 56.75 H 7.25 N 6.60 g) Allyl (1aS,3aR,6bS)-2-acetyl-5-(hydroxymethyl)-1-oxo-1,1a,2,3,3a,6b-hexahydro-4-oxa-2,6-diazacyclobut[cd]indene-6-carboxylate Was obtained in analogy to Example 28h) starting from allyl (1aS,3aR,6bS)-2-acetyl-5-(t-butyl-dimethyl-silanyloxymethyl)-1-oxo-1,1a,2,3,3a,6b-hexahydro-4-oxa-2,6a-diazacyclobut[cd]indene-6-carboxylate in 56% yield.

IR (film): 1779, 1712, 1658, 1617, 1419 cm$^{-1}$ MS(ISP): 326.4 (M+NH$_4$)$^+$; 309.5 (M+H)$^+$; 281.4 (M+H–CO)$^+$; 263.4 (M+H–CO–H$_2$O)$^+$ h) Allyl (1aS,3aR,6bS)-2-acetyl-5-(1-methyl-1H-tetrazo1-5-ylsulphanylmethyl)-1-oxo-1,1a,2,3,3a,6b-hexahydro-4-oxa-2,6a-diazacyclobut[cd]indene-6-carboxylate Was obtained in analogy to Example 29(d) starting from allyl (1aS,3aR,6bS)-2-acetyl-5-hydroxymethyl-1-oxo-1,1 a,2,3,3a,6b-hexahydro4-oxa-2,6-diazacyclobut[cd]indene-6-carboxylate and bis-(5-mercapto-1-methyltetrazolyl)-dithiocarbonate in 59% yield.

IR (KBr): 1781, 1711, 1660, 1615, 1415 cm$^{-1}$ MS (ISP): 424.5 (M+NH$_4$)$^+$; 407.4 (M+H)$^+$

EXAMPLE 36

(1aS,3aR,6bR)-2-t-Butoxycarbonyl-5-methyl-1-oxo-1a,2,3, 3a,4, 6b-hexahydro-4-oxa-2,6a-diazacyclobut[cd]indene-6-carboxylic acid sodium salt (1:1)

Dibenzyl (1aS,3aR,6bR)-5-methyl-1-oxo-1a,2,3,3a,4,6b-hexahydro-4-oxa-2,6a-diazacyclobut[cd]indene-2,6-dicarboxylate (334 mg; 0.76 mmol) was dissolved in THF/water (8:2; 15 ml) and hydrogenated over 10% Pd/C (100 mg). The mixture was filtered and concentrated. The residue consisted of crude 5-methyl-1-oxo-1a,2,3,3a,4,6b-hexahydro-4-oxa-2, 6a-diazacyclobut[cd]indene-6-carboxylic acid; this was dissolved in dioxan/water (2:1; 5 ml) and treated with sodium bicarbonate (57 mg; 0.68 mmol) and di-t-butyl dicarbonate (149 mg; 0.68 mmol). The mixture was stirred overnight. The dioxan was evaporated. The residue was fractionated over a polymeric, hydrophobic gel with water and water methanol 9:1. The fractions containing the product were combined and lyophilized. Yield: 44 mg (21%) of colourless powder.

IR (KBr): 1759, 1703, 1636 cm$^{-1}$ MS (ISP): (M+Na$^+$)333

The product can be converted with trifluoroacetic acid according to Example 2 (a) into (1aS,3aR,6bR)-5-methyl-1-oxo-1a,2,3,3a,4,6b-hexahydro-4-oxa-2,6a-diaza cyclobut[cd]indene-6-carboxylic acid trifluoroacetate.

The dibenzyl (1aS,3aR,6bR)-5-methyl-1-oxo-1a,2,3,3a,4,6b-hexahydro-4-oxa-2,6a-diazacyclobut[cd]indene-2,6-dicarboxylate used as the starting material was prepared as follows:

a) Benzyl (1S,4S,5S)-6-benzyloxycarbonylmethyl-7-oxo-4-(tetrahydropyran-2-yloxy)-2,6-diazabicyclo[3.2.0]heptane-2-carboxylate (diastereoisomeric mixture)

(1S,4S,5S)-2-Benzyloxycarbonyl-4-[(R)-and (S)-tetrahydropyran-2-yloxy]-2,6-diazabicyclo[3.2.0]heptan-7-one (1:1 mixture; 3.46 g; 10 mmol) (European Patent Publication 508 234, Example 14) was dissolved in abs. THF (100 ml) and treated at −78° C. with 1M bistrimethylsilyllithium amide solution in THF (11.5 ml) and benzyl bromoacetate (2.51 g; 11 mmol). The reaction mixture was warmed to −10° C., diluted with saturated aqueous sodium chloride solution and extracted with ether. The organic phase was dried over magnesium sulphate and concentrated. The residue was chromatographed over silica gel (0.0062–0.2 mm particle size) with ethyl acetate/n-hexane 1:1. Yield: 1.83 g (38%) of colourless oil.

IR (KBr): 1770, 1740, 1705 cm$^{-1}$ MS (ISP): 517.5 (M+Na$^+$) 512.5 (M+NH4$^+$), 512 (M+H$^+$)

b) (1S,4S,5S)-6-(1-Benzyloxycarbonyl-2-oxo-propyl)-4-hydroxy-7-oxo-2,6-diazabicyclo[3.2.0]heptane-2-carboxylate (diastereoisomeric mixture)

A solution of benzyl (1S,4S,5s)-6-benzyloxycarbonylmethyl-7-oxo-4-(tetrahydropyran-2-yloxy)-2,6-diazabicyclo[3.2.0]heptane-2-carboxylate (1.88 g, 3.82 mmol) was dissolved in abs. THF (40 ml) and treated at −70° C. with a 1M bis-trimethylsilyllithium amide solution in THF (4.77 ml, 4.77 mmol). The reaction mixture was warmed to −40° C., again cooled to −70° C. after 20 minutes and treated with a solution of acetyl chloride (0.59 ml, 8.40 mmol) in THF (10 ml). The reaction mixture was stirred at room temperature overnight, diluted with saturated aqueous ammonium chloride solution and extracted with ethyl acetate (3×50 ml). The organic phases were washed with saturated aqueous sodium chloride solution, dried over magnesium sulphate and concentrated. The residue was chromatographed over silica gel (0.0062–0.2 mm particle size) with ethyl acetate/n-hexane 3:7. Yield: 1.1 g (54%) of crude benzyl (1S,4S, 5S)-6-(1-benzyloxycarbonyl-2-oxo-propyl)-7-oxo-4-(tetrahydropyran-2-yloxy)-2,6-diazabicyclo[3.2.0]heptane-2-carboxylate as a colourless oil. This oil was dissolved in ethanol (15 ml) and treated with pyridinium (toluene-4-sulphonate) (110 mg) at 60° C. during 2 hours. The solvent was evaporated and the residue was taken up in ethyl acetate:and washed with water. The organic phase was dried over magnesium sulphate, concentrated and chromatographed over silica gel (0.0062–0.2 mm particle size) with ethyl acemte/n-hexane 1:1. Yield 483 mg (52%) of colourless oil.

IR (KBr): 3447, 1773, 1710, 1773 cm$^{-1}$ MS 475.3 (M+Na)$^+$ c) Dibenzyl (1aS,3aR,6bR)-5-methyl-1-oxo-1a,2,3,3a,4,6-hexahydro-4-oxa-2,6a-diazacyclobut[cd]indene-2,6-dicarboxylate A solution of benzyl (1S,4S,5S)-6-(1-benzyloxycarbonyl-2-oxo-propyl)-4-hydroxy-7-oxo-2,6-diazabicyclo[3.2.0]heptane-2-carboxylate (452 mg, 1 mmol) in 10 ml of abs. THF is treated at −10° C. with triphenylphosphine (340 mg, 1.3 mmol) and diethyl azodicarboxylate (226 mg, 1.3 mmol). The reaction mixture was stirred overnight, the solvent was evaporated and the residue was chromatographed over silica gel (0.0062–0.2 mm particle size) with ethyl acetate/CH$_2$Cl$_2$ 5:95. Yield: 362 mg (83%).

IR (KBr): 1781, 1713, 1617, 1423, 1214, 1097 cm$^{-1}$ MS: 457.3 (M+Na$^+$), 452.4 (M+NH$_4^+$), 435.3 (M+H$^+$)

EXAMPLE 37

(1aS,3aR,6bS)-5-(1-Cyclopropylcarbamoylmethyl-1H-tetrazol-5-ylsulphanylmethyl)-2-formyl-1-oxo-1,1a,2,3,3a,6b-hexahydro-4-oxa-2,6a-diazacyclobut[cd]indene-6-carboxylic acid sodium salt Formic acid-acetic acid anhydride (133 mg; 1.5 mmol) was added dropwise to a solution, cooled to 0° C., of (1aS,3aR,6bS)-5-(1-cyclopropylcarbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid (120 mg; 0.29 mmol; Example 29(g)) in DMF. The batch was stirred at room temperature for 1 hour. The reaction mixture was poured into 10 ml of water, adjusted to pH 7 with sodium bicarbonate and concentrated. The residue was taken up in a small amount of water and chromatographed over a hydrophobic polymer (eluent: water/acetonitrile). 36 mg (27%) were obtained as a white powder.

IR (KBr): 1765, 1667, 1594, 1390 cm$^{-1}$ MS (ISP): 480.2 (M+Na)$^+$; 458.2 (M+H)$^+$; 436.2 (M–Na+2H)$^+$

EXAMPLE 38

(a) (1aS,3aR,6bS)-2-Formyl-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Starting from (1aS,3aR,6bS)-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylic acid (67 mg; 0.21 mmol; Example 29(e)), formic acid (0.12 ml; 3.2 mmol) and dicyclohexylcarbodiimide (85 mg; 0.41 mmol) thee were obtained in analogy to Example 39 17 mg (22%) as a white powder.

IR (KBr): 1765, 1662, 1590, 1388 cm$^{-1}$ MS (ISP): 375.2 (M+H)$^+$; 371.4 (M–Na+H+NH$_4$)$^+$; 353.2 (M–Na+2H)$^+$

In analogy to this there were prepared:

(b) (1aS,3aR,6bS)-5-(1-Carbamoylmethyl-1H-tetrazol-5-ylsulfanylmethyl)-2-formyl-1-oxo-1,1a,2,3,3a,6b-hexahydro-4-oxa-2,6a-diaza-cyclobut[cd]indene-6-carboxylic acid sodium salt Starting from (1aS,3aR,6bS)-5-(1-carbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid (100 mg; 0.27 mmol; Example 29(j)) there were obtained 26 mg (23%) as a white powder.

IR (KBr): 1763, 1661, 1628, 1594, 1391 cm$^{-1}$ MS (ISP): 440.3 (M+Na)$^+$; 418.3 (M+H)$^+$; 413.3 (M–Na+H+NH$_4$)$^+$; 396.3 (M–Na+2H)$^+$ (c) (1aS,3aR,6bS)-2-Formyl-5-(1-(2-morpholin-4-yl-2-oxoethyl)-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt Starting from (1aS,3aR,6bS)-5-(1-(2-morpholin-4-yl-2-oxo-ethyl)-1H-tetrazol-5-ylsulphanylmethyl)-1-oxo-1,1a,2,3,3a,6b-hexahydro-4-oxa-2,6a-diazacyclobut[cd]indene-6-carboxylic acid (106 mg; 0.24 mmol; Example 29(1)) there were isolated 51 mg (43%) as a white powder.

IR (KBr): 1764, 1661, 1594, 1391 cm$^{-1}$ MS (ISN): 464.2 (M–Na)$^-$ (d) (1aS,3aR,6bS)-2-Formyl-1-oxo-5-(1-(trityloxycarbamoylmethyl)-1H-tetrazol-5-ylsulphanylmethyl)-1,1a,2,3,3a,6b-hexahydro-4-oxa-2,6a-diazacyclobut[cd]indene6-carboxylic acid sodium salt Starting from (1aS,3aR,6bS)-1-oxo-5-(1-(trityloxycarbamoylmethyl)-1H-tetrazol-5-ylsulphanylmethyl)-1,1a,2,3,3a,6b-hexahydro-4-oxa-2,6a-diazacyclobut[cd]indene-6-carboxylic acid (84 mg; 0.13 mmol; Example 29(n)) there were isolated 34 mg (38%) of white powder.

IR (KBr): 1761, 1665, 1629, 1599, 1388, 764, 704 cm$^{-1}$
MS (ISP): 698.4 (M+Na)$^+$; 676.3 (M+H)$^+$; 671 (M–Na+H+NH$_4$)$^+$; 654.3 (M–Na+2H)$^+$

EXAMPLE 39

(1aS,3aR,6bS)-5-(1-Carbamoylmethyl-1H-tetrazol-5-ylsulphanylmethyl)-1-oxo-2-trifluoroacetyl-1,1a,2,3,3a,6b-hexahydro-4-oxa-2,6a-diazacyclobut[cd]indene-6-carboxylic acid sodium salt Trifluoroacetic acid (0.31 ml; 4.1 mmol) and dicyclohexylcarbodiimide (111 mg; 0.54 mmol) were added to a solution of (1aS,3aR,6bS)-5-(1-carbamoylmethyl-1H-tetrazol-5-ylsulphanylmethyl)-1-oxo-1,1a,2,3,3a,6b-hexahydro-4-oxa-2,6a-diazacyclobut[cd]indene-6-carboxylic acid (100 mg; 0.27 mmol; Example 29(j)) in DMF. The reaction mixture was stirred for 1 hour. The resulting precipitate was filtered off. The filtrate was concentrated, taken up in a small amount of water, adjusted to pH 7 with sodium bicarbonate and chromatographed over a hydrophobic polymer (eluent: water/acetonitrile). 30 mg (23%) were obtained as a white powder.

IR (KBr): 1772, 1696, 1628, 1596, 1394, 1212 cm$^{-1}$
MS(ISP): 486.3 (M+H)$^+$; 481.2 (M–Na+H+NH$_4$)$^+$; 464.3 (M–Na+2H)$^+$

EXAMPLE 40

(a) (1aS,3aR,6bS)-5-(1-Methyl-1H-tetrazol-5-ylsulphanylmethyl)-1-oxo-4-thia-1,1a,2,3,3a,6b-hexahydro-2,6a-diazacyclobut[cd]indene-6-carboxylic acid Was prepared in analogy to Example 29(a) starting from diallyl (1aS,3aR,6bS)-5-(1-methyl-1H-tetrazol-5-ylsulphanylmethyl)-1-oxo-4-thia-1,1a,2,3,3a,6b-hexahydro-2,6a-diazacyclobut[cct]indene-2,6-dicarboxylate in 26% yield as a white powder.

IR (KBr): 1766, 1703, 1617, 1580, 1377 cm$^{-1}$ MS (ISN): 339.2 (M–Na)$^-$; 295.2 (M–CO$_2$–Na)$^-$

The diallyl (1aS,3aR,6bS)-5-(1-methyl-1H-tetrazol-5-ylsulphanylmethyl)-1-oxo-4-thia-1,1a,2,3,3a,6b-hexahydro-2,6a-diazacyclobut[cd]indene-2,6-dicarboxylate used as the starting material was prepared as follows:

a) 1:1:1:1 Mixture of allyl (1S, 4S, SS)-6-[(R) and (S)-1-allyloxycarbonyl-3-(t-butyl-dimethyl-silanyloxy)-2-oxopropyl]-4-methylsulphonyloxy-7-oxo-2,6-diaza-bicyclo[3.2.0]heptane-2-carboxylate A solution of 1:1:1:1 mixture of allyl (1S,4S,5S)-6-[(R)-and (S)-1-allyloxycarbonyl-3-(t-butyl-dimethyl-silanyloxy)-2-oxo-propyl]-4-hydroxy-7-oxo-2,6-diazabicyclo[3.2.0]heptane-2-carboxylate (3.08 g; 6.16 mmol; from Example 28f)) in methylene chloride (50 ml) was treated dropwise at –10° C. with mesyl chloride (1.15 ml, 14.78 mmol) and a solution of DABCO (1.8 g; 16.01 mmol) in methylene chloride (20 ml). The solution was stirred at room temperature for 20 minutes and then washed with cold water. The organic phase was dried and concentrated. The residue was chromatographed over silica gel with ethyl acetate/n-hexane 4:6. Yield: 2.8 g; (71%).

IR (film): 2934, 1786, 1716, 1412, 1366, 1174 cm$^{-1}$ MS (ISP): 656.5 (M+NH$_4$)$^+$)

b) Diallyl (1aS,3aaR,6bS)-5-(t-butyl-dimethyl-silanyloxymethyl)-1-oxo-1,1a,2,3,3a,6b-hexahydro-4-thia-2,6a-diazacyclobut[cd]indene-2,6-dicarboxylate Aluminium oxide (5 g; basic, activity grade I) is suspended in DMSO (15 ml) and treated with sodium hydrogen sulphide (780 mg) while stirring. The suspension was stirred for a further hour and was then concentrated. The powder obtained was dried in a high vacuum.

A solution of a 1:1:1:1 mixture of allyl (1S,4S,5S)-6-[(R) and (S)-1-allyloxycarbonyl-3-(t-butyl-dimethylsilanyloxy)-2-oxo-propyl]-4-methylsulphonyloxy-7-oxo-2,6-diaza-bicyclo[3.2.0]heptane-2-carboxylate (913 mg, 1.42 mmol) in methylene chloride (20 ml) was treated with the above-described reagent (2.84 g). The suspension was stirred overnight, suction filtered and rinsed with methylene chloride. The Filtrate was washed with water, dried and concentrated. The residue was chromatographed over silica gel with ethyl acetate/n-hexane (3:7). Yield: 540 mg (79%.)

IR (film): 2931, 1780, 1709, 1571, 1411 cm$^{-1}$ MS (ISP): 498.6 (M+NH$_4$$^+$); 481.6 (M+H$^+$)

c) Diallyl (1aS,3aR,6bS)-5-hydroxymethyl-1-oxo-1,1a,2,3,3a,6b-hexahydro-4-thia-2,6a-diazacyclobut[cd]indene-2,6-dicarboxylate A solution of diallyl (1aS,3aR,6bS)-5-(t-butyl-dimethylsilanyloxymethyl)-1-oxo-1,1a,2,3,3a,6b-hexahydro-4-thia-2,6a-diazacyclobut[cd]indene-2,6-dicarboxylate (7.5 g; 162 mmol) in acetonitrile (30 ml) was treated with a 2N hydrogen fluoride solution in acetonitrile (24.3 ml; 486 mmol). The solution was stirred at room temperature for 1.5 hours, then diluted with ethyl acetate and washed with a mixture of water and dilute sodium bicarbonate solution. The organic phase was dried and concentrated. The residue was chromatographed over silica gel with ethyl acetate/n-hexane (2:3). Yield: 4.0 g (68%.)

IR (KBr): 1775, 1707, 1648, 1574, 1412 cm$^{-1}$ MS (ISP): 482.3 (M+NH$_4$)$^+$; 465.4 (M+H)$^+$ d) Diallyl (1aS,3aR,6bS)-5-methylsulphonyloxymethyl-1-oxo-1,1a,2,3,3a,6b-hexahydro-4-thia-2,6a-diazacyclobut[cd]-indene-2,6-dicarboxylate A solution of diallyl (1aS,3aR,6bS)-5-hydroxymethyl-1-oxo-1,1a,2,3,3a,6b-hexahydro-4-thia-2,6a-diazacyclobut[cd]indene-2,6-dicarboxylate (4.02 g; 10.97 mmol) in methylene chloride (75 ml) was treated at –15° C. with triethylamine (1.44 g; 1.98 ml; 14.26 mmol) and mesyl chloride (1.50 g; 1.02 ml; 13.16 mmol). The reaction mixture was stirred at this temperature for 30 minutes, diluted with methylene chloride and washed in succession with saturated aqueous sodium bicarbonate solution and saturated aqueous sodium chloride solution. The organic phase was dried and concentrated. The residue was chromatographed over silica gel with ethyl acetate/n-hexane (1:1). Yield: 4.12 g (84%).

IR (film): 1770, 1702, 1577, 1415, 1363 cm$^{-1}$ MS (ISP): 462.4 (M+NH$_4$$^+$); 445.3 (M+H$^+$)

e) Diallyl (1aS,3aR,6bS)-5-(1-methyl-1H-tetrazol-5-ylsulphanylmethyl)-1-oxo-1,1a,2,3,3a,6b-hexahydro-4-thia-2,6a-diazacyclobut[cd]inden-2,6-dicarboxylate Was prepared in analogy to Example 29(c) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and 5-mercapto-1-methyl-1H-tetrazole.

IR (KBr): 1776, 1709, 1647, 1581, 1411 cm$^{-1}$ MS (ISP): 389.4 (M+Na)$^+$; 384 (M+NH$_4$)$^+$; 367.4 (M+H)$^+$; 339.3 (M+H– CO)$^+$ in analogy to the compound set forth under (a) there were prepared:

(b) (1aS,3aR,6bS)-1-(6-Carboxy-1-oxo-1,1a,2,3 ,3a,6b-hexahydro-4-thia-2,6a-diazacyclobut[cd]indene-5-ylmethyl)-pyridinium methylsulphonate Was prepared starting from (1aS,3aR,6bS)-1-(2,6-bis-allyloxycarbonyl-1-oxo-1,1a,2,3, 3 a,6b-hexahydro-4-thia-2,6a-diazacyclobut[cd]inden-5-ylmethyl)-pyridinium methylsulphonate.

IR (KBr): 1777, 1700, 1632, 1483 cm$^{-1}$ MS (ISP): 304.2 (M+H)$^+$

The (1aS,3aR,6bS)-1-(2,6-bis-allyloxycarbonyl-1-oxo-1,1a,2,3,3a,6b-hexahydro-4-thia-2,6a-diazacyclobut[cd]indene-5-ylmethyl)-pyridinium methylsulphonate used as the starting material was prepared in analogy to Example 40(a) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and pyridine.

IR (KBr): 1777, 1706, 1632, 1584 cm$^{-1}$ MS (ISP): 428.4 (M)$^+$ (c) (1aS,3aR,6bS)-5-(1-Methyl-imidazol-2-ylsulphanyl-methyl)-1-oxo-4-thia-1,1a,2,3,3a,6b-hexahydro-2,6a-diazacyclobut[cd]indene-6-carboxylic acid Was prepared starting from diallyl (1aS,3aR,6bS)-5-(1-methylimidazol-2-ylsulphanymethyl)-1-oxo-4-thia-1,1a,2,3,3a,6b-hexahydro-2,6a-diazacyclobut[cd]indene-2,6-dicarboxylate.

IR (KBr): 1741, 1608, 1374 cm$^{-1}$ MS (ISP): 383.1 (M+2Na–H)$^+$; 361.1 (M+Na)$^+$; 339.2 (M+H)$^+$

The diallyl (1aS,3aR,6bS)-5-(1-methyl-irnidazol-2-ylsulphanylmethyl)-1-oxo-4-thia-1,1a,2,3,3a,6b-hexahydro-2,6a-diazacyclobut[cd]indene-2,6-dicarboxylate used as the starting material was in prepared analogy to Example 40(a) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and 2-mercapto-1-methyl-imidazole.

IR (KBr): 1771, 1698, 1581 cm$^{-1}$ MS (ISP): 463.3 (M+H)$^+$ (d) (1aS,3aR,6bS)-5-(5-Hydroxy-4-methyl-4H—[1,2,4]-triazol-3-ylsulphanylmethyl)-1-oxo-4-thia-1,1a,2,3,3a,6b-hexahydro-2,6a-diazacyclobut[cd]indene-6-carboxylic acid Was prepared starting from diallyl (1aS,3aR,6bS)-5-(5-hydroxy-4-methyl-4H—[1,2,4]-triazol-3-ylsulphanylmethyl)-1-oxo-4-thia-1,1a,2,3,3a,6b-hexahydro-2,6a-diazacyclobut[cd]indene-2,6-dicarboxylate.

IR (KBr): 1741, 1707, 1606, 1577, 1376 cm$^{-1}$ MS (ISP): 356.2 (M+2H–Na)$^+$

The diallyl (1aS,3aR,6bS)-5-(5-hydroxy-4-methyl-4H-[1,2,4]-triazol-3-ylsulphanylmethyl)-1-oxo-4-thia-1,1a,2,3,3a,6b-hexahydro-2,6a-diazacyclobut[cd]indene-2,6-dicarboxylate used as the starting material was prepared in analogy to Example 40(a) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and 5-hydroxy-4-methyl-4H-[1,2,4]-triazole.

IR (KBr): 1778, 1708, 1411 cm$^{-1}$ MS (ISP): 480.2 (M+H)$^+$ (e) (1aS,3aR,6bS)-5-(5-Amino-1,3,4-thiadiazol-2-ylsulphanylmethyl)-1-oxo-4-thia-1,1a,2,3,3a,6b-hexahydro-2,6a-diazacyclobut[cd]indene-6-carboxylic acid Was prepared starting from diallyl (1aS,3aR,6bS)-5-(5-amino-1,3,4-thiadiazol-2-ylsulphanylmethyl)-1-oxo-4-thia-1,1a,2,3,3a,6b-hexahydro-2,6a-diazacyclobut[cd]indene-2,6-dicarboxylate.

IR (KBr): 1739, 1602, 1494 cm$^{-1}$ MS (ISP): 358.3 (M+H)$^+$

The diallyl (1aS,3aR,6bS)-5-(5-amino-1,3,4-thiadiazol-2-ylsulphanylmethyl)-1-oxo-4-thia-1,1a,2,3,3a,6b-hexahydro-2,6a-diazacyclobut[cd]indene-2,6-dicarboxylate used as the starting material was prepared in analogy to Example 40(a) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and 5-amino-2-mercapto-1,3,4-thiadiazole.

IR (KBr): 1775, 1707, 1493 cm$^{-1}$ MS (ISP): 482.3 (M+H)$^+$ (f) (1aS,3aR,6bS)-1-Oxo-5-(pyridin-4-ylsulphanyLmethyl)-4-thia-1,1a,2,3,3a,6b-hexahydro-2,6a-diazacyclobut[cd]indene-6-carboxylic acid Was prepared starting from diallyl (1aS,3aR,6bS)-1-oxo-5-(pyridin-4-ylsulphanylmethyl)-4-thia-1,1a,2,3,3a,6b-hexahydro-2,6a-diazacyclobut[cd]indene-2,6-dicarboxylate.

MS (ISP): 358.2 (M+H)$^+$; 336.2 (M–Na+2H)$^+$

The diallyl (1aS,3aR,6bS)-1-oxo-5-(pyridin-4-ylsulphanylmethyl)-4-thia-1,1a,2,3,3a,6b-hexahydro-2,6a-diazacyclobut[cd]-indene-2,6-dicarboxylate used as the starting material was prepared in analogy to Example 40(a) starting from diallyl (1aS,3aR,6bS)-5-methylsulphonyloxymethyl-1-oxo-1,1a,2,3, 3a,6b-hexahydro-4-thia-2,6a-diazacyclobut[cd]indene-2,6-dicarboxylate and 4-mercapto-pyridine.

IR (film): 1775, 1709, 1647, 1574 cm$^{-1}$ Microanalysis: $C_{21}H_{21}N_3O_5S_2$ Calc. C 54.89 H 4.61 N 9.14 Found C 55.06 H 4.70 N 8.90

(g) (1aS,3aR,6bS)-5-[1-(2-Morpholin-4-yl-2-oxo-ethyl)-1H-tetrazol-5-ylsulphanylmethyl]-1-oxo-4-thia-1,1a,2,3,3a,6b-hexahydro-2,6a-diazacyclobut[cd]indene-6-carboxylic acid Was prepared in analogy to Example 29(a) starting from diallyl (1aS,3aR,6bS)-5-[1-(2-morpholin-4-yl-2-oxo-ethyl)-1H-tetrazol-5-ylsulphanylmethyl]-1-oxo-4-thia-1,1a,2,3,3a,6b-hexahydro-2,6a-diazacyclobut[cd]indene-2,6-dicarboxylate in 90% yield as a white powder.

IR (KBr): 1742, 1660, 1609, 1465, 1376 cm$^{-1}$ MS (ISP): 476.3 (M+H)$^+$; 471.4 (M+H+Na+NH$_4$)$^+$; 454.4 (M+2H–Na)$^+$

The diallyl (1aS,3aR,6bS)-5-[1-(2-morpholin-4-yl-2-oxo-ethyl)-1H-tetrazol-5-ylsulphanylmethyl]-1-oxo-4-thia-1,1a,2,3,3a,6b-hexahydro-2,6a-diazacyclobut[cd]indene-2,6-dicarboxylate used as the starting material was prepared in analogy to Example 40(a) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and 5-mercapto-1-(2-morpholin-4-yl-2-oxo-ethyl)-1H-tetrazole.

IR (KBr): 1777, 1708, 1631, 1666, 1580 cm$^{-1}$ MS (ISP): 600 (M+Na)$^+$; 595.3 (M+NH$_4$)$^+$; 578.3 (M–H)$^+$ (h) (1aS,3aR,6bS)-5-[5-Methyl-1,3,4-thiadiazol-2-ylsulphanylmethyl]-1-oxo-4-thia-1,1a,2,3,3a,6b-hexahydro-2,6a-diazacyclobut[cd]indene-6-carboxylic acid Was prepared in analogy to Example 29(a) starting from diallyl (1aS,3aR,6bS)-5-[5-methyl-1,3,4-thiadiazol-2-ylsulphanylmethyl]-1-oxo-4-thia-1,1a,2,3,3a,6b-hexahydro-2,6a-diazacyclobut[cd]indene-2,6-dicarboxylate in 27% yield as a white powder.

IR (KBr): 1742, 1608, 1378 cm$^{-1}$ MS (ISN): 355.2 (M–Na)$^-$; 311.1 (M–Na–CO$_2$)$^-$

The diallyl (1aS,3aR,6bS)-5-[5-methyl-1,3,4-thiadiazol-2-ylsulphanylmethyl]-1-oxo-4-thia-1,1a,2,3,3a,6b-hexahydro-2,6a-diazacyclobut[cd]indene-2,6-dicarboxylate used as the starting material was prepared in analogy to Example 40(a) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and 5-mercapto-2-methyl-1,3,4-thiadiazole.

IR (film): 1775, 1707, 1579, 1411 cm$^{-1}$

EXAMPLE 41

(a) (1aS,3aR,6bS)-2-(4-Hydroxy-phenylcarbamoyl)-5-(6,7-dihydro-5H-1-pyrindin-4-ylsulphanylmethyl)-1-oxo-4-thia-1,1a,2,3,3a,6b-hexahydro-2,6a-diazacyclobut[cd]indene-6-carboxylic acid sodium salt Was obtained in analogy to Example 31(a) starting from (1aS,3aR,6bS)-5-(6,7-dihydro-5H-1-pyrindin-4-ylsulphanylmethyl)-1-oxo-4-thia-1,1a,2,3,3a,6b-hexahydro-2,6a-diazacyclobut[cd]indene-6-carboxylic acid and 4-hydroxyphenylcarbamic acid 2,5-dioxopyrrolidin-1-yl ester in 44% yield as a colourless powder.

IR (KBr): 1756, 1611, 1572, 1512 cm$^{-1}$ MS (ISP): 511.3 (M−Na+2H)$^+$

The (1aS,3aR,6bS)-5-(6,7-dihydro-5H-1-pyrindin-4-ylsulphanylmethyl)-1-oxo-4-thia-1,1a,2,3,3a,6b-hexahydro-2,6a-diazacyclobut[cd]indene-6-carboxylic acid used as the starting material was prepared in analogy to Example 29(a) and 40(a) starting from diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate and 2,3-cyclopenteno-1H- pyridine-4-thione.

IR (KBr): 1775, 1708, 1567, 1411 cm$^{-1}$ MS (ISP): 500.3 (M+H)$^+$

In analogy to this there were prepared:

(b) (1aS,3aR,6bS)-2-(4-Hydroxy-phenylcarbamoyl)-1-oxo-5-(pyridin-4-ylsulphanylmethyl)-4-thia-1,1a,2,3,3a,6b-hexahydro-2,6a-diazacyclobut[cd]indene-6-carboxylic acid sodium salt Was obtained in analogy to Example 31(a) starting from (1aS,3aR,6bS)-5-(pyridin-4-ylsulphanylmethyl)-1 ,oxo-4-thia-1,1a,2,3,3a,6b-hexahydro-2,6a-diazacyclobut[cd]indene-6-carboxylic acid and 4-hydroxy-phenylcarbamic acid 2,5-dioxopyrrolidin-1-yl ester in 68% yield as a colourless powder.

IR (KBr): 1750, 1609, 1580, 1538, 1512 cm$^{-1}$ MS (ISP): 493.2 (M+H)$^+$; 471.2 (M−Na+2H)$^+$ (c) (1aS,3aR,6bS)-2-(4-Hydroxy-phenylcarbamoyl)-5-(5-methyl-1,3,4-thiadiazol-2-ylsulphanylmethyl)-1-oxo-4-thia-1,1a,2,3,3a,6b-hexahydro-2,6a-diazacyclobut[cd]indene-6-carboxylic acid sodium salt Was obtained in analogy to Example 31(a) starting from (1aS,3aR,6bS)-5-(5-methyl-1,3,4-thiadiazol-2-ylsulphanylmethyl)-1-oxo-4-thia-1,1a,2,3,3a,6b-hexahydro-2,6a-diazacyclobut[cd]indene-6-carboxylic acid and 4-hydroxy-phenylcarbamic acid 2,5-dioxopyrrolidin-1-yl ester in 68% yield as a colourless powder.

IR (KBr): 1751, 1609, 1541, 1513 cm$^{-1}$ MS (ISN): 490.2 (M−Na)$^-$; 446.3 (M−Na−CO$_2$)$^-$ (d) (1aS,3aR,6bS)-2-(4-Hydroxy-phenylcarbamoyl)-5-(1-methyl-1H-tetrazol-5-ylsulphanylmethyl)-1-oxo-4-thia-1,1a,2,3,3a,6b-hexahydro-2,6a-diazacyclobut[cd]indene-6-carboxylic acid sodium salt Was obtained in analogy to Example 31(a) starting from (1aS,3aR,6bS)-5-(1-methyl-1H-tetrazol-5-ylsulphanylmethyl)-1-oxo-4-thia-1,1a,2,3,3a,6b-hexahydro-2,6a-diazacyclobut[cd]indene-6-carboxylic acid and 4-hydroxy-phenylcarbamic acid 2,5-dioxopyrrolidin-1-yl ester in 16% yield as a colourless powder.

IR (KBr): 1750, 1613, 1513 cm$^{-1}$ (1aS,3aR,6bS)-5-Hydroxymethyl-2-(4-hydroxy-phenylcarbamoyl)-1-oxo-4-thia-1,1a,2,3,3a,6b-hexahydro-2,6a-diazacyclobut[cd]indene-6-carboxylic acid was obtained as a byproduct.

IR (KBr): 1748, 1609, 1513,1438cm$^{-1}$ MS (ISN): 398.3 (M)$^-$; 376.3 (M−Na)$^-$.

EXAMPLE 42

(a) (1aS,3aR,6bS)-2-Acetyl-5-(5-methyl-1,3,4-thiadiazol-2-ylsulphanylmethyl)-1-oxo-4-thia-1,1a,2,3,3a,6b-hexahydro-2,6a-diazacyclobut[cd]indene-6-carboxylic acid sodium salt Was obtained in analogy to Example 33 starting from (1aS,3aR,6bS)-5-(5-methyl-1,3,4-thiadiazol-2-ylsulphanylmethyl)-1-oxo-4-thia-1,1a,2,3,3a,6b-hexahydro-2,6a-diazacyclobut[cd]indene-6-carboxylic acid and acetyl chloride in 77% yield as a colourless powder.

IR (KBr): 1759, 1616 cm$^{-1}$ MS (ISP): 443.2 (M+Na)$^+$; 421.2 (M+H)$^+$; 399.2 (M+H−Na)$^+$ (b) (1aS,3aR,6bS)-2-Acetyl-1-oxo-5-(pyridin-4-ylsulphanylmethyl)-4-thia-1,1a,2,3,3a,6b-hexahydro-2,6a-diazacyclobut[cd]Lndene-6-carboxylic acid sodium salt Was obtained in analogy to Example 32 starting from (1aS,3aR,6bS)-5-(pyridin-4-ylsulphanylmethyl)-1-oxo-4-thia-1,1a,2,3,3a,6b- hexahydro-2,6a-diazacyclobut[cd]indene-6-carboxylic acid and acetic anhydride in 42% yield as a colourless powder.

IR (KBr): 1752, 1614, 1576 cm$^{-1}$ MS (ISN): 393.3 (M−Na+NH$_3$)$^-$; 376.2 (M−Na)$^-$ (c) (1aS,3aR,6bS)-2-(2-Amino-1,3,4-thiadiazol-5-ylsulphanylacetyl)-5-(1-methyl-1H-tetrazol-5-ylsulphanylmethyl)-1-oxo-4-thia-1,1a,2,3,3a,6b-hexahydro-2,6a-diazacyclobut[cd]indene-6-carboxylic acid sodium salt Was obtained in analogy to Example 11 starting from (1aS,3aR,6bS)-5-(1-methyl-1H-tetrazol-5-ylsulphanylmethyl)-1-oxo-4-thia-1,1a,2,3,3a,6b-hexahydro-2,6a-diazacyclobut[cd]indene-6-carboxylic acid, bromoacetyl chloride and 2-amino-5-mercapto-1,3,4-thiadiazole in 27% yield as a grey powder.

IR (KBr): 1756, 1616, 1497, 1411 cm$^{-1}$ MS (ISP): 536.2 (M+H)$^+$; 514.2 (M−Na+2H)$^+$

EXAMPLE 43

(1aS,3aR,6bS)-5-(1-Methyl-1H-tetrazol-5-ylmethylsulphanylmethyl)-1-oxo-4-thia-1,1a,2,3,3a,6b-hexahydro-2,6a-diazacyclobut[cd]indene-6-carboxylic acid sodium salt Was prepared in analogy to Example 29(a) starting from diallyl (1aS,3aR,6bS)-5-(1-methyl-1H-tetrazol-5-ylmethylsulphanylmethyl)-1-oxo-4-thia-1,1a,2,3,3a,6b-hexahydro-2,6a-diazacyclobut[cd]indene-2,6-dicarboxylate in 28% yield as a white powder.

IR (KBr): 1740, 1606, 1466, 1573cm$^{-1}$ MS (ISP): 377.2 (M+H)$^+$; 355.2 (M+2H−Na)$^+$

The diallyl (1aS,3aR,6bS)-5-(1-methyl-1H-tetrazol-5-ylmethylsulphanylmethyl)-1-oxo-4-thia-1,1a,2,3,3a,6b-hexahydro-2,6a-diazacyclobut[cd]indene-2,6-dicarboxylate used as the starting material was prepared as follows:

A solution of diallyl (1aS,3aR,6bS)-5-methylsulphonyloxymethyl-1-oxo-1,1a,2,3,3a,6b-hexahydro-4-thia-2,6a-diazacyclobut[cd]indene-2,6-dicarboxylate (11 mg; 0.25 mmol) in 1N sodium hydroxide solution (0.5 ml) was treated at 0° C. with tetrabutylammonium bromide (32 mg; 0.1 mmol) and a solution of 5-mercaptomethyl-1H-1-methyltetrazole (65 mg; 0.5 mmol) in methylene chloride. The reaction mixture was stirred for 4 hours. The organic phase was separated and washed with water, then dried and concentrated. The residue was chromatographed with ethyl acetate/n-hexane (1:1). Yield 73 mg (63%).

IR (KBr): 1774, 1707, 1579, 1411 cm$^{-1}$ MS (ISP): 479.3 (M+H)$^+$

EXAMPLE 44

(1aS,3aR,6bS)-5-(5-Methylsulphanyl-1H-tetrazol-1-ylmethyl)-1-oxo-1,1a,2,3,3a,6b-hexahydro-4-thia-2,6a-diazacyclobut[cd]indene-6-carboxylic acid sodium salt Was obtained in analogy to Example 29(a) starting from diallyl (1aS,3aR,6bS)-5-(5-methylsulphanyl-1H-tetrazol-1-ylmethyl)-1-oxo-1,1a,2,3,3a,6b-hexahydro-4-thia-2,6a-diazacyclobut[cd]indene-2,6-dicarboxylate in 33% yield.

IR (KBr): 1745, 1614, 1384, 1351 cm$^{-1}$ MS (ISP): 363.2 (M+H)$^+$; 341.3 (M−Na+2H)$^+$

The starting material used was prepared in analogy to Example 29(c) from diallyl (1aS,3aR,6bS)-5-hydroxymethyl-1-oxo-1,1a,2,3,3a,6b-hexahydro-4-oxa-2,6-diazacyclobut[cd]indene-2,6-dicarboxylate and 5-methylsulphanyl-1H-tetrazole in 41% yield.

IR (KBr): 1774, 1701, 1700, 1418 cm$^{-1}$ MS (ISP): 487.3 (M+Na)$^+$; 482.3 (M+NH$_4$)$^+$; 365.3 (M+H)$^+$

EXAMPLE 45

(1aS,3aR,6bR)-1-Oxo-5-vinyl-1a,2,3,3a,4,6b-hexahydro-1H-2,6a-diazacyclobut[cd]indene-6-carboxylic acid trifluoroacetate Starting from di-t-butyl (1aS,3aR,6bR)-1-oxo-5-vinyl-1a,2,3,3a,4,6b-hexahyctro-1H-2,6a-diazacyclobut[cd]indene-2,6-dicarboxylate (185 mg; 0.49 mmol) there were obtained in analogy to Example 2(a) 120 mg (73%) as a yellowish solid.

IR (KBr): 1771, 1678, 1662, 1201 cm$^{-1}$ MS (ISP): (M+H)$^+$ 221.3

The di-t-butyl (1aS,3aR,6bR)-1-oxo-5-vinyl-1a,2,3,3a,4,6b-hexahydro-1H-2,6a-diazacyclobut[cd]indene-2,6-dicarboxylate used as the starting material was prepared as follows:

Tris (dibenzylidene acetone)-dipalladium(0) (10 mg; 0.011 mmol), zinc chloride (136 mg; 1.0 mmol), tri-(2-furyl)phosphine (4.5 mg; 0.019 mmol) and finally trimethylvinylstannane (114 mg; 0.60 mmol) were added in succession to a solution of di-t-butyl (1aS,3a-R,6bR)-1-oxo-5-trifluoromethylsulphonyloxy-1a,2,3,3a,4,6b-hexahydro-1H-2,6a-diazacyclobut[cd]indene-2,6-dicarboxylate (250 mg; 0.50 mmol; from Example 2(d)) in 1-methyl-2-pyrrolidinone (2 ml). The mixture was stirred at room temperature for 4.5 hours. The reaction mixture was poured into water (20 ml) and extracted with ethyl acetate (25 ml). The organic phase was washed with water (20 ml), dried over magnesium sulphate and concentrated. The residue was chromatographed on silica gel (eluent: ethyl acetate/n-hexane 1:4). 110 mg (61%) were obtained as a white solid.

IR(KBr): 1765, 1708, 1242, 1161, 990, 926 cm$^{-1}$ MS (ISP): 399.4 (M+Na)$^+$; 394.4 (M+NH$_4$)$^+$; 377.4 (M+H)$^+$

EXAMPLE 46

(a) (1aS,3aR,6bR)-2-(4-Hydroxy-phenylcarbamoyl)-1-oxo-5-vinyl-1a,2,3,3a,4,6b-hexahydro-1H-2,6a-diazacyclobut[cd]indene-6-carboxylic acid sodium salt Starting from (1aS,3aR,6bR)-1-oxo-5-vinyl-1a,2,3,3a,4,6b-hexahydro-1H-2,6a-diazacyclobut[cd]indene-6-carboxylic acid trifluoroacetate (133 mg; 0.40 mmol; from Example 45) there were isolated in analogy to Example 3(a) 75 mg (50%) as a white powder.

IR (KBr): 3417, 1745, 1606, 1513, 1393, 1244, 990, 905 cm$^{-1}$ MS (ISN): (M–Na)$^-$ 354.4

(b) (1aS,3aR,6bR)-2-(4-Carbamoyl-phenylcarbamoyl)-1-oxo-5-vinyl- 1a,2,3,3a,4,6b-hexahydro-1H-2,6a-diazacyclobut[cd]-indene-6-carboxylic acid sodium salt Starting from (1aS,3aR,6bR)-1-oxo-5-vinyl-1a,2,3,3a,4,6b-hexahydro-1H-2,6a-diazacyclobut[cd]indene-6-carboxylic acid trifluoroacetate (133 mg; 0.40 mmol; from Example 45) there were isolated in analogy to Example 3(a) 66 mg (41%) as a white powder.

IR (KBr): 3423, 1748, 1663, 1605, 1524, 1411, 990, 905, 853 cm$^{-1}$ MS (ISN): (M–Na)$^-$ 381.4

EXAMPLE 47

(1aS,3aR,6bR)-2-Acetyl-1-oxo-5-vinyl-1a,2,3,3a,4,6b-hexahydro-1H-2,6a-diazacyclobut[cd]indene-6-carboxylic acid sodium salt Starting from (1aS,3aR,6bR)-1-oxo-5-vinyl-1a,2,3,3a,4,6b-hexahydro-1H-2,6a-diazacyclobut[cd]indene-6-carboxylic acid trifluoroacetate (133 mg; 0.40 mmol; from Example 45) there were isolated in analogy to Example 3(ah) 54 mg (48%) as a beige powder.

IR (KBr): 1751, 1615, 1399, 990, 905 cm$^{-1}$ MS (ISN): (M–Na)$^-$ 278.4

EXAMPLE 48

(a) (Z)-(1aS,3aR,6bR)-5-(2-Cyanovinyl)-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (Z)-((1aS,3aR,6bR)-5-(2-cyanovinyl)-1-oxo-1a,2,3,3a,4,6b-hexahydro-1H-2,6a-diaza-cyclobut[cd]indene-2,6-dicarboxylate (500 mg; 1.25 mmol). Yield: 375 mg (84 %) as a yellow solid.

IR (KBr): 2208, 1781, 1676, 1596, 1201 cm$^{-1}$ MS (ISP): (M +H)$^+$ 246.2

(b) (E)-(1aS,3aR,6bR)-5-(2-Cyanovinyl)-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (E)-(1aS,3aR,6bR)-5-(2-cyanovinyl)-1-oxo-1a,2,3,3a,4,6b-hexahydro-1H-2,6a-diaza-cyclobut[cd]indene-2,6-dicarboxylate (500 mg; 1.25 mmol). Yield: 353 mg (79 %) as a beige solid.

IR (KBr): 2215, 1782, 1676, 1602, 1201 cm$^{-1}$ MS (ISP): (M+H)$^+$ 246.3

The starting materials used were prepared as follows:

a) Di-t-butyl (1aS,3aR,6bR)-5-formyl-1-oxo-1a,2,3,3a,4,6b-hexahydro-1H-2,6a-diazacyclobut[cd]indene-2,6-dicarboxylate This compound was prepared in the same manner as given in Example 1(c) starting from di-t-butyl (1aS,3aR,6bR)-5-hydroxy-methyl-1-oxo-1a,2,3,3a,4,6b-hexahydro-1H-2,6a-diazacyclobut[cd]indene-2,6-dicarboxylate (760 mg; 2.00 mmol). 757 mg (100%) are obtained as a beige solid.

IR (KBr): 2760, 1789, 1711, 1672 cm$^{-1}$ MS (EI): (M–$^t$BuO) 305 b) Di-t-butyl (Z)- and (E)-(1aS,3aR,6bR)-5-(2-cyanovinyl)-1-oxo-1a,2,3,3a,4,6b-hexahydro-1H-2,6a-diazacyclobut[cd]-indene-2,6-dicarboxylate Di-t-butyl (1aS,3aR,6bR)-5-formyl-1-oxo-1a,2,3,3a,4,6b-hexahydro-1H-2,6a-diazacyclobut[cd]indene-2,6-dicarboxylate (757 mg; 2.00 mmol) was dissolved in acetonitrile and treated at −20° C. with lithium perchlorate (212 mg; 2.00 mmol) and cyanomethylenetriphenylphosphorane (602 mg; 2.00 mmol). After 2 hours the solution was diluted with ethyl acetate (100 ml) and washed in succession with 1N aqueous hydrochloric acid (50 ml) and saturated aqueous sodium chloride solution (50 ml). The organic phase was dried over magnesium sulphate and concentrated. The separation of the Z and E isomers was effected by chromatography over silica gel (50 g; 0.040–0.063 mm particle size) with ethyl acetate/n-hexane 1:1.

Yield Z isomer: 217 mg (27%) as a yellow solid.

IR (KBr): 2208, 1708, 1707, 1597 cm$^{-1}$ MS (ISP): (M+NH$_4^+$) 419.4

Yield E isomer: 289 mg (36%) as a yellow viscous oil.

IR (KBr): 2216, 1781, 1707, 1602 cm$^{-1}$ MS (ISP): (M+NH$_4^+$) 419.4

EXAMPLE 49

(a) (Z)-(1a,3aR,6bR)-5-(2-Cyanovinyl)-2-(4-hydroxyphenylcarbamoyl)-1-oxo-aa,2,3,3a,4,6b-hexahydro-1H-2,6a-diazacyclobut[cd]indene-6-carboxylic acid sodium salt This compound was prepared in the same manner as given in Example 3(a) starting from (Z)-(1aS,3aR,6bR)-5-(2-cyanovinyl)-1-oxo-1a,2,3,3a,4,6b-hexahydro-1H-2,6a-diazacyclobut[cd]indene-6-carboxylic acid trifluoroacetate (195 mg; 0.6 mmol). Yield 85 mg (35%) as an orange powder.

IR (KBr): 2200, 1756, 1609, 1390, 1239 cm$^{-1}$ MS (ISN): (M–Na)$^-$ 379.2

(b) (E)-(1aS,3aR,6bR)-5-(2-Cyanovinyl)-2-(4-hydroxyphenylcarbamoyl)-1-oxo-1a,2,3,3a,4,6b-hexahydro-1H-2,6a-diazacyclobut[cd]indene-6-carboxylic acid sodium salt This compound was prepared in the same manner as given in Example 3(a) starting from (E)-(1aS,3aR,6bR)-5-(2-cyanovinyl)-1-oxo-1a,2,3,3a,4,6b-hexahydro-1H-2,6a-diazacyclobut[cd]indene-6-carboxylic acid trifluoroacetate (195 mg; 0.6 mmol). Yield: 98 mg (41%) as a pink-red powder.

IR (KBr): 2216, 1756, 1609, 1391, 1248 cm$^{-1}$ MS (ISN): (M–Na)$^-$ 379.0

EXAMPLE 50

(1aS,3aR,6bR)-[4-(6-Carboxy-1-oxo-1a,2,3,3a,4,6b-hexahydro-1H-2,6a-diazacyclobut[cd]indene-5-ylmethylsulphanyl)-pyridin-1-ylio]acetate trifluoroacetate This compound was prepared in the same manner as given in Example 2(a) starting from (1aS,3aR,6bR)-4-(2,6-bis-t-butoxycarbonyl-1-oxo-1a,2,3,3a,4,6b-hexahydro-1H-2,6a-diazacyclobut[cd]-indene-5-ylmethylsulphanyl)-1-t-butoxycarbonylmethyl-pyridinium bromide (370 mg; 0.604 mmol). Yield: 289 mg (98 %) as a light yellow solid.

IR (KBr): 1777, 1679, 1390, 1197 cm$^{-1}$ MS (ISP): (M+H)$^+$ 376.2

The starting material was prepared in analogy to Example 20 starting from di-t-butyl (1aS,3aR,6bR)-1-oxo-5-(pyridin-4-ylsulphanylmethyl)-1a,2,3,3a,4,6b-hexahydro-1H-2,6a-diazacyclobut[cd]indene-2,6-dicarboxylate (452 mg; 0.874 mmol; from Example 17) and t-butyl bromoacetate (0.64 ml; 4.37 mmol). Yield: 487 mg (85%) as a colourless powder.

IR (KBr): 1777, 1742, 1705, 163 1, 1494 cm$^{-1}$ MS (ISP): M$^+$ 588.5

EXAMPLE 51

(1aS,3aR,6bR)-[4-(2-Benzylcarbamoyl-6-carboxy-1-oxo-1a,2,3,3a,4,6b-hexahydro-1H-2,6a-diazacyclobut[cd]inden-5-ylmethylsulphanyl)-pyridin-2-ylio]-acetate sodium salt This compound was prepared in the same manner as given in Example 27(c) starting from (1aS,3aR,6bR)-[4-(6-carboxy-1-oxo-1a,2,3,3a,4,6b-hexahydro-1H,2,6a-diazacyclobut[cd]inden-5-ylmethylsulphanyl)-pyridin-1-ylio]acetate trifluoroacetate (377 mg; 0.77 mmol). Yield: 41 mg (10%) as a light yellow powder.

IR (KBr): 1752, 1632, 1541, 1492, 1374 cm$^{-1}$ MS (ISN): (M–H)$^-$ 507.2

EXAMPLE 52

(a) (1aS,3aR,6bR)-[4-(2-Acetyl-6-carboxy-1-oxo-1a,2,3,3a,4,6b-hexahydro-1H-2,6a-diaza-cyclobut[cd]inden-5-ylmethylsulphanyl)-pyridinio]-acetate bromoacetate (1:3.18) sodium salt (1:4.18)

(1aS,3a,R,6bR)-1-Oxo-5-(pyridin-4-ylsulphanylmethyl)-1a,2,3,3a,4,6b-hexahydro-1H-2,6a-diazacyclobut[cd]indene-6-carboxylic acid trifluoroacetate (165 mg; 0.3 mmol) was placed in dimethylformamide (2 ml) at 0° C. and treated with sodium bicarbonate (108 mg; 1.29 mmol) and acetyl chloride (0.026 ml; 0.36 mmol). After 1 hour sodium bicarbonate (60 mg; 0.72 mmol) and 2-bromoacetic acid (100 mg; 0.72 mmol) were added. The reaction mixture was subsequently stirred at room temperature for 20 hours and concentrated. The residue was dissolved in water (2 ml) and the pH value was adjusted to 7 with saturated aqueous sodium bicarbonate solution. the solution was chromatographed over a polymeric hydrophobic gel with water and lyophilised. Yield: 167 mg (59%) as a colourless powder.

IR (KBr): 1752, 1689, 1632, 1414 cm$^{-1}$ MS (ISP): (M+H)$^+$ 418.4; (M+Na)$^+$ 440.4; (M+2Na)$^+$ 462.4

(b) (1aS,3aR,6bR)-[4-(2-Trifluoroacetyl-6-carboxy-1-oxo-1a,2,3,3a,4,6b-hexahydro-1H-2,6a-diazacyclobut[cd]inden-5-ylmethylsulphanyl)-pyridin-1-ylio]-acemte sodium salt (1aS,3aR,6bR)-1-Oxo-5-(pyridin-4-ylsulphanylmethyl)-1a,2,3,3a,4,6b-hexahydro-1H-2,6a-diazacyclobut[cd]indene-6-carboxylic acid trifluoroacetate (165 mg; 0.3 mmol) was placed in dimethylformamide (2 ml) at room temperature and treated with sodium bicarbonate (28 mg; 0.33 mmol) and dicyclohexylcarbodiimide (74 mg; 0.36 mmol). After 1 hour sodium bicarbonate (38 mg; 0.45 mmol), 2-bromo acetic acid (63 mg; 0.45 mmol) and N-methyl-N-trtmethylsnyltrifluoroacetamide (0.2 ml; 1.0 mmol) were added. The reaction mixture was subsequently stirred at room temperature for 20 hours and concentrated. The residue was dissolved in water (2 ml) and the pH value was adjusted to 7 with saturated aqueous sodium bicarbonate solution. The solution was chromatographed over a polymeric hydrophobic gel with water and lyophilized. Yield: 32 mg (22%) as a yellow powder.

IR (KBr): 1765, 1695, 1631, 1369 cm$^{-1}$ MS (ISP): (M+H)$^+$ 494.4

(c) (1aS,3aR,6bR)-5-(1-Carbamoylmethyl-pyridixt-4-yliosulphanylmethyl)-1-oxo-2-trifluoroacetyl-1a,2,3,3a,4,6b-hexahydro-1H-2,6a-diazacyclobut[cd]indene-6-carboxylate This compound was prepared in analogy to Example 52(b) starting from (1aS,3aR,6bR)-1-oxo-5-(pyridin-4-ylsulphanylmethyl)-1a,2,3,3a,4,6b-hexahydro-1H-2,6a-diazacyclobut[cd]indene-6-carboxylic acid trifluoroacetate (165 mg; 0.3 mmol) and 2-bromoacetamide (125 mg; 0.90 mmol). Yield: 12 mg (9%) as a colourless powder.

IR (KBr): 1768, 1692, 1631, 1600, 1393 cm$^{-1}$ MS (ISP): (M+H)$^+$ 471.4

(d) (1aS,3aR,6bR)-5-(1-Benzyl-pyridin-4-yliosulphanylmethyl)-1-oxo-2-trifluoroacetyl-1a,2,3,3a,4,6b-hexahydro-1H-2,6a-diazacyclobut[cd]indene-6-carboxylate This compound was prepared in analogy to Example 52(b) starting from (1aS,3aR,6bR)-1-oxo-5-(pyridin-4-ylsulphanylmethyl)-1a,2,3,3a,4,6b-hexahydro-1H-2,6a-diazacyclobut[cd]indene-6-carboxylic acid trifluoroacetate (223 mg; 0.4 mmol) and benzyl bromide (0.12 ml; 1.0 mmol). Yield: 17 mg (8%) as a yellow powder.

IR (KBr): 1767, 1693, 1626, 1387 cm$^{-1}$ MS (ISP): (M+H)$^+$ 504.3

EXAMPLE 53

(1aS,3aR,6bR)-5-(2,5-Dihydro-6-hydroxy-2-methyl-5-oxo-1,2,4-triazin-3-ylsulphanylmethyl)-1-oxo-1a,2,3,3a,4,6b-hexahydro-1H-2,6a-diazacyclobut[cd]indene-6-carboxylic acid trifluoroacetate (1aS,3aR,6bR)-5-Acetoxymethyl-1-oxo-1a,2,3,3a,4,6b-hexahydro-1H-2,6a-diazacyclobut[cd]indene-6-carboxylic acid trifluoroacetate (370 mg; 1.00 mmol) and tetrahydro-2-methyl-3-thioxo-as-triazine-5,6-dione (167 mg; 1.05 mmol) were suspended in acetonitrile (2.5 ml) and treated with boron trifluoride in s acetonitrile (1.7 ml, 19%). After 2 hours at room temperature the reaction mixture was concentrated, triturated with abs. ether and suction filtered. Yield: 606 mg (84%) as a brown-beige powder.

IR (KBr): 1765, 1730, 1629 cm$^{-1}$ MS (ISP): (M+H)$^+$ 366.4

EXAMPLE 54

(1aS,3aR,6bR)-5-(2,5-Dihydro-6-hydroxy-2-methyl-5-oxo-1,2,4-triazin-3-ylsulphanylmethyl)-2-(4-hydroxy-phenylcarbamoyl)-1-oxo-1a,2,3,3a,4,6b-hexahydro-1H-2,6a-diazacyclobut[cd]indene-6-carboxylic acid sodium salt (1:2)

This compound was prepared in the same manner as given in Example 3(a) starting from (1aS,3aR,6bR)-5-(2,5-dihydro-6-hydroxy-2-methyl-5-oxo-1,2,4-triazin-3 -ylsulpbanylmethyl)-1-oxo-1a,2,3,3a,4,6b-hexahydro-1H-2,6a-diazacyclobut[cd]indene-6-carboxylic acid trifluoroacetate (300 mg; 0.41 mmol). Yield: 58 mg (17%) as a beige powder.

IR (KBr): 1748, 1630, 1604, 1546, 1401, 1241 cm$^{-1}$ MS (ISN): (M–2Na+H)$^-$ 499.2

EXAMPLE 55

(1aS,3aR,6bR)-2-Carboxymethylcarbamoyl-5-(piperidin-1-ylmethyl)-1-oxo-1a,2,3,3a,4,6b-hexahydro-1H-2,6a-diazacyclobut[cd]indene-6-carboxylic acid (1aS,3aR,6bR)-2-Benzyloxycarbonylmethylcarbamoyl-1-oxo-(5-pyridin-1-yliomethyl)-1a,2,3,3a,4,6b-hexahydro-1H-2,6a-diazacyclobut[cd]indene-6-carboxylate (400 mg; 0.84 mmol) is hydrogenated in water (100 ml) and acetonitrile (50 ml) over 10% Pd/C (100 mg). After 2 hours the reaction mixture was suction filtered, concentrated and chromatographed over a polymeric hydrophobic gel with water and [lyophilized. Yield: 200 mg (63%) as a yellow powder.

IR (KBr): 1757, 1700, 1608, 1537, 1395 cm$^{-1}$ MS (ISN): (M–H)$^-$ 391.4

EXAMPLE 56

(1aS,3aR,6bR)-5-(3-Benzyloxycarbonylmethyl-pyridin-1-yliomethyl)-1-oxo-1a,2,3,3a,4,6b-hexahydro-1H-2,6a-diazacyclobut[cd]indene-6-carboxylate trifluoroacetate This compound was prepared in the same manner as given in Example 2(a) starting from (1aS,3aR,6bR)-3-benzyloxycarbonylmethyl-1-(2,6-bis-t-butoxycarbonyl-1-oxo-1a,2,3,3a,4,6b-hexahydro-1H-2,6a-diazacyclobut[cd]inclen-5-ylmethyl)-pyridinium chloride (314 mg; 0.5 mmol). Yield: 179 mg (65%); as a colourless powder.

IR (KBr): 1782, 1737, 1677, 1636 cm$^{-1}$ MS (ISP): M$^+$ 434.5

By hydrogenolysis of the benzyl group with Pd/C there was obtained the 3-carboxymethyl compound with respect to the pyridine group.

The starting material was prepared as follows:

Di-t-butyl (1aS,3aR,6bR)-5-hydroxymethyl-1-oxo-1a;2,3,3a,4,6b-hexahydro-1H-2,6a-diazacyclobut[cd]indene-2,6-dicarboxylate (200 mg; 0.526 mmol) was placed in abs. methylene chloride (3 ml) at –40° C. and treated in succession with benzyl 3-pyridylacetate (300 mg; 1.315 mmol) and triflate anhydride (0.13 ml; 0.79 mmol). After 1 hour at this temperature the reaction mixture was diluted with methylene chloride (20 ml), dried with saturated aqueous sodium chloride solution (3 times 10 ml), dried over magnesium sulphate and concentrated. The residue obtained was triturated with abs. ether (20 ml) and filtered off under suction. Yield: 327 mg (100%) as a beige powder.

IR (KBr): 1779, 1705, 1630, 1160 cm$^{-1}$ MS (ISP): M+590.7

EXAMPLE 57

(a) (1aS,3aR,6bR)-5-(3-Benzyloxycarbonylmethyl-pyridin-1-yliomethyl)-2-(4-hydroxy-phenylcarbamoyl)-1-oxo-1a,2,3,3a,4,6b-hexahydro-1H-2,6a-diazacyclobut[cd]indene-6-carboxylate This compound was prepared in the same manner as given in Example 3(a) starting from (1aS,3aR,6bR)-5-(3-benzyloxycarbonylmethyl-pyridin-1-yliomethyl)-1-oxo-1a,2,3,3a,4,6b-hexahydro-1H-2,6a-diazacyclobut[cd]indene-6-carboxylate trifluoroacetate (170 mg; 0.31 mmol; from Example 56). Yield: 71 mg (40%) as a beige powder.

IR (KBr): 1765, 1616, 1512, 1381, 1243 cm$^{-1}$ MS (ISP): (M+H)$^+$ 569.5

(b) (1aS,3aR,6bR)-[1-[6-Carboxy-2-(4-hydroxy-phenylcarbamoyl)-1-oxo-1a,2,3,3a,4,6b-hexahydro-1H-2,6a-diazacyclobut[cd]inden-5-ylmethyl]-pyridin-3-ylio]-acetate (1aS,3aR,6bR)-5-(3-Benzyloxycarbonylmethyl-pyridin-1-yliomethyl)-2-(4-hydroxy-phenylcarbamoyl)-1-oxo-1a,2,3,3a,4, 6b-hexahydro-1H-2,6a-diazacyclobut[cd]Lndene-6-carboxylate (66 mg; 0.116 mmol) was dissolved in water (10 ml) and dimethylformamide (5 ml) and hydrogenated over 5% Pd/C. After 1 hour the suspension was suction filtered and concentrated. The residue was taken up in water and lyophilized. Yield: 50 mg (90%) as a yellow powder.

IR (KBr): 1764, 1710, 1636, 1612, 1512, 1436, 1242 cm$^{-1}$ MS (ISP): (M+H)$^+$479.3

EXAMPLE 58

(a) (1aS,3aR,6bR)-2-Acetyl-5-carbamoyloxymethyl-1-oxo-1a,2,3,3a,4,6b-hexahydro-1H-2,6a-diazacyclobut[cd]indene-6-carboxylic acid sodium salt (1aS,3aR,6bR)-5-Carbamoyloxymethyl-1-oxo-1a,2,3,3a, 4,6b-hexahydro-1H-2,6a-diazacyclobut[cd]indene-6-carboxylic acid trifluoroacetate (148 mg; 0.4 mmol) was suspended in methylene chloride (5 ml) and treated with N-methyl-N-trimethylsilyltrifluoroacetamide (0.171 ml; 0.88 mmol). After 10 minutes at room temperature sodium bicarbonate (41 mg; 0.48 mmol) and acetyl chloride (0.035 ml; 0.48 mmol) were added. The reaction mixture was stirred at room temperature for 2 hours and subsequently concentrated. The residue obtained was taken up in water (1 ml) and the pH value was adjusted to 7 with saturated aqueous sodium bicarbonate solution; The solution was chromatographed over a polymeric hydrophobic gel with water/acetonitrile and lyophilized. Yield: 72 mg (54%) as a yellowish powder.

IR (KBr): 1755, 1710, 1640, 1609, 1402 cm$^{-1}$ MS (ISP): (M+H)$^+$332.4

(b) (1aS,3aR,6bR)-5-Carbamoyloxymethyl-1-oxo-2-(thiophen-2-yl-acetyl)-1a,2,3,3a,4,6b-hexahydro-1H-2,6a-diazacyclobut[cd]indene-6-carboxylic acid sodium salt This compound was prepared in analogy to Example 19(d) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trifluoroacetate (148 mg; 0.4 mmol) and 2,5-dioxo-pyrrolidine-1-yl thiophen-2-yl-acetate(144 mg; 0.6 mmol). Yield: 32 mg (19%) as a beige powder.

IR (KBr): 1751, 1645, 1610, 1402, 1239, 1191 cm$^{-1}$ MS (ISN): (M–Na)$^-$390.3

(c) (1aS,3aR,6bR)-5-Carbamoyloxymethyl-2-methylsulphonyl-1-oxo-1a,2,3,3a,4,6b-hexahydro-1H-2,6a-diazacyclobut-[cd]indene-6-carboxylic acid sodium salt This compound was prepared in analogy to Example 19(e) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trifluoroacetate (148 mg; 0.4 mmol). Yield: 29 mg (20%) as a colourless powder.

IR (KBr): 1751, 1607, 1402, 1333, 1154 cm$^{-1}$ MS (ISN): (M–Na)$^-$344.2

(d) (1aS,3aR,6bR)-5-Carbamoyloxymethyl-1-oxo-2-trifluoroacetyl-1a,2,3,3a,4,6b-hexahydro-1H-2,6a-diazacyclobut[cd]indene-6-carboxylic acid sodium salt This compound was prepared in analogy to Example 19(c) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trifluoroacetate (166 mg; 0.45 mmol). Yield: 87 mg (50%) as a colourless powder.

IR (KBr): 1761, 1701, 1607, 1335, 1177 cm$^{-1}$ MS (ISN): (M–Na)$^-$362.4

(e) (1aS,3aR,6bR)-5-Carbamoyloxymethyl-2-(5-methyl-1,3,4-thiadiazol-2-ylsulphanylacetyl)-1-oxo-1a,2,3,3a,4,6b-hexahydro-1H-2,6a-diazacyclobut[cd]indene-6-carboxylic acid sodium salt (1aS,3aR,6bR)-5-Carbamoyloxymethyl-1-oxo-1a,2,3,3a,4,6b-hexahydro-1H-2,6a-diazacyclobut[cd]indene-6-carboxylic acid trifluoroacetate (130 mg; 0.35 mmol) was placed in dimethylformamide (2 ml) at –20° C. and treated with sodium bicarbonate (118 mg; 1.4 mmol) and bromoacetyl bromide (0.047 ml; 0.53 mmol). After 2.5 hours at this temperature 2-methyl-5-mercapto-1,3,4-thiadiazole (56 mg; 0.42 mmol) and further sodium bicarbonate (35 mg; 0.42 mmol) were added. After 2 hours at –20° C. and 2 hours at room temperature the reaction mixture was concentrated and the residue obtained was taken up in water (4 ml). The pH value was adjusted to 7 with saturated aqueous sodium bicarbonate solution. The solution was chromatographed over a polymeric hydrophobic gel with water/acetonitrile and lyophilised. Yield: 71 mg (44%) as a colourless powder.

IR (KBr): 1754, 1710, 1650, 1606, 1399 cm$^{-1}$ MS (ISP): (M+H)$^+$462.4

(f) (1aS,3aR,6bR)-2-(5-Amino-1,3,4-thiadiazol-2-ylsulphanyl-acetyl)-5-carbamoyloxymethyl-1-oxo-1a,2,3,3a,4,6b-hexahydro-1H-2,6a-diazacyclobut[cd]indene-6-carboxylic acid sodium salt This compound was prepared in analogy to Example 58(e) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trifluomacetate (130 mg; 0.35 mmol) and 2-amino-5-mercapto-1,3,4-thiadiazole (58 mg; 0.42 mmol). Yield: 67 mg (41%) as a colourless powder.

IR (KBr): 1750, 1606, 1402 cm$^{-1}$ MS (ISP): (M+H)$^+$ 463.4

(g) (1aS,3aR,6bR)-5-Carbamoyloxymethyl-1-oxo-2-pyridin-4-ylsulphanylacetyl-1a,2,3,3a,4,6b-hexahydro-1H-2,6a-diazacyclobut[cd]indene-6-carboxylic acid sodium salt This compound was prepared in analogy to Example 58(e) starting from (1aS,3aR,6bR)-5-carbamoyloxymethyl-1-oxo- 1a,2,3,3a,4,6b-hexahydro-1H-2,6a-diazacyclobut[cd]indene-6-carboxylic acid trifluoroacetate (130 mg; 0.35 mmol) and 4-mercapto-pyridine (61 mg; 0.52 mmol). Yield: 81 mg (53%) as a colourless powder.

IR (KBr): 1756, 1644, 1608, 1406, 1234 cm$^{-1}$ MS (ISP): (M–Na+2H)$^+$419.4; (M+H)$^+$441.4

(h) (1aS,3aR,6bR)-5-Carbamoyloxymethyl-1-oxo-2-phenylaminoacetyl-1a,2,3,3a,4,6b-hexahydro-1H-2,6a-diazacyclobut[cd]indene-6-carboxylic acid sodium salt This compound was prepared in analogy to Example 58(e) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trifluoroacetate (130 mg; 0.35 mmol) and aniline (0.048 ml; 0.52 mmol). Yield: 57 mg (39%) as a colourless powder.

IR (KBr): 1751, 1650, 1604, 1405 cm$^{-1}$ MS (ISP): (M–Na+2H)$^+$401.4; (M+H)$^+$423.4

(i) (1aS,3aR,6bR)-2-Formyl-5-carbamoyloxymethyl-1-oxo-2-phenylaminoacetyl-1a,2,3,3 a,4,6b-hexahydro-1H-2,6a-diazacyclobut[cd]indene-6-carboxylic acid sodium salt This compound was prepared in the same manner as given in Example 19(k) starting from (1aS,3aR6bR)-5-carbamoyloxymethyl-1-oxo-1a,2,3,3a,4,6b-hexahydro-1H-2,6a-diazacyclobut[cd]indene-6-carboxylic acid trifluoroacetate (100 mg; 0.27 mmol). Yield: 69 mg (81%) as a yellow powder.

IR (KBr): 1760, 1696, 1612, 1400 cm$^{-1}$ MS (ISN): (M–Na)$^-$ 294.1

EXAMPLE 59

(a) (1aS,3aR,6bR)-5-Carbarmoyloxymethyl-2-(4-hydroxyphenylcarbamoylmethyl)-1-oxo-1a,2,3,3a,4,6b-hexahydro-1H-2,6a-diazacyclobut[cd]indene-6-carboxylic acid sodium salt (1aS,3aR,6bR)-5-Carbamoyloxymethyl-1-oxo-1a,2,3,3a,4,6b-hexahydro-1H-2,6a-diazacyclobut[cd]indene-6-carboxylic acid trifluoroacetate (148 mg; 0.4 mmol) was dissolved in dimethylformamide and treated at room temperature with N-methyl-N-trimethylsilyltrifluoroacetamide (0.17 ml; 0.88 mmol). After 15 minutes sodium bicarbonate (41 mg; 0.48 mmol) and 2-bromo-4'-hydroxyacetanilide (111 mg; 0.48 mmol) were added. After 5 hours the reaction mixture was concentrated and the residue obtained was taken up in water (2 ml). The pH value was adjusted to 7 with saturated aqueous sodium bicarbonate solution and the solution was chromatographed over a polymeric hydrophobic gel with water/acetonitrile and lyophilized. Yield: 99 mg (56%) as colourless powder.

IR (KBr): 1750, 1728, 1668, 1602, 1402 cm$^{-1}$ MS (ISP): (M+H)$^+$439.5

(b) (1aS,3aR,6bR)-5-Carbamoyloxymethyl,2-methoxycarbonylmethyl-1-oxo-1a,2,3,3a,4,6 1>hexahydro-1H-2,6a-diazacyclobut[cd]indenc-6-carboxylic acid sodium salt This compound was prepared in analogy to Example 59(a) starting from (1aS,3aR,6bR)-5-carbamoyloxymethyl-1-oxo-1a,2,3,3a,4,61b-hexahydro-1H-2,6a-diazacyclobut[cd]indene-6-carboxylic acid trifluoroacetate (148 mg; 0.4 mmol) and methyl bromoacetate (0.046 ml; 0.48 mmol). Yield: 73 mg (50%) as a yellowish powder.

IR (KBr): 1750, 1734, 1602, 1401 cm$^{-1}$ MS (ISN): (M–Na)$^-$338.2

(c) (1aS,3aR,6bR)-5-Carbamoyloxymethyl-2-ethyl-1-oxo-1a,2,3,3a,4,6b-hexahydro-1H-2,6a-diazacyclobut[cd]indene-6-carboxylic acid sodium salt This compound was prepared in anology to Example 59(a) starting from (1aS,3aR,6bR)-5-carbamoyloxymethyl-1-oxo-1a,2,3,3a,4,6b-hexahydro-1H-2,6 a-diazacyclobut[cd]indene-6-carboxylic acid trifluoroacetate (148 mg; 0.4 mmol) and ethyl iodide (0.049 ml; 0.60 mmol). Yield: 40 mg (31%) as a yellow powder.

IR (KBr): 1750, 1731, 1605, 1401 cm$^{-1}$ MS (ISN): (M–Na)$^-$294.3

(d) (1aS,3aR,6bR)-2-Carbamoylmethyl-5-carbamoyloxymethyl-1-oxo-1a,2,3,3a,4,6b-hexahydro-1H-2,6a-diazacyclobut[cd]indene-6-carboxylic acid sodium salt This compound was prepared in analogy to Example 59(a) starting from (1aS,3aR,6bR)-5-carbamoyloxymethyl-1-oxo-1a,2,3,3a,4,6b-hexahydro-1H-2,6a-diazacyclobut[cd]indene-6-carboxylic acid trifluoroacetate (148 mg; 0.4 mmol) and 2-bromacetamide (68 mg; 0.48 mmol); Yield: 19 mg (14%) as a colourless powder.

IR (KBr): 1750, 1700, 1676, 1602, 1400 cm$^{-1}$ MS (ISN): (M–Na)$^-$323.3

EXAMPLE 60

(Z)-(1aS,3aR,6bR)-2-[(2-Amino-thiazol-4-yl)-methoxyimino-acetyl]-5-carbamoyloxymethyl-1-oxo-1a,2,3,3,a,4, 6b-hexahydro-1H-2,6a-diazacyclobut[cd]indene-6-carboxylic acid (1aS,3aR,6bR)-5-Carbamoyloxymethyl-1-oxo-1a,2,3,3a,4,6b-hexahydro-1H-2,6a-diazacyclobut[cd]indene-6-carboxylic acid trifluoroacetate (150 mg; 0.39 mmol) was dissolved in dimethylformamide (5 ml) and treated at room temperature with 2-(2-aminothiazol-4-yl)-2-(Z)-methoxyimino-acetic acid 2-benzthiazolylthioester (115 1 mg; 0.43 mmol). After 1 hour the reaction mixture was concentrated and the oily residue was triturated with ethyl acetate (20 ml). The precipitated product was filtered off under suction, washed with acetone and ether and dried. Yield: 82 mg (46%) as a beige powder.

IR (KBr): 1768, 1716, 1645, 1610, 1534, 1400, 1048 cm$^{-1}$ MS (ISP): (M+H)$^+$451.3

EXAMPLE 61

(a) (1aS,3aR,6bR)-2-Methoxycarbonylmethyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid This compound was prepared in analogy to Example 59(a) starting from (1aS,3aR,6bR)-5-(1-methyl-tetrazol-5-ylsulphanylmethyl)-1-oxo-1a,2,3,3a,4,6b-hexahydro-1H-2,6a-diazacyclobut[cd]indene-6-carboxylic acid trifluoroacetate (200 mg; 0.415 mmol) and methyl 2-bromo acetate (0.046 ml; 0.50 mmol). Yield: 35 mg (21%) as a yellow powder.

IR (KBr): 1739, 1602, 1391 cm–1 MS (ISP): (M+H)$^+$ 395.5

(b) (1aS,3aR,6bK)-2-(4-Hydroxy-phenylcarbamoylmethyl)-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt This compound was prepared in the same manner as given in Example 59(a) starting from (1aS,3aR,6bR)-5-(1-methyl;tetrazol-5-yl-sulphanylmethyl)-1-oxo-1a,2,3,3a,4,6b-hexahydro-1H-2,6a-diazacyclobut[ cd]indene-6-carboxylic acid trifluoroacetate (200 mg; 0415 mmol). Yield: 25 mg (12%) as a colourless powder.

IR (KBr): 1741, 1670, 1603, 1513 cm$^{-1}$ MS (ISN): (M–Na)$^-$470.4

EXAMPLE 62

(1aS,3aR,6bR)-5-(1-Methyl-1H-tetrazol-5-ylsulphanylmethy)-1-oxo-1a,2,3,3a,4,6b-hexahydro-1H-2,6a-diazacyclobut[cd]indene-2,6-dicarboxylic acid 2-ethyl ester This compound was prepared in analogy to Example 3(a) starting from (1aS,3aR,6bR)-5-(1-methyl-1H-tetrazol-5-yl-sulphanylmethyl)-1-oxo-1a,2,3,3a,4,6b-hexahydro-1H-2,6a-diazacyclobut[cd]indene-6-carboxylic acid trifluoroacetate (200 mg; 0.415 mmol) and ethyl N-hydroxysuccinimidyl carbonate (217 mg; 1.16 mmol). Yield: 62 mg.(31%) as a colourless powder.

IR (KBr): 1774, 1707, 1628,cm$^{-1}$ MS (ISP): (M+H)$^+$ 395.4

EXAMPLE 63

(1aS,3aR,6bR)-5-(5-Methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacerate.

This compound was prepared in the same manner as given in Example 2(a) starting from di-t-butyl (1aS,3aR,6bR)-5-(5-methyl-1,3,4-thiadiazol-2-ylsulphanylmethyl)-1-oxo-1a,2,3, 3a,4,6b-hexahydro-1H-2,6a-diazacyclobut[cd]indene-2,6-dicarboxylate (2.3 g; 4.73 mmol). Yield: 1.95 g (93%) as a reddish product.

IR (KBr): 1781, 1700, 1677, 1199 cm$^{-1}$ MS (ISN): (M–H)$^-$337.3

The starting material used was prepared in analogy to Example 17 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (1.8 g; 4.73 mmol) and 2-methyl-5-mercapto-1,3,4-thiadiazol (937 mg; 7.09 mmol). Yield: 2.3 g (100%) as a colourless solid foam.

IR (KBr): 1775, 1703, 1625 cm$^{-1}$ MS (ISP): (M+H)$^+$ 495.5

EXAMPLE 64

(1aS,3aR,6bR)-2-(4-Hydroxy-phenylcarbamoyl)-5-(5-methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid sodium salt This compound was prepared in the same manner as given in Example 3(a) starting from (1aS,3aR,6bR)-5-(5-methyl-1,3,4-thiadiazol-2-ylsulphanylmethyl)-1-oxo-1a,2,3,3a,4, 6b-hexahydro-1H-2,6a-diazacyclobut[cd]indene-6-carboxylic acid trifluoroacetate (133 mg; 0.3 mmol). Yield: 60 mg (47%) as a colourless powder.

IR (KBr): 1747, 1650, 1603 cm$^{-1}$ MS (ISN): (M–Na)$^-$ 472.3

EXAMPLE 65

(a) (1aS,3aR,6bR)-2-Acetyl-5-(5-methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-(5-methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacetate(177 mg; 0.4 mmol) in DMF (5 ml). Yield: 52 mg (38%) as an orange powder.

IR (KBr): 1751, 1660, 1601, 1412 cm$^{-1}$ MS (ISP): (M+H)$^+$381.3

(b) (1aS,3aR,6bR)-5-(5-Methyl-1,3,4-thiadiazol-2-ylsulphanylmethyl)-1-oxo-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR6bR)-5-(5-methyl-1,3,4-thiadiazol-2-ylsulphanylmethyl)-1-oxo-1a,2,3,3a,4, 6b-hexahydro-1H-2,6a-diazacyclobut[cd]indene-6-carboxylic acid trifluoroacetae (177 mg; 0.4 mmol). Yield: 30 mg (19%) as an orange powder.

IR (KBr): 1759, 1693, 1609, 1390 cm$^{-1}$ MS (ISN): (M–Na)$^-$433.3

(c) (1aS,3aR,6bR)-5,(5-Methyl-1,3,4-thiadiazol-2-ylsulphanylmethyl)-1-oxo-2-(pyridin-4-ylsulphanylacetyl)-1a,2,3, 3a,4,6b-hexahydro-1H-2,6a-diazacyclobut[cd]indene-6-carboxylic acid sodium salt This compound was prepared in analogy to Example 58(e) starting from (1aS,3aR,6bR)-5-(5-methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacetate (177 mg; 0.4 mmol) and 4-mercaptopyridine(53 mg; 0.48 mmol). Yield: 41 mg (2096) as a yellowish powder.

IR (KBr): 1754, 1647, 1604, 1409 cm$^{-1}$ MS (ISP): (M–Na+2H)$^+$490.4

(d) (1aS,3aR,6bR)-2-(3-Carbamoyl-pyridin-1-ylioacetyl)-5-(5-methyl-1,3,4-thiadiazol-2-ylsulphanylmethyl), 1-oxo-1a, 2,3,3a,4,6b-hexahydro-1H-2,6a-diazacyclobut[cd]indene-6-carboxylic acid sodium salt This compound was prepared in analogy to Example 58(e) starting from (1aS,3aR,6bR)-5-(5-methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid trifluoroacetate (295 mg; 0.666 mmol) and isonicotinamide (122 mg; 1.00 mmol). Yield: 55 mg (16%) as a yellowish powder.

IR (KBr): 1757, 1669, 1604, 1386 cm$^{-1}$ MS (ISP): (M+H)$^+$501.4

(e) (1aS,3aR,6bR)-2-Formyl-5-(5-methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid sodium salt This compound was prepared in the same manner as given in Example 19(k) starting from (1aS,3aR,6bR)-5-(5-methyl-1,3,4-thiadiazol-2-ylsulphanylmethyl)-1-oxo-1a,2,3,3 a,4,6b-hexahydro-1H-2,Ga-diazacyclobut[cd]indene-6-carboxylic acid trifluoroacetate (177 mg; 0.4 mmol). Yield: 59 mg (38%) as an orange powder.

IR (KBr): 1753, 1661, 1593, 1391 cm$^{-1}$ MS (ISP): (M+H)$^+$367.2

(f) (1aS,3aR,6bR)-2-(2-Amino-1,3,4-thiadiazol-5-ylsulphanylacetyl)-5-(5-methyl-1,3,4-thiadiazol-2-ylsulphanylmethyl)-1-oxo-1a,2,3,3a,4,6b-hexahydro-1H-2,6a-diazacyclobut[cd]indene-6-carboxylic acid sodium salt This compound was prepared in analogy to Example 58(e) starting from (1aS,3aR,6bR)-5-(5-methyl-1,3,4-thiadiazol-2-ylsulphanylmethyl)-1-oxo-1a,2,3,3a,4,6b-hexahydro-1H-2,6a-diazacycobut[cd]indene-6-carboxylic acid trifluoroacetate (177 mg; 0.4 mmol) and 2-amino-5-mercapto-1,3,4-thiadiazole (66 mg; 0.48 mmol). Yield: 54 mg (27%).

IR (KBr): 1751, 1650, 1600, 1389 cm$^{-1}$ MS (ISP): (M−Na+2H)$^+$512.2

(g) (1aS,3aR,6bR)-2-Carbamoylmethylsulphanylacetyl-5-(5-methyl-1,3,4-thiadiazol-2-ylsulphanylmethyl)-1-oxo-1a,2,3,3a,4,6b-hexalaydro-1H-2,6a-diazacyclobut[cd]indene-6-carboxylic acid sodium salt This compound was prepared in analogy to Example 58(e) starting from (1aS,3aR,6bR)-5-(5-methyl-1.3.4-thiadiazol-2-ylsulphanylmethyl)-1-oxo-1a,2,3,3 a,4,6b-hexahydro-1H-2,6a-diazacyclobut[cd]indene-6-carboxylic acid trifluoroacetate (177 mg; 0.4 mmol) and 2-mercaptoacetamide (44 mg; 0.48 mmol). Yield: 43 mg (22%).

IR (K. Br): 1752, 1673, 1596, 1382 cm$^{-1}$ MS (ISP): (M−Na+2H)$^+$470,3; (M+H)$^+$492.2

EXAMPLE 66

(1aS,3aR,6bR)-1-Oxo-5-(4-pyridin-3-yl-thiazol-2-ylsulphanylmethyl)-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-1-oxo-5-(4-pyridin-3-yl-thiazol-2-ylsulphanylmethyl)-1a,2,3,3a,4,6b-hexahydro-1H-2,6a-diazacyclobut[cd]indene-2,6-dicarboxylate (1.11 g; 2.00 mmol). Yield: 966 mg (86%) as an orange powder.

IR (KBr): 1778, 1678, 1630 cm$^{-1}$ MS (ISP): (M+H)$^+$ 401.3

The starting material used was prepared in analogy to Example 17 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (760 mg; 2.0 mmol) and 2-mercapto-4-pyridin-3-yl-1,3-thiazole (583 mg; 3.0 mmol). Yield: 1.11 g (100%) as a colourless solid foam.

IR (KBr): 1775, 1703, 1625, 1250, 1164 cm$^{-1}$ MS (ISP): (M+H)$^+$557.4

EXAMPLE 67

(a) (1aS,3aR,6bR)-2-Acetyl-1-oxo-5-(4-pyridin-3-yl-thiazol-2-ylsulphanylmethyl)-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-1-oxo-5-(4-pyridin-3-yl-thiazol-2-ylsulphahylmethyl)-1a,2,3,3a,4,6b-hexahydro-1H-2,6a-diazacyclobut[cd]indene-6<arboxylic acid trifluoroacetate (225 mg; 0.4 mmol) in DMF (5 ml). Yield: 87 mg (47%) as a colourless powder.

IR (KBr): 1748, 1650, 1596, 1404 cm$^{-1}$ MS (ISP): (M−Na+2H)$^+$443.4

(b) (1aS,3aR,6bR)-1-Oxo-5-(4-pyridin-3-yl-thiazol-2-ylsulphanylmethyl)-2-trifluoroacetyl-1a,2,3,3a,4,6b-hexahydro-1H-2,6a-diazacyclobut[cd]indene-6-carboxylic acid sodium salt This compound was prepared in the same manner as in Example 19(c) starting from (1aS,3aR,6bR)-1-oxo-5-(4-pyridin-3-yl-thiazol-2-ylsulphanylmethyl)-1a,2,3,3a,4,6b-hexahydro-,1H-2,6a-diazacyclobut[cd]indene-6-carboxylic acid trifluoroacetate (225 mg; 0.4 mmol). Yield: 127 mg (6196) as an orange powder.

IR (KBr): 1764, 1689, 1624, 1406 cm$^{-1}$ MS (ISP): (M−Na+2H)$^+$497.2

EXAMPLE 68

(1aS,3aR,6bR)-5-[(R)-2-Amino-2-(3-methyl-1,2,4-oxadiazol-5yl)ethylsulphanylmethyl[-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-[(R)-2-t-butoxycarbonylamino-2-(3-methyl-1,2,4-oxadiazol-5-yl)-ethylsulphanylmethyl]-1-oxo-1a,2,3,3a,4,6b-hexahydro-1H-2,6a-diazacyclobut[cd]indene-2,6-dicarboxylate (3 10 mg; 0.5 mmol). Yield: 25 1 mg (100%) as a beige powder.

IR (KBr): 1776, 1677, 1203 cm$^{-1}$ MS (ISP): (M+H)$^+$ 366.4

The starting material used was prepared in analogy to Example 17 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (190 mg; 0.5 mmol). Yield: 310 mg (100%) as a yellow solid foam.

IR (KBr): 1778, 1710, 1585, 1513, 1251, 1165 cm$^{-1}$ MS (ISP): (M+H)$^+$622,4; (M+NH$_4$)$^+$639.4

EXAMPLE 69

(1aS,3aR,6bR)-5-(1-Carbamoylmethyl-1H-tetrazol-5-ylsulphanylmethyl)-1-oxo-1 a2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-(1-carbamoylmethyl-1H-tetrazol-5-ylsulphanylmethyl)-1-oxo-1a,2,3,3a,4,6b-hexahydro-1H-2,6a-diazacyclobut[cd]indene-2,6-dicarboxylate (1.00 g; 1.92 mmol). Yield: 830 mg (90%) as a pale pink solid.

IR (KBr): 1780, 1693, 1624 cm$^{-1}$ MS (ISP): (M+H)$^+$ 366.3

The starting material used was prepared in analogy to Example 17 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (700 mg; 1.84 mmol) and 5-mercapto-1H-tetrazole-1-acetamide (439 mg; 2.76 mmol). Yield: 960 mg (100%) as a yellow solid.

IR (KBr): 1777, 1703, 1625, 1251 cm$^{-1}$ MS (ISP): (M+H)$^+$522,5; (M+NH$_4$)$^+$539.5

EXAMPLE 70

(a) (1aS,3aR,6bR)-2-Acetyl-5-(1-carbamoylmethyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-(1-carbamoylmethyl-1H-tetrazol-5-ylsulphanylmethyl)-1-oxo-1a,2,3,3a,4,6b-hexahydro-1H-2,6 a-diazacyclobut[cd]indene-6-carboxylic acid trifluoroacetate (240 mg; 0.5 mmol) in dimethylformamide (5 ml). Yield: 123 mg (57%) as an orange powder.

IR (KBr): 1749, 1694, 1622, 1397 cm$^{-1}$ MS (ISP): (M+H)$^+$408.4; (M+NH$_4$)$^+$425.4; (M+Na)$^+$430.4

(b) (1aS;3aR,6bR)-5-(1-Carbamoylmethyl-1H-tetrazol-5-yl-sulphanylmethyl)-2-trifluoroacetyl-1-oxo-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR),5-(1-carbamoylmethyl-1H-tetrazol-5-ylsulphanylmethyl)-1-oxo-1a,2,3,3a,4,6b-hexahydro- 1H-2,6a-diazacyclobut[cd]indene-6-carboxylic acid trifluoroacetate (300 mg; 0.625 mmol) in dimethylformamide (5 ml). Yield: 160 mg (53%) as an orange powder.

IR (KBr): 1763, 1692, 1606 cm$^{-1}$ MS (ISP): (M+H)$^+$462, 3; (M+NH$_4$)$^+$479,3; (M+Na)$^+$484.3

(c) (1aS,3aR,6bR)-5-(1-Carbamoylmethyl-1H-tetrazol-5-yl-sulphanylmethyl)-2-formyl-1-oxo-1a,2,3,3a,4,6b-hexahydro-1H-2,6a-diazacyclobut[cd]indene-6-carboxylic acid sodium salt This compound was prepared in the same manner as given in Example 19(k) starting from (1aS,3aR,6bR)-5-(1-carbamoylmethyl-1H-tetrazol-5-ylsulphanylmethyl)-1-oxo-1a,2,3,3a,4,6b-hexahydro-1H-2,6a-diazacyclobut[cd]indene-6-carboxylic acid trifluoroacetate (300 mg; 0.625 mmol). Yield: 54 mg (42%) as an orange powder.

IR (KBr): 1753, 1693, 1659, 1601, 1395 cm$^{-1}$ MS (ISP): (M+H)$^+$394.1; (M+NH$_4$)$^+$411.3; (M+Na)$^+$416.2

EXAMPLE 71

(1aS,3aR,6bR)-1-Oxo-5-(pyrimidin-2-ylsulphanylmethyl)-1a,2,3,3a,4,6b-hexahydro-1H-2,6a-diazacyclobut[cd]indene-6-carboxylic acid trifluoroacetate This compound was-prepared in, the same manner as given in Example 2(a) starting from di-t-butyl (1aS,3aR, 6bR)-1-oxo-5-(pyrimidin-2-ylsulphanylmethyl)-1a,2,3,3a, 4,6b-hexahydro-1H-2,6a-diazacyclobut[cd]indene-2,6-dicarboxylate (560 mg; 1.18 mmol). Yield: 500 mg (93%) as a yellow powder.

IR (KBr): 1780, 1676, 1630, 1200 cm$^{-1}$ MS (ISN): (M−H)$^-$ 17.2

The starting material used was prepared in analogy to Example 17 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (450 mg; 1.18 mmol) and 2-mercapto-pyrimidine (185 mg; 1.61 mmol). Yield: 560 mg (100%) as a yellow powder.

IR (KBr): 1775, 1704, 1381, 1164 cm$^{-1}$ MS (ISP): (M+H)$^+$475,4; (M+Na)$^+$497.4

EXAMPLE 72

(a) (1aS,3aR,6bR)-2-Acetyl-1-oxo-5-(pyrimidin-2-ylsulphanylmethyl)-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-1-oxo-5-(pyrimidin-2-ylsulphanylmethyl)-1a,2,3,3a,4,6b-hexahydro-1H-2,6a-diazacyclobut[cd]indene-6-carboxylic acid trifluoroacetate (182 mg; 0.4 mmol) in dimethylformamide (4 ml). Yield: 58 mg (35%) as an orange powder.

IR (KBr): 1749, 1650, 1599, 1380 cm$^{-1}$ MS (ISP): (M+2H-Na)$^+$361.2; (M+H)$^+$383.2; (M+Na)$^+$405.2

(b) (1aS,3aR,6bR)-1-Oxo-5-(pyrimidin-2-ylsulphanylmethyl)-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-1-oxo-5-(pyrimidin-2-ylsulphanylmethyl)-1a,2,3,3a,4,6b-hexahydro-1H-2,6a-diazacyclobut[cd]indene-6-carboxylic acid trifluoroacetate (182 mg; 0,4 mmol). Yield: 75 mg (43%) as a yellow powder.

IR (KBr):. 1749, 1650, 1599, 1380 cm$^{31\ 1}$ MS (ISP): (M+2H-Na)$^+$415.3; (M+H)$^+$437.3

EXAMPLE 73

(1aS,3aR,6bR)-5-(1-Methylcarbamoylmethyl-1H-tetrazol-5-ylsulphanylxnethyl)-1-oxo-1a,2,3,3a,4,6b-hexahydro-1H-2,6a-diazacyclobut[cd]indene-6-carboxylic acid trifluoroacetate This compound was prepared in the same manner as given in Example 2(a)starting from di-t-butyl (1aS,3aR,6bR)-5-(1-methylcarbarnoylmethyl-1H-tetrazol-5-ylsulphanylmethyl)-1-oxo-1a,2,3,3a,4,6b-hexahydro-1H-2,6a-diazacyclobut[cd]indene-2,6-dicarboxylate (632 mg; 1.18 mmol). Yield: 600 mg (100%) as a pale yellow powder.

IR (KBr): 1781, 1680, 1630, 1570, 1200 cm$^{-1}$

The starting material used was prepared in analogy to Example 17 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (190 mg; 0.5 mmol) and N-methyl-2-(5-mercapto-1H-tetrazol-1-yl)-acetamide (280 mg; 1.62 mmol). Yield: 630 mg (100%) as a yellow solid foam.

IR (KBr): 1777, 1701, 1640, 1557, 1251 cm$^{-1}$ MS (ISP): (M+H)$^+$536.4; (M+NH$_4$)$^+$553.4

EXAMPLE 74

(a) (1aS,3aR,6bR)-2-Acetyl-5-(1-methylcarbamoylmethyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-(1-methylcarbamoylmethyl-1H-tetrazol-5-ylsulphanylmethyl)-1-oxo-1a,2,3,3a, 4,6b-hexahydro-1H-2,6a-diazacyclobut[cd]indene-6-carboxylic acid trifluoroacetate (247 mg; 0.487 mmol) in dimethylformamide (4 ml). Yield: 71 mg (33%) as a pale yellow powder.

IR (KBr): 1751, 1686, 1640, 1603, 1550, 1409 cm$^{-1}$ MS (ISP): (M+2H-Na)$^+$422.4; (M+H-Na+NH$_4$)$^+$439.4; (M+H)$^+$ 444.3

(b) (1aS,3aR,6bR)-5-(1-Methylcarbamoylmethyl-1H-tetrazol-5-ylsulphanylmethyl)-1-oxo-2-trifluoroacetyl-1 a,2,3,3a, 4,6b-hexahydro-1H-2,6a-diazacyclobut[cd]indene-6-carboxylic acid sodium salt This compound was prepared in the same manner as given in Example 19(c) starting from (1aS,3aR,6bR)-5-(1-methylcarbamoylmethyl-1H-retrazol-5-ylsulphanylmethyl)-1-oxo-1a,2,3,3a,4,6b-hexahydro-1H-2,6a-diazacyclobut[cd]

indene-6-carboxylic acid trifluoroacetate (247 mg; 0.487 mmol). Yield: 63 mg (26%) as a pale yellow powder.

IR (KBr): 1764, 1692, 1605, 1560, 1399, 1155 cm$^{-1}$ MS (ISP): (M+2H-Na)$^+$476.3; (M+H-Na+NH$_4$)$^+$493.3; (M+H)$^+$ 498.2

EXAMPLE 75

(1aS,3aR,6bR)-1-Oxo-5-(1H-1,2,4-triazol-3-ylsulphanylmethyl)-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-1-oxo-5-(1H-1,2,4-triazol-3-ylsulphanylmethyl)-1a,2,3,3a,4,6b-hexahydro-1H-2,6a-diazacyclobut[cd]indene-2,6-dicarboxylate (533 mg; 1.18 mmol). Yield: 430 mg (89%) as an orange powder.

IR (KBr): 1778, 1700, 1676 cm$^{-1}$ MS (ISP): (M+H)$^+$ 308.2

The starting material used was prepared in analogy to Example 17 starting from di-t-butyl (1aS,3aR,6bR)-5-hydroxymethyl-1-oxo-1a,2,33a,4,6b-hexahydro-1H-2,6a-diazacyclobut[cd]indene-2,6-dicarboxylate (450 mg; 1.18 mmol) and 1H-1,2,4-triazole-3-thiol (280 mg; 1.62 mmol). Yield: 530 mg (100%) as a pale yellow solid foam.

IR (KBr): 1775, 1704, 1633, 1368 cm$^{-1}$ MS (ISP): (M+H)$^+$464,4; (M+Na)$^+$486.4

EXAMPLE 76

(a) (1aS,3aR,6bR)-2-Acetyl-1-oxo-5-(1H-1,2,4-triazol-3-ylsulphanylmethyl)-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-1-oxo-5-(1H-1,2,4-triazol-3-ylsulphanylmethyl)-1a,2,3,3a,4,6b-hexahydro-1H-2,6a-diazacyclobut[cd]indene-6-carboxylic acid trifluoroacetate (205 mg; 0.5 mmol) in dimethylformamide (5 ml). Yield: 84 mg (45%) as a yellow powder.

IR (KBr): 1749, 1660, 1598, 1401 cm$^{-1}$ MS (ISN): (M−Na)$^-$348.2

(b) (1aS,3aR,6bR)-1-Oxo-5-(1H-1,2,4-triazol-3-ylsulphanylmethyl)-2-trifhoroacetyl-1a,2,3,3a,4,6b-hexahydro-1H-2,6a-diazacyclobut[cd]indene-6-carboxylic acid sodium salt This compound was prepared in the same manner as given in Example 19(c)' starting from (1aS,3aR,6bR)-1-oxo-5-(1H-1,2,4-triazol-3-ylsulphanylmethyl)-1a,2,3,3a,4,6b-hexahydro-1H-2,6a-diazacyclobut[cd]indene-6-carboxylic acid trifluoroacetate (205 mg; 0.5 mmol). Yield: 73 mg (34%) as a beige powder.

IR (KBr): 1762, 1695, 1598, 1399 cm$^{-1}$ MS (ISP): (M+H)$^+$ 404.3; (M+Na)$^+$ 426.3

EXAMPLE 77

(1aS,3aR6bR)-5-[1-(4-Hydroxy-phenylcarbamoylmethyl)-1H-tetrazol-5-ylsulphanylmethyl]-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-[1-(4-hydroxy-phenylcarbamoylmethyl)-1H-tetrazol-5-ylsulphanylmethyl]-1-oxo-1a,2,3,3a,4,6b-hexahydro-1H-2,6a-diazacyclobut[cd]indene-2,6-dicarboxylate (724 mg; 1.18 mmol). Yield: 650 mg (99%) as a beige powder.

IR (KBr): 1779, 1678, 1621, 1513, 1250, 1202 cm$^{-1}$ MS (ISN): (M−H)$^-$ 456.3

The starting material used was prepared in analogy to Example 17 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (450 mg; 1.18 mmol) and N-(4-hydroxy-phenyl)-2-(5-mercapto-1H-tetrazol-5-yl)-acetamide (477 mg; 1.62 mmol). Yield: 720 mg (100%) as a beige powder.

IR (KBr): 1776, 1701, 1680, 1615, 1557, 1367, 1250 cm$^{-1}$ MS (ISP): (M+H)$^+$ 614.3; (M+NH$_4$)$^+$ 631.3

EXAMPLE 78

(a) (1aS,3aR,6bR)-2-Acetyl-5-[1-(4-hydroxy-phenylcarbamoylmethyl)-1H-tetrazol-5-ylsulphanylmethyl]-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR6bR)-5-[1-(4-hydroxy-phenylcarbamoyl-methyl)-1H-tetrazol-5-ylsulphanylmethyl]-1-oxo-1a,2,3,3a,4,6b-hexahydro-1H-2,6a-diazacyclobut[cd]indene-6-carboxylic acid trifluoroacetate (279 mg; 0.5 mmol) in dimethylformamide (5 ml). Yield: 97 mg (37%) as a beige powder.

IR (KBr): 1750, 1686, 1614, 1399, 1251 cm$^{-1}$ MS (ISP): (M+H)+ 500.4; (M+Na)$^+$ 522.3

(b) (1aS,3aR6bR)-5-[1-(4-Hydroxy-phenylcarbamoylmethyl)-1H-tetrazol-5-ylsulphanylmethyl]-1-oxo-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c)starting from (1aS,3aR,6bR)-5-[1-(4-hydroxyphenylcarbamoylmethyl)-1H-tetrazol-5-ylsulphanylmethyl ]-1-oxo-1a,2,3,3a,4,6b-hexahydro-1H-2,6a-diazacyclobut[cd]indene-6-carboxylic acid trifluoroacetate (279 mg; 0.5 mmol). Yield: 79 mg (27%) as a colourless powder.

IR (KBr): 1763, 1680, 1605, 1398, 1250, 1208, 1157 cm$^{-1}$ MS (ISP): (M+H)$^+$ 554.2; (M+Na)$^+$ 576.2

EXAMPLE 79

(1aS,3aR,6bR)-1-Oxo-5-[1-(phenethylcarbamoylmethyl)-1H-tetrazol-5-ylsulphanylmethyl]-1a,2,3,3 a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-1-oxo-5-[1-(phenethylcarbamoylmethyl)-1H-tetrazol-5-ylsulphanylmethyl]-1a,2,3,3a,4,6b-hexahydro-1H-2,6a-diazacyclobut[cd]indene-2,6-dicarboxylate (1.18 g; 1.89 mmol). Yield: 850 mg (81%) as a pink-red powder.

IR (KBr): 1778, 1678, 1650, 1558, 1242, 1200 cm$^{-1}$ Ms (ISN): (M−H)$^-$ 468.4

The starting material used was prepared in analogy to Example 17 starting from di-t-butyl (1aS,3aR,6bR)-B-hydroxymethyl-1-oxo-1a,2,3,3a,4,6b-hexahydro-1H-2,6a-diazacyclobut[cd]indene-2,6-dicarboxylate (720 mg; 1.89 mmol) and N-(2-phenylethyl)-2-(5-mercapto-1H-tetrazol-B-yl)-acetamide (680 mg; 2.58 mmol). Yield: 1.18 g (100%) as a yellow powder.

IR (KBr): 1773, 1699, 1670, 1554, 1252 cm$^{-1}$ MS (ISP): (M+H)$^+$ 626; (M+Na)$^+$ 648; (M+K)$^+$ 664

EXAMPLE 80

(a) (1aS,3aR,6bR)-2-Acetyl-1-oxo-5-[1-(phenethylcarbamoylmethyl)-1H-tetrazol-5-ylsulphanylmethyl]-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-1-oxo-5-[1-(phenethyl-carbamoylmethyl)-1H-tetrazol-5-ylsulphanylmethyl]-1a,2,3,3a,4,6b-hexahydro-1H-2,6a-diazacyclobut[cd]indene-6-carboxylic acid trifluoroacetate (278 mg; 0.5 mmol) in dimethylformamide (5 ml). Yield: 99 mg (37%) as a beige powder.

IR (KBr): 1750, 1685, 1606, 1560, 1403 cm$^{-1}$ MS (ISP): (M+H)$^+$ 512.2; (M+NH$_4$)$^+$ 529.2; (M+Na)$^+$ 534.2

(b) (1aS,3aR,6bR)-1-Oxo-5-[1-(phenethylcarbamoylmethyl)-1H-tetrazol-5-ylsulphanylmethyl]-2-trifluoroacetyl-1a,2,3,3a,4,6b-hexahydro- 1H-2,6a-diazacyclobut[cd]indene-6-carboxylic acid sodium salt This compound was prepared in the same manner as given in Example 19(c) starting from (1aS,3aR6bR)-1-oxo-5-[1-(phenethylcarbamoylmethyl)-1H-tetrazol-5-ylsulphanylmethyl]-1a,2,3,3a,4,6b-hexahydro-1H-2,6a-diazacyclobut[cd]indene-6-carboxylic acid trifluoroacetate (292 mg; 0.52 mmol). Yield: 91 mg (29%) as a beige powder.

IR (KBr): 1763, 1692, 1606, 1551, 1398 cm$^{-1}$ MS (ISP): (M+H)$^+$ 565.9; (M+NH$_4$)$^+$ 582.9; (M+Na)$^+$ 587.9

EXAMPLE 81

(1aS,3aR,6bR)-5-Azidomethyl-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-azidomethyl-1-oxo-1a,2,3,3a,4,6b-hexahydro-1H-2,6a-diazacyclobut[cd]indene-2,6-dicarboxylate (450 mg; 1.2 mmol). Yield: 390 mg (95%) as a beige powder.

IR (KBr): 2109, 1782, 1676, 1201 cm$^{-1}$ MS (ISP): (M+H)$^+$ 250.4; (M+NH$_4$)$^+$ 267.5

The starting material used was prepared as follows:
Di-t-butyl (1aS,3aR,6bR)-5-azidomethyl-1-oxo-1a,2,3,3a,4,6b-hexahydro-1H-2,6a-diazacyclobut[cd]indene-2,6-dicarboxylate Di-t-butyl (1aS,3aR,6bR)-5-hydroxymethyl-1-oxo-1a,2,3,3a,4,6b-hexahydro-1H-2,6a-diazacyclo but [cd]indene-2,6-dicarboxylate (190 mg; 0.5 mmol) in dimethylformamide (2.0 ml) was treated at −20° C. with triethylamine (0.097 ml; 0.7 mmol) and methanesulphonyl chloride (0.054 ml; 0.7 mmol). After 15 minutes at this temperature the mixture was diluted with dimethylformamide (9 ml) and sodium azide (49 mg; 0.75 mmol) was added. Subsequently, the reaction mixture was stirred at 0° C. for 1 hour and poured into a mixture of ethyl acetate (90 ml) and water (45 ml). The organic phase was washed in succession with water (2×20 ml) and saturated aqueous sodium chloride solution (30 ml), dried over magnesium sulphate and concentrated. The residue was treated with n-hexane and suction filtered. Yield: 200 mg (97%) as a light yellow powder.

IR (KBr): 2110, 1768, 1708, 1644 cm$^{-1}$ MS (H): (M-$^t$BUO.) 332

EXAMPLE 82

(1aS,3aR,6bR)-5-Azidomethyl-2-(4-hydroxy-phenylcarbamoyl)-1-oxo-1a,2,3,3a,4,6b-hexahydro-1H-2,6a-diazacyclobut[cd]indene-6-carboxylic acid sodium salt This compound was prepared in the same manner as given in Example 3(a) starting from (1aS,3aR,6bR)-5-azidomethyl-1-oxo-1a,2,3,3a,4,6b-hexahydro-1H-2,6a-diazacyclobut[cd]indene-6-carboxylic acid trifluoroacetate (130 mg; 0.37 mmol). Yield: 50 mg (33%) as a yellowish powder.

IR (KBr): 2107, 1747, 1650, 1606 cm$^{-1}$ MS (ISP): (M+H)$^+$ 407.4; (M−Na+2H)$^+$ 385.5

EXAMPLE 83

(a) (1aS,3aR,6bR)-2-Acetyl-5-azidomethyl-1-oxo-1a,2,3,3a,4, 6b-hexahydro-1H-2,6a-diazacyclobut[cd]indene-6-carboxylic acid sodium salt This compound was prepared in the same manner as given in Example 19(a) starting from (1aS,3aR,6bR)-5-azidomethyl-1-oxo- 1a,2,3,3a,4,6b-hexahydro-1H-Z,6a-diazacyclobut[cd]Lndene-6-carboxylic acid trifluoroacetate (130 mg; 0.37 mmol). Yield: 35 mg (30%) as a brown powder.

IR (KBr): 2103, 1752, 1650, 1613 cm$^{-1}$ MS (ISN): (M−Na)$^-$ 290.3

(b) (1aS,3aR,6bR)-5-Azidomethyl-2-trifluoroacetyl-1-oxo-1a,2,3,3 a,4,6b-hexahydro-1H-2,6a-diazacyclobut[cd]indene-6-carboxylic acid sodium salt This compound was prepared in the same manner as given in Example 19(c) starting from (1aS,3aR,6bR)-5-azidomethyl-1-oxo-1a,2,3,3a,4,6b-hexahydro-1H-2,6a-diazacyclobut[cd]indene-6-carboxylic acid trifluoroacetate (126 mg; 0.36 mmol). Yield: 34 mg (26%) as a brown powder.

IR (KBr): 2107, 1762, 1696, 1612 cm$^{-1}$

EXAMPLE 84

(1aS,3aR6bR)-5-Acetylaminomethyl-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-acetylaminomethyl-1-oxo-1a,2,3,3a,4,6b-hexahydro-1H-2,6a-diazacyclobut[cd]indene-2,6-dicarboxylate (350 mg; 0.83 mmol). Yield: 255 mg (82%) as a beige powder.

IR (KBr): 1781, 1675, 1640, 1551, 1200 cm$^{-1}$ MS (ISN): (M−H)$^-$ 264.3

The starting material used was prepared as follows:
a) Di-t-butyl(1aS,3aR,6bR)-5-aminomethyl-1-oxo-1a,2,3,3a,4,6b-hexa-hydro-1H-2,6a-diazacyclobut[cd]indene-2,6-dicarboxylate hydrochloride Di-t-butyl (1aS,3aR,6bR)-5-azidomethyl-1-oxo-1a,2,3,3a,4,6b-hexahydro-1H-2,6a-diazacyclobut[cd]indene-2,6-dicarboxylate hydrochloride (520 mg; 1.28 mmol; from Example 81) was dissolved in methanol (50 ml) and 1N aqueous hydrochloric acid (1.3 ml) and hydrogenated over 10% Pd/C (125 mg). After 1 hour the reaction mixture was suction filtered and concentrated. Yield: 530 mg (100%) as a colourless powder.

IR (KBr):1777, 1705, 1368, 1163 cm$^{-1}$ MS (ISP): (M+H)$^+$ 380.5 b) Di-t-butyl (1aS,3aR,6bR)-5-acetylaminomethyl-1-oxo-1a,2,3,3a,4,6b-hexahydro-1H-2,6a-diazacyclobut[cd]indene-2,6-dicarboxylate Di-t-butyl (1aS,3aR,6bR)-5-aminomethyl-1-oxo-1a,2,3,3a,4,6b-hexahydro-1H-2,6a-diazacyclobut[cd]indene-2,6-dicarboxylate hydrochloride (490 mg; 1.16 mmol) was dissolved in methylene chloride (5 ml) and treated at −15° C. with methylamine (0.33 ml; 2.4 mmol) and acetyl chloride (0.093 ml; 1.3 mmol). After 10 minutes the reaction mixture was diluted with methylene chloride (25 ml) and washed in succession with water (10 ml) and saturated aqueous sodium chloride solution (10 ml). The organic phase was dried over magnesium sulphate and concentrated. Yield: 350 mg (60%) as a colourless powder.

IR (KBr): 1775, 1705, 1660, 1535 cm$^{-1}$ MS (ISP): (M+NH$_4$)$^+$ 439.6

EXAMPLE 85

(1aS,3aR,6bR)-5-Acetylaminomethyl-2-(4-hydroxy-phenylcarbamoyl)-1-oxo-1a,2,3,3a,4,6b-hexahydro-1H-2,6a- diazacyclobut[cd]indene-6-carboxylic acid sodium salt

This compound was prepared in the same manner as given in Example 3(a) starting from (1aS,3aR,6bR)-5-acetylaminomethyl-1-oxo-1a,2,3,3a,4,6b-hexahydro-1H-2,6a-diazacyclobut[cd]indene-6-carboxylic acid trifluoroacetate (100 mg; 0.267 mmol). Yield: 34 mg (30%) as a colourless powder.

IR (KBr): 1747, 1646, 1604, 1513, 1374 cm$^{-1}$ MS (ISN): (M–Na)$^-$ 399.4

EXAMPLE 86

(1aS,3aR,6bR)-5-Acetylaminomethyl-1-oxo-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-5-acetylaminomethyl-1-oxo-1a,2,3,3a,4,6b-hexahydro-1H-2,6a-diazacyclobut[cd]indene-6-carboxylic acid trifluoroacetate (130 mg; 0.348 mmol). Yield: 24 mg (18%) as a colourless powder.

IR (KBr): 1759, 1698, 1607, 1542, 1401 cm$^{-1}$ MS (ISP): (M–Na+2H)$^+$ 362.4; (M–Na+H+NH$_4$)$^+$ 379.4; (M+H)$^+$ 384.4

EXAMPLE 87

(1aS,3aR,6bR)-5-Methylsulphonylaminomethyl-1-oxo-1a,2,3,3a,4,6b-hexahydro-1H-2,6a-diazacyclobut[Cd]indene-6-carboxylic acid trifluoroacetate This compound was prepared in the same manner as given in Example 2(a) starting from di-t-butyl (1aS,3aR,6bR)-5-methylsulphonylaminomethyl-1-oxo-1a,2,3,3a,4,6b-hexahydro-1H-2,6a-diazacyclobut[cd]indene-2,6-dicarboxylate (600 mg; 1.3 mmol). Yield: 530 mg (97%) as a beige powder.

IR (KBr): 1779, 1677, 1630, 1315, 1148 cm$^{-1}$ MS (ISP): (M+H)$^+$ 302.3

The starting material used was prepared as follows:

Di-t-butyl (1aS,3aR,6bR)-5-aminomethyl-1-oxo-1a,2,3,3a,4,6b-hexahydro-1H-2,6a-diazacyclobut[cd]indene-2,6-dicarboxylate hydrochloride (800 mg; 1.9 mmol; from Example 84) was dissolved in methylene chloride (8 ml) and treated at –40° C. with triethylamine (0.59 ml; 4.2 mmol) and mesyl chloride (0.18 ml; 2.3 mmol). After 20 minutes the reaction mixture was diluted with ethyl acetate (40 ml) and washed in succession with water (20 ml) and saturated aqueous sodium chloride solution (20 ml). The organic phase was dried over magnesium sulphate and concentrated. The residue obtained was crystallized from ethyl acetate/n-hexane and filtered off under suction. Yield: 660 mg (76%) as a colourless powder.

IR (KBr): 1757, 1693, 1639 cm$^{-1}$ MS (ISP): (M+NH$_4$)$^+$ 475.5

EXAMPLE 88

(a) (1aS,3aR,6bR)-2-Acetyl-5-methylsulphonylaminomethyl-1-oxo-1a,2,3,3a,4,6b-hexaliydro-1H-2,6a-diazacyclobut[cd]indene-6-carboxylic acid sodium salt This compound was prepared in analogy to Example 19(a) starting from (1aS,3aR,6bR)-5-methylsulphonylaminomethyl-1-oxo-1a,2,3,3a,4,6b-hexahydro-1H-2,6a-diazacyclobut[cd]indene-6-carboxylic acid trifluoroacetate (220 mg; 0.523 mmol) in dimethylformamide (6 ml). Yield: 105 mg (55%) as a colourless powder.

IR (KBr): 1751, 1614, 1403, 1311, 1148 cm$^{-1}$ MS (ISN): (M–Na)$^-$ 342.3

(b) (1aS,3aR,6bR)-5-Methylsulphonylaminomethyl-1-oxo-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-5-methylsulphonylaminomethyl-1-oxo-1a,2,3,3a,4,6b-hexahydro-1H-2,6a-diazacyclobut[cd]indene-6-carboxylic acid trifluoroacetate (220 mg; 0.523 mmol). Yield: 83 mg (38%) as a colourless powder.

IR (KBr): 1758, 1694, 1604, 1401, 1149 cm$^{-1}$ MS (ISN): (M–Na)$^-$ 396.3; (M–Na+NH$_3$)$^-$ 413.3

EXAMPLE 89

(1aS,3aR,6bR)-5-(4-Hydroxy-phenylcarbamoyloxymethyl)-1-oxo-1a,2,3,3a,4,6b-hexahydro-1H-2,6ardiazacyclobut[cd]indene-6-carboxylic acid trifluoroacetate This compound was prepared in the same manner as given in Example 2(a) starting from di-t-butyl (1aS,3aR,6bR)-5-(4-hydroxyphenylcarbamoyloxymethyl)-1-oxo-1a,2,3,3a,4,6b-hexahydro-1H-2,6a-diazacyclobut[cd]indene-2,6-dicarboxylate (640 mg; 1.24 mmol). Yield: 670 mg (100%) as a colourless powder.

IR (KBr): 1775, 1677, 1516 cm$^{-1}$ MS (ISN): (M–H)$^-$ 358.3

The starting material used was prepared as follows:

Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (770 mg; 2.03 mmol) was dissolved in methylene chloride (24 ml) and treated with 0.4 nm molecular sieve (1 g), di-(N-succinimidyl) carbonate (624 mg; 2.44 mmol) and triethylamine (0.68 ml; 4.86 mmol) at room temperature. After 1 hour 4-aminophenol (270 mg; 2.44 mmol) and triethylamine (0.56 ml; 4.05 mmol) were added. After 1 hour the reaction mixture was diluted with methylene chloride (100 ml) and washed in succession with saturated aqueous sodium bicarbonate solution (20 ml) and saturated aqueous sodium chloride solution (20 ml), dried over magnesium sulphate and concentrated. The residue obtained was chromatographed over silica gel (50 g; 0.040–0.063 mm particle size) with ethyl acetate/n-hexane 6:4. Yield: 640 mg (61%) as a colourless solid.

IR (KBr): 1776, 1708, 1516 cm$^{-1}$ MS (ISP): (M+H)$^+$ 516,4; (M+NH$_4$)$^+$ 533,4; (M+Na)$^+$ 538.3

EXAMPLE 90

(a) (1aS,3aR,6bR)-2-Acetyl-5-(4-hydroxy-phenylcarbamoyloxymethyl)-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-(4-hydroxy-phenylcarbamoyloxymethyl)-1-oxo-1a,2,3,3a,4,6b-hexahydro-1H-2,6a-diazacyclobut[cd]indene-6-carboxylic acid trifluoroacetate (220 mg; 0.47 mmol) in dimethylformamide (6 ml). Yield: 154 mg (77%) as a yellowish powder.

IR (KBr): 1751, 1720, 1606, 1404, 1221 cm$^{-1}$ MS (ISN): (M–Na)$^-$ 400.31

(b) (1aS,3aR,6bR)-5-(4-Hydroxy-phenylcarbamoyloxymethyl)-2-trifluoroacetyl-1-oxo-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-5-(4-hydroxy-phenylcarbamoyloxymethyl)-1-oxo-1a,2,3,3a,4,6b-hexahydro-1H-2,6a-diazacyclobut[cd]indene-6-carboxylic acid trifluoroacetate (220 mg; 0.47 mmol). Yield: 120 mg (53%) as a yellowish powder.

IR (KBr): 1759, 1694, 1605, 1402, 1222 cm$^{-1}$ MS (ISN): (M–Na)$^-$ 454.2

EXAMPLE 91

(1aS,3aR,6bR)-1-Oxo-5-(2,2,2-trifluoroethylcarbamoyloxymethyl)-1a,2,3,3a,4,6b-hexahydro-1H-2,6a -diazacyclobut[cd]indene-6-carboxylic acid trifluoroacetate This compound was prepared in the same manner as given in Example 2(a) starting from di-t-butyl (1aS,3aR,6bR)-1-oxo-5-(2,2,2-trifluoroethylcarbamoyloxymethyl)-1a,2,3,3a, 4,6b-hexahydro-1H-2,6a-diazacyclobut[cd]indene-2,6-dicarboxylate (408 mg; 0.81 mmol). Yield: 217 mg (69%) as a yellowish powder.

IR (KBr): 1773, 1725, 1679, 1625, 1549, 1403, 1241, 1156 cm$^{-1}$ MS (ISP): (M+H)$^+$ 350.3; (M+NH$_4$)$^+$ 367.3

The starting material used was prepared in analogy to Example 89 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (400 mg; 1.05 mmol) and 2,2,2-trifluoroethylamine (0.1 ml; 1.26 mmol). Yield: 435 mg (82%) as a colourless solid.

IR (KBr): 1776, 1709, 1539, 1240, 1158 cm$^{-1}$ MS (ISP): (M+H)$^+$ 506.4; (M+NH$_4$)$^+$ 523.4

EXAMPLE 92

(a) (1aS,3aR,6bR)-2-Acetyl-1-oxo-5-(2,2,2-trifluoroethylcarbamoyloxymethyl)-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-1-oxo-5-(2,2,2-trifluoroethylcarbamoyloxymethyl)-1a,2,3,3a,4,6b-hexahydro-1H-2, 6a-diazacyclobut[cd]indene-6-carboxylic acid trifluoroacetate (95 mg; 0.24 mmol) in dimethylformamide (3 ml). Yield: 35 mg (35%) as a yellowish powder.

IR (KBr): 1758, 1730, 1618, 1408, 1151 cm$^{-1}$ MS (ISP): (M+NH$_4$)$^+$ 409.3; (M+Na)$^+$ 414.2

(b) (1aS,3aR,6bR)-1-Oxo-2-trifluoroacetyl-5-(2,2,2-trifluoroethylcarbamoyloxymethyl)-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-1-oxo-5-(2,2,2-trifluoroethylcarbamoyloxymethyl)-1a,2,3,3a,4,6b-hexahydro-1H-2,6a-diazacyclobut[cd]indene6-carboxylic acid trifluoroacetate (120 mg; 0.307 mmol). Yield: 56 mg (39%) as a beige powder.

IR (KI3r): 1762, 1695, 1608, 1546, 1403, 1152 cm$^{-1}$ MS (ISP): (M+NH$_4$)$^+$ 463.2

EXAMPLE 93

(1aS,3aR,6bR)-5-Cyclopropylcarbamoyloxymethyl-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-cyclopropylcarbamoyloxymethyl-1-oxo-1a,2,3,3a,4,6b-hexahydro-1H-2,6a-diazacyclobut[cd]indene-2,6-dicarboxylate (490 mg; 1.05 mmol). Yield: 330 mg (78%) as a beige powder.

IR (KBr): 1780, 1700, 1681, 1625, 1410, 1203 cm$^{-1}$ MS (ISP): (M+H)+308.3

The starting material used was prepared in analogy to Example 89 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (500 mg; 1.32 mmol) and cyclopropylamine (0.11 ml; 1.58 mmol). Yield: 533 mg (88%) as a colourless powder.

IR (KBr): 1781, 1709, 1686 cm$^{-1}$ MS (ISP): (M+H)$^+$ 464.4; (M+NH$_4$)$^+$ 481.4; (M+Na)$^+$ 486.4

EXAMPLE 94

(a) (1aS,3aR,6bR)-2-Acetyl-5-cyclopropylcarbamoyloxymethyl-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-cyclopropylcarbamoyloxymethyl-1-oxo-1a,2,3,3a,4,6b-hexahydro-1H-2,6a-diazacyclobut[cd]indene-6-carboxylic acid trifluoroacetate (150 mg; 0,37 mmol) in dimethylformamide (2.5 ml). Yield: 71 mg (51%) as a colourless powder.

IR (KBr): 1754, 1708, 1640, 1606, 1529, 1406, 1263 cm$^{-1}$ MS (ISP): (M+H)$^+$ 350.3; (M+NH$_4$)$^+$ 367.4; (M+Na)$^+$ 372.3

(b) (1aS,3aR,6bR)-5-Cyclopropylcarbamoyloxymethyl-1-oxo-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-5-cyclopropylcarbamoyloxymethyl-1-oxo-1a,2,3,3a,4,6b-hexahydro-1H-2,6a-diazacyclobut[cd]indene-6-carboxylic acid trifluoroacetate (150 mg; 0.37 mmol). Yield: 67 mg (42%) as a pale brown powder.

IR (KBr): 1764, 1697, 1607, 1520, 1404 cm$^{-1}$ MS (ISN): (M–Na)$^-$ 402.2

EXAMPLE 95

(1aS,3aR,6bR)-5-Carbamoylmethylcarbamoyloxymethyl-1-oxo- 1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-carbamoylmethylcarbamoyloxymethyl-1-oxo-1a,2,3,3a,4, 6b-hexahydro-1H-2,6a-diazacyclobut[cd]indene-2,6-dicarboxylate (317 mg; 0.66 mmol). Yield: 236 mg (79%) as a beige powder.

IR (KBr): 1774, 1700, 1679, 1610, 1426, 1203 cm$^{-1}$ MS (ISP): (M+H)+ 325.3

The starting material used was prepared in analogy to Example 89 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (500 mg; 1.31 mmol) and glycinamide hydrochloride (175 mg; 1.58 mmol). Yield: 260 mg (41%) as a colourless solid.

IR (KBr): 1776, 1710, 1690, 1525, 1244 cm$^{-1}$ MS (ISP): (M+H)$^+$ 481.4; (M+NH$_4$)$^+$ 498.5; (M+Na)$^+$ 503.5

EXAMPLE 96

(a) (1aS,3aR,6bR)-2-Acetyl-5-carbamoylmethylcarbamoyloxymethyl- 1-oxo-1a,2,3,3a,4,6b-hexahydro-1H-2,6a-diazacyclobut[cd]indene- 6-carboxylic acid sodium salt This compound was prepared in analogy to Example 19(a) starting from (1aS,3aR,6bR)-5-carbamoylmethylcarbamoyloxymethyl- 1-oxo-1a,2,3,3a,4,6b-hexahydro-1H-2, 6a-diazacyclobut[cd]indene- 6-carboxylic acid trifluoroacetate (100 mg; 0.22 mmol) in dimethylformamide (2 ml). Yield: 26 mg (30%) as an orange powder.

IR (KBr): 1755, 1680, 1621, 1540, 1402 cm$^{-1}$ MS (ISN): (M–Na)$^-$ 365.2

(b) (1aS,3aR,6bR) 5-Carbamoylmethylcarbamoyloxymethyl-1-oxo-2-trifluoroacetyl-1a,2,3,3a,4,6b-hexahydro-1H-2,6a-diazacyclobut[cd]indene- 6-carboxylic acid sodium salt This compound was prepared in the same manner as given in Example 19(c) starting from (1aS,3aR,6bR)-5-carbamoylmethylcarbamoyloxymethyl- 1-oxo-1a,2,3,3a,4,6b-hexahydro-1H-2,6a-diazacyclobut[cd]indene- 6-carboxylic acid trifluoroacetate (100 mg; 0.22 mmol). Yield: 28 mg (29%) as a brownish powder.

IR (KBr): 1763, 1690, 1606, 1529, 1403 cm$^{-1}$ MS (ISP): (M+H)$^+$ 443.2

EXAMPLE 97

(1aS,3aR,6bR)-5-Methylcarbamoyloxymethyl-1-oxo-1a,2,3,3a,4,6b-hexahydro- 1H-2,6a-diazacyclobut[cd]indene-6-carboxylic acid trifluoroacetate This compound was prepared in the same manner as given in Example 2(a) starting from di-t-butyl (1aS,3aR,6bR)-5-methylcarbamoyloxymethyl- 1-oxo-1a,2,3,3a,4,6b-hexahydro-1H-2,6a-diazacyclobut[cd]indene- 2,6-dicarboxylate (600 mg; 1.37 mmol). Yield: 490 mg (92%) as a light beige powder.

IR (KBr): 1776, 1710, 1680, 1539, 1201 cm$^{-1}$ MS (ISN): (M−H)$^-$ 280.2

The starting material used was prepared in analogy to Example 89 starting from di-t-butyl (1aS,3aR,6bR)-5-hydroxymethyl-1-oxo-1a,2,3,3a,4,6b-hexahydfo-1H-2,6a-diazacyclobut[cd]indene-2,6-dicarboxylate (600 mg; 1.58 mmol) and methylamine hydrochloride (126 mg; 1.89 mmol). Yield: 600 mg (87%) as a colourless foam.

IR (KBr): 1776, 1708, 1634, 1532, 1246 cm$^{-1}$ MS (ISP): (M+H)$^+$ 438.5; (M+NH$_4$)$^+$ 455.5; (M+Na)$^+$ 460.4

EXAMPLE 98

(a) (1aS,3aR,6bR)-2-Acetyl-5-methylcarbamoyloxymethyl-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-methylcarbamoyloxymethyl-1-oxo-1a,2,3,3a,4,6b-hexahydro-1H-2,6a-diazacyclobut[cd]indene-6-carboxylic acid trifluoroacetate (100 mg; 0.26 mmol) in dimethylformamide (2 ml). Yield: 41 mg (46%) as an orange powder.

IR (KBr): 1754, 1704, 1624, 1540, 1405 cm$^{-1}$ MS (ISN): (M−Na)$^-$ 322.2

(b) (1aS,3aR,6bR)-5-Methylcarbamoyloxymethyl-1-oxo-2-trifluoroacetyl-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-5-methylcarbamoyloxymethyl- 1-oxo-1a,2,3,3a,4,6b-hexahydro-1H-2,6a-diazacyclobut[cd]indene-6-carboxylic acid trifluoroacetate (200 mg; 0.506 mmol). Yield: 70 mg (34%) as a yellow-brown powder.

IR (KBr): 1768, 1696, 1610, 1537, 1405 cm$^{-1}$ MS (ISP): (M+H)$^+$ 378.2; (M+NH$_4$)$^+$ 395.3; (M+Na)$^+$ 400.2

EXAMPLE 99

(1aS,3aR,6bR)-1-Oxo-5-(pyridin-4-ylmethylcarbamoyloxymethyl)-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-1-oxo-5-(pyridin- 4-ylmethylcarbamoyloxymethyl)-1-oxo-1a,2,3,3a,4,6b-hexahydro- 1H-2,6a-diazacyclobut[cd]indene-2,6-dicarboxylate (1.00 g; 1.94 mmol). Yield: 1.17 g (100%) as a light beige powder.

IR (KBr): 1782, 1710, 1678, 1511, 1198 cm$^{-1}$ MS (ISP): (M+H)$^+$ 359.3

The starting material used was prepared in analogy to Example 89 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (900 mg; 2.37 mmol) and 4-picolylamine (0.29 ml; 2.8 mmol). Yield: 657 mg (54%) as a colourless solid.

IR (KBr):.1774, 1706, 1690, 1243 cm$^{-1}$ MS (ISP): (M+H)+5 15.4

EXAMPLE 100

(a) (1aS,3aR,6bR)-2-Acetyl-1-oxo-5-(pyridin-4-ylmethylcarbamoyloxymethyl)- 1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-1-oxo-5-(pyridin-4-ylmethylcarbamoyloxymethyl)-1a,2,3,3a,4,6b-hexahydro-1H-2,6a-diazacyclobut[cd]indene- 6-carboxylic acid trifluoroacetate (200 mg; 0.33 mmol) in dimethylformamide (3 ml). Yield: 80 mg (57%) as a beige powder.

IR (KBr): 1755, 1712, 1640, 1604, 1418 cm$^{-1}$ MS (ISP): (M+2H−Na)$^+$ 401.3

(b) (1aS,3aR,6bR)-1-Oxo-5-(pyridin4-ylmethylcarbamoyloxymethyl)-2-trffiuoroacetyl- 1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-1-oxor5-(pyridin-4-ylmethylcarbamoyloxymethyl)- 1a,2,3,3a,4,6b-hexahydro-1H-2,6a-diazacyclobut[cd]indene-6-carboxylic acid trifluoroacetate (200 mg; 0.33 mmol). Yield: 90 mg (57%) as a colourless powder.

IR (KBr): 1762, 1712, 1698, 1605, 1401 cm$^{-1}$ MS (ISN): (M−Na)$^-$ 453.3

(c) (1aS,3aR,6bR)-2-[(R) -N-(Benzyloxycarbonyl)-2-phenyl-glycyl]-1-oxo-5-(pyridin-4-ylmethylcarbamoyloxymethyl)-1a,2,3,3a,4,6b-hexahydro-1H-2,6a-diazacyclobut[cd]indene-6-carboxylic acid potassium salt This compound was prepared in analogy to Example 19(c) starting from (1aS,3aR,6bR)-1-oxo-5-(pyridin-4-ylmethylcarbamoyloxymethyl)-1a,2,3,3a,4,6b-hexahydro-1H-2,6a-diazacyclobut[cd]indene-6-carboxylic acid trifluoroacetate (500 mg; 0.83 mmol), N-benzyloxycarbonyl-D-(−)[R] -2-phenylglycine (515 mg; 2.5 mmol) and potassium carbonate (250 mg; 1.8 mmol) in dimethylformamide (5 ml). Yield: 97 mg (19%) of brownish powder.

IR (KBr): 1756, 1713, 1605, 1523 cm$^{-1}$ MS (ISP): (M+H)$^+$ 626.3

(1aS,3aR,6bR)-2-[(R)-2-phenyl-glycyl]-1-oxo-5-(pyridin-4-ylmethylcarbamoyloxymethyl)-1a,2,3,3a,4,6b-hexahydro-1H-2,6a-diazacyclobut[cd]indene-6-carboxylic acid hydrochloride (1aS,3aR,6bR)-2-[(R)-Benzyloxycarbonylamino-phenylacetyl]-1-oxo-5-(pyridin-4-ylmethylcarbamoyloxymethyl)-1a,2,3,3a,4,6b-hexahydro-1H-2,6a-diazacyclobut[cd]indene-6-carboxylic acid potassium salt (85 mg; 0.136 mmol) was hydrogenated in methanol (20 ml) and 1N aqueous hydrochloric acid (0.41 ml) over 10% Pd/C (20 mg). After 2.5 hours the suspension was suction filtered, concentrated, triturated with ether and suction filtered. Yield: 43 mg (56%) as a yellow-orange powder.

IR (KBr): 1760, 1720, 1643 cm$^{-1}$ MS (ISP): (M+H)$^+$ 492.4

EXAMPLE 101

(1aS,3aR,6bR)-5-[(4-Hydroxy-benzyl)-carbamoyloxymethyl]-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3ag,6bR)-5-[(4-hydroxybenzyl)-carbamoyloxymethyl]-1-oxo-1a,2,3,3a,4,6b-hexahydro-1H-2,6a-diazacyclobut[cd]indene-2,6-dicarboxylate (380 mg; 0.72 mmol). Yield: 280 mg (84%) as a beige powder.

IR (KBr): 1774, 1710, 1696, 1615, 1515, 1203 cm$^{-1}$ MS (ISP): (M+H)$^+$ 374.2; (M+NH$_4$)$^+$ 391.3; (M+Na)$^+$ 396.2

The starting material used was prepared in analogy to Example 89 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (600 mg; 1.58 mmol) and 4-hydroxybenzylamine (270 mg; 2.2 mmol). Yield: 320 mg (38%) as a colourless solid.

IR (KBr): 1775, 1705, 1516, 1367, 1242, 1161 cm$^{-1}$ MS (ISP): (M+H)$^+$ 530.4; (M+NH$_4$)$^+$ 547.4; (M+Na)$^+$ 552.4

EXAMPLE 102

(a) (1aS,3aR,6bR)-2-Acetyl-5-[(4-hydroxy-benzyl)-carbamoyloxymethyl]-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5[(4-hydroxy-benzyl)-carbamoyloxymethyl]-1-oxo-1a,2,3,3a,4,6b-hexahydro-1H-2,6a-diazacyclobut[cd]indene-6-carboxylic acid trifluoroacetate (110 mg; 0.24 mmol) in dimethylformamide (2 ml). Yield: 36 mg (35%) as a beige powder.

IR (KBr): 1758, 1710, 1613, 1515, 1406 cm$^{-1}$ MS (ISP): (M+H)$^+$ 415.9; (M+NFI4)$^+$ 433.0; (M+Na)$^+$ 438.0

(b) (1aS,3aR,6bR)-5-[(4-Hydroxy-benzyl)-carbamoyloxymethyl]-2-trifluoroacetyl-1-oxo-1a,2,3,3a,4,6b-hexahydro-1H-2,6a-diazacyclobut[cd]indene-6-carboxylic acid sodium salt This compound was prepared in the same manner as given in Example 19(c) starting from (1aS,3aR,6bR)-5-[(4-hydroxy-benzyl)carbamoyloxymethyl]-1-oxo-1a,2,3,3a,4,6b-hexahydro-1H-2,6a-diazacyclobut[cd]indene-6-carboxylic acid trifluoroacetate (120 mg; 0.26 mmol). Yield: 29 mg (23%) as a brown powder.

IR (KBr): 1765, 1694, 1612, 1516, 1403 cm$^{-1}$ MS (ISP): (M+H)$^+$ 470.0; (M+NH$_4$)$^+$ 487.1; (M+Na)$^+$ 492.1

EXAMPLE 103

(1aS,3aR,6bR)-5-(4-Methyl-piperazin-1-ylcarbonyloxymethyl)-1-oxo-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-5-(4-methylpiperazin-1-ylcarbonyloxymethyl)-1-oxo-1a,2,3,3a,4,6b-hexahydro-1H-2,6a-diazacyclobut[cd]indene-2,6-dicarboxylate (900 mg; 1.78 mmol). Yield: 807 mg (76%) as a beige powder.

IR (KBr): 1779, 1700, 1679, 1201 cm$^{-1}$ MS (ISP): (M+H)$^+$ 351

The starting material used was prepared in analogy to Example 89 starting from di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate (600 mg; 1.58 mmol) and 4-methyl-piperazine (0.19 ml; 1.89 mmol). Yield: 805 mg (100%) as a colourless resinous solid.

IR (KBr): 1774, 1702, 1366, 1160 cm$^{-1}$ MS (ISP): (M+H)$^+$ 507

EXAMPLE 104

(a) (1aS,3aR,6bR)-2-Acetyl-5-(4-methyl-piperazin-1-ylcarbonyloxymethyl)-1-oxo-1a,2,3,3a,4,6b-hexahydro-1H-2,6a-diazacyclobut[cd]indene-6-carboxylic acid sodium salt This compound was prepared in analogy to Example 19(a) starting from (1aS,3aR,6bR)-5-(4-methyl-piperazin-1-ylcarbonyloxymethyl)-1-oxo-1a,2,3,3a,4,6b-hexahydro-1H-2,6a-diazacyclobut[cd]indene-6-carboxylic acid trifluoroacetate (200 mg; 0.33 mmol) in dimethylformamide (4 ml). Yield: 40 mg (29%) as a brown powder.

IR (KBr): 1757, 1694, 1640, 1608, 1427, 1236 cm$^{-1}$ MS (ISP): (M+H)$^+$ 393.1

(b) (1aS,3aR,6bR)-5-(4-Methyl-piperazin-1-ylcarbonyloxymethyl)-2-trifluoroacetyl-1-oxo-1a,2,3,3a,4,6b-hexahydro-1H-2,6a-diazacyclobut[cd]indene6-carboxylic acid sodium salt This compound was prepared in the same manner as given in Example 19(c) starting from (1aS,3aR,6bR)-5-(4-methyl-piperazin-1-ylcarbonyloxymethyl)-1-oxo-1a,2,3,3a,4,6b-hexahydro-1H-2,6a-diazacyclobut[cd]indene-6-carboxylic acid trifluoroacetate (200 mg; 0.33 mmol). Yield: 82 mg (52%) as a yellowish powder.

IR (KBr): 1756, 1710, 1661, 1614, 1402, 1207 cm$^{-1}$ MS (ISN): (M–Na)$^-$ 445.2

EXAMPLE 105

(1aS,3aR,6bR)-1-Oxo-5-(tetrazol-5-yl-amino-carbonyloxymethyl)-1a,2,3,3a,4,6b-hexahydro-1H-2,6a-diazacyclobut[cd]indene-6-carboxylic acid trifluoroacetate This compound was prepared in the same manner as given in Example 2(a) starting from di-t-butyl (1aS,3aR,6bR)-1-oxo-5-(tetrazol-5-yl-aminocarbonyloxymethyl)-1-oxo-1a,2,3,3a,4,6b-hexahydro-1H-2,6a-diazacyclobut[cd]indene-2,6-dicarboxylate (750 mg; 1.52 mmol). Yield: 410 mg (60%) as a yellow-brown solid.

IR (KBr): 1773, 1700, 1677, 1611, 1401, 1203, 1135 cm$^{-1}$ MS (ISP): (M+H)$^+$ 336.3

The starting material used was prepared in analogy to Example 89 starting from di-t-butyl ((1aS,3aR,6bR)-5-hydroxymethyl-1-oxo-1a,2,3,3a,4,6b-hexahydro-1H-2,6a-diazacyclobut[cd]indene-2,6-dicarboxylate (1.00 g; 2.63 mmol) and 5-amino-tetrazole (270 mg; 3.15 mmol). Yield: 750 mg (58%) as a colourless powder.

IR (KBr): 1774, 1735, 1703, 1607, 1367, 1242 cm$^{-1}$ MS (ISP): (M+Na)$^+$ 514; (M+K)$^+$ 530

EXAMPLE 106

(1aS,3aR,6bR)-5-Methoxy-1-oxo-1a,2,3,3a,4,6b-hexahydro-1H-2,6a-diazacyclobut[cd]indene-6-carboxylic acid trifluoroacetate Starting from di-t-butyl (1aS,3aR,6bR)-5-methoxy-1-oxo-1a,2,3,3a,4,6b-hexahydro-1H-2,6a -diazacyclobut[cd]indene-2,6-dicarboxylate (1.43 g; 3.8 mmol) there were obtained in analogy to Example 2(a) 1.12 g (70%) as a yellowish solid.

IR (KBr): 1772, 1679, 1613, 1369, 1201, 1134 cm$^{-1}$ MS (ISP): (M+H)$^+$ 225.3 Microanalysis: $C_{12}H_{13}N_2O_6F_3$ .0.33 H$_2$O.0.65 (CH$_3$CH$_2$)$_2$O.0.27 CF$_3$COOH Calc. C 42.97 H 4.87 N 6.62 F 17.11 Found C 43.14 H 4.85 N 6.39 F 17.14

The di-t-butyl (1aS,3aR,6bR)-5-methoxy-1-oxo-1a,2,3, 3a,4,6b-hexahydro- 1H-2,6a-diazacyclobut[cd]indene-2,6-dicarboxylate used as the starting material was prepared as follows:

A solution of di-t-butyl (1aS,3aR,6bR)-5-hydroxy-1-oxo-1a,2,3,3a,4,6b-hexahydro-2,6a-diazacyclobut[cd]indene-2,6-dicarboxylate (2.00 g; 5.5 mmol; from Example 1) in THF (50 ml) was treated at 0° C. with a solution of diazomethane in diethyl ether (a total of 12 ml, divided into portions of 2 ml and 2×5 ml). The mixture was stirred at room temperature for 4 hours. It was diluted with ethanol (10ml) and concentrated. The residue was chromatographed on silica gel (eluent ethyl acetate/n-hexane 2:1). 1.66 g (80%) were obtained as a white solid.

IR(KBr): 1761, 1705, 1627, 1236, 1162, 1112 cm$^{-1}$ MS (ISP): (M+Na)$^+$ 403; (M+H)$^+$ 381.5 Microanalysis: $C_{19}H_{28}N_2O_6 \cdot 0.043$ $H_2O$ Calc. C 59.86 H 7.43 N 7.05 Found C 60.02 H 7.52 N 7.35

EXAMPLE 107

(1aS,3aR,6bR)-2-(4-Hydroxy-phenylcarbamoyl)-5-methoxy-1-oxo-1a,2,3,3a,4,6b-hexahydro-1H-2,6a-diazacyclobut[cd]indene-6-carboxylic acid sodium salt Starting from (1aS,3aR,6bR)-5-methoxy-1-oxo-1a,2,3,3a,4,6b-hexahydro-1H-2,6a-diazacyclobut[cd]indene-6-carboxylic acid trifluoroacetate (150 mg; 0.35; mmol; from Example 107) there were isolated in analogy to Example 3(a) 81 mg (61%) as a white powder.

IR(KBr): 3400, 1745, 1633, 1513, 1410, 1244, 1112, 1006, 835 cm$^{-1}$ MS (ISN): (M−Na)$^-$ 358.3

EXAMPLE 108

(a) (1aS,3aR,6bR)-2-Acetyl-5-methoxy-1-oxo-1a,2,3,3a,4,6b-hexahydro-1H-2,6a-diazacyclobut[cd]indene-6-carboxylic acid sodium salt Starting from (1aS,3aR,6bR)-5-methoxy-1-oxo-1a,2,3,3a,4,6b-hexahydro-1H-2,6a-diazacyclobut[cd]indene-6-carboxylic acid trifluoroacetate (200 mg; 0.47 mmol; from Example 107) there were obtained in analogy to Example 3(aa) 90 mg (66%) of a white powder.

IR (KBr): 1750, 1633, 1414, 1114 cm$^{-1}$ MS (ISP): (M+Na)$^+$ 311.3; (M+H)$^+$ 289.3; (M−Na+2H)$^+$ 267.3

(b) (1aS,3aR,6bR)-5-Methoxy-1-oxo-2-trifluoroacetyl-1a,2,3,3a, 4,6b-hexahydro-1H-2,6a-diazacyclobut[cd]indene-6-carboxylic acid sodium salt Starting from (1aS,3aR,6bR)-5-methoxy-1-oxo-1a,2,3,3a,4, 6b-hexahydro-1H-2,6a-diazacyclobut[cd]indene-6-carboxylic acid trifluoroacetate (150 mg; 0.35 mmol; from Example 12) there were isolated in analogy to Example 3(ab) 66 mg (49%) as a white powder.

IR (KBr): 1757, 1699, 1633, 1603, 1409, 1156 cm$^{-1}$ MS (ISN): (M−Na)$^-$ 3 19.3 Microanalysis: $C_{12}H_{10}N_2O_5F_3Na$. 1.96 $H_2O \cdot 0.05$ $NaHCO_3$ Calc. C 37.92 H 3,69 N 7.34 F 14.93 Na 6.32 Found C 37.79 H 3,89 N 7.41 F 15.08 Na6.44

EXAMPLE A

Production of dry ampoules for intramuscular administration:

A lyophilizate of 0.5 g of the sodium salt of (1aS,3aR,6bR)-5-carbamoyloxymethyl-2-(4-hydroxy-phenylcarbamoyl)-1-oxo-1a,2,3,3a,4,6b-hexahydro-1H-2,6a-diazacyclobut[cd]indene-6-carboxylic acid and 1 g of the disodium salt of (6R,7R)-7-[2-amino-4-thiazolyl)-2-(Z-methoxyimino) acetamido]-3{[(2,5-dihydro-6-hydroxy-2-methyl-5-oxo-as-triazin-3-yl)thio]methyl}-8-oxo-5-thia-1-azabicyclo [4.2.0]oct-2-ene-2-carboxylic acid is prepared in the usual manner and filled into an ampoule. Prior to administration the lyophilizate is treated with 4 ml of a 2% aqueous lidocaine hydrochloride solution.

If desired, the two active ingredients can be filled separately into two different ampoules.

Another compound of formula I can also be used, e.g.

(1aS,3aR,6bR)-5-carbamoyloxymethyl-2-(4-carbamoylphenylcarbamoyl)-1-oxo-1a,2,3,3a,4,6b-hexahydro-1H-2,6a-diazacyclobut[cd]indene-6-carboxylic acid sodium salt, (1aS,3aR,6bR)-2-(4-carbamoyl-phenylcarbamoyl)-1-oxo-5-(pyridin4-ylsulphanylmethyl)-1a,2,3,3a,4,6b-hexahydro-1H-2,6a-diazacyclobut[cd]indene-6-carboxylic acid, (1aS,3aR,6bR)-5-(5-amino-1,3,4-thiadiazol-2-ylsulphanylmethyl)-2-(4-hydroxy-phenylcarbamoyl)-1-oxo-1a,2,3,3a,4,6b-hexahydro-1H-2,6a-diazacyclobut[cd]indene-6-carboxylic acid sodium salt, (1aS,3aR,6bR)-5-(5-amino-1,3,4-thiadiazol-2-ylsulphanyl)-2-(4-hydroxyphenylcarbamoyl)-1-oxo-1a,2,3,3a, 4,6b-hexahydro-1H-2,6a-diazacyclobut[cd]indene-6-carboxylic acid sodium salt, (1aS,3aR,6bR)-5-carbamoyloxymethyl-1-oxo-2-trifluoroacetyl-1a,2,3,3a,4,6b-hexahydro-1H-2,6a-diazacyclobut[cd]indene-6-carboxylic acid sodium salt, (1aS,3aR,6bR)-1-oxo-5-(pyridin-4-ylsulphanylmethyl)-2-trifluoroacetyl-1a,2,3,3a,4,6b-hexahydro-1H-2,6a-diazacyclobut[cd]indene-6-carboxylic acid sodium salt, (1aS,3aR,6bR)-5-(1-carbamoylmethyl-1H-tetrazol-5-ylsulphanylmethyl)-2-formyl-1-oxo-1a,2,3,3a,4,6b-hexahydro-1H-2,6a-diazacyclobut[cd]indene-6-carboxylic acid sodium salt, (1aS,3aR,6bR)-2-methylsulphonyl-5-(1-methyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt, (1aS,3aR,6bR)-2-acetyl-5-(1-carbamoylmethyl-1H-tetrazol-5-ylsulphanylmethyl)-1-oxo-1a,2,3,3a,4,6b-hexahydro-1H-2,6a-diazacyclobut[cd]indene-6-carboxylic acid sodium salt, (1aS,3aR,6bS)-2-acetyl-5-(1-methyl-1H-tetrazol-5-ylsulphanylmethyl)-1-oxo-1,1a,2,3,3a,6b-hexahydro-4-oxa-2,6a-diazacyclobut[cd]indene-6-carboxylic acid sodium salt.

What is claimed is:

1. A compound of the formula

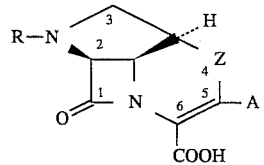

in which Z signifies oxygen or sulphur and R signifies hydrogen, lower (cyclo)alkyl optionally substituted by carboxy, lower alkoxycarbonyl, carbamoyl, lower alkylcarbamoyl, phenylcarbamoyl or hydroxyphenylcarbamoyl, lower alkenylmethyl, lower alkenylmethoxycarbonyl, formyl, lower (cyclo)alkanoyl or (cyclo)alkylsulphonyl optionally substituted by halogen, cyano, carbamoyl-lower-alkoxy, carbamoyl-lower alkylthio or carbamoyl-lower alkylamino, carbamoyl optionally substituted by lower (cyclo)alkyl, lower alkoxycarbonyl-lower alkyl, benzyloxycarbonyl-lower alkyl or carboxy-lower alkyl or a ring structure of the formulae Q—X—CO— (a1)

Q—X—SO₂— (a2)

wherein Q represents a 5- or 6-membered ring optionally containing nitrogen, sulphur and/or oxygen and X represents a direct bond or one of the groups —CH₂—, —CH₂CH₂—, —CH=CH—, —NH—, —NHCH₂—, —CH₂NH—, —CH(NH₂)—, —CH₂CH₂NH—, —C(=NOCH₃)—, —OCH₂— and —SCH₂—; and wherein further A signifies lower alkyl, hydroxy-lower alkyl, vinyl, cyanovinyl, lower alkoxy, optionally phenyl-substituted lower (cyclo)alkanoyloxy or (cyclo)alkylsulphonyloxy, optionally lower-(cyclo)alkyl-substituted benzoyloxy or phenylsulphonyloxy, a residue —S-Het or —S—CH₂-Het, wherein Her represents a 5- or 6-membered heterocycle containing nitrogen, sulphur and/or oxygen, or a residue —CH₂-L, wherein L represents optionally phenyl-substituted lower (cyclo)alkanoyloxy or (cyclo)alkylsulphonyloxy, optionally lower (cyclo)alkyl-substituted benzoyloxy or phenylsulphonyloxy, carbamoyloxy, lower (cyclo)alkoxycarbonyl, carboxy, azido, amino, lower (cyclo)alkanoylamino, lower (cyclo)alkylsulphonylamino, lower (cyclo)alkylamino, di-lower (cyclo)alkylamino, a 5- or 6-membered ring bonded to a nitrogen atom or a residue —S-Het or —S—CH₂-Het, wherein Het has the above significance, and pharmaceutically compatible, readily hydrolyzable esters and salts of these compounds.

2. The compound of claim 1, wherein R signifies a group of the formula

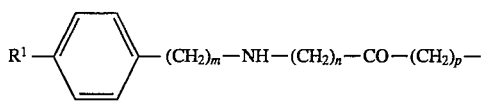
(b)

wherein $R^1$ signifies hydrogen, hydroxy, carbamoyl or sulphamoyl and each of m, n and p represent 0 or 1.

3. The compound of claim 2, wherein R represents the group

(b1)

wherein $R^1$ has the significance given in claim 2.

4. The compound of claim 2, wherein R represents the group

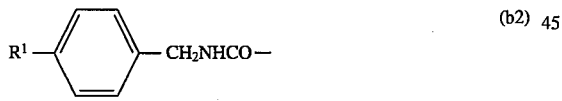
(b2)

wherein $R^1$ has the significance given in claim 3.

5. The compound of claim 2, wherein R represents the group

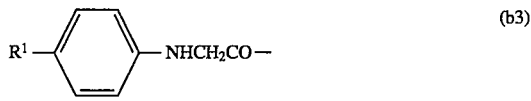
(b3)

wherein $R^1$ has the significance given in claim 2.

6. The compound of claim 3, wherein R represents the group

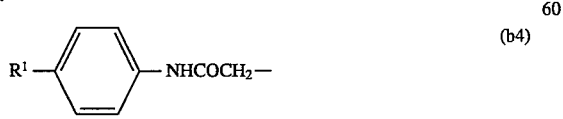
(b4)

wherein R has the significance given in claim 2.

7. The compound of claim 3, wherein R represents the 4-hydroxyphenylcarbamoyl group.

8. The compound of claim 3, wherein R represents the 4-carbamoylphenylcarbamoyl group.

9. The compound of claim 1, wherein R represents an optionally fluoro- or cyano-substituted lower alkanoyl or lower alkylsulphonyl group.

10. The compound of claim 9, wherein R represents the formyl group.

11. The compound of claim 9, wherein R represents the acetyl group.

12. The compound of claim 9, wherein R represents the trifluoroacetyl group.

13. The compound of claim 9, wherein R represents the cyanoacetyl group.

14. The compound of claim 9, wherein R represents the methylsulphonyl group.

15. The compound of claim 1, wherein R represents one of the groups hydrogen,
2-oxo-pyrrolidin-3-ylcarbamoyl,
thien-2-yl-methylcarbamoyl,
3,4-dihydroxy-benzylcarbamoyl,
2-oxo-tetrahydrothien-3-ylcarbamoyl,
4-sulphamoyl-benzylcarbamoyl,
3-methoxy-isoxazol-5-ylmethylcarbamoyl,
3-hydroxy-isoxazol-5-ylmethylcarbamoyl,
1,1-dioxo-tetrahydrothien-3-ylmethylcarbamoyl,
(2-amino-thiazol-4-yl)-methoxyiminoacetyl,
1-methyl-1H-tetrazol-5-ylsulphanylacetyl,
3-carbamoyl-pyridin-1-ylioacetyl.

16. The compound of claim 1, wherein R represents one of the groups 2-t-butoxycarbonyl-ethylcarbamoyl,
4-hydroxy-benzylcarbamoyl,
trifluoromethylsulphonyl,
benzyloxycarbonylcarbamoyl,
benzylcarbamoyl,
cyclopropylcarbamoyl,
4-sulphamoyl-benzylcarbamoyl,
2-thiophen-2-yl-ethylcarbamoyl,
5-methyl-1,3,4-thiadiazol-2-yl-sulphonylacetyl,
5-amino-1,3,4-thiadiazol-2-yl-sulphonylacetyl,
pyridin-4-ylsulphahylacetyl,
phenylaminoacetyl,
4-hydroxy-phenylcarbamoylmethyl,
methoxycarbonylmethyl,
ethyl,
carbamoylmethyl,
pyridin-4-ylsulphanylacetyl,
3-carbamoyl-pyridin-1-ylioacetyl,
carbamoylmethylsulphanylacetyl,
(R)-benzyloxycarbonylamino-phenyl-acetyl,
(R)-amino-phenyl-acetyl,
carboxymethylcarbamoyl.

17. The compound of claim 1, wherein A represents a residue —CH₂-L.

18. The compound of claim 17, wherein L signifies a group of the formula

—OCONR²R³ (c)

wherein $R^2$ represents hydrogen and $R^3$ represents hydrogen, lower (cyclo)alkyl, halo-lower alkyl, carbamoylmethyl or a residue —(CH$_2$)$_q$Q, wherein q is 0, 1 or 2 and Q has the above significance, or R$^2$ and R$^3$ together with the nitrogen atom represent a saturated N-heterocycle optionally containing sulphur, oxygen or additional nitrogen.

19. The compound of claim 18, wherein R$^2$ represents hydrogen and R$^3$ represents hydrogen or one of the groups methyl, cyclopropyl, 2,2,2-trifluoroethyl, phenyl, p-hydroxyphenyl, benzyl, p-hydroxybenzyl, 4-pyridylmethyl, carbamoylmethyl, 1H-tetrazol-5-yl.

20. The compound of claim 18, wherein —NR$^2$R$^3$ represents one of the groups piperazinyl, 4-methyl-piperazinyl, 4-morpholinyl, 4-thiomorpholinyl.

21. The compound of claim 19, wherein A represents the carbamoyloxymethyl group.

22. The compound of claim 1, wherein A represents a group of the formula

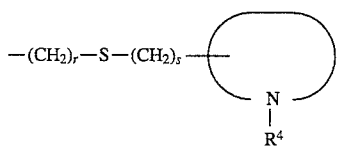

(d)

in which each of r and s represent 0 or 1 and

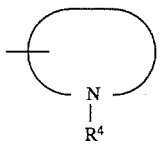

represents a 5- or 6-membered N-heterocycle optionally containing a sulphur or oxygen atom; and in which R$^4$ signifies lower alkyl, sulphonylmethyl or a group of the formula —CH$_2$CONR$^5$R$^6$  (d1)

and R$^5$ signifies hydrogen and R$^6$ signifies hydrogen, lower (cyclo)alkyl, hydroxy, carbamoylmethyl, halo-lower alkyl or a residue —(CH$_2$)$_q$Q, wherein q is 0, 1 or 2 and Q has the above significance, or R$^5$ and R$^6$ together with the nitrogen atom to which they are bound represent a saturated N-heterocycle optionally containing sulphur, oxygen or additional nitrogen.

23. The compound of claim 22, wherein the residue

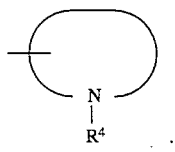

represents a 1-R$^4$-substituted 1H-tetrazol-5-yl residue.

24. The compound of claim 23, wherein R$^4$ represents methyl.

25. The compound of claim 22, wherein R$^4$ represents group (d1) in which R$^5$ signifies hydrogen and R$^6$ signifies hydrogen, methyl, cyclopropyl, phenyl, p-hydroxyphenyl, benzyl, phenethyl, carbamoylmethyl or hydroxy or R$^5$ and R$^6$ together with the nitrogen atom to which they are bound signify piperazinyl, 4-methyl-piperazinyl, 4-morpholinyl or 4-thiomorpholinyl.

26. The compound of claim 24, wherein A represents the 1-methyl-1H-tetrazol-5-ylsulphanylmethyl group.

27. The compound of claim 24, wherein A represents the 1-carbamoylmethyl-1H-tetrazol-5-ylsulphanylmethyl group.

28. The compound of claim 1, wherein A represents a group of the formula

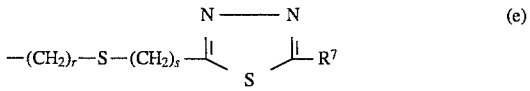

(e)

in which each of r and s represent 0 or 1 and R$^7$ represents methyl, amino, acetylamino or pyridinioacetylamino.

29. The compound of claim 28, wherein A represents the 5-amino-1,3,4-thiadiazol-2-yl-sulphanylmethyl group or the 5-amino-1,3,4-thiadiazol-2-yl-sulphanyl group.

30. The compound of claim 1, wherein A signifies a group of the formula

(f)

in which each of r and s represent 0 or 1 and R$^8$ represents the pyridin-4-yl group or the group

(g)

and R$^9$ signifies methyl, benzyl, carboxymethyl or carbamoylmethyl.

31. The compound of claim 30, wherein A represents the pyridin-4-ylsulphanylmethyl group.

32. The compound of claim 1, wherein A represents one of the groups selected from 1-methyl-1H-tetrazol-5-ylsulphanyl, 5-methyl-1,3,4-thiadiazol-2-ylsulphanyl, 5-(pyridin-1-ylioacetylamino)-1,3,4-thiadiazol-2-ylsulphanyl, 1-methyl-pyridin-4-yliosulphanylmethyl, pyridin-1-yliomethyl, methylsulphonyloxy, 4-methyl-phenylsulphonyloxy, carboxymethyl, methoxycarbonylmethyl, methyl, vinyl, and acetoxymethyl.

33. The compound of claim 1, wherein A represents one of the groups selected from 2-carbamoyl-5-methyl[1,2,4]triazolo[1,5-a]pyrimidin-7-ylsulphanylmethyl, 1-(cyclopropyl-carbamoylmethyl)-1H-tetrazol-5-ylsulphanylmethyl, 1-(phenylethyl-carbamoylmethyl)-1H-tetrazol-5-ylsulphanylmethyl, 1-(carbamoylmethyl-carbamoylmethyl)-1H-tetrazol-5-ylsulphanylmethyl, 1-methylcarbamoylmethyl-1H-tetrazol-5-ylsulphanylmethyl, 1-(2-morpholin-4-yl-2-oxo-ethyl)-1H-tetrazol-5-ylsulphanylmethyl, 1-(4-hydroxyphenyl-carbamoylmethyl)-1H-tetrazol-5-ylsulphanylmethyl, 1-(hydroxy-carbamoylmethyl)-1H-tetrazol -5-ylsulphahylmethyl, 1-sulphonylmethyl-1H-tetrazol-5-ylsulphanylmethyl, 1-methyl-imidazol-2-ylsulphanylmethyl, 5-hydroxy-4-methyl-4H-[1,2,4]-triazol-3-ylsulphanylmethyl, 6,7-dihydro-5H-1-pyrindin-4-ylsulphanylmethyl, 5-methyl-1,3,4- thiadiazol-2-ylsulphahylmethyl, 1-methyl-1H-tetrazol-5-yl-methylsulphanylmethyl, 5-methylsulphanyl-1H-tetrazol-1-ylmethyl, 4-methyl-4-pyridiniosulphanyl, carbamoylmethylsulphanyl, 5-(1,4-dimethyl-1H-1,2,4-triazol-4-ium)-methylsulphanyl, pyridin-4-ylsulphanyl, 5-acetylamino-1,3,4-thiadiazol-2-ylsulphanylmethyl, 2-cyanovinyl (Z and E isomers), 1-carboxymethyl-pyridin-4-yliosulphanylmethyl, 1-carbamoylmethyl-pyridin-4-yliosulphanylmethyl, 1-benzyl-pyridin-4-yliosulphanylmethyl, 2,5-dihydro-6-hydroxy-2-methyl-5-oxo-1,2,4-triazin-3-ylsulphanylmethyl, piperidin-1-ylmethyl, 3-benzyloxycarbonylmethyl-pyridin-1-yliomethyl, 3-carboxymethyl-pyridin-1-yliomethyl, 4-pyridin-3-yl-thiazol-2-ylsulphahylmethyl, pyrimidin-2-ylsulphanyl, 1H-1,2,4-triazol-3-ylsulphanylmethyl, azidomethyl, acetylaminomethyl, methylsulphonylaminomethyl, 4-hydroxy-phenylcarbamoyloxymethyl, 2,2,2-trifluoroethylcarbamoyloxymethyl, cyclopropylcarbamoyloxymethyl, carbamoylmethylcarbamoyloxymethyl, methylcarbamoyloxymethyl, pyridinylcarhamoyloxymethyl, 4-hydroxy-benzylcarbamoyloxymethyl, 4-methyl-piperazin-1-ylcarbonyloxymethyl, 1H-tetrazol-5-yl-amino-carbonyloxymethyl, and methoxy.

34. A compound of the formula

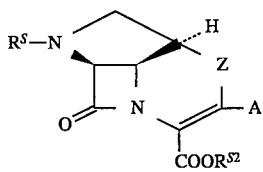

II in which Z signifies oxygen or sulphur, A signifies lower alkyl, hydroxy-lower alkyl, vinyl, cyanovinyl, optionally phenyl-substituted lower (cyclo)alkanoyloxy or (cyclo)alkylsulphonyloxy, optionally lower-(cyclo)alkyl- substituted benzoyloxy or phenylsulphonyloxy, a residue —S-Het or —S—$CH_2$-Het, wherein Het represents a 5- or 6-membered heterocycle containing nitrogen, sulphur and/ or oxygen, or a residue —$CH_2$-L, wherein L represents optionally phenyl-substituted lower (cyclo)alkanoyloxy or (cyclo)alkylsulphonyloxy, optionally lower (cyclo)alkyl- substituted benzoyloxy or phenylsulphonyloxy, carbamoyloxy, lower (cyclo)alkoxycarbonyl, carboxy, azido, amino, lower (cyclo)alkanoylamino, lower (cyclo)alkylsulphonylamino, lower (cyclo)alkylamino, di-lower (cyclo)aikylamino, a 5- or 6-membered ring bonded to a nitrogen atom or a residue —S-Het or —S—$CH_2$-Het, wherein Het has the above significance, $R^S$ signifies an amino protecting group or hydrogen, lower (cyclo)alkyl optionally substituted by carboxy, lower alkoxycarbonyl, carbamoyl, lower alkylcarbamoyl, phenylcarbamoyl or hydroxyphenylcarbamoyl, lower alkenylmethyl, lower alkenylmethoxycarbonyl, formyl, lower (cyclo)alkanoyl or (cyclo)alkylsulphonyl optionally substituted by halogen, cyano, carbamoyl-loweralkoxy, carbamoyl-lower alkylthio or carbamoyl-lower alkylamino, carbamoyl optionally substituted by lower (cyclo)alkyl, lower alkoxycarbonyl-lower alkyl, benzyloxycarbonyl-lower alkyl or carboxy-lower alkyl or a ring structure of the formulae $$Q—X—CO—$$ (a1)

$$Q—X—SO_2$$ (a2)

wherein Q represents a 5- or 6-membered ring optionally containing nitrogen, sulphur and/or oxygen and X represents a direct bond or one of the groups —$CH_2$—, —$CH_2CH_2$—, —CH=CH—, —NH—, —$NHCH_2$—, —$CH_2NH$—, —$CH(NH_2)$—, —$CH_2CH_2NH$—, —$C(=NOCH_3)$—, —$OCH_2$- and —$SCH_2$— and $R^{S2}$ represents a carboxy protecting group.

35. The compound of claim 34, wherein Z represents oxygen or sulphur, $R^{S2}$ represents allyl and $R^S$ represents allyloxycarbonyl.

36. A compound of the formula

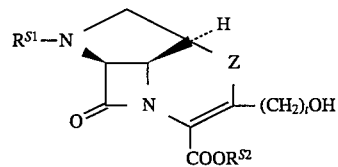

in which Z signifies oxygen or sulphur, $R^{S1}$ represents an amino protecting group, $R^{S2}$ represents a carboxy protecting group and t represents the number 0 or 1.

37. The compound of claim 36, wherein Z represents oxygen or sulphur, $R^{S2}$ represents allyl and $R^{S1}$ represents allyloxycarbonyl or acetyl.

38. A pharmaceutical composition comprising a therapeutically effective amount of a compound of the formula

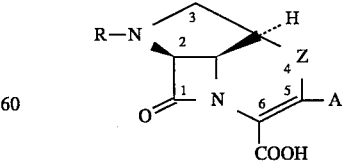

I in which Z signifies oxygen or sulphur and R signifies hydrogen, lower (cyclo)alkyl optionally substituted by carboxy, lower alkoxycarbonyl, carbamoyl, lower alkylcarbamoyl, phenylcarbamoyl or hydroxyphenylcarbamoyl, lower alkenylmethyl, lower alkenylmethoxycarbonyl, formyl, lower (cyclo)alkanoyl or (cyclo)alkylsulphonyl optionally substituted by halogen, cyano, carbamoyl-lower-alkoxy, carbamoyl-lower alkylthio or carbamoyl-lower alkylamino, carbamoyl optionally substituted by lower (cyclo)alkyl, lower alkoxycarbonyl-lower alkyl, benzyloxycarbonyl-lower alkyl or carboxy-lower alkyl or a ring structure of the formulae Q—X—CO— (a1)

Q—X—SO₂— (a2)

wherein Q represents a 5- or 6-membered ring optionally containing nitrogen, sulphur and/or oxygen and X represents a direct bond or one of the groups —CH₂—, —CH₂CH₂—, —CH=CH—, —NH—, —NHCH₂—, —CH₂NH—, —CH(NH₂)—, —CH₂CH₂NH—, —C(=NOCH₃)—, —OCH₂— and —SCH₂—; and wherein further A signifies lower alkyl, hydroxy-lower alkyl, vinyl, cyanovinyl, lower alkoxy, optionally phenyl-substituted lower (cyclo)alkanoyloxy or (cyclo)alkylsulphonyloxy, optionally lower-(cyclo)alkyl-substituted benzoyloxy or phenylsulphonyloxy, a residue —S-Het or —S—CH₂-Het, wherein Het represents a 5- or 6-membered heterocycle containing nitrogen, sulphur and/or oxygen, or a residue —CH₂-L, wherein L represents optionally phenyl-substituted lower (cyclo)alkanoyloxy or (cyclo)alkylsulphonyloxy, optionally lower (cyclo)alkyl-substituted benzoyloxy or phenylsulphonyloxy, carbamoyloxy, lower (cyclo)alkoxycarbonyl, carboxy, azido, amino, lower (cyclo)alkanoylamino, lower (cyclo)alkylsulphonylamino, lower (cyclo)alkylamino, di-lower (cyclo)alkylamino, a 5- or 6-membered ring bonded to a nitrogen atom or a residue —S-Het or —S—CH₂-Het, wherein Het has the above significance, or a pharmaceutically compatible, readily hydrolyzable ester or salt of one of these compounds, and a pharmaceutically acceptable carrier.

39. The pharmaceutical composition of claim 38 further comprising a β-lactam antibiotic or a pharmaceutically acceptable salt thereof.

40. The pharmaceutical composition of claim 39 wherein the compound of formula I and the β-lactam antibiotic are present in a ratio of from about 1:20 to about 1:1.

41. The pharmaceutical composition of claim 40 wherein the β-lactam antibiotic is selected from the group consisting of penicillins, cephalosporins, penems or carbapenems, or their respective pharmaceutically acceptable salts.

42. The pharmaceutical composition of claim 41, wherein the β-lactam antibiotic is a penicillin.

43. The pharmaceutical composition of claim 42, wherein the penicillin is selected from the group benzylpenicillin, piperacillin, phenoxymethylpenicillin, carbenicillin, apalcillin, methicillin, propicillin, tricarcillin, ampicillin, amoxicillin or mecillinam.

44. The pharmaceutical composition of claim 41, wherein the β-lactam antibiotic is a cephalosporin.

45. The pharmaceutical composition of claim 44, wherein the cephalosporin is selected from the group ceftriaxone, ceftazidime, cefetamet, cefatamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R, 7R)-7-[(Z)-2-(2-amino-4-thiazolyl)-2-(methoxyimino)acetamido]-3-(azidomethyl)-8-oxo-5-thia-1-azabicyclo[4.2.0]oct-2-ene-2-carboxylic acid or (E)-2-(isobutoxycarbonyl)-2-pentenyl (6R,7R)-7-[(Z)- 2-(2-amino-4-thiazolyl)-2-(methoxyimino)acetamido]-3-(azidomethyl)-8-oxo-5-thia-1-azabicyclo[4.2.0]oct-2-ene-2-carboxylate.

46. The pharmaceutical composition of claim 41, wherein the β-lactam antibiotic is a penem.

47. The pharmaceutical composition of claim 46, wherein the penem is imipenem.

48. The pharmaceutical composition of claim 41, wherein the β-lactam antibiotic is a carbapenem.

49. The pharmaceutical composition of claim 48, wherein the carbapenem is meropenem.

50. The pharmaceutical composition of claim 45 wherein the cephalosporin is ceftriaxone or one of its pharmaceutically compatible salts.

51. The pharmaceutical composition of claim 50 containing ceftriaxone disodium salt hemiheptahydrate.

52. The pharmaceutical composition of claim 38 which is in unit dosage form.

53. The pharmaceutical composition of claim 52 wherein the unit dosage form is selected from tablets, dragees, suppositories, hard gelatin capsules, soft gelatin capsules, solutions, suspensions, or emulsions.

54. The pharmaceutical composition of claim 39 which is in unit dosage form.

55. The pharmaceutical composition of claim 54 wherein the unit dosage form is selected from tablets, dragees, suppositories, hard gelatin capsules, soft gelatin capsules, solutions, suspensions, or emulsions.

56. A pharmaceutical composition comprising (a) a therapeutically effective mount of a compound of the formula

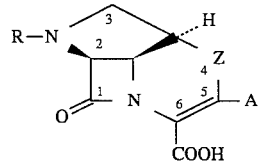

in which Z signifies oxygen or sulphur and R signifies hydrogen, lower (cyclo)alkyl optionally substituted by carboxy, lower alkoxycarbonyl, carbamoyl, lower alkylcarbamoyl, phenylcarbamoyl or hydroxyphenylcarbamoyl, lower alkenylmethyl, lower alkenylmethoxycarbonyl, formyl, lower (cyclo)alkanoyl or (cyclo)alkylsulphonyl optionally substituted by halogen, cyano, carbamoyl-lower-alkoxy, carbamoyl-lower alkylthio or carbamoyl-lower alkylamino, carbamoyl optionally substituted by lower (cyclo)alkyl, lower alkoxycarbonyl-lower alkyl, benzyloxycarbonyl-lower alkyl or carboxy-lower alkyl or a ring structure of the formulae —Q—X—CO— (a1)

—Q—X—SO₂— (a2)

wherein Q represents a 5- or 6-membered ring optionally containing nitrogen, sulphur and/or oxygen and X represents a direct bond or one of the groups —CH₂—, —CH₂CH₂—, —CH=CH—, —NH—, —NHCH₂—, —CH₂NH—, —CH(NH₂)—, —CH₂CH₂NH—, —C(=NOCH₃)—, —OCH₂— and —SCH₂—; and wherein further A signifies lower alkyl, hydroxy-lower alkyl, vinyl, cyanovinyl, lower alkoxy, optionally phenyl-substituted lower (cyclo)alkanoyloxy or (cyclo)alkylsulphonyloxy, optionally lower-(cyclo)alkyl-substituted benzoyloxy or phenylsulphonyloxy, a residue —S-Het or —S—CH₂-Het, wherein Het represents a 5- or 6-membered heterocycle containing nitrogen, sulphur and/or oxygen, or a residue —CH₂-L, wherein L represents optionally phenyl-substituted lower (cyclo)alkanoyloxy or (cyclo)alkylsulphonyloxy, optionally lower (cyclo)alkyl-substituted benzoyloxy or phenylsulphonyloxy, carbamoyloxy, lower (cyclo)alkoxycarbonyl, carboxy, azido, amino, lower (cyclo)alkanoylamino, lower (cyclo)alkylsulphonylamino, lower (cyclo)alkylamino, di-lower (cyclo)alkylamino, a 5- or 6-membered ring bonded to a nitrogen atom or a residue —S-Het or —S—CH$_2$-Het, wherein Het has the above significance, or a pharmaceutically compatible, readily hydrolyzable ester or salt of one of these compounds; and (b) a β-lactam antibiotic or a pharmaceutically acceptable salt thereof;

and a pharmaceutically acceptable carrier.

57. The pharmaceutical composition of claim 56 which is in unit dosage form.

58. The pharmaceutical composition of claim 57 wherein the unit dosage form is selected from tablets, dragees, suppositories, hard gelatin capsules, soft gelatin capsules, solutions, suspensions, or emulsions.

59. The pharmaceutical composition of claim 56 wherein the compound of formula I and the β-lactam antibiotic are present in a ratio of from about 1:20 to about 1:1.

60. The pharmaceutical composition of claim 59 wherein the β-lactam antibiotic is selected from the group consisting of penicillins, cephalosporins, penems, or carbapenems.

61. The pharmaceutical composition of claim 60, wherein the β-lactam antibiotic is a penicillin.

62. The pharmaceutical composition of claim 61, wherein the penicillin is selected from the group benzylpenicillin, piperacillin, phenoxymethylpenicillin, carbenicillin, apalcillin, methicillin, propicillin, tricarcillin, ampicillin, amoxicillin or mecillinam.

63. The pharmaceutical composition of claim 60, wherein the β-lactam antibiotic is a cephalosporin.

64. The pharmaceutical composition of claim 63, wherein the cephalosporin is selected from the group ceftriaxone, ceftazidime, cefetamet, cefetamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R, 7R)-7-[(Z)-2-(2-amino-4-thiazolyl)-2-(methoxyimino)acetamido]- 3-(azidomethyl)-8-oxo-5-thia-1-azabicyclo[4.2.0]oct-2-ene-2-carboxylic acid or (E)-2-(isobutoxycarbonyl)-2-pentenyl (6R,7R)-7-[(Z)- 2-(2-amino-4-thiazolyl)-2-(methoxyimino)acetamido]-3-(azidomethyl)- 8-oxo-5-thia-1-azabicyclo[4.2.0]oct-2-ene-2-carboxylate.

65. The pharmaceutical composition of claim 60, wherein the β-lactam antibiotic is a penem.

66. The pharmaceutical composition of claim 65, wherein the penem is imipenem.

67. The pharmaceutical composition of claim 60, wherein the β-lactam antibiotic is a carbapenem.

68. The pharmaceutical composition of claim 67, wherein the carbapenem is meropenem.

69. A method of treating bacterial infections in a mammal in need of such treatment which comprises administering a therapeutically effective mount of a compound of the formula

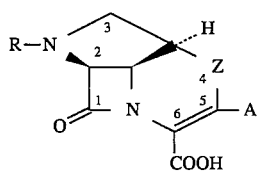

in which Z signifies oxygen or sulphur and R signifies hydrogen, lower (cyclo)alkyl optionally substituted by carboxy, lower alkoxycarbonyl, carbamoyl, lower alkylcarbamoyl, phenylcarbamoyl or hydroxyphenylcarbamoyl, lower alkenylmethyl, lower alkenylmethoxycarbonyl, formyl, lower (cyclo)alkanoyl or (cyclo)alkylsulphonyl optionally substituted by halogen, cyano, carbamoyl-lower-alkoxy, carbamoyl-lower alkylthio or carbamoyl-lower alkylamino, carbamoyl optionally substituted by lower (cyclo)alkyl, lower alkoxycarbonyl-lower alkyl, benzyloxycarbonyl-lower alkyl or carboxy-lower alkyl or a ring structure of the formulae Q—X—CO— (a1)

Q—X—SO$_2$— (a2)

wherein Q represents a 5- or 6-membered ring optionally containing nitrogen, sulphur and/or oxygen and X represents a direct bond or one of the groups —CH$_2$—, —CH$_2$CH$_2$—, —CH=CH—, —NH—, —NHCH$_2$—, —CH$_2$NH—, —CH(NH$_2$)—, —CH$_2$CH$_2$NH—, —C(=NOCH$_3$)—, —OCH$_2$— and —SCH$_2$—; and wherein further A signifies lower alkyl, hydroxy-lower alkyl, vinyl, cyanovinyl, lower alkoxy, optionally phenyl-substituted lower (cyclo)alkanoyloxy or (cyclo)alkylsulphonyloxy, optionally lower-(cyclo)alkyl-substituted benzoyloxy or phenylsulphonyloxy, a residue —S-Het or —S—CH$_2$-Het, wherein Het represents a 5- or 6-membered heterocycle containing nitrogen, sulphur and/or oxygen, or a residue —CH$_2$-L, wherein L represents optionally phenyl-substituted lower (cyclo)alkanoyloxy or (cyclo)alkylsulphonyloxy, optionally lower (cyclo)alkyl-substituted benzoyloxy or phenylsulphonyloxy, carbamoyloxy, lower (cyclo)alkoxycarbonyl, carboxy, azido, amino, lower (cyclo)alkanoylamino, lower (cyclo)alkylsulphonylamino, lower (cyclo)alkylamino, di-lower (cyclo)alkylamino, a 5- or 6-membered ring bonded to a nitrogen atom or a residue —S-Het or —S—CH$_2$-Het, wherein Het has the above significance, or a pharmaceutically compatible, readily hydrolyzable ester or salt of one of these compounds; and a pharmaceutically acceptable carrier.

70. The method of claim 69 which further comprises administering a therapeutically effective amount of a β-lactam antibiotic and their pharmaceutically acceptable salts.

71. The method of claim 70 wherein the compound of formula I and the β-lactam antibiotic are present in a ratio of from about; 1:20 to about 1:1.

72. The method of claim 70 wherein the β-lactam antibiotic is selected from the group consisting of penicillins, cephalosporins, penems or carbapenems, or their respective pharmaceutically acceptable salts.

73. A method of treating bacterial infection in a mammal in need of such treatment comprising administering (a) a therapeutically effective mount of a compound of the formula

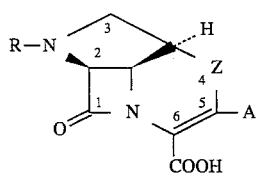

in which Z signifies oxygen or sulphur and R signifies hydrogen, lower (cyclo)alkyl optionally substituted by carboxy, lower alkoxycarbonyl, carbamoyl, lower alkylcarbamoyl, phenylcarbamoyl or hydroxyphenylcarbamoyl, lower alkenylmethyl, lower alkenylmethoxycarbonyl, formyl, lower (cyclo)alkanoyl or (cyclo)alkylsulphonyl optionally substituted by halogen, cyano, carbamoyl-lower-alkoxy, carbamoyl-lower alkylthio or carbamoyl-lower alkylamino, carbamoyl optionally substituted by lower (cyclo)alkyl, lower alkoxycarbonyl-lower alkyl, benzyloxycarbonyl-lower alkyl or carboxy-lower alkyl or a ring structure of the formulae Q—X—CO— (a1)

Q—X—SO$_2$— (a2)

wherein Q represents a 5- or 6-membered ring optionally containing nitrogen, sulphur and/or oxygen and X represents a direct bond or one of the groups —CH$_2$—, —CH$_2$CH$_2$—, —CH=CH—, —NH—, —NHCH$_2$—, —CH$_2$NH—, —CH(NH$_2$)—, —CH$_2$CH$_2$NH—, —C(=NOCH$_3$)—, —OCH$_2$— and —SCH$_2$—; and wherein further A signifies lower alkyl, hydroxy-lower alkyl, vinyl, cyanovinyl, lower alkoxy, optionally phenyl-substituted lower (cyclo)alkanoyloxy or (cyclo)alkylsulphonyloxy, optionally lower-(cyclo)alkyl-substituted benzoyloxy or phenylsulphonyloxy, a residue —S-Het or —S—CH$_2$-Het, wherein Het represents a 5- or 6-membered heterocycle containing nitrogen, sulphur and/or oxygen, or a residue —CH$_2$-L, wherein L represents optionally phenyl-substituted lower (cyclo)alkanoyloxy or (cyclo)alkylsulphonyloxy, optionally lower (cyclo)alkyl-substituted benzoyloxy or phenylsulphonyloxy, carbamoyloxy, lower (cyclo)alkoxycarbonyl, carboxy, azido, amino, lower (cyclo)alkanoylamino, lower (cyclo)alkylsulphonylamino, lower (cyclo)alkylamino, di-lower (cyclo)alkylamino, a 5- or 6-membered ring bonded to a nitrogen atom or a residue —S-Het or —S—CH$_2$-Het, wherein Het has the above significance, or a pharmaceutically compatible, readily hydrolyzable ester or salt of one of these compounds: and (b) a β-lactam antibiotic or a pharmaceutically acceptable salt thereof;

and a pharmaceutically acceptable carrier.

74. The method of claim 73 wherein the compound of formula I and the β-lactam antibiotic are present in a ratio of from about 1:20 to about 1:1.

75. The method of claim 74 wherein the β-lactam antibiotic is selected from the group consisting of penicillins, cephalosporins, penems, or carbapenems.

* * * * *

UNITED STATES PATENT AND TRADEMARK OFFICE
CERTIFICATE OF CORRECTION

PATENT NO. : 5,494,666
DATED : February 27, 1996
INVENTOR(S) : Markus Bohringer, Christian Hubschwerlen, Philippe Pflieger, Jean-Luc Specklin It is certified that error appears in the above-indentified patent and that said Letters Patent is hereby corrected as shown below:

In claim 1, column 114, line 63, delete "aIkyl" and insert therefor -- alkyl --.

In claim 1, column 115, line 12, delete "Her" and insert therefor -- Het --.

In claim 16, column 116, line 46, delete "pyridin-4-vlsulphahylacetyl" and insert therefor -- pyridin-4-ylsulphanylacetyl --.

In claim 33, column 119, line 15, delete "-2-ylsulphahylmethyl" and insert therefor -- -2-ylsulphanylmethyl --.

In claim 33, column 119, line 36, delete "-2-vlsulphahylmethyl" and insert therefor -- -2-ylsulphanylmethyl --.

In claim 34, column 120, line 9, delete "(cyclo)aiky-" and insert therefor -- (cyclo)alky- --.

In claim 56, column 122, line 27, delete "mount" and insert therefor -- amount --.

In claim 56, column 122, lines 50-53, delete

"-Q-X-CO-        (a1)
 -Q-X-SO$_2$-    (a2)"

and insert therefor

-- Q-X-CO-       (a1)
   Q-X-SO$_2$-   (a2) --.

UNITED STATES PATENT AND TRADEMARK OFFICE
CERTIFICATE OF CORRECTION

PATENT NO. : 5,494,666
DATED : February 27, 1996
INVENTOR(S) : Markus Bohringer, Christian Hubschwerlen, Philippe Pflieger, Jean-Luc Specklin It is certified that error appears in the above-indentified patent and that said Letters Patent is hereby corrected as shown below:

In claim 33, column 119, lines 7-8, delete "-5-ylsulphahylmethyl" and insert therefor -- -5-ylsulphanylmethyl --.

In claim 33, column 119, line 49, delete "pyridinylcarhamoyloxymethyl" and insert therefor -- pyridinylcarbamoyloxymethyl --.

In claim 69, column 123, line 66, delete "mount" and insert therefor -- amount --.

In claim 71, column 124, line 58, delete "about;" and insert therefor -- about --.

In claim 73, column 124, line 66, delete "mount" and insert therefor -- amount --.

In claim 73, column 126, line 20, delete "compounds:" and insert therefor -- compounds; --.

Signed and Sealed this

Ninth Day of July, 1996

Attest:

BRUCE LEHMAN

*Attesting Officer*    *Commissioner of Patents and Trademarks*